(12) United States Patent
Paquet et al.

(10) Patent No.: US 8,470,999 B2
(45) Date of Patent: Jun. 25, 2013

(54) OLIGONUCLEOTIDES FOR TREATING INFLAMMATION AND NEOPLASTIC CELL PROLIFERATION

(76) Inventors: Luc Paquet, Sherbrooke (CA); Helene D'Anjou, Boucherville (CA); Nicolay Ferrari, Boucherville (CA)

(*) Notice: Subject to any disclaimer, the term of this patent is extended or adjusted under 35 U.S.C. 154(b) by 0 days.

(21) Appl. No.: 12/992,885

(22) PCT Filed: Mar. 31, 2009

(86) PCT No.: PCT/CA2009/000415
§ 371 (c)(1),
(2), (4) Date: Feb. 23, 2011

(87) PCT Pub. No.: WO2009/137912
PCT Pub. Date: Nov. 19, 2009

(65) Prior Publication Data
US 2011/0144183 A1    Jun. 16, 2011

Related U.S. Application Data

(60) Provisional application No. 61/053,327, filed on May 15, 2008.

(51) Int. Cl.
*C07H 21/04*    (2006.01)
*C12N 15/11*    (2006.01)
*C12Q 1/68*     (2006.01)
*C12N 5/00*     (2006.01)
*C12N 5/02*     (2006.01)

(52) U.S. Cl.
USPC ........... 536/24.5; 514/44 A; 435/6.1; 435/375

(58) Field of Classification Search
None
See application file for complete search history.

(56) References Cited

U.S. PATENT DOCUMENTS

| | | | | |
|---|---|---|---|---|
| 5,861,279 A | * | 1/1999 | Zhang et al. | 435/69.1 |
| 7,250,496 B2 | * | 7/2007 | Bentwich | 536/23.1 |
| 7,696,342 B1 | * | 4/2010 | Bentwich | 536/24.5 |
| 2005/0221354 A1 | | 10/2005 | Mounts | |
| 2006/0088836 A1 | * | 4/2006 | Wohlgemuth et al. | 435/6 |

FOREIGN PATENT DOCUMENTS

| WO | 9741154 | 11/1997 |
|---|---|---|
| WO | WO 2004058052 A2 * | 7/2004 |
| WO | 2006045202 | 5/2006 |
| WO | 2007048244 | 5/2007 |

OTHER PUBLICATIONS

Gauvreau et al., "Antisense Therapy against CCR3 and the Common Beta Chain Attenuates Allergen-induced Eosinophilic Responses," Am J Respir Crit Care Med 177:952-958 (2008).

Allakhverdi et al., "Multitargeted Appoach Using Antisense Oligonucleotides for the Treatment of Asthma," Ann. N.Y. Acad. Sci. 1082:62-73 (2006).

Fortin et al., "Effects of Antisense Oligodeoxynucleotides Targeting CCR3 on the Airway Response to Antigen in Rats," Oligonucletotides 16:203-212 (2006).

Allakhverdi, Z. et al., "Inhibition of Antigen-induced Eosinophilia and Airway Hyperresponsiveness by Antisense Oligonucleotides Directed Against the Common Beta Chain of IL-3, IL-5, GM-CS Receptors in a Rat Model of Allergic Asthma", American Journal of Respiratory and Critical Care Medicine, 2002, 165:1015-1021.

* cited by examiner

*Primary Examiner* — Dana Shin
(74) *Attorney, Agent, or Firm* — Pepper Hamilton, LLP

(57) ABSTRACT

There is provided oligonucleotides directed against the CCR3 receptor and the common beta sub-unit of IL-3, IL-5 and GM-CSF receptors. The oligonucleotides are useful to inhibit general inflammation, including inflammation associated with asthma, COPD, allergy, Cystic fibrosis (CF), hypereosinophilia and neoplastic cell proliferation such as cancer.

18 Claims, 15 Drawing Sheets

US 8,470,999 B2

OLIGONUCLEOTIDES FOR TREATING INFLAMMATION AND NEOPLASTIC CELL PROLIFERATION

CROSS-REFERENCE TO RELATED APPLICATIONS

This application is a U.S. National Stage application under 35 U.S.C. §371, which claims priority to International Application Serial No. PCT/CA2009/000415, filed Mar. 31, 2009, which claims priority to U.S. Provisional Application No. 61/053,327, filed on May 15, 2008, each of which is incorporated herein by reference in its entirety.

FIELD OF THE INVENTION

The invention relates to the use of antisense oligonucleotides directed against specific cellular receptors, alone or in combination, in order to inhibit general inflammation, including inflammation associated with asthma, COPD, allergy, Cystic fibrosis (CF), and hypereosinophilia. The invention also relates to the use of antisense oligonucleotides to inhibit neoplastic cell proliferation such as cancer.

BACKGROUND OF THE INVENTION

Antisense oligonucleotides (AONs) are complementary to a region of a target gene and are capable of hybridizing to the target gene sequence and inhibiting gene expression. Gene expression is inhibited through hybridization of an AON to a specific messenger RNA (mRNA) sense target according to the Watson-Crick base pairing in which adenosine and thymidine (uracil in mRNA) or guanosine and cytidine interact through hydrogen bonding. Two mechanisms are generally thought to account for these effects, the first being hybridization with impaired translation of targeted mRNA, the second being the induction of RNase H or similar enzymes with associated degradation of target mRNA. A major advantage of this strategy is the specificity of action with the potential for reduced side effects and lower toxicity, especially when applied directly to the site of action (topical treatment). This therapeutic strategy could potentially be applied to any disease in which overexpression of one or several genes is believed to be responsible for the presence or persistence of the disease. As a result, there have been numerous studies investigating the use of AONs as therapeutic agents for cancer and viral diseases.

The alveolar and airway epithelium is recognized as a dynamic barrier that plays an important role in regulating inflammatory and metabolic responses to oxidative stress, sepsis, endotoxemia, and other critical illnesses in the lung. The respiratory epithelium, in particular, is a primary target of inflammatory conditions/infections at the epithelial-blood interface, and is itself capable of amplifying an inflammatory signal by recruiting inflammatory cells and producing inflammatory mediators.

Asthma is a disease that affects 5 to 10% of the population that has doubled in prevalence in the last 25 years. This increase has been noted especially in infants after a viral infection of the airways (bronchiolitis), in children and in occupation-induced asthma. The recurrent breathing problems associated with asthma are often triggered by allergens but the exact cause of asthma remains to be elucidated. However, it is believed that agents such as viruses are involved in the perpetuation of the abnormal inflammation that is found in the airways of patients with asthma and, thus, the persistence of the disease.

For this reason, the current recommendation for first line therapy of asthma is a potent anti-inflammatory medication such as those containing corticosteroids and anti-leukotrienes. Although this approach is effective in many patients, some patients are not controlled with current anti-inflammatory medications. Corticosteroids are also potent immunosuppressives with long term side effects and have not been shown to be effective in the prevention of allergy or asthma. Anti-leukotrienes have some effect in allergy and asthma but are not as effective as corticosteroids.

Several inflammatory mediators play a role in the appearance and perpetuation of inflammation in the airways of patients with asthma. Some mediators attract the inflammatory cells into the airways either through chemotaxis of eosinophils (the chemokines: RANTES, eotaxins 1, 2, 3, MCP-3, 4 that act mostly in asthmatic inflammation through a receptor called CCR3) or through endothelial cell activation (IL-4, -13). Other mediators cause the priming and increased survival of inflammatory cells in the airways (IL-3, -4, -5, GM-CSF). These mediators thus consist of either specific chemokines for eosinophils or cytokines of the T helper lymphocyte type 2 phenotype (Th2: IL-3, -4, -5, -6, -9, -10, -13 and GM-CSF), (John A E. and Lukacs N W., 2003 Sarcoidosis Vasc Diffuse Lung Dis., 20:180-189; Blease et al., 2003, Expert Opin Emerg Drugs. 8:71-81). An improvement in asthma and general respiratory inflammation has been demonstrated when there is a decrease in these inflammatory mediators in the airways.

Allergy is a hypersensitivity to an allergen causing an undesirable immune response. Allergy is a disease that is extremely prevalent, for example atopic rhinitis, eczema and allergic conjunctivitis affect around 30% of the population. Allergy is characterized by abnormal IgE production and inflammation to an allergen. In the presence of IgE and allergen, effector cells, such as the mast cells degranulate and release inflammatory mediators leading to the recruitment of the same inflammatory cells that are found in asthma. In allergic rhinitis (i.e. hayfever), allergic conjunctivitis, nasal polyposis, chronic sinusitis, eczema, and atopic dermatitis, one finds the same excess in inflammatory mediators as those present in asthma. IL-4 and IL-13 are necessary for the production of IgE and the induction of the cells with a Th2 phenotype (Barnes P J., 2003, Cytokine Growth Factor Rev. 14:511-522; Schuh et al., 2003, Cytokine Growth Factor Rev. 2003, 14:503-510). Atopic disease is a generic name for allergic diseases which are developed by exposure to allergens, especially in individuals with a genetic propensity for being easily sensitized to allergens. Individuals having these predisposing factors readily develop an abnormal immune response to alimentary antigens and inhalants. Some specific examples of allergic diseases are bronchial asthma, atopic dermatitis, urticaria, allergic rhinitis, allergic conjunctivitis and allergic enterogastritis.

Chronic Obstructive Pulmonary Disease (COPD) is another example of an inflammatory airway and alveolar disease where persistent upregulation of inflammation is thought to play a role. Inflammation in COPD is characterized by increased infiltration of neutrophils, CD8 positive lymphocytes, and macrophages into the airways. Neutrophils and macrophages play an important role in the pathogenesis of airway inflammation in COPD because of their ability to release a number of mediators including elastase, metalloproteases, and oxygen radicals that promote tissue inflammation and damage. It has been suggested that inflammatory cell accumulation in the airways of patients with COPD is driven by increased release of pro-inflammatory cytokines and of chemokines that attract the inflammatory cells into the airways, activate them and maintain their presence. The cells that are present also release enzymes (like metalloproteases) and oxygen radicals which have a negative effect on tissue and perpetuate the disease. A vast array of pro-inflammatory cytokines and chemokines has been shown to be increased within the lungs of patients with COPD. Among them, important roles are played by tumor necrosis factor alpha (TNF-alpha), granulocyte-macrophage colony stimulating factor (GM-CSF) and interleukin 8 (IL-8), levels of which are increased in the airways of patients with COPD.

Cystic fibrosis (CF) is yet another example of an airway inflammatory disease. Lack of CF transmembrane conductance regulator (CFTR) Cl⁻ channel function leads to progressive pulmonary damage, and ultimately results in death. The loss of functional CFTR in airway epithelial cells promotes depletion and increased oxidation of the airway surface liquid. Activated neutrophils present in airways produce large amounts of proteases and reactive oxygen species (ROS). Together these changes are associated with reduced mucociliary clearance of bacteria, activation of epithelial cell signalling through multiple pathways, and subsequent hyperinflammatory responses in CF airways. Both the NF-kappaB pathway and $Ca^{2+}$ mobilization in airway epithelial cells are believed to be factors in the control of lung inflammation via regulated production of mediators such as IL-8 that participate in recruitment and activation of neutrophils, modulation of apoptosis, and control of epithelial barrier integrity. Excessive and persistent inflammation sustained by bacterial infections and an ongoing accumulation of airway neutrophils is a key factor in lung destruction in CF patients, and has prompted investigation into anti-inflammatory therapies.

Other examples of respiratory diseases where inflammation seems to play a role include: eosinophilic cough, bronchitis, acute and chronic rejection of lung allograft, sarcoidosis, pulmonary fibrosis, rhinitis and sinusitis.

Eosinophilic cough is characterized by chronic cough and the presence of inflammatory cells, mostly eosinophils, within the airways of patients in the absence of airway obstruction or hyperresponsiveness. Several cytokines and chemokines are increased in this disease, although they are mostly eosinophil directed. Eosinophils are recruited and activated within the airways and potentially release enzymes and oxygen radicals that play a role in the perpetuation of inflammation and cough.

Acute bronchitis is an acute disease that occurs during an infection or irritating event for example by pollution, dust, gas or chemicals, of the lower airways. Chronic bronchitis is defined by the presence of cough and phlegm production on most days for at least 3 months of the year, for 2 years. One can also find inflammatory cells, mostly neutrophils, with a broad array of chemokines and cytokines, within the airways in cases of acute or chronic bronchitis. These mediators are thought to play a role in the inflammation, symptoms and mucus production that occur during these diseases.

Lung transplantation is performed in patients with end stage lung disease. Acute and more importantly chronic allograft rejection occur when the inflammatory cells of our body, lymphocytes, do not recognize the donor organ as "self". Inflammatory cells are recruited by chemokines and cytokines and release a vast array of enzymes that lead to tissue destruction and in the case of chronic rejection a disease called bronchiolitis obliterans.

Sarcoidosis is a disease of unknown cause where chronic non-caseating granulomas occur within tissue. The lung is the organ most commonly affected. Lung bronchioalveolar lavage shows an increase in mostly lymphocytes, macrophages and sometimes neutrophils and eosinophils. These cells are also recruited and activated by cytokines and chemokines and are thought to be involved in the pathogenesis of the disease.

Pulmonary fibrosis is a disease of lung tissue characterized by progressive and chronic fibrosis (scarring) which lead to chronic respiratory insufficiency. Different types and causes of pulmonary fibrosis exist but all are characterized by inflammatory cell influx and persistence, activation and proliferation of fibroblasts with collagen deposition in lung tissue. These events seem related to the release of cytokines and chemokines within lung tissue.

Acute rhinitis is an acute disease that occurs during an infection or irritating event, for example, by pollution, dust, gas or chemicals, of the nose or upper airways. Chronic rhinitis is defined by the presence of a constant chronic runny nose, nasal congestion, sneezing and pruritus. One can also find within the upper airways during acute or chronic rhinitis inflammatory cells with a broad array of chemokines and cytokines. These mediators are thought to play a role in the inflammation, symptoms and mucus production that occur during these diseases.

Acute sinusitis is an acute, usually infectious disease of the sinuses characterized by nasal congestion, runny, purulent phlegm, headache or sinus pain, with or without fever. Chronic sinusitis is defined by the persistence for more than 6 months of the symptoms of acute sinusitis. One can also find during acute or chronic sinusitis within the upper airways and sinuses inflammatory cells with a broad array of chemokines and cytokines. These mediators are thought to play a role in the inflammation, symptoms and phlegm production that occur during these diseases.

A neoplasm is an abnormal tissue growth that is uncontrollable and progressive. A malignant neoplasm is often characterized as a cancer. Cancer is the second leading cause of death in humans and is a general term for more than 100 diseases characterized by abnormal proliferation of immortalized cells. One of the mechanisms involved in the persistence and increase in cellular proliferation is the release of growth factors that act through cognate receptors. Amongst these growth factors, GM-CSF has been shown to be an important growth factor for several tumour cells. The chemokine receptor CCR3 was recently characterized in malignant B lymphocytes recovered from patients with chronic lymphocytic leukemia (CLL) and with hairy cell leukemia (HCL), (Trentin et al., 2004, Blood, 104, 502-508). Indeed, the transactivation of Epidermal Growth Factor Receptor (EGFR) through CCR3 chemokine receptor was found to be a critical pathway that elicits MAP kinase activation and cytokine production in bronchial epithelial cells (Adachi et al., 2004, Biochem. Biophys. Res. Commun. 320, 292-396). Inhibition of cancer cell proliferation via blockage of receptors for growth factors and/or chemokines may be important in the therapy of certain cancers.

Eosinophils are a type of white blood cell. They are granular leukocytes with a nucleus that usually has two lobes connected by a slender thread of chromatin, and cytoplasm containing course, round granules that are uniform in size and stainable by eosin. Hypereosinophilia is characterized by an increased number of eosinophils, often associated with allergies, asthmas and infections.

Uses of oligonucleotides directed against specific nucleic acid sequences coding for receptors for inhibition of inflammatory reactions is known. Co-owned International Patent Application Publication Nos. WO 99/66037 and WO 06/045202 describe AONs used for treating and/or preventing asthma, allergy, hypereosinophilia, general inflammation and cancer.

For potential clinical uses, AONs should exhibit stability against degradation by serum and cellular nucleases, show low non-specific binding to serum and cell proteins, exhibit enhanced recognition of the target mRNA sequence, demonstrate cell-membrane permeability and elicited cellular nucleases when complexed with complementary mRNA. It is well documented that oligonucleotides containing natural sugars (D-ribose and D-2-deoxyribose) and phosphodiester (PO) linkages are rapidly degraded by serum and intracellular nucleases, which limit their utility as effective therapeutic agents. Chemical strategic modifications have been described for oligonucleotides in order to improve their stability and efficacy as therapeutic agents. The main chemical changes included, modification of the sugar moiety, the base moiety, and/or modification or replacement of the internucleotide phosphodiester linkage. To date the most widely studied analogues are the phosphorothioate (PS) oligodeoxynucleotides, in which one of the non-bridging oxygen atoms in the phosphodiester backbone is replaced with a sulfur (Eckstein F., 1985, Ann. Rev. Biochem., 54: 367-402). Several AON generations have been developed and used for in vitro and for in vivo studies (Goodchild J., 2004, Curr. Opin. Mol. Ther., 2004, 6:120-128; Urban E. and R. Noe C R., 2003, Farmaco. 58:243-258).

It would be desirable to have improved AONs directed against nucleic acid sequences coding for pro-inflammatory receptors for inhibiting these receptors. Such AONs would be useful in the therapy and/or prevention of asthma, allergy, hypereosinophilia, general inflammation and cancer.

SUMMARY OF THE INVENTION

In accordance with one aspect, there is provided an oligonucleotide directed against a nucleic acid sequence coding for a protein selected from the group consisting of a CCR3 chemokine receptor and a common beta sub-unit of IL-3, IL-5 and GM-CSF receptors, wherein the oligonucleotide is one of (i) having a base sequence corresponding to any one of SEQ ID NOs. 1-698 and (ii) a modified oligonucleotide of any one of SEQ ID NOs. 1-698.

Preferably, the oligonucleotide has the base sequence corresponding to any one of SEQ ID NOs. 1-698.

Preferably, at least one adenosine of the oligonucleotide is replaced by a modified nucleotide, preferably a 2-amino-2'-deoxyadenosine (DAP).

In some embodiments, at least one of the nucleotides of the oligonucleotide is an arabinose modified oligonucleotide, preferably 2'-deoxy-2'-fluoroarabinonucleotide (FANA).

In some embodiments, the oligonucleotide contains at least one internucleotide linkage selected from the group consisting of phosphodiester, phosphotriester, phosphorothioate, methylphosphonate, boranophosphate and any combination thereof. Preferably, the oligonucleotide is phosphorothioate or phosphodiester oligonucleotide or an oligonucleotide with a combination of phosphorothioate and phosphodiester bonds.

In accordance with a further aspect, there is provided a pharmaceutical composition comprising at least one of the oligonucleotide described herein and pharmaceutically acceptable carrier.

In accordance with a further aspect, there is provided a method for treating and/or preventing at least one of asthma, COPD, allergy, CF, hypereosinophilia, general inflammation and cancer in a patient comprising administering to said patient a pharmaceutical composition described herein.

In accordance with a further aspect, there is provided a use of a pharmaceutical composition described herein for treating and/or preventing at least one of asthma, COPD, allergy, CF, hypereosinophilia, general inflammation and cancer.

In accordance with a further aspect, there is provided a use of a pharmaceutical composition described herein in the preparation of a medicament for treating and/or preventing at least one of asthma, COPD, allergy, CF, hypereosinophilia, general inflammation and cancer.

In accordance with a further aspect, there is provided a method for decreasing common beta sub-unit of IL-3, IL-5 and GM-CSF receptors expression in a patient comprising administering to said patient an oligonucleotide described herein the base sequence of the oligonucleotide having one of SEQ ID NOs. 1-672.

In accordance with a further aspect, there is provided a use of an oligonucleotide described herein for decreasing common beta sub-unit of IL-3, IL-5 and GM-CSF receptors expression, the base sequence of the oligonucleotide having one of SEQ ID NOs. 1-672.

In accordance with a further aspect, there is provided a use of an oligonucleotide described herein in the preparation of a medicament decreasing common beta sub-unit of IL-3, IL-5 and GM-CSF CSF receptors expression, the sequence of the oligonucleotide having one of SEQ ID NOs. 1-672.

In accordance with a further aspect, there is provided an oligonucleotide described herein for decreasing common beta sub-unit of IL-3, IL-5 and GM-CSF receptors expression, the base sequence of the oligonucleotide having one of SEQ ID NOs. 1-672.

In accordance with a further aspect, there is provided a method for decreasing CCR3 chemokine receptor expression in a patient comprising administering to said patient an oligonucleotide described herein, the base sequence of the oligonucleotide having one of SEQ ID NOs. 673-698.

In accordance with a further aspect, there is provided a use of an oligonucleotide described herein for decreasing CCR3 chemokine receptor expression, the base sequence of the oligonucleotide having one of SEQ ID NOs. 673-698.

In accordance with a further aspect, there is provided a use of an oligonucleotide described herein in the preparation of a medicament decreasing CCR3 chemokine receptor expression, the base sequence of the oligonucleotide having one of SEQ ID NOs. 673-698.

In accordance with a further aspect, there is provided an oligonucleotide described herein for decreasing CCR3 chemokine receptor expression, the base sequence of the oligonucleotide having one of SEQ ID NOs. 673-698.

In accordance with a further aspect, there is provided a commercial package comprising a pharmaceutical composition described herein together with instructions for its use for treating and/or preventing at least one of asthma, COPD, allergy, CF, hypereosinophilia, general inflammation and cancer; for decreasing common beta sub-unit of IL-3, IL-5 and GM-CSF receptors expression in a patient, the base sequence of the oligonucleotide having one of SEQ ID NOs. 1-672; or for decreasing CCR3 chemokine receptor expression in a patient, the base sequence of the oligonucleotide having one of SEQ ID NOs. 673-698.

In accordance with a further aspect, there is provided a double-stranded siRNA, the two strands comprising one of SEQ ID NOs. 699 and 700; 701 and 702; 703 and 704; 705 and 706; 707 and 708; 709 and 710; 711 and 712; 713 and 714; 715 and 716; 717 and 718; 719 and 720; 721 and 722; 723 and 724; 725 and 726; 727 and 728; 729 and 730; 731 and 732; 733 and 734; 735 and 736; 737 and 738; 739 and 740; 741 and 742; 743 and 744; 745 and 746; 747 and 748; 749 and 750; 752 and 752; 753 and 754; 755 and 756; 757 and 758; 759 and 760; 761 and 762; 763 and 764; 765 and 766; 767 and 768; 769 and 770; 771 and 772; 773 and 774; 775 and 776; 777 and 778; 779 and 780; 781 and 782; 783 and 784; 785 and 786; 787 and 788; 789 and 790; 791 and 792; 793 and 794; 795 and 796; 797 and 798; 799 and 800; 801 and 802; 803 and 804; 805 and 806; 807 and 808; 809 and 810; 811 and 812; 813 and 814; 815 and 816; 817 and 818; 819 and 820; 821 and 822; 823 and 824; 825 and 826; 827 and 828; 829 and 830; 831 and 832; 833 and 834; 835 and 836; 837 and 838; 839 and 840; 841 and 842; 843 and 844; 845 and 846; 847 and 848; 849 and 850; 851 and 852; 853 and 854; 855 and 856; 857 and 858; 859 and 860; 861 and 862; 863 and 864; 865 and 866; 867 and 868; 869 and 870; 871 and 872; 873 and 874; 875 and 876; 877 and 878; 879 and 880; 881 and 882; 883 and 884; 885 and 886; 887 and 888; 889 and 890; 891 and 892; 893 and 894; 895 and 896; 897 and 898; 899 and 900; 901 and 902; 903 and 904; 905 and 906; 907 and 908; 909 and 910; 911 and 912; 913 and 914; 915 and 916; 917 and 918; 919 and 920; 921 and 922; 923 and 924; 925 and 926; 927 and 928; 929 and 930; 931 and 932; 933 and 934; 935 and 936; 937 and 938; 939 and 940; 941 and 942; 943 and 944; 945 and 946; 947 and 948; 949 and 950; 951 and 952; 953 and 954; 955 and 956; 957 and 958; 959 and 960; 961 and 962; 963 and 964; 965 and 966; 967 and 968; 969 and 970; 971 and 972; 973 and 974; 975 and 976; 977 and 978; 979 and 980; 981 and 982; 983 and 984; 985 and 986; 987 and 988; 989 and 990; 991 and 992; 993 and 994; 995 and 996; 997 and 998; 999 and 1000; 1001 and 1002; 1003 and 1004; 1005 and 1006; 1007 and 1008; 1009 and 1010; 1011 and 1012; 1013 and 1014; 1015 and 1016; 1017 and 1018; 1019 and 1020; 1021 and 1022; 1023 and 1024; 1025 and 1026; 1027 and 1028; 1029 and 1030; 1031 and 1032; 1033 and 1034; 1035 and 1036; 1037 and 1038; 1039 and 1040; 1041 and 1042; 1043 and 1044; 1045 and 1046; 1047 and 1048; 1049 and 1050; 1051 and 1052; 1053 and 1054; 1055 and 1056; 1057 and 1058; 1059 and 1060; 1061 and 1062; 1063 and 1064; 1065 and 1066; 1067 and 1068; 1069 and 1070; 1071 and 1072; 1073 and 1074; 1075 and 1076; 1077 and 1078; 1079 and 1080; 1081 and 1082; 1083 and 1084; 1085 and 1086; 1087 and 1088; 1089 and 1090; 1091 and 1092; 1093 and 1094; 1095 and 1096; 1097 and 1098; 1099 and 1100; 1101 and 1102; 1103 and 1104; 1105 and 1106; 1107 and 1108; 1109 and 1110; 1111 and 1112; 1113 and 1114; 1115 and 1116; 1117 and 1118; 1119 and 1120; 1121 and 1122; 1123 and 1124; 1125 and 1126; 1127 and 1128; 1129 and 1130; 1131 and 1132; 1133 and 1134; 1135 and 1136; 1137 and 1138; 1139 and 1140; 1141 and 1142; 1143 and 1144; 1145 and 1146; 1147 and 1148; 1149 and 1150; 1151 and 1152; 1153 and 1154; 1155 and 1156; 1157 and 1158; 1159 and 1160; 1161 and 1162; 1163 and 1164; 1165 and 1166; 1167 and 1168; 1169 and 1170; 1171 and 1172; 1173 and 1174; 1175 and 1176; 1177 and 1178; 1179 and 1180; 1181 and 1182; 1183 and 1184; 1185 and 1186; 1187 and 1188; 1189 and 1190; 1191 and 1192; 1193 and 1194; 1195 and 1196; 1197 and 1198; 1199 and 1200; 1201 and 1202; 1203 and 1204; 1205 and 1206; 1207 and 1208; 1209 and 1210; 1211 and 1212; 1213 and 1214; 1215 and 1216; 1217 and 1218; 1219 and 1220; 1221 and 1222; 1223 and 1224; 1225 and 1226; 1227 and 1228; 1229 and 1230; 1231 and 1232; 1233 and 1234; 1235 and 1236; 1237 and 1238; 1239 and 1240; 1241 and 1242; 1243 and 1244; 1245 and 1246; 1247 and 1248; 1249 and 1250; 1251 and 1252; 1253 and 1254; 1255 and 1256; 1257 and 1258; 1259 and 1260; 1261 and 1262; 1263 and 1264; 1265 and 1266; 1267 and 1268; 1269 and 1270; 1271 and 1272; 1273 and 1274; 1275 and 1276; 1277 and 1278; 1279 and 1280; 1281 and 1282; 1283 and 1284; 1285 and 1286; 1287 and 1288; 1289 and 1290; 1291 and 1292; 1293 and 1294; 1295 and 1296; 1297 and 1298; 1299 and 1300; 1301 and 1302; 1303 and 1304; 1305 and 1306; 1307 and 1308; 1309 and 1310; 1311 and 1312; 1313 and 1314; 1315 and 1316; 1317 and 1318; 1319 and 1320; 1321 and 1322; 1323 and 1324; 1325 and 1326; 1327 and 1328; 1329 and 1330; 1331 and 1332; 1333 and 1334; 1335 and 1336; 1337 and 1338; 1339 and 1340; 1341 and 1342; 1343 and 1344; 1345 and 1346; 1347 and 1348; 1349 and 1350; 1351 and 1352; 1353 and 1354; 1355 and 1356; 1357 and 1358; 1359 and 1360; 1361 and 1362; 1363 and 1364; 1365 and 1366; 1367 and 1368; 1369 and 1370; 1371 and 1372; 1373 and 134; 1375 and 1376; 1377 and 1378; 1379 and 1380; 1381 and 1382; 1383 and 1384; 1385 and 1386; 1387 and 1388; 1389 and 1390; 1391 and 1392; 1393 and 1394; 1395 and 1396; 1397 and 1398; 1399 and 1400; 1401 and 1402; 1403 and 1404; 1405 and 1406; 1407 and 1408; 1409 and 1410; 1411 and 1412; 1413 and 1414; 1415 and 1416; 1417 and 1418; 1419 and 1420; 1421 and 1422; 1423 and 1424; 1425 and 1426; 1427 and 1428; 1429 and 1430; 1431 and 1432; 1433 and 1434; 1435 and 1436; 1437 and 1438; 1439 and 1440; 1441 and 1442; 1443 and 1444; 1445 and 1446; 1447 and 1448; 1449 and 1450; 1451 and 1452; 1453 and 1454; 1455 and 1456; 1457 and 1458; 1459 and 1460; 1461 and 1462; 1463 and 1464; 1465 and 1466; 1467 and 1468; 1469 and 1470; 1471 and 1472; 1473 and 1474; 1475 and 1476; 1477 and 1478; 1479 and 1480; 1481 and 1482; 1483 and 1484; 1485 and 1486; 1487 and 1488; 1489 and 1490; 1491 and 1492; 1493 and 1494; 1495 and 1496; 1497 and 1498; 1499 and 1500; 1501 and 1502; 1503 and 1504; 1505 and 1506; 1507 and 1508; 1509 and 1510; 1511 and 1512; 1513 and 1514; 1515 and 1516; 1517 and 1518; 1519 and 1520; 1521 and 1522; 1523 and 1524; 1525 and 1526; 1527 and 1528; 1529 and 1530; 1531 and 1532; 1533 and 1534; 1535 and 1536; 1537 and 1538; 1539 and 1540; 1541 and 1542; 1543 and 1544; 1545 and 1546; 1547 and 1548; 1549 and 1550; 1551 and 1552; 1553 and 1554; 1555 and 1556; 1557 and 1558; 1559 and 1560; 1561 and 1562; 1563 and 1564; 1565 and 1566; 1567 and 1568; 1569 and 1570; and 1571 and 1572, preferably for decreasing common beta sub-unit of IL-3, IL-5 and GM-CSF receptors expression.

In accordance with a further aspect, there is provided a double-stranded siRNA, the two strands comprising one of SEQ ID NOs. 1573 and 1574; 1575 and 1576; and 1577 and 1578, preferably for decreasing CCR3 chemokine receptor expression.

In accordance with a further aspect, there is provided the siRNA described herein for treating and/or preventing at least one of asthma, COPD, allergy, CF, hypereosinophilia, general inflammation and cancer.

In accordance with a further aspect, there is provided the siRNA described herein, wherein at least one nucleotide of the siRNA is FANA.

In accordance with a further aspect, there is provided the siRNA described herein wherein at least one adenosine nucleotide of the siRNA is substituted with DAP or an analog thereof.

In accordance with a further aspect, there is provided a method for decreasing common beta sub-unit of IL-3, IL-5 and GM-CSF receptors expression in a patient comprising administering the siRNA described herein.

In accordance with a further aspect, there is provided a method for decreasing CCR3 chemokine receptor expression in a patient comprising administering the siRNA described herein.

In accordance with a further aspect, there is provided a method for treating and/or preventing at least one of asthma, COPD, allergy, CF, hypereosinophilia, general inflammation and cancer in a patient comprising administering the siRNA described herein.

In accordance with a further aspect, there is provided use of the siRNA described herein for decreasing common beta sub-unit of IL-3, IL-5 and GM-CSF receptors expression or CCR3 chemokine receptor expression or for treating and/or preventing at least one of asthma, COPD, allergy, CF, hypereosinophilia, general inflammation and cancer.

In accordance with a further aspect, there is provided a use of the siRNA described herein in the preparation of a medicament for decreasing common beta sub-unit of IL-3, IL-5 and GM-CSF receptors expression; or for decreasing CCR3 chemokine receptor expression; or for treating and/or preventing at least one of asthma, COPD, allergy, CF, hypereosinophilia, general inflammation and cancer.

In accordance with a further aspect, there is provided a double-stranded or single-stranded miRNA comprising a pair of oligonucleotides or single oligonucleotide selected from the group consisting of SEQ ID NOs: 1634 and 1635; 1636 and 1637; 1638 and 1639; 1640 and 1641; 1642 and 1643; 1644 and 1645; 1646 and 1647; 1648; 1649 and 1650; 1651 and 1652; 1653 and 1654; 1655 and 1656; 1657 and 1658; 1659; 1660; 1661; 1662; 1663; 1664; 1665; 1666 and 1667; 1668 and 1669; 1670 and 1671; 1672 and 1673; 1674 and 1675; 1676 and 1677; 1678; 1679 and 1680; 1681 and 1682; 1683 and 1684; 1685 and 1686; 1687 and 1688; 1689 and 1690; 1691 and 1692; 1693; 1694; 1695 and 1696; 1697; 1698; 1699 and 1700; 1701; 1702 and 1703; 1704; 1705; 1706; 1707; 1708; 1709; 1710; 1711; 1712 and 1713; 1714 and 1715; 1716; 1717 and 1718; 1719; 1720 and 1721; 1722 and 1723; 1724; 1725 and 1726; 1727; 1728; 1729 and 1730; 1731 and 1732; 1733 and 1734; 1735; 1736; 1737; 1738 and 1739; 1740 and 1741; 1742; 1743 and 1744; 1745; 1746 and 1747; 1748 and 1749; 1750 and 1751; 1752; 1753; 1754; 1755; 1756; 1757; 1758; 1759; 1760; 1761 and 1762; 1763; 1764 and 1765; 1766; 1767 and 1768; 1769; 1770; 1771; 1772; 1773; 1774 and 1775; 1776; 1777; and 1778, preferably for decreasing common beta sub-unit of IL-3, IL-5 and GM-CSF receptors expression.

In accordance with a further aspect, there is provided the miRNA described herein, wherein at least one nucleotide of the miRNA is FANA.

In accordance with a further aspect, there is provided the miRNA described herein wherein at least one adenosine nucleotide of the miRNA is substituted with DAP or an analog thereof.

In accordance with a further aspect, there is provided a method for decreasing common beta sub-unit of IL-3, IL-5 and GM-CSF receptors expression in a patient comprising administering the miRNA described herein.

In accordance with a further aspect, there is provided a method for treating and/or preventing at least one of asthma, COPD, allergy, CF, hypereosinophilia, general inflammation and cancer in a patient comprising administering the miRNA described herein.

In accordance with a further aspect, there is provided use of the miRNA described herein for decreasing common beta sub-unit of IL-3, IL-5 and GM-CSF receptors expression or for treating and/or preventing at least one of asthma, COPD, allergy, CF, hypereosinophilia, general inflammation and cancer.

In accordance with a further aspect, there is provided a use of the miRNA described herein in the preparation of a medicament for decreasing common beta sub-unit of IL-3, IL-5 and GM-CSF receptors expression; or for treating and/or preventing at least one of asthma, COPD, allergy, CF, hypereosinophilia, general inflammation and cancer.

In accordance with a further aspect, there is provided an AON capable of hybridizing under highly stringent conditions with a nucleic acid sequence coding for a protein selected from the group consisting of a CCR3 chemokine receptor and a common beta sub-unit of IL-3, IL-5 and GM-CSF receptors, wherein at least one nucleotide in the oligonucleotide is a 2'-deoxy-2'-fluoroarabinonucleotide (FANA).

In accordance with a further aspect, there is provided an AON capable of hybridizing under highly stringent conditions with a nucleic acid sequence coding for the common beta sub-unit of IL-3, IL-5 and GM-CSF receptors, wherein at least one adenosine nucleotide in the oligonucleotide is substituted with 2-amino-2'-deoxyadenosine (DAP).

In accordance with a further aspect, there is provided a method of improving the therapeutic efficacy to toxicity ratio of an oligonucleotide administered to a mammal comprising: (a) identifying the oligonucleotide as being intended for administration to the lung and where lowered toxicity is desired; and (b) replacing at least one non-FANA nucleotide with a corresponding FANA nucleotide and/or replacing one adenosine with 2-amino-2'-deoxyadenosine. Preferably, the administration of the resulting oligonucleotide to the mammal results in enhanced potency and/or reduced toxicity compared to administration of an unmodified oligonucleotide.

In accordance with a further aspect, there is provided an AON capable of hybridizing under highly stringent conditions with a nucleic acid sequence coding for a protein selected from the group consisting of a CCR3 chemokine receptor and a common beta sub-unit of IL-3, IL-5 and GM-CSF receptors, wherein the internucleotide linkages of the oligonucleotide comprise both phosphodiester and phosphorothioate linkages.

BRIEF DESCRIPTION OF THE DRAWINGS

FIG. 1a shows the efficacy of AON sequences TOP057 (SEQ ID No: 8) to TOP073 (SEQ ID No: 24). TF-1 cells (668 nM) or 293-βc-GFP cells (267 nM) were transfected for 24 hours and β-chain mRNA expression level was quantified using Quantigene. Results are expressed as mean percentage of β-chain mRNA inhibition (normalized to β2M)±SEM (compilation from two experiments in TF-1 cell line and two experiments in 293-CCR3-GFP cell line) compared to untransfected control cells. The specific activities of AON sequences TOP057 (SEQ ID No: 8), TOP062 (SEQ ID No: 13) and TOP063 (SEQ ID No: 14) were compared to corresponding sense control sequences (TOP057s (SEQ ID No: 1779), TOP062s (SEQ ID No: 1780) and TOP063s (SEQ ID No: 1781)) in FIG. 1b 293-βc-GFP cells (267 nM) and; FIG. 1c TF-1 cells (500 nM). Cells were transfected for 24 hours and β-chain mRNA expression levels were quantified using Quantigene. Results are expressed as mean normalized ratio β-chain/β2M±SEM. The percentage inhibition of β-chain mRNA relative to the corresponding sense control AON is indicated. Statistical analysis was performed using the ANOVA test (Dunnett's post test, n=3, **p<0.01).

FIG. 2a describes the efficacy of AON sequences TOP020 (SEQ ID No: 673) to TOP045 (SEQ ID No: 698). TF-1 cells (668 nM) or 293-CCR3-GFP cells (267 nM) were transfected with indicated AONs. Twenty-four hours post-transfection CCR3 mRNA expression levels were quantified using Quantigene. Results are provided as mean percentage of CCR3 mRNA expression inhibition±SEM (compilation from 2 experiments in TF-1 and 4 experiments in 293-CCR3-GFP cells) compared to non-transfected control cells. FIG. 2b illustrates the specific activities of AON sequences TOP030 (SEQ ID No: 683) and TOP031 (SEQ ID No: 684) compared to corresponding sense control sequences (TOP030s (SEQ ID No: 1782) and TOP031s (SEQ ID No: 1783)) in 293-CCR3-GFP cells (267 nM). FIG. 2c illustrates similar results obtained for TF-1 cells (668 nM). Cells were transfected and 24 hours post-transfection CCR3 mRNA expression levels were quantified using Quantigene. Results are expressed as mean±SEM normalized ratio CCR3/β2M±SEM. The percentage inhibition of CCR3 mRNA expression relative to the corresponding sense control AON is indicated. Statistical analysis was performed using the ANOVA test (Dunnett's post test, n=3, **p<0.01).

FIG. 3a illustrates the efficacy of siRNA sequences at reducing β-chain mRNA expression in 293-βc-GET cells 24 hours post-transfection at doses of 0.04, 0.12 and 0.24 µM. FIGS. 3b and 3c compare the efficacy of β-chain AON (TOP062 (SEQ ID No: 13)) and siRNA sequences at reducing β-chain mRNA expression levels in TF-1 cells. For the dose-response experiment, cells were transfected with the indicated AON or siRNA at doses of 0.25 µM, 0.5 µM and 1 µM (FIG. 3b). For the time-course study, cells were transfected with 1 µM of the indicated AON or siRNA and β-chain mRNA expression quantification was performed 24, 48 or 72 hours post-transfection using the Quantigene assay (FIG. 3c). Results are expressed as the mean ratios (±SEM) of β-chain relative luminescence units (RLU) normalized to β2M control gene RLU. Statistical analysis was performed using one-way ANOVA followed by a Dunnett post-test with TOP062 (SEQ ID No: 13) as control reference (*p<0.05, **p<0.01, n=3 replicates per condition).

FIG. 4a illustrates the efficacy of siRNA sequences at reducing CCR3 mRNA expression levels following transfection in 293-CCR3-GFP cells. Cells were transfected with siRNAs at doses ranging from 0.04 µM to 0.24 uM and CCR3 mRNA expression determined 24 hours post-transfection. FIG. 4b compares the efficacy of indicated AON and siRNA sequences at reducing CCR3 mRNA expression levels in 293-CCR3-GFP cells. 293-CCR3-GFP cells were transfected with indicated AON or siRNA at a concentration of 300 nM, and CCR3 mRNA expression quantification was performed 24, 48 or 72 hours post-transfection. Total RNA was extracted from transfected cells, purified, and subjected to CCR3 mRNA quantification using the Quantigene assay. Results are expressed as the mean ratios (±SEM) of CCR3 relative luminescence units (RLU) normalized to β2M control gene RLU. Statistical analysis was performed using one-way ANOVA followed by a Dunnett post-test with TOP030 (SEQ ID No: 683) as control reference (*p<0.05, **p<0.01, n=3 replicates per condition).

In FIGS. 5a and 5c, results are expressed as the mean percentage±SEM of 293-βc-GFP and 293-CCR3-GFP cells positive for the expression of βc-GFP and CCR3-GFP proteins, respectively. In FIGS. 5b and 5d, results are expressed as the average mean fluorescence intensity (MFI)±SEM of β-chain and CCR3 protein expression, respectively, in TF-1 cells. The percentage of inhibition of target protein expression relative to the corresponding sense control AON is indicated. Statistical analysis was performed using the unpaired t test, with n=3 and p<0.01, *p<0.001.

FIGS. 15a and 15b illustrate a comparison of the efficacy of miRNA mimic sequences at reducing β-chain mRNA expression and protein expression levels, respectively. mRNA expression level results are given as the average±SD normalized ratio β-chain/β2M (FIG. 15a) while protein expression results are given as the mean percentage±SD of cells expressing β-chain protein (FIG. 15b). Statistical analyses were carried out using a One Way ANOVA (Dunnett) against the untransfected cells (Control NT); **p<0.01, n=3-6.

BRIEF DESCRIPTION OF THE TABLES

Figure 1:
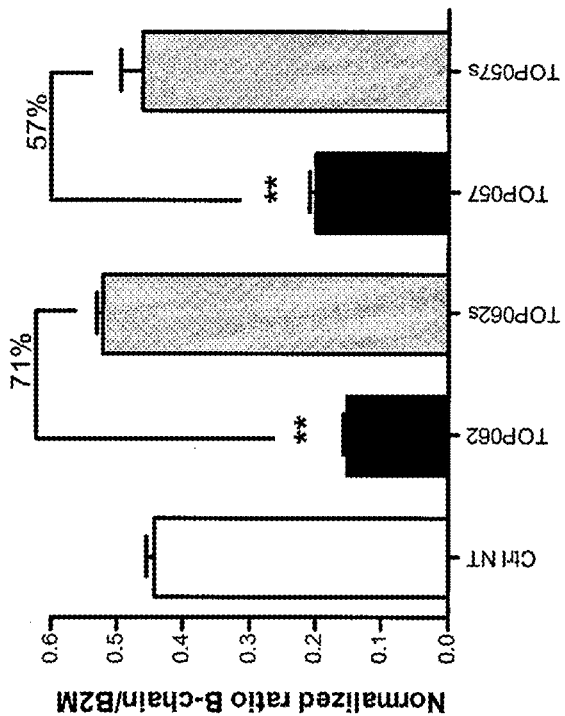
FIG. 1 illustrates the efficacy of AON sequences at reducing the β-chain mRNA expression.
Figure 1:
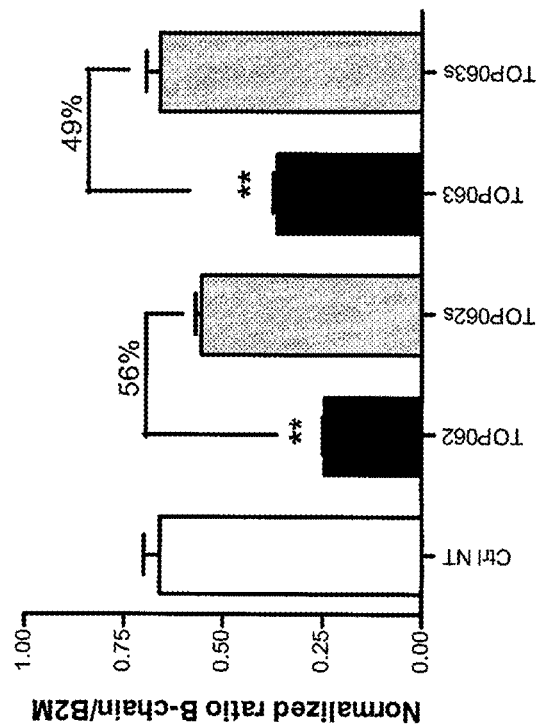

Table 1a identifies AON sequences with specificity for the common beta subunit (β-chain) of IL-3, IL-5 and GM-CSF receptors in accordance with the present invention.

Table 1b identifies AON sequences with specificity against the CCR3 chemokine receptor in accordance with the present invention.

Table 2a identifies siRNA sequences designed against the common beta subunit (β-chain) of IL-3, IL-5 and GM-CSF receptors in accordance with the present invention.

Table 2b identifies siRNA sequences designed against CCR3 chemokine receptor in accordance with the present invention.

Table 3a identifies AON sequences containing FANA modification with specificity against the common beta subunit (β-chain) of IL-3, IL-5 and GM-CSF receptors in accordance with the present invention.

Table 3b identifies AON sequences containing FANA modification with specificity against the CCR3 chemokine receptor in accordance with the present invention.

Table 3c identifies AON sequences containing DAP modification with specificity against the common beta subunit (β-chain) of IL-3, IL-5 and GM-CSF receptors in accordance with the present invention.

Table 4 identifies AON sequences with specificity against the rat common beta subunit (β-chain) of IL-3, IL-5 and GM-CSF receptors and the rat CCR3 chemokine receptor in accordance with the present invention.

Table 5 identifies primary treatment-related histopathologic changes in the lungs of monkeys treated with 2'F-ANA modified AONs (TPI 1100) or non 2'F-ANA modified AONs (TPI ASM8).

Table 6 identifies AON sequences TPI 1100 and TPI ASM8.

Table 7 identifies miRNA mimic sequences with specificity against the common beta subunit (β-chain) of IL-3, IL-5 and GM-CSF receptors in accordance with the present invention.

Table 8 identifies sense oligonucleotide sequences TOP057s (SEQ ID NO: 1779), TOP062s (SEQ ID NO: 1780), TOP063s (SEQ ID NO: 1781), TOP030s (SEQ ID NO: 1782), and TOP031s (SEQ ID NO: 1783), as well as nonspecific antisense oligonucleotide sequence TOP4005 (SEQ ID NO: 1784), each of which is used as a control in an experiment-dependent manner.

DETAILED DESCRIPTION OF THE INVENTION

Several inflammatory mediators play a role in the appearance and perpetuation of inflammation in the airways of patients with asthma. Some mediators attract the inflammatory cells into the airways through chemotaxis of eosinophils. Many of these chemokines act mostly in asthmatic or allergic inflammation through the CCR3 receptor. Other mediators cause the priming and increased survival of inflammatory cells in the airways or skin such as IL-3, IL-5, and GM-CSF. An improvement in asthma has been shown when there is a decrease in these inflammatory mediators in the airways.

Furthermore, cancer, characterized by abnormal proliferation of immortalized cells, can be caused by the release of inflammatory mediators and/or growth factors that act through receptors and lead to cellular proliferation. Amongst these, GM-CSF has been shown to be an important growth factor for several tumour cells. The chemokine receptor CCR3 was characterized in malignant B lymphocytes recovered from patients with chronic lymphocytic leukemia (CLL) and with hairy cell leukemia (HCL), (Trentin et al., 2004, Blood, 104, 502-508). Indeed, the transactivation of EGFR through CCR3 was found to be a critical pathway that elicits MAP kinase activation and cytokine production in bronchial epithelial cells (Adachi et al., 2004, Biochem. Biophys. Res.

Commun. 320, 292-396). The inhibition of proliferation and metastasis of cancerous cells by blocking the receptors for growth factors or the chemokine receptor CCR3 could be important in the therapy of certain cancers.

In accordance with one aspect, there is provided an oligonucleotide directed against a nucleic acid sequence coding for a protein selected from the group consisting of a CCR3 chemokine receptor and a common beta sub-unit of IL-3, IL-5 and GM-CSF receptors, wherein the oligonucleotide is one of (i) having a base sequence corresponding to any one of SEQ ID NOs. 1-698 and (ii) a modified oligonucleotide of any one of SEQ ID NOs. 1-698.

Preferably, the oligonucleotide has the base sequence corresponding to any one of SEQ ID NOs. 1-698 and is preferably the oligonucleotide of any one of SEQ ID NOs. 1-698.

Preferably, at least one adenosine is substituted with a nucleotide substitute selected from the group consisting of 2-amino-2'-deoxyadenosine and analogs. Preferred 2-amino-2'-deoxyadenosine analogs include 2,6-diamino-deoxyadenosine hemisulfate, 2-amino-9-(B-D-2'-deoxyribofuranosyl)adenosine, 7-deaza-2'-deoxyadenosine, N6-methyl-2'-deoxyribofuranosyl adenosine, 2-aminoadenosine/2,6-diaminopurine riboside, salts and functional derivatives thereof.

Preferably, at least one of the nucleotides of the oligonucleotide is an arabinose modified nucleotide, preferably having a 2' substituent selected from the group consisting of fluorine, hydroxyl, amino, azido, alkyl, alkoxy, and alkoxyalkyl groups. Preferably, the alkyl group is selected from the group consisting of methyl, ethyl, propyl, butyl, and functionalized alkyl groups, the alkoxy group is selected from the group consisting of methoxy, ethoxy, propoxy and functionalized alkoxy groups and the alkoxyalkyl group is selected from the group consisting of methoxyethyl, and ethoxyethyl.

Preferably, the functionalized alkyl group is selected from the group consisting of ethylamino, propylamino and butylamino group and the functionalized alkoxy group is selected from the group consisting of —O(CH$_2$)$_q$—R, where q=2-4 and —R is a —NH$_2$, —OCH$_3$, or —OCH$_2$CH$_3$ group.

Preferably the arabinose modified nucleotide is 2'-deoxy-2'-fluoroarabinonucleotide (FANA).

In some embodiments, the at least one arabinose modified nucleotide is at the 5' end or the 3' end of the oligonucleotide; or at both ends.

In some embodiments, the oligonucleotide has between 1-7 arabinose modified nucleotides independently at the 5' end and 3' end of the oligonucleotide. Preferably, there is between 1-6, 1-5, 1-4, or 1-3 arabinose modified nucleotides independently at the 5' end and 3' end of the oligonucleotide.

In some embodiments, the oligonucleotide contains at least one internucleotide linkage selected from the group consisting of phosphodiester, phosphotriester, phosphorothioate, methylphosphonate, boranophosphate and any combination thereof. Preferably, the oligonucleotide is phosphorothioate or phosphodiester oligonucleotide or an oligonucleotide with a combination of phosphorothioate and phosphodiester bonds.

In accordance with a further aspect, there is provided a pharmaceutical composition comprising at least one of the oligonucleotides described herein and a pharmaceutically acceptable carrier.

In accordance with a further aspect, there is provided a method for treating and/or preventing at least one of asthma, COPD, allergy, CF, hypereosinophilia, general inflammation and cancer in a patient comprising administering to said patient a pharmaceutical composition described herein.

In accordance with a further aspect, there is provided a use of a pharmaceutical composition described herein for treating and/or preventing at least one of asthma, COPD, allergy, CF, hypereosinophilia, general inflammation and cancer.

In accordance with a further aspect, there is provided a use of a pharmaceutical composition described herein in the preparation of a medicament for treating and/or preventing at least one of asthma, COPD, allergy, CF, hypereosinophilia, general inflammation and cancer.

In accordance with a further aspect, there is provided a method for decreasing common beta sub-unit of IL-3, IL-5 and GM-CSF receptors expression in a patient comprising administering to said patient an oligonucleotide described herein, the base sequence of the oligonucleotide having one of SEQ ID NOs. 1-672.

In accordance with a further aspect, there is provided a use of an oligonucleotide described herein for decreasing common beta sub-unit of IL-3, IL-5 and GM-CSF receptors expression, the base sequence of the oligonucleotide having one of SEQ ID NOs. 1-672.

In accordance with a further aspect, there is provided a use of an oligonucleotide described herein in the preparation of a medicament decreasing common beta sub-unit of IL-3, IL-5 and GM-CSF receptors expression, the base sequence of the oligonucleotide having one of SEQ ID NOs. 1-672.

In accordance with a further aspect, there is provided an oligonucleotide described herein for decreasing common beta sub-unit of IL-3, IL-5 and GM-CSF receptors expression, the base sequence of the oligonucleotide having one of SEQ ID NOs. 1-672.

In accordance with a further aspect, there is provided a method for decreasing CCR3 chemokine receptor expression in a patient comprising administering to said patient an oligonucleotide described herein, the base sequence of the oligonucleotide having one of SEQ ID NOs. 673-698.

In accordance with a further aspect, there is provided a use of an oligonucleotide described herein for decreasing CCR3 chemokine receptor expression, the base sequence of the oligonucleotide having one of SEQ ID NOs. 673-698.

In accordance with a further aspect, there is provided a use of an oligonucleotide described herein in the preparation of a medicament decreasing CCR3 chemokine receptor expression, the base sequence of the oligonucleotide having one of SEQ ID NOs. 673-698.

In accordance with a further aspect, there is provided an oligonucleotide described herein for decreasing CCR3 chemokine receptor expression, the base sequence of the oligonucleotide having one of SEQ ID NOs. 673-698.

In accordance with a further aspect, there is provided a commercial package comprising a pharmaceutical composition described herein together with instructions for its use for treating and/or preventing at least one of asthma, COPD, allergy, CF, hypereosinophilia, general inflammation and cancer; for decreasing common beta sub-unit of IL-3, IL-5 and GM-CSF receptors expression in a patient, the base sequence of the oligonucleotide having one of SEQ ID NOs: 1-672; or for decreasing CCR3 chemokine receptor expression in a patient, the base sequence of the oligonucleotide having one of SEQ ID NOs: 673-698.

In accordance with a further aspect, there is provided a double-stranded siRNA, the two strands comprising one of SEQ ID NOs: 699 and 700; 701 and 702; 703 and 704; 705 and 706; 707 and 708; 709 and 710; 711 and 712; 713 and 714; 715 and 716; 717 and 718; 719 and 720; 721 and 722; 723 and 724; 725 and 726; 727 and 728; 729 and 730; 731 and 732; 733 and 734; 735 and 736; 737 and 738; 739 and 740; 741 and 742; 743 and 744; 745 and 746; 747 and 748; 749 and 750; 752 and 752; 753 and 754; 755 and 756; 757 and 758; 759 and 760; 761 and 762; 763 and 764; 765 and 766; 767 and 768; 769 and 770; 771 and 772; 773 and 774; 775 and 776; 777 and 778; 779 and 780; 781 and 782; 783 and 784; 785 and 786; 787 and 788; 789 and 790; 791 and 792; 793 and 794; 795 and 796; 797 and 798; 799 and 800; 801 and 802; 803 and 804; 805 and 806; 807 and 808; 809 and 810; 811 and 812; 813 and 814; 815 and 816; 817 and 818; 819 and 820; 821 and 822; 823 and 824; 825 and 826; 827 and 828; 829 and 830; 831 and 832; 833 and 834; 835 and 836; 837 and 838; 839 and 840; 841 and 842; 843 and 844; 845 and 846; 847 and 848; 849 and 850; 851 and 852; 853 and 854; 855 and 856; 857 and 858; 859 and 860; 861 and 862; 863 and 864; 865 and 866; 867 and 868; 869 and 870; 871 and 872; 873 and 874; 875 and 876; 877 and 878; 879 and 880; 881 and 882; 883 and 884; 885 and 886; 887 and 888; 889 and 890; 891 and 892; 893 and 894; 895 and 896; 897 and 898; 899 and 900; 901 and 902; 903 and 904; 905 and 906; 907 and 908; 909 and 910; 911 and 912; 913 and 914; 915 and 916; 917 and 918; 919 and 920; 921 and 922; 923 and 924; 925 and 926; 927 and 928; 929 and 930; 931 and 932; 933 and 934; 935 and 936; 937 and 938; 939 and 940; 941 and 942; 943 and 944; 945 and 946; 947 and 948; 949 and 950; 951 and 952; 953 and 954; 955 and 956; 957 and 958; 959 and 960; 961 and 962; 963 and 964; 965 and 966; 967 and 968; 969 and 970; 971 and 972; 973 and 974; 975 and 976; 977 and 978; 979 and 980; 981 and 982; 983 and 984; 985 and 986; 987 and 988; 989 and 990; 991 and 992; 993 and 994; 995 and 996; 997 and 998; 999 and 1000; 1001 and 1002; 1003 and 1004; 1005 and 1006; 1007 and 1008; 1009 and 1010; 1011 and 1012; 1013 and 1014; 1015 and 1016; 1017 and 1018; 1019 and 1020; 1021 and 1022; 1023 and 1024; 1025 and 1026; 1027 and 1028; 1029 and 1030; 1031 and 1032; 1033 and 1034; 1035 and 1036; 1037 and 1038; 1039 and 1040; 1041 and 1042; 1043 and 1044; 1045 and 1046; 1047 and 1048; 1049 and 1050; 1051 and 1052; 1053 and 1054; 1055 and 1056; 1057 and 1058; 1059 and 1060; 1061 and 1062; 1063 and 1064; 1065 and 1066; 1067 and 1068; 1069 and 1070; 1071 and 1072; 1073 and 1074; 1075 and 1076; 1077 and 1078; 1079 and 1080; 1081 and 1082; 1083 and 1084; 1085 and 1086; 1087 and 1088; 1089 and 1090; 1091 and 1092; 1093 and 1094; 1095 and 1096; 1097 and 1098; 1099 and 1100; 1101 and 1102; 1103 and 1104; 1105 and 1106; 1107 and 1108; 1109 and 1110; 1111 and 1112; 1113 and 1114; 1115 and 1116; 1117 and 1118; 1119 and 1120; 1121 and 1122; 1123 and 1124; 1125 and 1126; 1127 and 1128; 1129 and 1130; 1131 and 1132; 1133 and 1134; 1135 and 1136; 1137 and 1138; 1139 and 1140; 1141 and 1142; 1143 and 1144; 1145 and 1146; 1147 and 1148; 1149 and 1150; 1151 and 1152; 1153 and 1154; 1155 and 1156; 1157 and 1158; 1159 and 1160; 1161 and 1162; 1163 and 1164; 1165 and 1166; 1167 and 1168; 1169 and 1170; 1171 and 1172; 1173 and 1174; 1175 and 1176; 1177 and 1178; 1179 and 1180; 1181 and 1182; 1183 and 1184; 1185 and 1186; 1187 and 1188; 1189 and 1190; 1191 and 1192; 1193 and 1194; 1195 and 1196; 1197 and 1198; 1199 and 1200; 1201 and 1202; 1203 and 1204; 1205 and 1206; 1207 and 1208; 1209 and 1210; 1211 and 1212; 1213 and 1214; 1215 and 1216; 1217 and 1218; 1219 and 1220; 1221 and 1222; 1223 and 1224; 1225 and 1226; 1227 and 1228; 1229 and 1230; 1231 and 1232; 1233 and 1234; 1235 and 1236; 1237 and 1238; 1239 and 1240; 1241 and 1242; 1243 and 1244; 1245 and 1246; 1247 and 1248; 1249 and 1250; 1251 and 1252; 1253 and 1254; 1255 and 1256; 1257 and 1258; 1259 and 1260; 1261 and 1262; 1263 and 1264; 1265 and 1266; 1267 and 1268; 1269 and 1270; 1271 and 1272; 1273 and 1274; 1275 and 1276; 1277 and 1278; 1279 and 1280; 1281 and 1282; 1283 and 1284; 1285 and 1286; 1287 and 1288; 1289 and 1290; 1291 and 1292; 1293 and 1294; 1295 and 1296; 1297 and 1298; 1299 and 1300; 1301 and 1302; 1303 and 1304; 1305 and 1306; 1307 and 1308; 1309 and 1310; 1311 and 1312; 1313 and 1314; 1315 and 1316; 1317 and 1318; 1319 and 1320; 1321 and 1322; 1323 and 1324; 1325 and 1326; 1327 and 1328; 1329 and 1330; 1331 and 1332; 1333 and 1334; 1335 and 1336; 1337 and 1338; 1339 and 1340; 1341 and 1342; 1343 and 1344; 1345 and 1346; 1347 and 1348; 1349 and 1350; 1351 and 1352; 1353 and 1354; 1355 and 1356; 1357 and 1358; 1359 and 1360; 1361 and 1362; 1363 and 1364; 1365 and 1366; 1367 and 1368; 1369 and 1370; 1371 and 1372; 1373 and 134; 1375 and 1376; 1377 and 1378; 1379 and 1380; 1381 and 1382; 1383 and 1384; 1385 and 1386; 1387 and 1388; 1389 and 1390; 1391 and 1392; 1393 and 1394; 1395 and 1396; 1397 and 1398; 1399 and 1400; 1401 and 1402; 1403 and 1404; 1405 and 1406; 1407 and 1408; 1409 and 1410; 1411 and 1412; 1413 and 1414; 1415 and 1416; 1417 and 1418; 1419 and 1420; 1421 and 1422; 1423 and 1424; 1425 and 1426; 1427 and 1428; 1429 and 1430; 1431 and 1432; 1433 and 1434; 1435 and 1436; 1437 and 1438; 1439 and 1440; 1441 and 1442; 1443 and 1444; 1445 and 1446; 1447 and 1448; 1449 and 1450; 1451 and 1452; 1453 and 1454; 1455 and 1456; 1457 and 1458; 1459 and 1460; 1461 and 1462; 1463 and 1464; 1465 and 1466; 1467 and 1468; 1469 and 1470; 1471 and 1472; 1473 and 1474; 1475 and 1476; 1477 and 1478; 1479 and 1480; 1481 and 1482; 1483 and 1484; 1485 and 1486; 1487 and 1488; 1489 and 1490; 1491 and 1492; 1493 and 1494; 1495 and 1496; 1497 and 1498; 1499 and 1500; 1501 and 1502; 1503 and 1504; 1505 and 1506; 1507 and 1508; 1509 and 1510; 1511 and 1512; 1513 and 1514; 1515 and 1516; 1517 and 1518; 1519 and 1520; 1521 and 1522; 1523 and 1524; 1525 and 1526; 1527 and 1528; 1529 and 1530; 1531 and 1532; 1533 and 1534; 1535 and 1536; 1537 and 1538; 1539 and 1540; 1541 and 1542; 1543 and 1544; 1545 and 1546; 1547 and 1548; 1549 and 1550; 1551 and 1552; 1553 and 1554; 1555 and 1556; 1557 and 1558; 1559 and 1560; 1561 and 1562; 1563 and 1564; 1565 and 1566; 1567 and 1568; 1569 and 1570; and 1571 and 1572, preferably for decreasing common beta sub-unit of IL-3, IL-5 and GM-CSF receptors expression.

In accordance with a further aspect, there is provided a double-stranded siRNA, the two strands comprising one of SEQ ID NOs: 1573 and 1574; 1575 and 1576; and 1577 and 1578, preferably for decreasing CCR3 chemokine receptor expression.

In accordance with a further aspect, there is provided the siRNA described herein, wherein at least one nucleotide of the siRNA is FANA.

In accordance with a further aspect, there is provided the siRNA described herein wherein at least one adenosine nucleotide of the siRNA is substituted with DAP or an analog thereof.

In accordance with a further aspect, there is provided the siRNA described herein for treating and/or preventing at least one of asthma, COPD, allergy, CF, hypereosinophilia, general inflammation and cancer.

In accordance with a further aspect, there is provided a method for decreasing common beta sub-unit of IL-3, IL-5 and GM-CSF receptors expression in a patient comprising administering a siRNA described herein.

In accordance with a further aspect, there is provided a method for decreasing CCR3 chemokine receptor expression in a patient comprising administering a siRNA described herein.

In accordance with a further aspect, there is provided a method for treating and/or preventing at least one of asthma, COPD, allergy, CF, hypereosinophilia, general inflammation and cancer in a patient comprising administering a siRNA described herein.

In accordance with a further aspect, there is provided use of a siRNA described herein for decreasing common beta sub-unit of IL-3, IL-5 and GM-CSF receptors expression or CCR3 chemokine receptor expression or for treating and/or preventing at least one of asthma, COPD, allergy, CF, hypereosinophilia, general inflammation and cancer.

In accordance with a further aspect, there is provided a use of a siRNA described herein in the preparation of a medicament for decreasing common beta sub-unit of IL-3, IL-5 and GM-CSF receptors expression; or for decreasing CCR3 chemokine receptor expression; or for treating and/or preventing at least one of asthma, COPD, allergy, CF, hypereosinophilia, general inflammation and cancer.

In accordance with a further aspect, there is provided a double-stranded or single-stranded miRNA comprising a pair of oligonucleotides or single oligonucleotide selected from the group consisting of SEQ ID NOs: 1634 and 1635; 1636 and 1637; 1638 and 1639; 1640 and 1641; 1642 and 1643; 1644 and 1645; 1646 and 1647; 1648; 1649 and 1650; 1651 and 1652; 1653 and 1654; 1655 and 1656; 1657 and 1658; 1659; 1660; 1661; 1662; 1663; 1664; 1665; 1666 and 1667; 1668 and 1669; 1670 and 1671; 1672 and 1673; 1674 and 1675; 1676 and 1677; 1678; 1679 and 1680; 1681 and 1682; 1683 and 1684; 1685 and 1686; 1687 and 1688; 1689 and 1690; 1691 and 1692; 1693; 1694; 1695 and 1696; 1697; 1698; 1699 and 1700; 1701; 1702 and 1703; 1704; 1705; 1706; 1707; 1708; 1709; 1710; 1711; 1712 and 1713; 1714 and 1715; 1716; 1717 and 1718; 1719; 1720 and 1721; 1722 and 1723; 1724; 1725 and 1726; 1727; 1728; 1729 and 1730; 1731 and 1732; 1733 and 1734; 1735; 1736; 1737; 1738 and 1739; 1740 and 1741; 1742; 1743 and 1744; 1745; 1746 and 1747; 1748 and 1749; 1750 and 1751; 1752; 1753; 1754; 1755; 1756; 1757; 1758; 1759; 1760; 1761 and 1762; 1763; 1764 and 1765; 1766; 1767 and 1768; 1769; 1770; 1771; 1772; 1773; 1774 and 1775; 1776; 1777; and 1778, preferably for decreasing common beta sub-unit of IL-3, IL-5 and GM-CSF receptors expression.

In accordance with a further aspect, there is provided the miRNA described herein, wherein at least one nucleotide of the miRNA is FANA.

In accordance with a further aspect, there is provided the miRNA described herein wherein at least one adenosine nucleotide of the miRNA is substituted with DAP or an analog thereof.

In accordance with a further aspect, there is provided a method for decreasing common beta sub-unit of IL-3, IL-5 and GM-CSF receptors expression in a patient comprising administering the miRNA described herein.

In accordance with a further aspect, there is provided a method for treating and/or preventing at least one of asthma, COPD, allergy, CF, hypereosinophilia, general inflammation and cancer in a patient comprising administering the miRNA described herein.

In accordance with a further aspect, there is provided use of the miRNA described herein for decreasing common beta sub-unit of IL-3, IL-5 and GM-CSF receptors expression or for treating and/or preventing at least one of asthma, COPD, allergy, CF, hypereosinophilia, general inflammation and cancer.

In accordance with a further aspect, there is provided a use of the miRNA described herein in the preparation of a medicament for decreasing common beta sub-unit of IL-3, IL-5 and GM-CSF receptors expression; or for treating and/or preventing at least one of asthma, COPD, allergy, CF, hypereosinophilia, general inflammation and cancer.

In accordance with a further aspect, there is provided an AON capable of hybridizing under highly stringent conditions with a nucleic acid sequence coding for a protein selected from the group consisting of a CCR3 chemokine receptor and a common beta sub-unit of IL-3, IL-5 and GM-CSF receptors, wherein at least one nucleotide in the oligonucleotide is a 2'-deoxy-2'-fluoroarabinonucleotide (FANA).

In accordance with a further aspect, there is provided an AON capable of hybridizing under highly stringent conditions with a nucleic acid sequence coding for the protein common beta sub-unit of IL-3, IL-5 and GM-CSF receptors, wherein at least one adenosine nucleotide in the oligonucleotide is substituted with 2-amino-2'-deoxyadenosine (DAP).

In accordance with a further aspect, there is provided a method for improving the therapeutic efficacy to toxicity ratio of an oligonucleotide administered to a mammal comprising: (a) identifying the oligonucleotide as being intended for administration to the lung and where lowered toxicity is desired; and (b) replacing at least one non-FANA nucleotide with a corresponding FANA nucleotide, and/or substituting at least one adenosine nucleotide with 2-amino-2'-deoxyadenosine (DAP). Preferably, the administration of the resulting oligonucleotide to the mammal results in increased potency of the oligonucleotide and/or decreased toxicity compared to administration of an unmodified oligonucleotide.

In accordance with a further aspect, there is provided an AON capable of hybridizing under highly stringent conditions with a nucleic acid sequence coding for a protein selected from the group consisting of a CCR3 chemokine receptor and a common beta sub-unit of IL-3, IL-5 and GM-CSF receptors, wherein the internucleotide linkages of the oligonucleotide comprise both phosphodiester and phosphorothioate linkages.

AONs directed against the common beta subunit of IL-3, IL-5 and GM-CSF, and the CCR3, receptors, and against nucleic acids coding therefor, are, thus, provided. Pharmaceutical compositions comprising the oligonucleotides with a pharmaceutically acceptable carrier are also provided. Uses of the oligonucleotides and methods comprising administering the oligonucleotides for treating and/or preventing at least one of asthma, allergy, CF, hypereosinophilia, general inflammation and cancer are described.

The terms "nucleic acid" and "nucleic acid molecule" as used interchangeably herein, refer to a molecule comprised of nucleotides, i.e., ribonucleotides, deoxyribonucleotides, or both. The term includes monomers and polymers of ribonucleotides and deoxyribonucleotides, with the ribonucleotide and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs.

"Bases" includes any one of the natively found purine and pyrimidine bases, adenine (A), thymine (T), cytosine (C), guanine (G) and uracil (U), but also any modified or analogous forms thereof. Examples of non-naturally occurring bases that are capable of forming base-pairing relationships include, but are not limited to, aza and deaza pyrimidine analogues, aza and deaza purine analogues, and other heterocyclic base analogues, wherein one or more of the ring atoms and/or functional groups of the purine and pyrimidine rings have been substituted by heteroatoms, e.g., carbon, fluorine, nitrogen, oxygen, sulfur, and the like. Preferably, such bases include, but are not limited to, inosine, 5-methylcytosine, 2-thiothymine, 4-thiothymine, 7-deazaadenine, 9-deazaadenine, 3-deazaadenine, 7-deazaguanine, 9-deazaguanine, 6-thioguanine, isoguanine, 2,6-diaminopurine, hypoxanthine, and 6-thiohypoxanthine. Bases may also include, but are not limited to, 5-fluorocytosine, 5-bromocytosine, 5-iodocytosine, isocytosine, $N^4$-methylcytosine, 5-iodouracil, 5-fluorouracil, 4-thiouracil, 2-thiouracil, (E)-5-(2-bromovinyl)uracil, $N^6$-methyladenine, 2-chloroadenine, 2-fluoroadenine, 2-chloroadenine, N6-cyclopropyl-2,6-diaminopurine, nicotinamide, 2-aminopurine, 1,2,4-triazole-3-carboxamide.

The term "nucleic acid backbone" as used herein refers to the structure of the chemical moiety linking nucleotides in a molecule. This may include structures formed from any and all means of chemically linking nucleotides. A modified backbone as used herein includes modifications to the chemical linkage between nucleotides, as well as other modifications that may be used to enhance stability and affinity, such as modifications to the sugar structure. For example an α-anomer of deoxyribose may be used, where the base is inverted with respect to the natural β-anomer. In a preferred embodiment, the 2'-OH of the sugar group may be altered to 2'-O-alkyl, R- and S-constrained 2'-O-methyl (R-cMOE and S-cMOE) or 2'-O-alkyl-n(O-alkyl), which provides resistance to degradation without comprising affinity.

The term "oligonucleotide" as used herein refers to a nucleic acid molecule comprising from about 1 to about 100 nucleotides, more preferably from 1 to 80 nucleotides, and even more preferably from about 4 to about 35 nucleotides. This may include nucleic acid molecules of variable length that correspond either to the sense strand or to the non-coding strand of a target nucleic acid sequence.

Oligonucleotide compounds in accordance with the present invention also include siRNAs (small interfering RNAs) and the RISCs (RNA-induced silencing complexes) containing them that result from the RNAi (RNA interference) approach. The RNAi approach, which has been described recently, is considered as a new tool for the inhibition of target gene expression. As already known some years ago, RNAi is based on an ancient anti-viral defense mechanism in lower eukaryotes. It is induced by double-stranded RNA and its processing to typically 21-23 nt siRNAs, which cause the degradation of homologous endogenous mRNA after hybridizing to the target mRNA in a single stranded fashion with the assistance of the RISC complex. The way in which RNAi inhibits target gene expression remains to be fully elucidated, but presently, RNAi serves as a first choice approach to generate loss-of-function phenotypes across a broad spectrum of eukaryotic species, such as nematodes, flies, plants, fungi and mammals.

Oligonucleotide compounds in accordance with the present invention also include microRNA (miRNA). MicroRNA are single-stranded RNA molecules, typically of about 21-23 nucleotides in length, which regulate gene expression in a hybridization dependent manner. Typically, miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, typically at the 3' end of the mRNA, and their main function is to downregulate gene expression.

Oligonucleotide compounds in accordance with the present invention also include ribozymes and short nucleotide sequences, single or double stranded, RNA or DNA, which may incorporate chemical modifications as described above, capable of inhibiting gene transcription and/or translation in vitro and/or in vivo.

The term "modified oligonucleotide" and "modified nucleic acid molecule" includes oligonucleotide compounds that have been modified without significant adverse effect to their activity, for example, by the insertion, substitution or deletion of 1 or more bases. In particular, the addition or deletion of bases at the terminal ends of the oligonucleotides that exhibit 100% complementation to the gene they are directed against can generally be made without significant loss of inhibitory activity. Such modifications may be made in order to increase activity or to provide enhanced stability of the oligonucleotide. In addition, substitution of 1 or more bases in the present oligonucleotide compounds may also be made without adverse effect to activity, for example, substitution of purine with another purine (adenine, guanine) and pyrimidine with pyrimidine (cytosine, thymine, uracil). Modified oligonucleotide and modified nucleic acid molecule as used herein also include nucleic acids, including oligonucleotides, with one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. Modified nucleotides may include a nucleotide substitute selected from the group consisting of 2-amino-2'-deoxyadenosine and analogs. Preferred adenosine analogs include 2,6-diaminoadenosine hemisulfate, 2-amino-9-(B-D-2'-deoxyribofuranosyl)adenosine, 7-deaza-2'-deoxyadenosine, N6-methyl-2'-deoxyribofuranosyl adenosine, 2-aminoadenosine/2,6-diaminopurine riboside, salts and functional derivatives thereof. The internucleoside phosphate linkages can be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate and/or sulfone internucleotide linkages, or 3'-3', 2'-5' or 5'-5'linkages, and combinations of such similar linkages (to produce mixed backbone modified oligonucleotides). The modifications can be internal (single or repeated) or at the end(s) of the oligonucleotide molecule and can include additions to the molecule of the internucleoside phosphate linkages, such as cholesteryl, diamine compounds with varying numbers of carbon residues between amino groups and terminal ribose, deoxyribose and phosphate modifications which cleave or cross-link to the opposite chains or to associated enzymes or other proteins. Electrophilic groups such as ribose-dialdehyde may be covalently linked with an epsilon amino group of the lysyl-residue of such a protein. A nucleophilic group such as n-ethylmaleimide tethered to an oligomer could covalently attach to the 5' end of an mRNA or to another electrophilic site. The term modified oligonucleotides also includes oligonucleotides comprising modifications to the sugar moieties such as 2'-substituted ribonucleotides, or deoxyribonucleotide monomers, any of which are connected together via 5' to 3' linkages. Modified oligonucleotides may also be comprised of PNA or morpholino modified backbones where target specificity of the sequence is maintained. The term modified oligonucleotides also includes oligonucleotide compounds, as defined herein, of a form that does not significantly adversely affect their activity to reduce activity or inhibit expression of a target protein, but which may enhance this activity.

Modified oligonucleotides also include oligonucleotides that are based on or constructed from arabinonucleotide or modified arabinonucleotide residues, including but not limited to AON constructs based on beta-arabinofuranose and its analogues. Aribonucleosides are stereoisomers of ribonucleosides, differing only in the configuration at the 2'-position of the sugar ring. International Patent Application Publication No. WO 99/67378 discloses arabinonucleic acid (ANA) oligomers and their analogues for improved sequence specific inhibition of gene expression via association to complementary messenger RNA. International Patent Application Publication No. WO 99/67378 further teaches sugar-modified oligonucleotides that form a duplex with its target RNA sequence resulting in a substrate for RNaseH. Specifically, oligomers comprising beta-D-arabinonucleotides and 2'-deoxy-2'-fluoro-beta-D-arabinonucleosides (FANA or 2'F-ANA) are disclosed. International Patent Application Publication No. WO 02/20773 discloses oligonucleotide chimeras used to inhibit gene transcription and expression in a sequence specific manner. Specifically, International Patent Application Publication No. WO 02/20773 teaches AONs constructed from arabinonucleotides flanking a series of deoxyribose nucleotide residues of variable length. AONs so constructed are used to hybridize and induce cleavage of complementary RNA. International Patent Application Publication No. WO 03/037909 discloses oligonucleotides having an internal acyclic linker residue. AONs prepared with an acyclic linker are used to prevent or deplete function of a target nucleic acid of interest such RNA. International Patent Application Publication No. WO 03/064441 discloses oligonucleotides having alternating segments of sugar-modified nucleosides and 2' deoxynucleosides and also alternating segments of sugar-modified nucleotides and 2' deoxynucleotides. AONs having these alternating segments are disclosed to be used to prevent or deplete function of a target nucleic acid of interest such as RNA.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of highly stringent conditions involves the use of higher temperatures in which the washes are identical to those above except the temperature of the final two 30 min. washes in 0.2×SSC, 0.5% SDS was increased to 60° C. Another preferred set of very highly stringent conditions involves the use of two final washes in 0.1×SSC, 0.1% SDS at 65° C.

The term "substantially nuclease resistant" refers to nucleic acids that are resistant to nuclease degradation, as compared to naturally occurring or unmodified nucleic acids. Modified nucleic acids of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant nucleic acids include, but are not limited to, nucleic acids with modified backbones such as phosphorothioates, methylphosphonates, ethylphosphotriesters, 2'-O-methylphosphorothioates, 2'-O-methyl-p-ethoxy ribonucleotides, 2'-O-alkyls, 2'-O-alkyl-n(O-alkyl), 3'-O-alkyls, 3'-O-alkyl-n(O-alkyl), 2'-fluoros, 2'-deoxy-erythropentofuranosyls, 2'-O-methyl ribonucleosides, R- and S-constrained 2'-O-methyl ribonucleosides (R-cMOE and S-cMOE), methyl carbamates, and methyl carbonates; nucleic acids with modified bases such as inverted bases (e.g., inverted T's); or chimeric versions of any of the above.

The term "CCR3 and common beta-chain for IL-3/IL-5/GM-CSF receptors AON" as used herein refers to an oligonucleotide that is targeted to sequences specific for the CCR3 chemokine receptor and the common beta-chain for IL-3/IL-5/GM-CSF receptors, and inhibits CCR3 and common beta-chain for IL-3/IL-5/GM-CSF receptors expression and/or activity. These include, but are not limited to, CCR3 chemokine receptor and the common beta-chain for IL-3/IL-5/GM-CSF receptors, DNA coding sequences, DNA promoter sequences, DNA enhancer sequences, intron-exon junctions, 5' and 3' UTR, mRNA coding sequences, and the like.

As discussed above, one embodiment of the present invention provides AON targeted to sequences that affect CCR3 chemokine receptor and the common β-chain for IL-3/IL-5/GM-CSF receptors expression and/or activity. In one embodiment, the AON may comprise fragments or variants of these sequences, as will be understood by a person skilled in the art, that may alter the oligonucleotide make-up and/or length, but which maintains or increases the activity of the oligonucleotide to down-regulate gene expression. In another embodiment the present invention provides for combinations of at least two AON from the sequences described herein.

The terms "treatment", "treating", "therapy" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or amelioration of an adverse effect attributable to the disease. "Treatment" as used herein covers any treatment of a disease in a subject as previously defined, particularly a human, and includes:
  (a) preventing a disease from occurring in a subject which may be predisposed to the disease but has not yet been diagnosed as having it;
  (b) inhibiting a disease, i.e., arresting its development; or
  (c) relieving a disease, i.e., causing regression of the disease.

The term "pharmaceutically acceptable" as it is used herein with respect to carriers, surfactants and compositions refers to substances which are acceptable for use in the treatment of a subject patient that are not toxic or otherwise unacceptable for administration by any of the routes herein described.

The invention is generally directed toward the treatment of subjects by the administration of therapeutically effective amounts of AON compounds in accordance with the present invention, including siRNA; miRNA and miRNA mimics; ribozymes; short nucleotide sequences, single or double stranded, including RNA and/or DNA that may be complementary to a target nucleic acid, or may optionally be modified as described above; an RNA oligonucleotide having at least a portion of said RNA oligonucleotide capable of hybridizing with RNA to form an oligonucleotide-RNA duplex; or a chimeric oligonucleotide, that will downregulate or inhibit the expression of an endogenous gene in vivo.

By "therapeutically effective" amount is meant a nontoxic but sufficient amount of an antisense oligonucleotide compound to provide the desired therapeutic effect. In the present case, that dose of AON compound effective to relieve, ameliorate, or prevent symptoms of the condition or disease being treated, e.g. disease associated with allergy, asthma, inflammatory disease such as inflammatory respiratory disease.

The term "allergy" as used herein, describes any undesirable immune response by the body to a substance to which it has become hypersensitive.

The formulations of the present invention are preferably administered directly to the site of action and, thus, preferably are topical, including but not limited to, oral, intrabuccal, intrapulmonary, rectal, intrauterine, intratumor, nasal, intrathecal, inhalable, transdermal, intradermal, intracavitary, iontophoretic, ocular, vaginal, intraarticular, optical, transmucosal, rectal, slow release or enteric coating formulations. Without limiting any of the foregoing, formulations of the present invention may also be intracranial, intramuscular, subcutaneous, intravascular, intraglandular, intraorgan, intralymphatic, intraperitoneal, intravenous, and implantable. The carriers used in the formulations may be, for example, solid and/or liquid carriers.

Reference may be made to "Remington's Pharmaceutical Sciences", 17th Ed., Mack Publishing Company, Easton, Pa., 1985, for other carriers that would be suitable for combination with the present oligonucleotide compounds to render compositions/formulations suitable for administration to treat respiratory disease.

Optionally, the presently described oligonucleotides may be formulated with a variety of physiological carrier molecules. The presently described oligonucleotides may also be complexed with molecules that enhance their ability to enter the target cells. Examples of such molecules include, but are not limited to, carbohydrates, polyamines, amino acids, peptides, lipids, and molecules vital to cell growth. For example, the oligonucleotides may be combined with a lipid, the resulting oligonucleotide/lipid emulsion, or liposomal suspension may, inter alia, effectively increase the in vivo half-life of the oligonucleotide.

The pharmaceutical compositions provided herein may comprise oligonucleotide compounds described above and one or more pharmaceutically acceptable surfactants. Suitable surfactants or surfactant components for enhancing the uptake of the oligonucleotides of the invention have been previously described in U.S. Application Publication No. 2003/0087845, the contents of which are incorporated herein with respect to surfactants. The application states that suitable surfactants " . . . include synthetic and natural as well as full and truncated forms of surfactant protein A, surfactant protein B, surfactant protein C, surfactant protein D and surfactant protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, Brij 35™, Triton X-100™ and synthetic surfactants ALEC™, Exosurf™, Survan™ and Atovaquone™, among others. These surfactants may be used either as single or part of a multiple component surfactant in a formulation, or as covalently bound additions to the 5' and/or 3' ends of the AONs."

The oligonucleotide component of the present compositions may be contained in a pharmaceutical formulation within a lipid particle or vesicle, such as a liposome or microcrystal. As described in U.S. Pat. No. 6,025,339, the lipid particles may be of any suitable structure, such as unilamellar or plurilamellar, so long as the oligonucleotide is contained therein. Positively charged lipids such as N-[1-(2,3-dioleoyloxi) propyl]-N,N,N-trimethyl-ammoniumethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.; 4,921,757 to Wheatley et al.; etc.

The composition of the invention may be administered by any means that transports the oligonucleotide compound to the desired site, such as for example, the lung. The oligonucleotide compounds disclosed herein may be administered to the lungs of a patient by any suitable means, but are preferably administered by inhalation of an aerosol comprised of respirable particles that comprise the oligonucleotide compound.

The oligonucleotides may be formulated to be administered in a dry powder inhaler, metered dose inhaler, nebulizer, soft mist inhaler and by any other suitable device having the capacity to deliver oligonucleotides to the lungs via inhalation route.

The composition of the present invention may be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. Particles of non-respirable size that are included in the aerosol tend to deposit in the throat and be swallowed, and the quantity of non-respirable particles in the aerosol is preferably thus minimized. For nasal administration, a particle size in the range of 10-500 µM is preferred to ensure retention in the nasal cavity.

A solid particulate composition comprising the oligonucleotide compound may optionally contain a dispersant that serves to facilitate the formation of an aerosol as well as other therapeutic compounds. A suitable dispersant is lactose, which may be blended with the antisense compound in any suitable ratio, e.g., a 1 to 1 ratio by weight.

Liquid pharmaceutical compositions of active compound (the oligonucleotide compound(s)) for producing an aerosol may be prepared by combining the oligonucleotide compound with a suitable vehicle, such as sterile pyrogen free water or phosphate buffered saline.

The oligonucleotide compositions may be administered in an anti-bronchoconstriction, anti-allergy(ies) and/or anti-inflammatory effective amount, which amount depends upon the degree of disease being treated, the condition of the subject patient, the particular formulation, the route of administration, the timing of administration to a subject, etc. In general, intracellular concentrations of the oligonucleotide of from 0.05 to 50 µM, or more particularly 0.2 to 5 µM, are desirable. For administration to a mammalian patient such as a human, a dosage of about 0.001, 0.01, 0.1, or 1 mg/Kg up to about 50, or 100 mg/Kg or more is typically employed. However, other doses are also contemplated. Depending on the solubility of the active compound in any particular formulation, the daily dose may be divided among one or several unit dose administrations.

The aerosols of liquid particles comprising the oligonucleotide compound may be produced by any suitable means, such as with a nebulizer. Nebulizers are commercially available devices that transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers comprise the active oligonucleotide ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, anti-oxidants, anti-bacterials, flavorings, volatile oils, buffering agents and emulsifiers and other formulation surfactants.

The aerosols of solid particles comprising the active oligonucleotide compound(s) and a pharmaceutically acceptable surfactant may likewise be produced with any solid particulate medicament aerosol generator. Aerosol generators for administering solid particulate medicaments to a subject produce particles that are respirable, as explained above, and generate a volume of aerosol containing a predetermined metered dose of a medicament at a rate suitable for human administration. The active oligonucleotide ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 µL, to produce a fine particle spray containing the active ingredient. Suitable propellants include certain chlorofluorocarbon compounds, for example, dichlorodifluoromethane, trichlorofluoromethane, dichlorotetrafluoroethane or hydrofluoroalkanes and mixtures thereof. The formulation may additionally contain one or more co-solvents, for example, ethanol, emulsifiers and other formulation surfactants, such as oleic acid or sorbitan trioleate, anti-oxidants and suitable flavoring agents.

The aerosol, whether formed from solid or liquid particles, may be produced by the aerosol generator at a rate of from about 1 to 150 liters per minute.

In a further aspect of the present invention, an article of manufacture is provided which includes packaging material contained within which is a pharmaceutically acceptable oligonucleotide composition that is therapeutically effective to treat conditions associated with allergy, asthma, rhinitis and inflammatory disease. In one embodiment, the composition comprises an oligonucleotide compound that is effective to inhibit CCR3 chemokine receptor or the common beta-chain for IL-3/IL-5/GM-CSF receptors gene expression, said oligonucleotide compound being at least 50% complementary to the gene. In another aspect, the composition comprises at least 2 oligonucleotide compounds, each oligonucleotide compound being capable of downregulating expression of each of the CCR3 chemokine receptor and the common beta-chain for IL-3/IL-5/GM-CSF receptors genes, each oligonucleotide compound being present at a concentration at which the oligonucleotide compound is practically ineffective on its own to downregulate the gene it is directed against, the combination of the oligonucleotide compounds being effective to downregulate at least one of the genes that the oligonucleotides are directed against.

In one embodiment, the packaging material of the article comprises a label which indicates that the composition can be used to treat inflammatory respiratory disease and may additionally include an indication that the disease is one of allergy, rhinitis, COPD, CF, and asthma.

In another embodiment, the packaging material of the article comprises a label which indicates that the composition can be used to treat inflammatory respiratory disease, and may additionally include an indication that the disease is one of allergy, asthma, hypereosinophilia, bronchitis, COPD, rhinitis or sinusitis.

For the purposes of the present invention, the packaging material may be any suitable material for packaging a nucleotide-containing composition in accordance with the present invention, including a bottle or other container (either plastic or glass), a carton, a tube, or other protective wrapping. As will be appreciated, the packaging may vary with the nature of the oligonucleotide composition, for example, a liquid formulation may be packaged differently than an aerosol formulation.

The present invention will be more readily understood by referring to the examples that are given to illustrate the following invention rather than to limit its scope. With respect to these examples, the following were methods and materials were used.

EXAMPLES

Methods

Cell Culture

TF-1 cells were cultured in RPMI-1640 medium containing 2 mM L-glutamine, 1.5 g/l sodium bicarbonate, 4.5 g/l D-glucose, 10 mM HEPES, 1 mM sodium pyruvate, 10% fetal bovine serum, 2 ng/ml rhGM-CSF, 100 U/ml penicillin and 100 µg/ml streptomycin. 293-βc-GFP and 293-CCR3-GFP cells stably expressing β-chain-GFP and CCR3-GFP fusion cDNA, respectively, were cultured in DMEM containing 2 mM L-glutamine, 4.5 g/l glucose, 10% fetal bovine serum, 15 µg/ml Blasticidin, 100 µg/ml Hygromycin B, 100 U/ml penicillin and 100 µg/ml Streptomycin. NIH-3T3 cells were cultured in DMEM containing 2 mM L-glutamine, 4.5 g/l glucose, 10% calf bovine serum, 100 U/ml penicillin and 100 µg/ml Streptomycin.

Design and Preparation of AON, siRNA and miRNA Mimic Sequences

Phosphorothioate-DNA AONs (Sigma Genosys), DAP-modified phosphorothioate-DNA AONs (Sigma Genosys) and phosphorothioate-2'F-ANA AONs (Topigen, Montreal or UcDNA, Calgary) were designed to target the coding regions of the β-chain and CCR3 mRNAs. Phosphorothioate-DNA AONs, specifically, were designed to target regions along the entire coding region of the β-chain mRNA, as well as within the 5' UTR, 3' UTR and regions extending across intron/exon junctions. Online reference sequences (NCBI Genbank entries) used for the design of β-chain and CCR3 AON were: Genbank accession numbers BC070085 (TOP050 (SEQ ID No: 1)-TOP076 (SEQ ID NO: 27), TOP195 (SEQ ID No: 146), and TOP254 (SEQ ID NO: 205)-TOP259 (SEQ ID No: 210)); NM_000395.2 (TOP077 (SEQ ID NO: 28)-TOP194

(SEQ ID NO: 145), TOP196 (SEQ ID No: 147)-253 (SEQ ID No: 204), TOP260 (SEQ ID No: 211)-TOP346 (SEQ ID No: 297) and TOP517 (SEQ ID No: 468)-TOP721 (SEQ ID No: 672)); and NG_008040 (TOP347 (SEQ ID No: 298)-TOP516 (SEQ ID No: 467)) for β-chain; and NM_001837 (TOP020 (SEQ ID NO. 673) -TOP045 (SEQ ID NO. 698)) for CCR3. SiRNA sequences were designed using conventional Tuschl-based design (Qiagen siRNA design tool), High Performance (HP) OnGuard algorithm (Genome Wide siRNA, Qiagen), Thermoscientific Dharmacon RNAi Technologies siDESIGN Center Custom siRNA Design Tool, Invitrogen's BLOCK-IT™ RNAi Designer, or EMBOSS.

MiRNA mimics were selected using publicly available algorithms to identify miRNAs with homology to the 3' UTR of the β-chain gene. Algorithms employed for identification of miRNAs were TargetScan, miRBase, miRANDA, miR-GEN, and DIANA microT.

All oligonucleotides were resuspended in sterile water and their concentrations determined by spectrophotometry.

Cell Transfection

TF-1 cells in exponential growth phase (0.6 to $0.8 \times 10^6$ cells/ml) were grown at a density of $1.25 \times 10^6$ cells/ml in complete growth medium without antibiotics. Cells were immediately transfected with AON-, siRNA- or miRNA mimic-Lipofectamine 2000 complexes diluted in Opti-MEM and previously incubated for 20 minutes at room temperature at a ratio of 1 μg oligonucleotide: 1 μl Lipofectamine 2000. Cells were transfected with AON concentrations ranging between 83.5 nM and 2.67 μM, siRNA concentrations ranging between 0.25 and 1.0 μM, and miRNA mimics at concentrations of 0.5 μM and 1 μM, then incubated at 37° C. for 18 to 72 hours.

293-βc-GFP and 293-CCR3-GFP cells were cultured in complete growth medium without antibiotics. Cells were transfected as described above with AON concentrations between 67 nM and 534 nM or siRNA concentrations between 40 nM and 1.0 μM. CCR3-GFP or β-chain-GFP expression was induced with 100 ng/ml doxycycline for 2 hours (mRNA) or 18 hours (protein) prior to harvesting.

NIH 3T3 cells were transfected as described above with 0.2 μg pCMVscript rat CCR3 or 0.3 μg pGL2-Luciferase, and 0.2 μg of AON.

Quantification of mRNA Expression

Quantification of the mRNA expression levels of CCR3 and β-chain was performed using the Quantigene 2.0 assay. Briefly, cells were resuspended in 1× Quantigene lysis mixture and incubated at 53-55° C. for 30 minutes. The only exception was for CCR3 mRNA quantification in TF-1 cells for which total RNA was first extracted from cell pellets using the RNAeasy mini kit and quantified using the Ribogreen assay according to the manufacturer protocols. Cell lysates or purified RNA were then hybridized overnight at 55° C. using specific probe sets and signal detection performed according to the Quantigene 2.0 assay procedure. Gene expression was normalized relative to the expression of a control gene (β2M).

Quantification of βc-GFP and CCR3-GFP Protein Expression in 293 Cells by Flow Cytometry Cells were harvested with trypsin 24 hours post-transfection, washed twice with PBS, resuspended in 1× permeabilization solution and incubated for 10 minutes at room temperature. Cells were then washed twice with PBS containing 0.5% BSA, resuspended in 50 μL PBS containing 5 μg/ml FITC-conjugated anti-GFP antibody and incubated for 1 hour at 4° C. Cells were washed twice with PBS and fixed in 2% paraformaldehyde before analysis by flow cytometry (488 nM) using the GUAVA EasyCyte apparatus.

Quantification of Endogenous Protein Expression in TF-1 by FACS

TF-1 cells were harvested at indicated time points post-transfection and washed twice with PBS. The staining was performed on 50,000 cells using the Eotaxin Fluorokine kit for CCR3 receptor quantification or the IL-3 Fluorokine kit for common β-chain of IL-3, IL-5 and GM-CSF receptors. In these assays, biotinylated eotaxin or biotinylated IL-3 binds to the specific cell surface receptor and is detected using avidin-fluorescein. Cells were fixed in 4% paraformaldehyde solution and green fluorescence was detected by FACS (488 nM) using the GUAVA EasyCyte apparatus.

AON Serum Stability Assay

AON were dried down and resuspended in DMEM supplemented with 50% fetal bovine serum at a final concentration of 1 μg/μl. AONs were incubated at 37° C. and samples (20 μl) collected at different time points between 0 and 96 hours and stored at −80° C. until analysis. Samples were dried down, resuspended in 100 μl dH$_2$O and loaded on Protein-Pak™ DEAE-5PW anion exchange column (7.5×75 mm) for HPLC analysis.

Antisense Efficacy in a Rat Model of Allergen-Induced Airway Inflammation

Animal studies were conducted at Mispro Biotech Services, Montréal, QC and were approved by Mispro's Animal Ethic Committees. Brown Norway (BN) rats (6 to 8 weeks old) were obtained from Harlan Sprague-Dawley Inc. Active sensitization was performed by subcutaneous injection of 1 ml of saline containing 1 mg of chicken egg ovalbumin (OVA) and 3.5 mg of aluminum hydroxide gel. Fourteen days after sensitization, rats were injected intra-tracheally (i.t.) with either sterile saline (50 μl) or 50 μg of a combination of TOP006 (SEQ ID No: 1626) and TOP007 (SEQ ID No: 1628) (ratio w/w 1:1) or 50 μg of a combination TOP006-F2 (SEQ ID No: 1627) and TOP007-F8 (SEQ ID No: 1629) (ratio w/w 1:1) in 50 μl sterile saline. Rats were challenged 10 minutes later by exposure to OVA aerosols (5% in saline) in a closed chamber for 15 minutes. Challenge was repeated 24 hours later. To determine the effect of AON treatment on cellular influx to the lungs, rats were sacrificed 15 hours following second OVA challenge, and bronchioalveolar lavages (BAL) were performed. Cells were recovered by centrifugation and total leukocyte counts were performed using a hemacytometer. Differential cell counts were performed on cytospin slides stained with Hema-3 stain kit. At least 200 cells were counted under oil immersion microscopy. Lungs were collected following BAL and processed for mRNA (right lung) or immunohistochemistry (left lung).

Animal Inhalation Studies

Monkey Study Design

All studies were performed at ITR Laboratories Canada (Baie d'Urfe, QC) in compliance with GLP regulations. Briefly, male and female cynomolgus monkeys (weighing 1.5-2.5 kg) received 14 consecutive doses of vehicle or 0.05, 0.25 or 2.5 mg/kg of TPI ASM8 (in saline) or TPI 1100 (in phosphate-buffered saline; PBS) administered daily as aerosols using a inhalation exposure system. The animals were examined 1-2 times daily for clinical symptoms including a qualitative assessment of food consumption, and body weight was measured weekly. Electrocardiographic (ECG) activity was recorded and ophthalmic examinations were conducted for animals pre-study and on Day 14.

One day after the last dose (Day 15), 24 monkeys (3/sex/group) were euthanized. All remaining animals were euthanized upon completion of the recovery period (14 day after the last dose for the TPI ASM8 study or 28 days after the last dose for the TPI 1100 study). Terminal procedures included complete gross necropsy examination, collection and preservation of approximately 40 tissues, and measurement of the weights of all major organs. Respiratory tract tissues (nasal cavity, nasopharynx, larynx, pharynx, trachea, bronchi, lungs including carina and bronchial lymph nodes) from all animals were examined by light microscopy, and all collected tissues was examined for all high dose and control group animals. In addition, portions of the trachea, lung, liver and kidney were collected for analysis of AON content.

Rodent Study Design

Studies in rat (TPI ASM8) and in mice (TPI 1100) were conducted as described for the monkey studies. Male and female CD-1 mice received 14 consecutive doses of vehicle or 0.05, 0.25 or 2.5 mg/kg of TPI 1100 administered daily as aerosols using an inhalation exposure system. Male and female Sprague-Dawley rats received 14 consecutive doses of vehicle or 0.02, 0.07, 0.2 0.1 or 5 mg/kg of TPI ASM8 administered daily as aerosols using an inhalation exposure system.

Example 1

Efficacy of AON Sequences Directed to the Common Beta Subunit of IL-3, IL-5 and GM-CSF Receptors The sequence and composition of the AON sequences directed against the common beta subunit (β-chain) of IL-3, IL-5 and GM-CSF receptors are presented in Table 1a. All AONs were purified and desalted. The potency of some selected sequences is demonstrated in FIG. 1a which shows the reduction in gene expression in vitro following transfection with indicated AON in 293-βc-GFP and TF-1 cell lines. AON activity listed in Table 1a, is expressed as the average percentage inhibition of β-chain mRNA relative to untransfected controls. The 293-βc-GFP cell line was engineered to artificially express β-chain/green fluorescent protein (GFP) fusion mRNA and protein while TF-1 cells express β-chain mRNA and protein endogenously.

Specificity of some selected AON sequences was assessed by comparing their efficacy at reducing β-chain mRNA expression levels compared to their respective control sense sequence in 293-βc-GFP cells (FIG. 1b) and in TF-1 cells (FIG. 1c). In each cell line, respective control sense sequences which are not complementary to the β-chain mRNA were inactive. In addition, inhibitory activity of AON targeting β-chain was also observed at the protein level upon analysis by flow cytometry. FIGS. 5a and 5b show that 293-βc-GFP and TF-1 cells had decreased levels of β-chain protein expression following transfection with specific AON and overnight incubation while control sequences had no effect.

Example 2

Efficacy of AON Sequences Directed to the CCR3 Chemokine Receptor

Figure 2:
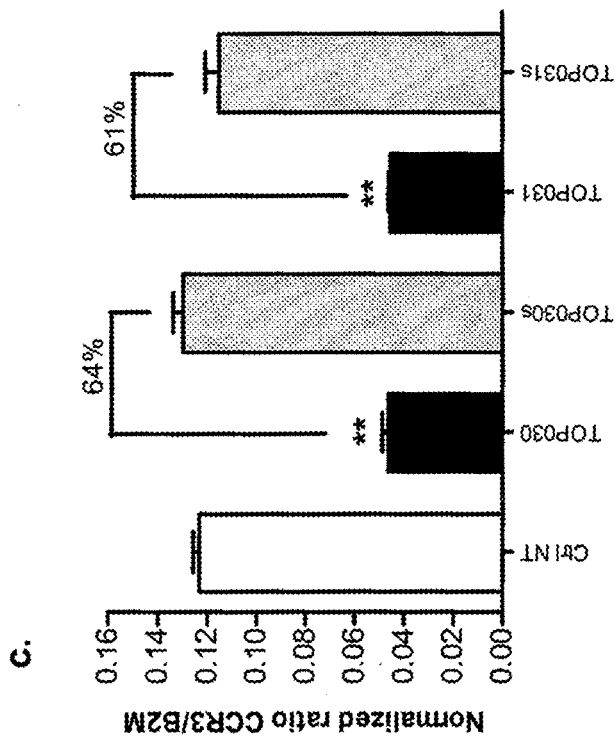
FIG. 2 illustrates the efficacy of AON sequences at reducing the CCR3 mRNA expression.
Figure 2:
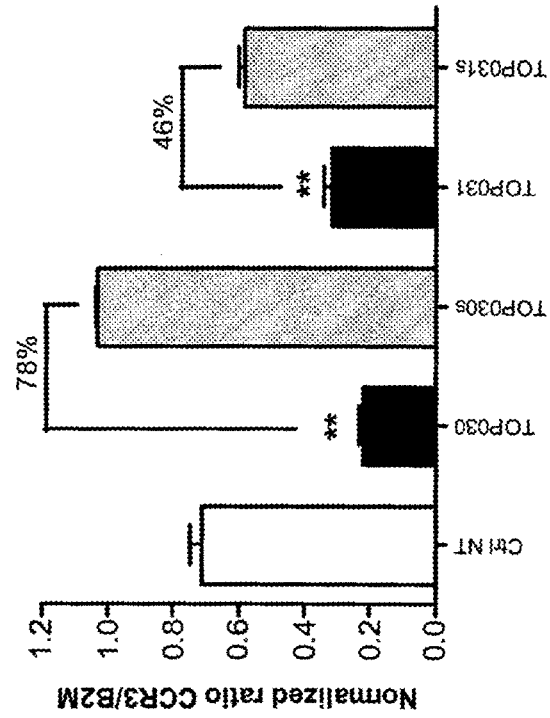

The list of AON sequences targeting CCR3 is presented in Table 1b. All AON were prepared and purified as described above. The potency of some selected sequences is demonstrated in FIG. 2a which shows the reduction in gene expression in vitro following transfection with indicated AON in 293-CCR3-GFP and TF-1 cell lines. The 293-CCR3-GFP cell line was engineered to express a CCR3/green fluorescent protein (GFP) fusion product while TF-1 cells express CCR3 mRNA and protein endogenously. FIGS. 2b and 2c show the specific reduction in CCR3 mRNA expression levels in 293-CCR3-GFP and TF-1 cells, respectively, 24 hours post-transfection with AONs against CCR3, whereas respective control sense sequences were inactive. AON activity given in Table 1b is expressed as the average percentage inhibition of CCR3 mRNA expression relative to untransfected controls.

The inhibitory activity of AON targeting CCR3 was also observed at the protein level upon analysis by flow cytometry. FIGS. 5c and 5d show that 293-CCR3-GFP and TF-1 cells had decreased levels of CCR3 protein expression 24 hours post-transfection with indicated AON, while control sequences had no effect.

Example 3

Comparison Between AON and siRNA Sequences at Reducing β-Chain mRNA Expression

Figure 3:
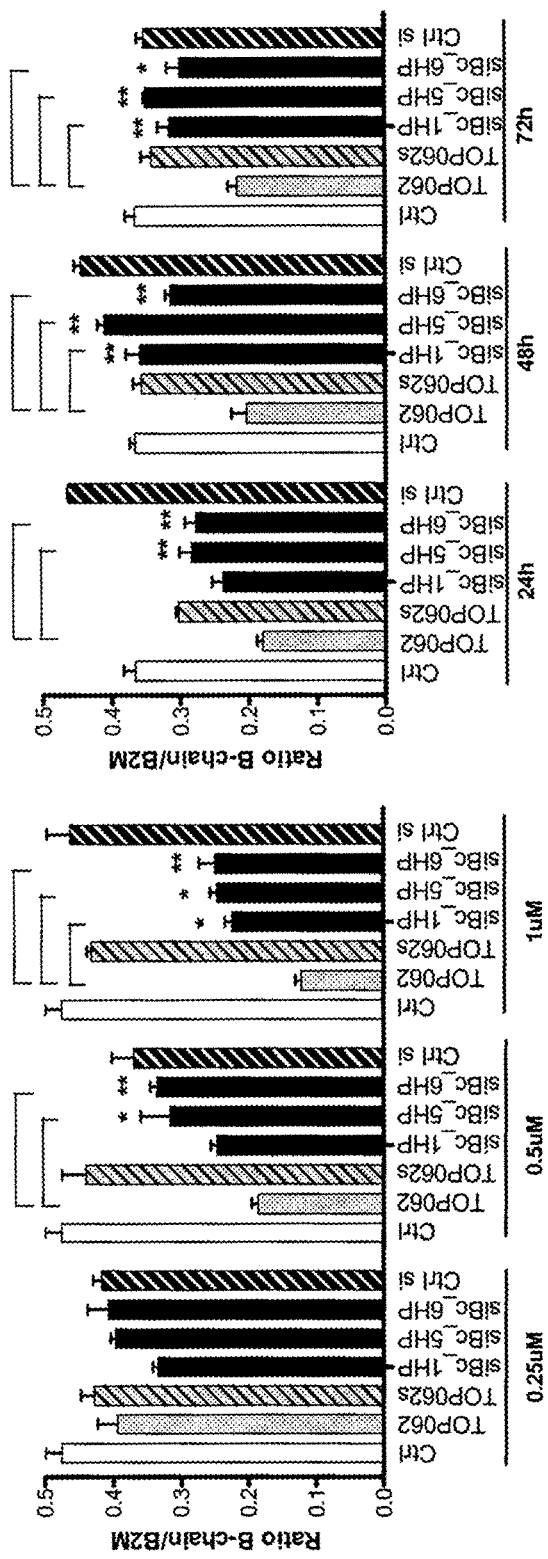
FIG. 3 illustrates the efficacy of siRNA sequences at reducing β-chain mRNA expression levels.

In addition to AON sequences, siRNA molecules were designed (Table 2a) and tested for their efficacy at reducing β-chain mRNA expression (FIG. 3). FIG. 3a shows the efficacy of some selected siRNA sequences at reducing β-chain mRNA expression levels in 293-βc-GFP cells compared to untransfected cells (Ctl NT) and to an irrelevant siRNA sequence (siCtl). The efficacy of AON TOP062 (SEQ ID No: 13) at reducing β-chain mRNA expression in TF-1 cells was compared to different siRNA sequences designed to target common β-chain. Results indicated that AON TOP062 (SEQ ID No: 13) (0.5 and 1 μM) exhibited superior efficacy at reducing β-chain mRNA expression compared to the siRNA sequences (FIG. 3b). In addition, time-course experiments indicated that inhibition of β-chain mRNA expression in cells transfected with AON TOP062 (SEQ ID No: 13) was maintained up to 72 h post-transfection while all the siRNA sequences evaluated were ineffective at reducing expression at this time point (FIG. 3c).

Example 4

Comparison Between AON and siRNA Sequences at Reducing CCR3 mRNA Expression

Figure 4:
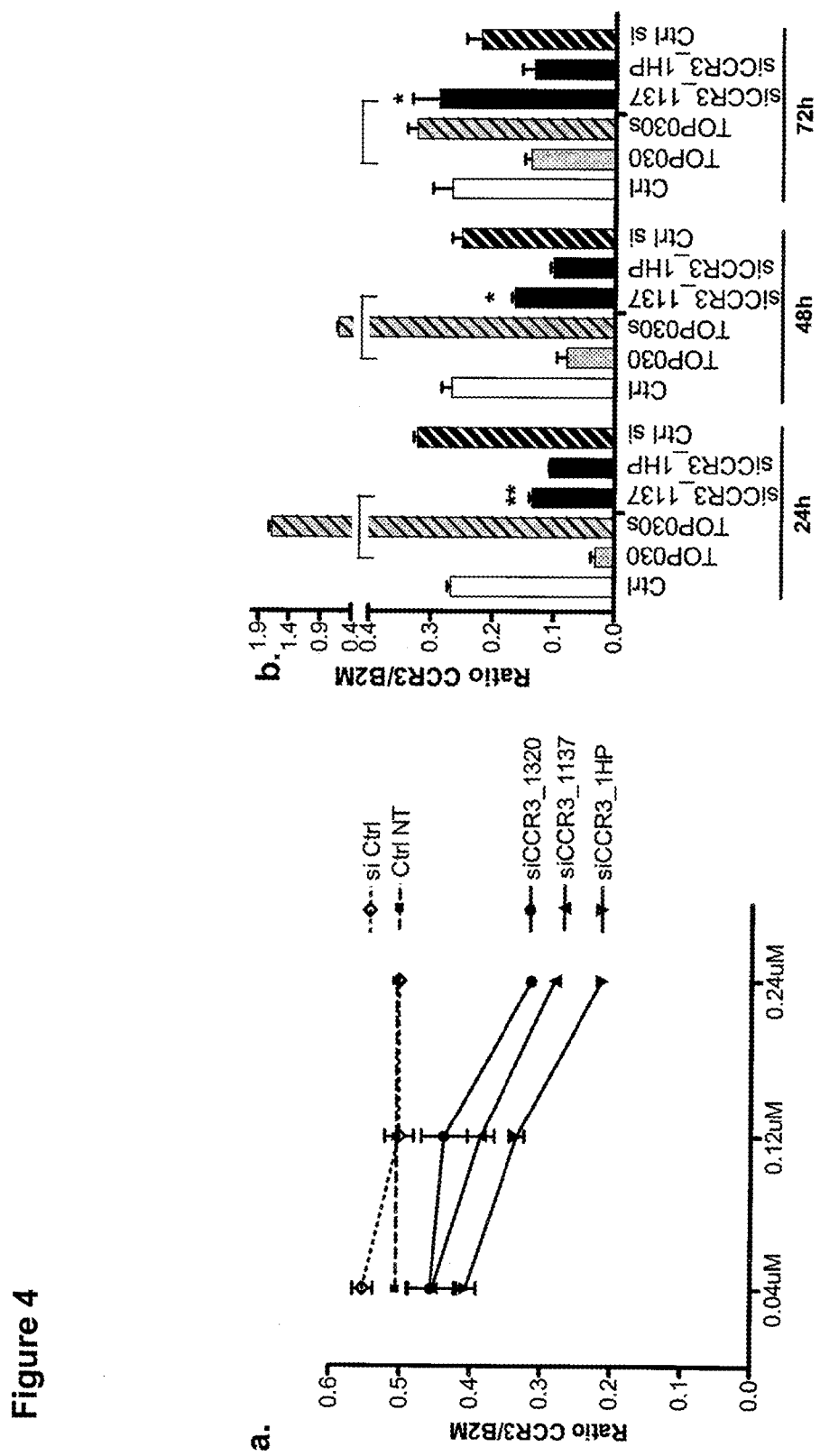
FIG. 4 illustrates the efficacy of siRNA sequences at reducing CCR3 mRNA expression levels.

In addition to AON sequences, siRNA molecules were designed (Table 2b) and tested for their efficacy at reducing CCR3 mRNA expression (FIG. 4). FIG. 4a shows the efficacy of some selected siRNA sequences at reducing CCR3 mRNA expression levels in 293-CCR3-GFP cells compared to untransfected cells (Ctl NT) and to an irrelevant siRNA sequence (siCtl). The efficacy of AON TOP030 (SEQ ID No: 683) at reducing CCR3 mRNA expression in 293-CCR3-GFP cells was compared to different siRNA sequences designed to target CCR3 (FIG. 4b). Time-course experiments indicated that inhibition of CCR3 mRNA expression in cells transfected with AON TOP030 (SEQ ID No: 683) was maintained up to 72 hours post-transfection while only one siRNA sequence (siCCR3_1HP) maintained inhibitory activity at this time point.

Example 5

Figure 6:
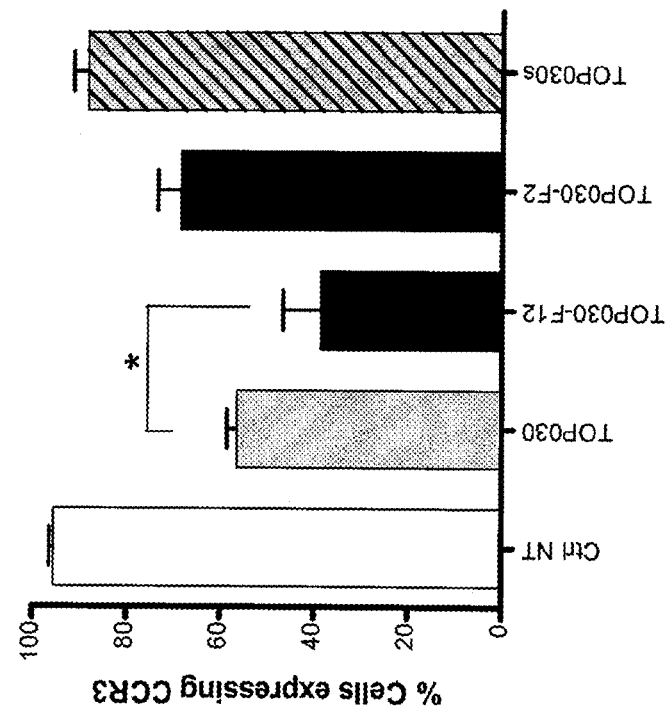
FIG. 6 illustrates the efficacy of FANA-containing TOP062 (SEQ ID No: 13) and TOP030 (SEQ ID No: 683) AONs at reducing β-chain (293-βc-GFP cells) and CCR3 (TF-1 cells) protein levels, respectively. 293-βc-GFP cells were transfected with 200 nM AON while TF-1 cells were transfected with 668 nM AON. Protein expression levels were measured by flow cytometry 24 hours post-transfection. Results are expressed as the main percentage of cells positive for β-chain (FIG. 6a) and CCR3 (FIG. 6b) protein expression±SEM. Statistical analysis was performed using the ANOVA test (Dunnett's post test), with n=3 or 4, *p<0.05 and **p<0.01.
Figure 6:
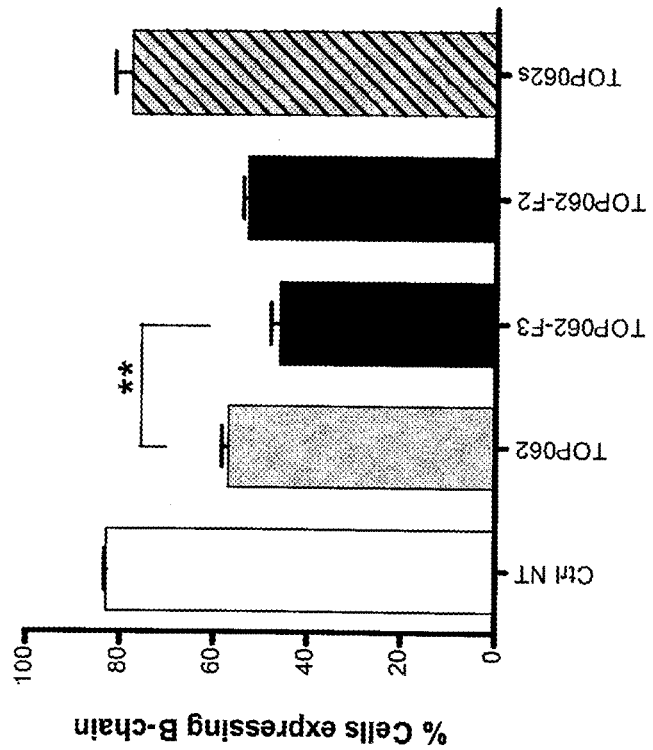

AONs Modified with FANA Chemistry Demonstrated Increased Efficacy and Prolonged Serum Stability This example relates to the enhanced efficacy and prolonged serum stability of β-chain and CCR3-specific AONs when ANA modifications are incorporated into the chemistry of the AON. Tables 3a and 3b describe the compositions of AON modified with FANA residues. In FIG. 6a, results obtained for β-chain expression in 293-βc-GFP cells transfected with β-chain-specific AONs (unmodified DNA with phosphorothioate backbone or FANA modified as indicated) are provided. Modification of TOP062 (SEQ ID No: 13) sequence with FANA (TOP062-F2 (SEQ ID No: 1582) and TOP062-F3 (SEQ ID No: 1583)) enhanced the efficacy of the AON as shown by the increased inhibition of target protein expression, clearly indicating an advantage of this modification for AON activity. Similarly, modification of TOP030 (SEQ ID No: 683) sequence with FANA (TOP030-F12) (SEQ ID No: 1610) enhanced its efficacy to inhibit CCR3 protein expression, again supporting the advantage of this modification for AON activity (FIG. 6b). The FANA modifications also enabled the incorporation of natural phosphodiester linkages without affecting the activity of the AON on expression of the respective mRNA target (TOP062-F14 (SEQ ID No: 1594) to F18 and TOP030-F12 (SEQ ID No: 1610)) (Table 3a and 3b). This was surprising as phosphodiester-containing AONs are commonly believed to be more susceptible to nuclease degradation, resulting in reduced antisense inhibitory activity compared to phosphorothioate-containing AON counterparts.

Figure 5:
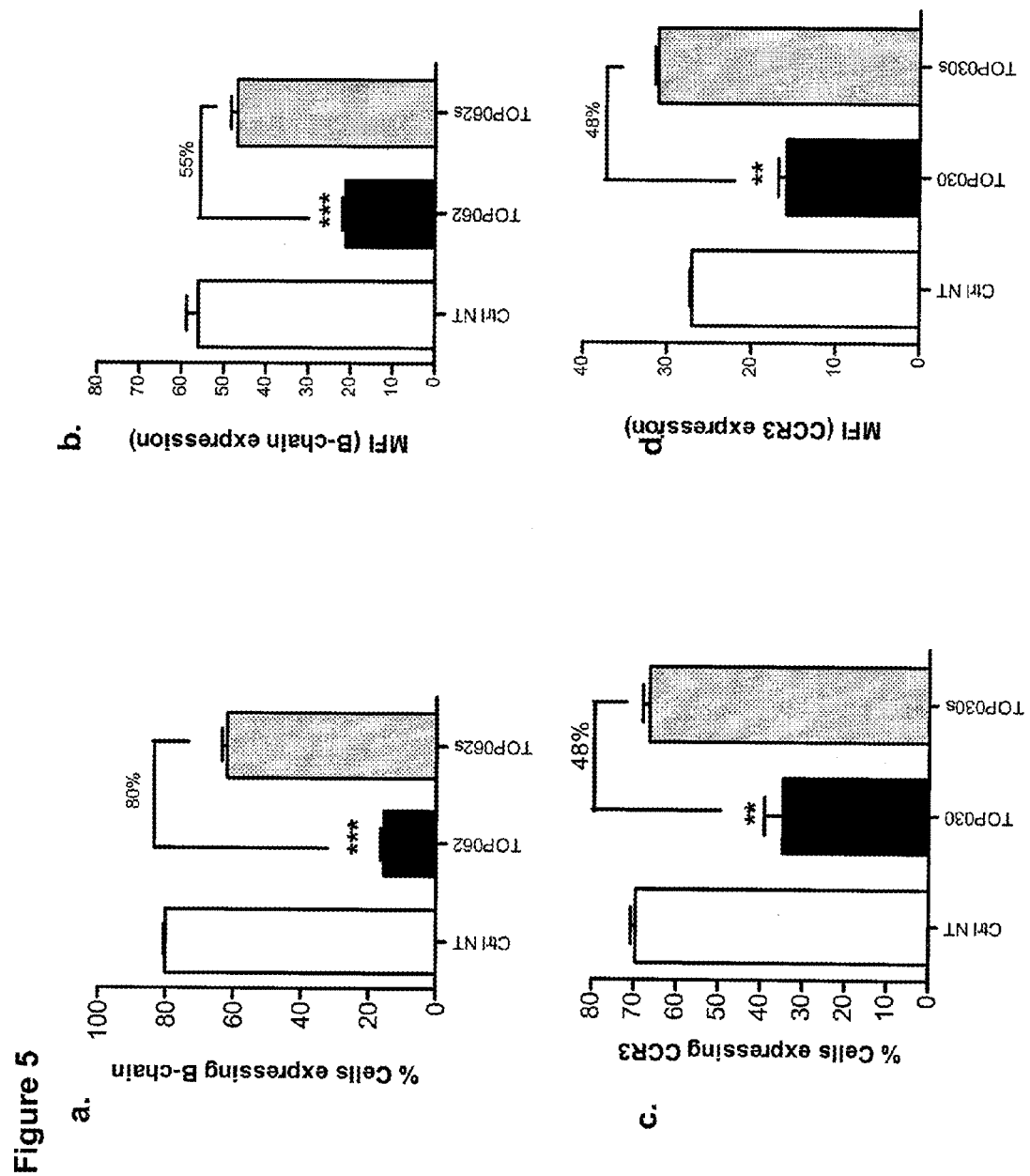
FIG. 5 illustrates the efficacy of selected AON sequences at reducing β-chain or CCR3 protein expression. Cells were transfected with indicated AONs or their control sense sequence (267 nM of AON was transfected into 293-βc-GFP and 293-CCR3-GFP cells; 667 nM of AON was transfected into TF-1 cells) and protein levels were analyzed by flow cytometry 24 hours post-transfection.
Figure 7:
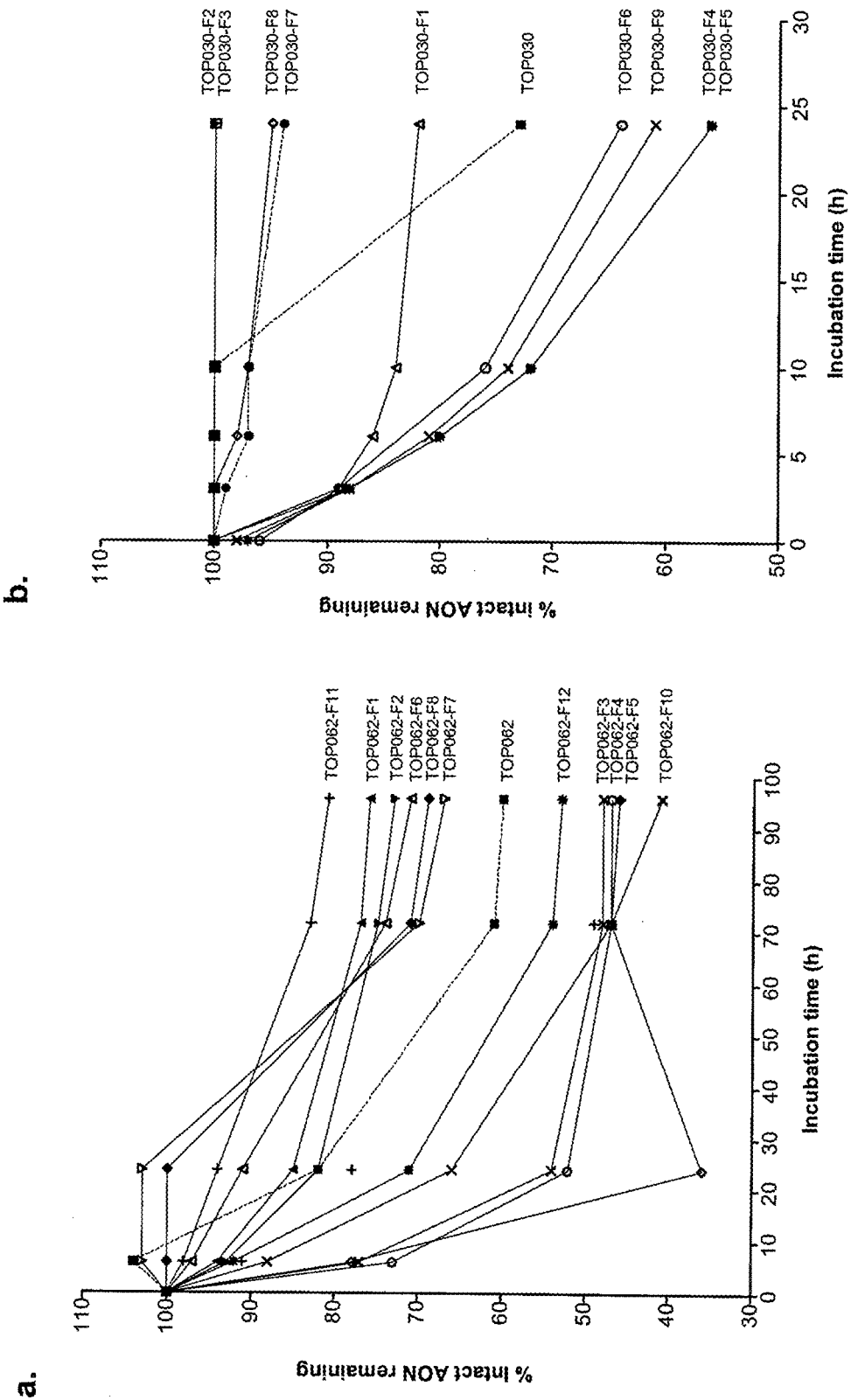
FIG. 7 illustrates the increased serum stability of FANA-containing TOP062 (SEQ ID No: 13) (FIG. 7a) and TOP030 (SEQ ID No: 683) (FIG. 7b) AONs. AONs were incubated at 37° C. in DMEM containing 50% fetal bovine serum. Samples were collected at different time points and analyzed using anion exchange HPLC. The percentage of intact AON remaining was determined by comparing the corresponding peak area to the value of the peak area at time point 0 hours set at 100%.

FANA modifications are expected to enhance the stability of the AON, rendering it more resistant to nucleosidase digestion, further resulting in prolonged AON activity. FIG. 5 presents the comparison of different formulations of TOP062 (SEQ ID No: 13) (β-chain) and TOP030 (SEQ ID No: 683) (CCR3) diluted DMEM containing 50% fetal bovine serum and incubated at 37° C. for indicated time period. Aliquots were collected at different time points and the presence of intact AON analyzed using HPLC. Results showed that incorporation of FANA modified nucleotides in TOP062 (SEQ ID No: 13) (FIG. 7a) and TOP030 (SEQ ID No: 683) (FIG. 7b) conferred significant resistance to serum-mediated degradation.

Example 6

Figure 8:
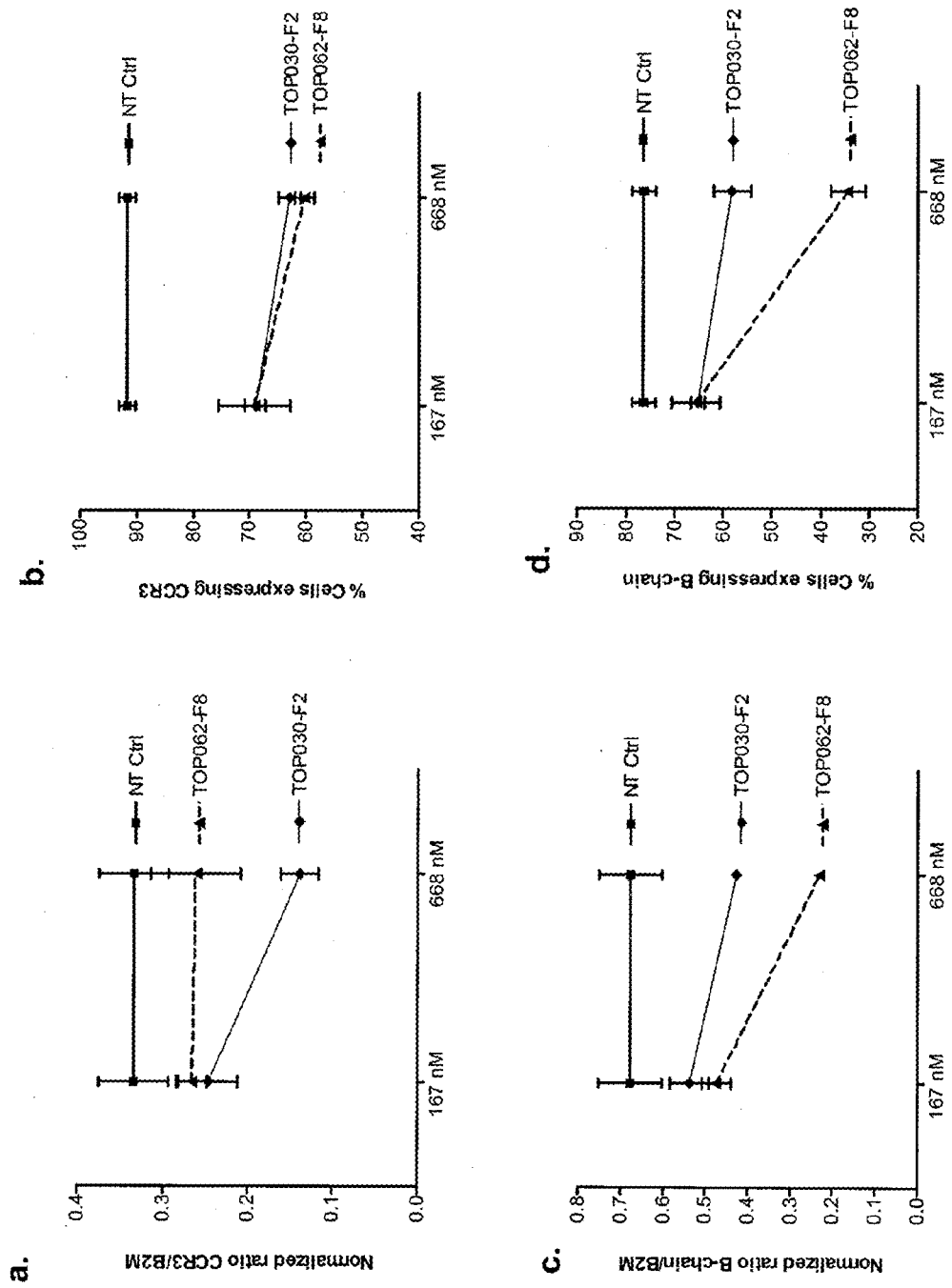
FIG. 8 illustrates the cross-target effect of TOP062-F8 (SEQ ID No: 1588) (β-chain AON) on CCR3 expression and TOP030-F2 (SEQ ID No: 1600) (CCR3 AON) on β-chain expression. TF-1 cells were transfected with either AON singly at a concentration of 167 nM or 668 nM. Twenty-four hours post-transfection cells were analyzed for mRNA and protein expression levels of CCR3 (FIGS. 8a and 8b) and β-chain (FIGS. 8c and 8d). The mRNA expression level results are given as the average±SEM of normalized ratio CCR3 or β-chain/β2M while protein expression results are given as the mean percentage±SEM of cells expressing CCR3 or β-chain protein.
Figure 9:
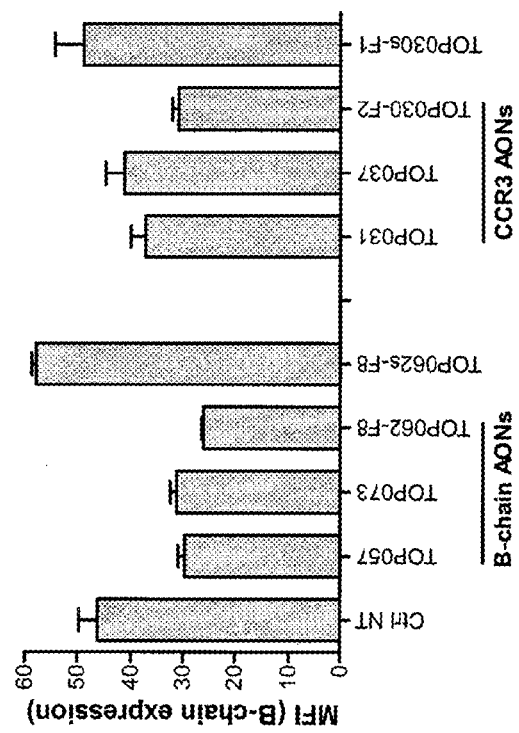
FIG. 9 illustrates the cross target effect of TOP62-F8 (SEQ ID No: 1588) and TOP30-F2 (SEQ ID No: 1600)(TPI2200) AONs on CCR3 (FIG. 9a) and β-chain (FIG. 9b) protein expression. TF-1 cells were transfected with indicated AON sequences at a concentration of 668 nM. Twenty-four hours post-transfection protein expression levels were measured by flow cytometry. Results were expressed as the mean fluorescence intensity (MFI±SEM).
Figure 9:
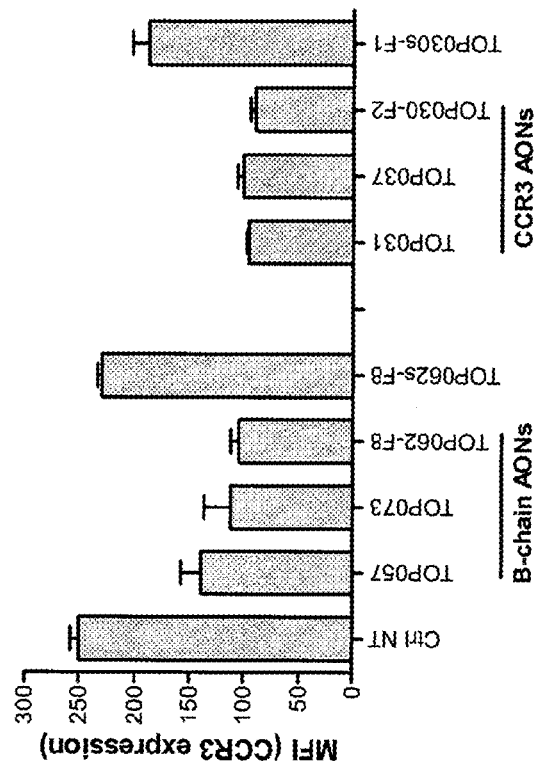

Cross-Target Effect of an AON Specific for One Receptor on the Expression of Another Receptor This example relates to the effect of inhibition of a single receptor on mRNA production of a different receptor. The experiments were conducted in TF-1 cells. Although AON sequences were specifically designed against their respective target, results in FIG. 8 and FIG. 9 show that several AON were found not only to inhibit their specific targets but were able to down regulate mRNA corresponding to other receptors (cross-target effect). CCR3 specific AON TOP030-F2 (SEQ ID No: 1600) not only provided inhibition of its specific target (FIGS. 8a and 8b) but also downregulated mRNA (FIG. 8c) and protein (FIG. 8d) expression of common β-chain.

Similarly, AONs TOP031 (SEQ ID No: 684) and TOP037 (SEQ ID No: 690) downregulated expression of CCR3 (FIG. 9a) and additionally demonstrated inhibitory activity towards common β-chain protein expression (FIG. 9b).

Conversely, besides downregulating expression of its specific target, common β-chain (FIGS. 8c and 8d), TOP062-F8 (SEQ ID No: 1588) was also shown to be effective at reducing CCR3 mRNA (FIG. 8a) and protein (FIG. 8b) expression levels. The cross-target inhibitory effect was not restricted to TOP062-F8 (SEQ ID No: 1588), and was also observed with additional AON sequences (TOP057 (SEQ ID No: 8) and TOP073 (SEQ ID No: 24)) targeting β-chain (FIG. 9a and FIG. 9b).

Example 7

Figure 10:
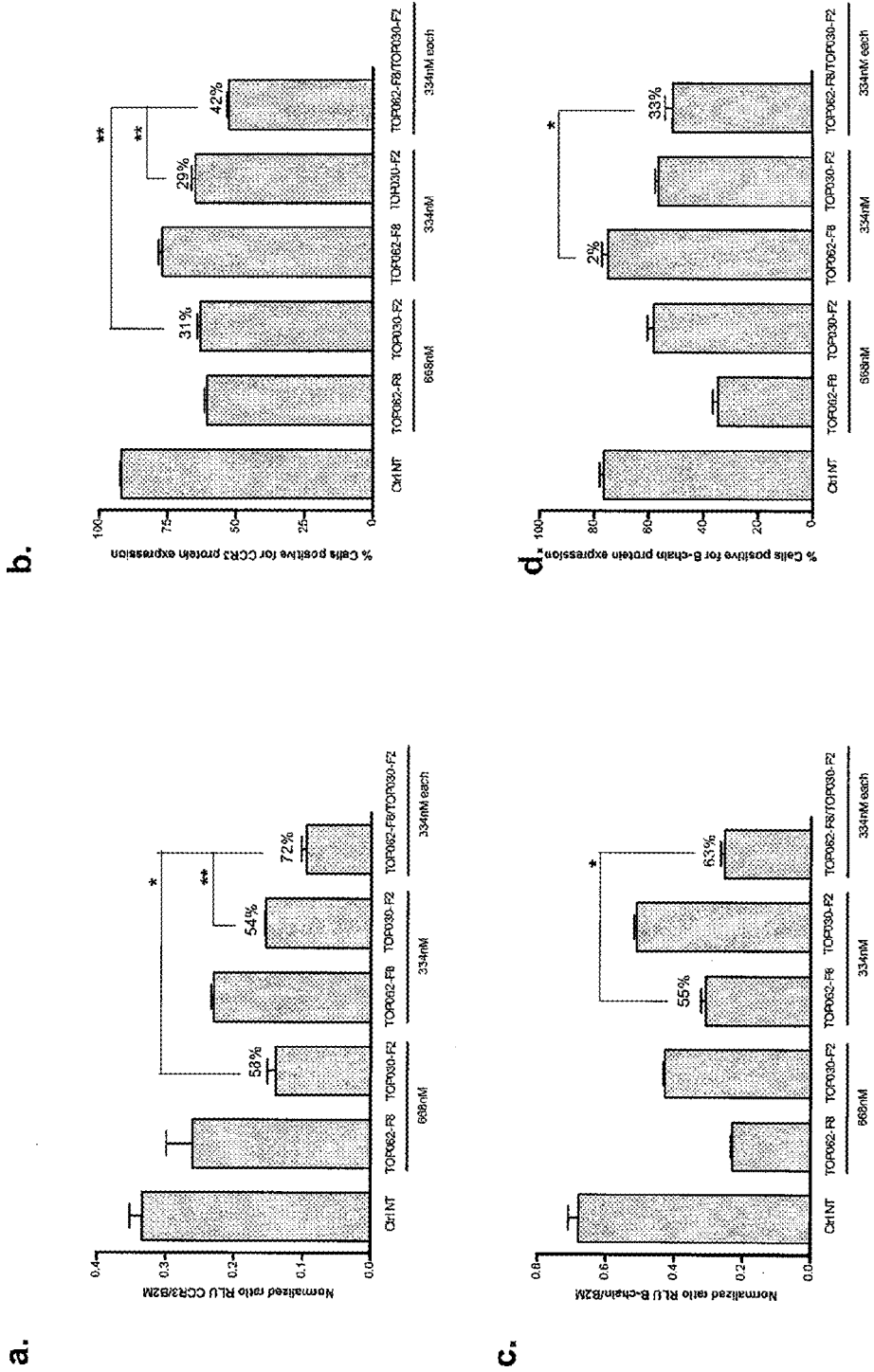
FIG. 10 illustrates the efficacy of TOP062-F8 (SEQ ID No: 1588) and TOP030-F2 (SEQ ID No: 1600) alone or in combination on inhibition of CCR3 and β-chain mRNA and protein expression. TF-1 cells were transfected with one AON alone (334 nM or 668 nM) or in combination (334 nM each AON). Twenty-four hours post-transection mRNA and protein levels of CCR3 (FIGS. 10a and 10b) and β-chain (FIGS. 10c and 10d) were quantified. mRNA expression results are given as the average±SEM normalized ratio CCR3 or β-chain/β2M while protein expression results are given as the mean percentage±SEM of cells expressing CCR3 or β-chain protein. The percentage of expression inhibition relative to untransfected control cells is indicated. Statistical analysis was performed using unpaired t test with n=3, *p<0.05 and **p<0.01.

Multiple Gene Knock-Down Effect of Combining Two AON Derived from the Nucleotide Sequences of Two Different Target Genes This example relates to the effect of the combination of specific AONs on β-chain and CCR3 gene expression. The effects of combining two separate AONs on β-chain and CCR3 mRNA expression in TF-1 cells expressing both receptors endogenously was assessed (FIG. 10). Each AON was transfected into cells singly or in combination. Cells were analyzed for mRNA or protein expression 24 hours post-transfection. The combination of TOP030-F2 (SEQ ID No: 1600) and TOP062-F8 (SEQ ID No: 1588) was demonstrated to be significantly more effective at decreasing CCR3 mRNA (FIG. 10a) and protein (FIG. 10b) expression levels compared to TOP030-F2 (SEQ ID No: 1600) alone. Similarly, the combination of a lower concentration of TOP062-F8 (SEQ ID No: 1588) relative to concentration of TOP030-F2 (SEQ ID No: 1600) exhibited a strong synergistic effect on the expression levels of β-chain mRNA (FIG. 10c) and protein (FIG. 10d) compared to TOP062-F8 (SEQ ID No: 1588) alone.

Example 8

Antisense Efficacy in a Rat Model of Allergen-Induced Airway Inflammation

Figure 11:
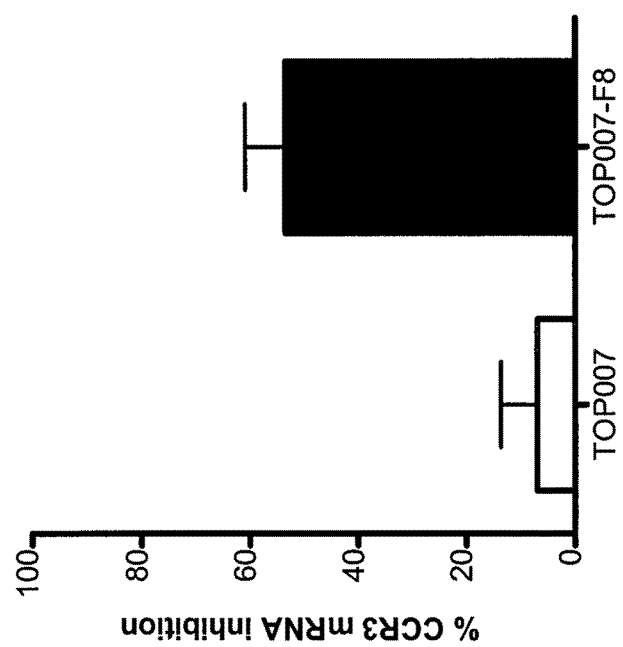
FIG. 11 illustrates the activity of FANA-containing TOP007 (SEQ ID No: 1628) AON at reducing the rat CCR3 mRNA expression levels. NIH-3T3 cells were co-transfected with 0.2 µg of an expression plasmid containing the rat CCR3 cDNA (pCMVscript rat CCR3) and 0.2 µg of the indicated AON. Twenty-four hours post-transfection CCR3 mRNA expression levels were quantified. CCR3 mRNA expression levels post-transfection were normalized against the expression levels of a control plasmid (pGL2-Luciferase). The results are expressed as the percentage of CCR3 mRNA expression inhibition relative to the corresponding mRNA expression inhibition levels in cells expressing a mismatch control AON.

This example relates to the enhanced efficacy of AON targeting the rat β-chain and rat CCR3 when FANA modifications are incorporated into the chemistry of the AON in vitro and in an in vivo model of allergic asthma in rats. Table 4 describes the compositions of AONs targeting the rat β-chain and rat CCR3 and modification with FANA residues. In FIG. 8, NIH 3T3 cells, engineered to transiently express the rat CCR3 mRNA, were transfected with a rat CCR3-specific AON (unmodified DNA with phosphorothioate linkage (TOP007 (SEQ ID No: 1628)) or incorporating FANA-modified nucleotides (TOP007-F8) (SEQ ID No: 1629) as indicated), and analyzed 24 hours post-transfection. The results showed that modification of TOP007 (SEQ ID No: 1628) sequence with FANA monomers (TOP007-F8 (SEQ ID No: 1629)) enhanced the efficacy of the AON with respect to inhibition of target mRNA expression, clearly showing an advantage of this modification for AON activity (FIG. 11).

Figure 12:
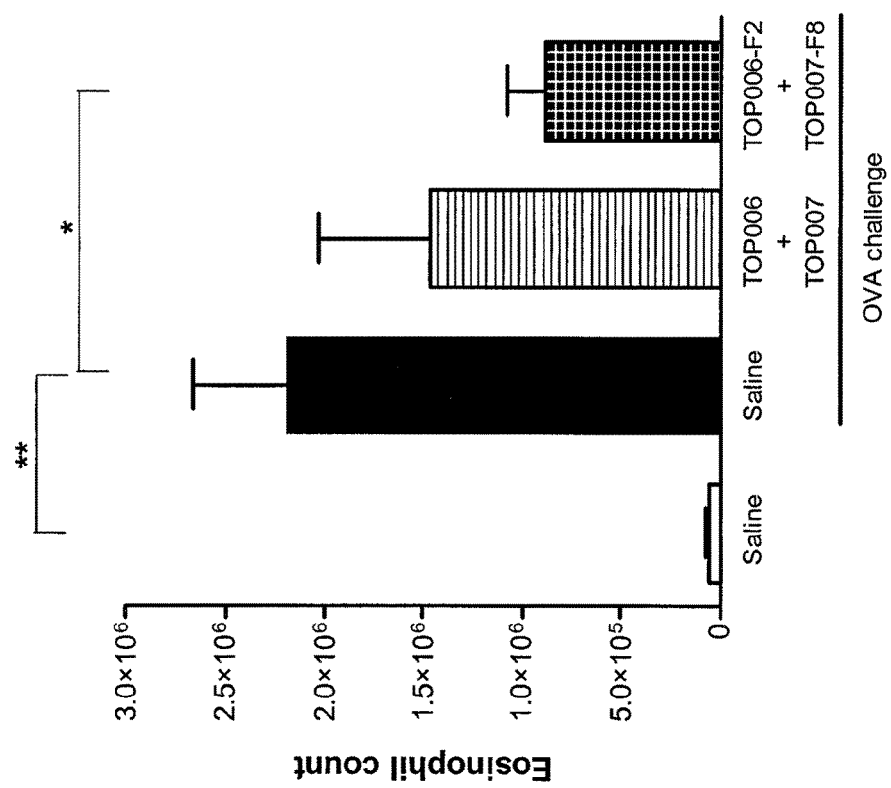
FIG. 12 illustrates a comparison of the effect of combinations of AONs targeting the rat β-chain (TOP006 (SEQ ID No: 1626)) and CCR3 (TOP007 (SEQ ID No: 1628)) to combinations of FANA-modified versions of the same AONs (TOP006-F2 (SEQ ID No: 1627) and TOP007-F8 (SEQ ID No: 1629), respectively) on allergen-induced eosinophil influx into the lungs of sensitized BN rats. Fourteen days following OVA-sensitization, rats were either unchallenged or treated with a single intra-tracheal administration of vehicle or 25 µg of each combination of AON (total of 50 µg per animal) as indicated prior to the OVA challenge. Rats were sacrificed 15 hours after OVA challenge, and differential cell counts from the BAL fluid were performed. Data represent mean total cell number +/−SEM from 3 separate experiments. One-way ANOVA followed by Dunnett's multiple comparison test (versus treated with vehicle and OVA challenged) (*p<0.05; **p<0.01); n=14 to 23 rats per group.

The enhanced activity of FANA-modified AONs targeting rat β-chain and rat CCR3 was also demonstrated in an in vivo model of allergic asthma in Brown Norway (BN) rats. In this model of asthma, BN rats are challenged with ovalbumin (OVA) 14 days following sensitization, resulting in a marked influx of eosinophils in the lungs of the animals (FIG. 12). Eosinophils are a key cell underlying the allergic response in asthma. When BN rats were treated prior to challenge with 50 µg of a combination (ratio 1:1 w/w) of one unmodified AON targeting rat β-chain (TOP006 (SEQ ID No: 1626)) and one unmodified AON targeting rat CCR3 (TOP007 (SEQ ID No: 1628)), no significant reduction of the allergen-induced eosinophil influx was observed (FIG. 12). However, when sensitized BN rats were treated with 50 µg of a combination (ratio 1:1 w/w) of FANA-containing AONs (TOP006-F2 (SEQ ID No: 1627) and TOP007-F8 (SEQ ID No: 1629)), the allergen-induced eosinophil influx to the lung was reduced by 60% (FIG. 12).

Example 9

Figure 13:
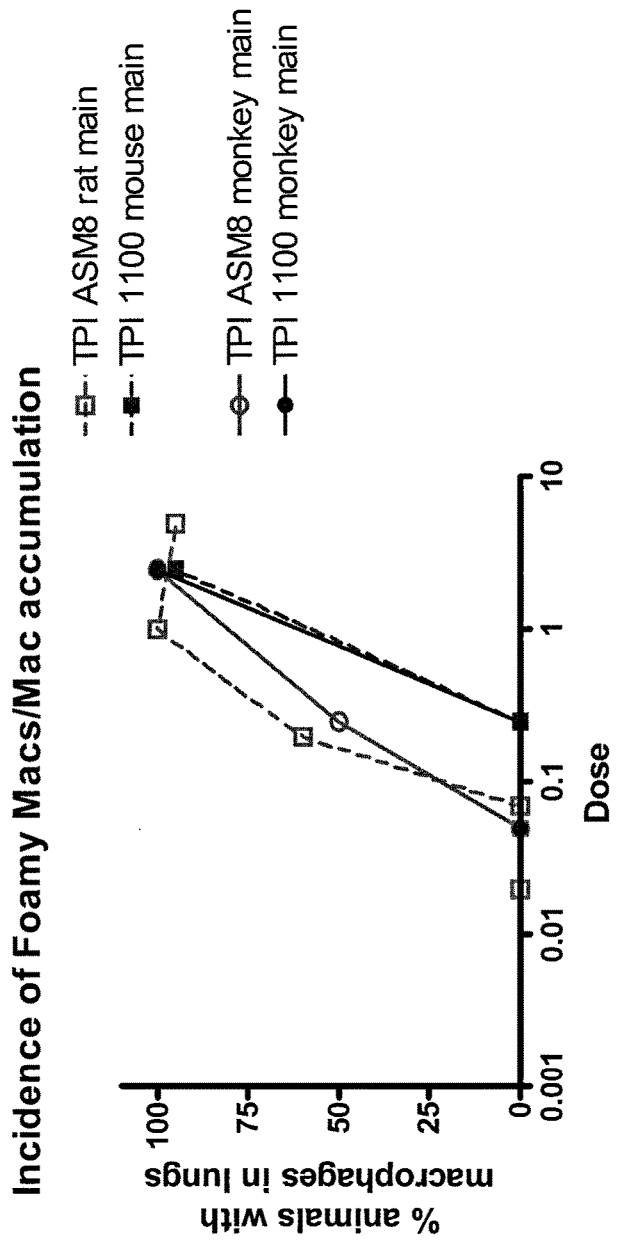
FIG. 13 illustrates a comparison of the effects of FANA modified AONs (TPI 1100) to non-FANA modified AONs (TPI ASM8) on the percentage incidence of foamy macrophages in the lung of rodents (mice and rats) and of monkeys following chronic dosing.

Macrophage Influx into the Lungs Following Chronic Delivery of 2'F-ANA Modified AONs The example relates to the relative reduction in infiltration of alveolar macrophages following chronic dosing administration of FANA-modified AONs for 14 consecutive days in rodents and monkeys. FIG. 13 shows the percentage incidence of alveolar macrophages in the lungs of rodents (mice and rats) and of monkeys following chronic dosing of FANA modified AONs (TPI 1100) and of non-2'F-ANA modified AONs (TPI ASM8 (TOP004 (SEQ ID NO: 1630) and TOP005 (SEQ ID NO: 1631)). Lung histology was assessed 24 h following the last AON exposure (Day 15). Results indicated that animals receiving FANA modified AONs (TPI 1100 (TOP1572 (SEQ ID NO: 1632) and TOP1731 (SEQ ID NO:1633), $IC_{50}$~1 mg/kg) had a lower incidence of alveolar macrophages compared to animals receiving non-2'F-ANA-containing AONs (TPI ASM8, $IC_{50}$~0.1 mg/kg), and was species-independent (rodent or primate).

Example 10

Figure 14:
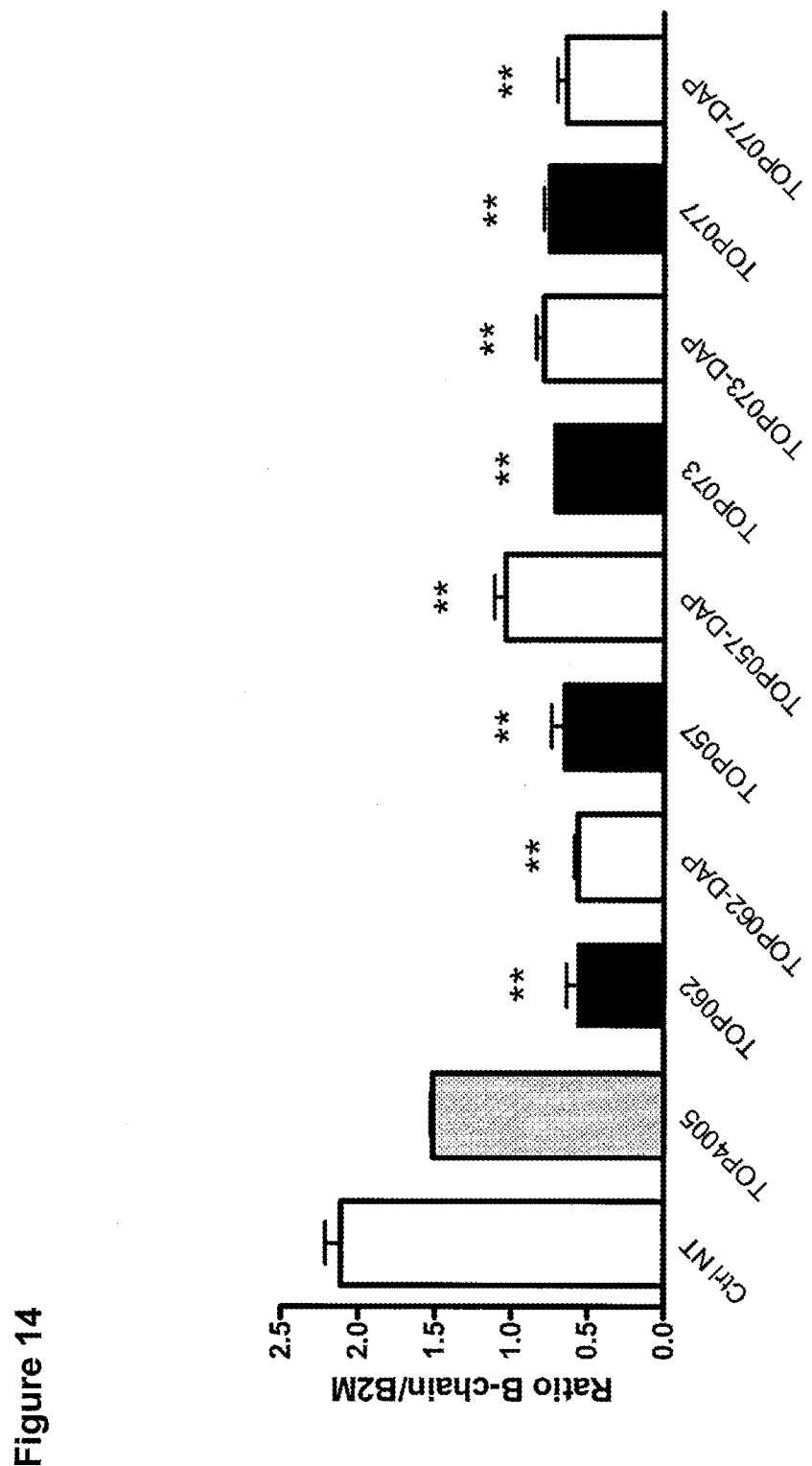
FIG. 14 illustrates a comparison of the efficacy of select AONs targeting the β-chain (TOP062 (SEQ ID No: 13), TOP057 (SEQ ID No: 8), TOP073 (SEQ ID No: 24) and TOP077 (SEQ ID No: 28)) to the efficacy of DAP-modified versions of the same AON (TOP062-DAP (SEQ ID No: 1621), TOP057-DAP (SEQ ID No: 1622), TOP073-DAP (SEQ ID No: 1623) and TOP077-DAP (SEQ ID No: 1624), respectively) at reducing β-chain mRNA expression levels determined using Quantigene. 293-βc-GFP cells were transfected with 267 nM AON and 24 hours post-transfection RNA was extracted and β-chain mRNA expression levels quantified. mRNA expression levels are given as the average±SD normalized ratio β-chain/β2M. Statistical analyses were carried out using a One Way ANOVA (Dunnett) against the negative control oligonucleotide TOP4005 (SEQ ID No: 1784); **p<0.01, n=3.

Efficacy of 2-amino-2'-deoxyadenosine-Containing AON Sequences at Reducing β-Chain mRNA Expression This example relates to the efficacy of β-chain-specific AONs incorporating 2-amino-2'-deoxyadenosine (DAP) modifications in the chemistry of the AON. Table 3c describes the compositions of AON modified with DAP residues. The potency of some selected sequences is demonstrated in FIG. 14 which shows the reduction in gene expression in vitro following transfection with indicated AONs in 293-βc-GFP cells. Specificity of the AON sequences was assessed by comparing their efficacy at reducing β-chain mRNA expression levels compared to an irrelevant AON sequence (TOP4005 (SEQ ID No: 1784)).

Example 11

Figure 15:
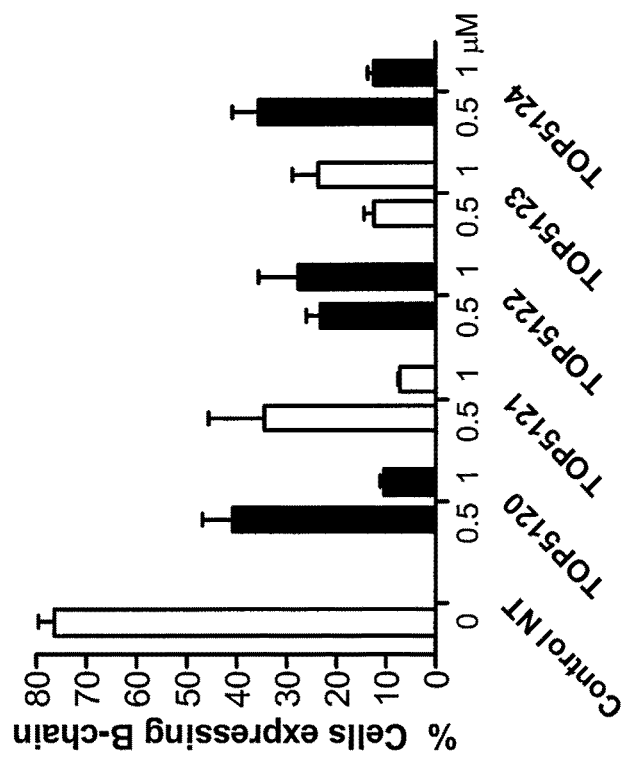
FIG. 15 illustrates the efficacy of selected miRNA mimic sequences TOP5120 (SEQ ID NOs: 1636 and 1637), TOP5121 (SEQ ID NOs: 1638 and 1639), TOP5122 (SEQ ID NOs: 1640 and 1641), TOP05123 (SEQ ID NOs: 1642 and 1643) and TOP5124 (SEQ ID NOs: 1644 and 1645) at reducing β-chain mRNA and protein expression levels. TF-1 cells were transfected with 0.5 or 1 µM miRNA. Twenty-four hours post-transfection expression levels were determined.
Figure 15:
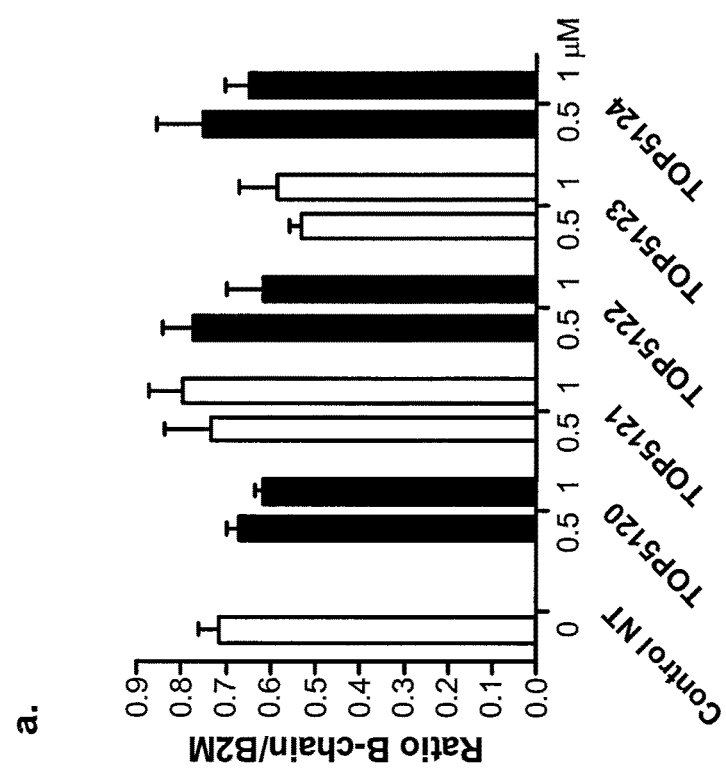

Efficacy of miRNA Mimic Sequences at Reducing β-Chain mRNA and Protein Expression In addition to AON sequences and siRNA, miRNA mimic molecules were designed (Table 7) and tested for their efficacy at reducing β-chain mRNA and protein expression (FIG. 15). FIG. 15a shows the efficacy of some selected miRNA mimic sequences at reducing β-chain mRNA levels in TF-1 cells compared to non-transfected cell controls (Control NT). In line with the mechanism of action of miRNA, no effect on β-chain mRNA levels were measured. The inhibitory activity of miRNA on β-chain protein expression was also analyzed by fluorescence activated cell sorting (FACS). FIG. 15b shows that TF-1 cells had dose-dependent decreases in levels of β-chain protein expression following transfection with specific miRNA and overnight incubation compared to untransfected control cells.

All references cited are incorporated by reference herein. Although preferred embodiments of the invention have been described herein, it will be understood by those skilled in the art that variations may be made thereto without departing from the spirit of the invention or the scope of the appended claims.

TABLE 1a

| Seq ID | AON ID | AON sequence (5'-3') | Activity |
|---|---|---|---|
| 1 | TOP050 | gctggtgtagtcgttgtagcag | <20% |
| 2 | TOP051 | gcaggtgatgtggctggtgtag | <20% |
| 3 | TOP052 | ggctccaggaggtcctcattc | <20% |
| 4 | TOP053 | ggctgaccagggcatgtcatc | <20% |
| 5 | TOP054 | ctcaggaggctggacatgctg | <20% |
| 6 | TOP055 | ggccacactccaggtcagc | 20-40% |
| 7 | TOP056 | ccacctccttcctcacctc | <20% |
| 8 | TOP057 | gaccgagctggccacctcc | 20-40% |
| 9 | TOP058 | ctgtctccatccttggtcac | 20-40% |
| 10 | TOP059 | gtcttgctgtccttccacgtgg | 20-40% |
| 11 | TOP060 | ctcactccactcgctccagatc | 20-40% |
| 12 | TOP061 | tcctctatggtgagaggtgac | <20% |
| 13 | TOP062 | ctctccacttccacggcctg | >40% |
| 14 | TOP063 | cagaggccactccagggtcctc | 20-40% |
| 15 | TOP064 | ggttcttgatctcaggaccg | 20-40% |
| 16 | TOP065 | agccgcttgtagaccacctc | 20-40% |
| 17 | TOP066 | tggcctgggaggtgttggag | <20% |
| 18 | TOP067 | tcctgagagccgagaacctg | 20-40% |
| 19 | TOP068 | ctccacttgctgggacgtcc | 20-40% |
| 20 | TOP069 | ctggagtcgtgtcaggccca | <20% |
| 21 | TOP070 | agagggaccagttgcacctg | <20% |
| 22 | TOP071 | cggccttctctccactccca | 20-40% |
| 23 | TOP072 | ctcagtgtcccagagctca | <20% |
| 24 | TOP073 | tccactggccagcccaggac | 20-40% |
| 25 | TOP074 | ttggagggagctccacatag | <20% |
| 26 | TOP075 | ggattgttccttggtgacct | <20% |
| 27 | TOP076 | tggtctaggttcttgatctc | <20% |
| 28 | TOP077 | aagagtcctgaagccgcttgt | >40% |
| 29 | TOP078 | aggaggatggctgcgtcctc | <20% |
| 30 | TOP079 | gcatgaggtgctctggcc | <20% |
| 31 | TOP080 | gccacgtaggtgctgctg | 20-40% |
| 32 | TOP081 | gccaggcgggtccgtactc | <20% |
| 33 | TOP082 | tactcgggccacgtaggt | 20-40% |
| 34 | TOP083 | acctctgggctccacttg | 20-40% |
| 35 | TOP084 | cctggctgggagtcccagcaa | <20% |
| 36 | TOP085 | gggctgggcctcatccc | <20% |
| 37 | TOP086 | gaagcactccaggttctg | 20-40% |
| 38 | TOP087 | catctccctggtcagctctg | <20% |
| 39 | TOP088 | ggccagcaccatctccctgg | <20% |

TABLE 1a-continued

| Seq ID | AON ID | AON sequence (5'-3') | Activity |
|---|---|---|---|
| 40 | TOP089 | gcagcccctgggccagcacc | <20% |
| 41 | TOP090 | gccatggagagcagcccctg | <20% |
| 42 | TOP091 | ggccagcagggccatggaga | <20% |
| 43 | TOP092 | cccagcacagggccagcagg | <20% |
| 44 | TOP093 | aggctgcgctcccagcacag | <20% |
| 45 | TOP094 | tgcccctgccaggccgcgct | <20% |
| 46 | TOP095 | tggtttcttctgcccctgcca | <20% |
| 47 | TOP096 | cgttgtagcagcgcaggtc | <20% |
| 48 | TOP097 | cccacctgcaggtgatgtgg | <20% |
| 49 | TOP098 | tgggtgtctgcccacctgca | <20% |
| 50 | TOP099 | ctgggcatcctgggtgtctg | <20% |
| 51 | TOP100 | tgacgagccgctgggcatcc | <20% |
| 52 | TOP101 | agggtcacgttgacgagccg | <20% |
| 53 | TOP102 | ccggcgaatgagggtcacgt | 20-40% |
| 54 | TOP103 | cctcattcacccggcgaatg | 20-40% |
| 55 | TOP104 | ggacactggctccaggaggt | 20-40% |
| 56 | TOP105 | tgaggtcacaggacactggc | <20% |
| 57 | TOP106 | atgtcatcactgaggtcaca | <20% |
| 58 | TOP107 | gggggcaggctgaccagggc | <20% |
| 59 | TOP108 | cagcggggatgggggcaggc | <20% |
| 60 | TOP109 | cctgggcacgcagcgggat | <20% |
| 61 | TOP110 | tgacacatctcctgggcacg | <20% |
| 62 | TOP111 | tggcagggaatgacacatctc | <20% |
| 63 | TOP112 | gacaaaactctggcagggaa | 20-40% |
| 64 | TOP113 | cgtcagtgacgacaaaactct | <20% |
| 65 | TOP114 | aagtagtcaacgtcagtgac | <20% |
| 66 | TOP115 | ttggaatgagaattagtcaa | <20% |
| 67 | TOP116 | gcctgtctggttggaatgag | <20% |
| 68 | TOP117 | gtgcccagaggcctgtctgg | <20% |
| 69 | TOP118 | ggtgagccgggtgcccagag | <20% |
| 70 | TOP119 | tcagagtgacggtgagccgg | <20% |
| 71 | TOP120 | acatgctgggtcagagtgac | 20-40% |
| 72 | TOP121 | ccctgggctcaggaggctgg | <20% |
| 73 | TOP122 | atctgcaggtccctgggctca | <20% |
| 74 | TOP123 | gtcggtgctgatctgcaggt | <20% |
| 75 | TOP124 | agtggtcctggtcggtgctg | <20% |
| 76 | TOP125 | gtcagcaggaagtggtcctg | <20% |
| 77 | TOP126 | tcccaagggccacactccag | <20% |
| 78 | TOP127 | ctctggggactcccaagggcca | 20-40% |
| 79 | TOP128 | caaccagtggctctggggac | <20% |
| 80 | TOP129 | cctggggacaaccagtgg | <20% |
| 81 | TOP130 | aactccagatcccctgggga | <20% |
| 82 | TOP131 | ccacctcaaactccagatcc | n.d. |
| 83 | TOP132 | gcctcactccactcgctcca | 20-40% |
| 84 | TOP133 | ccaggagcgcgcctcactcc | <20% |
| 85 | TOP134 | actcggtgtcccaggagcgc | <20% |
| 86 | TOP135 | ggcagcaccgactcggtgtc | 20-40% |
| 87 | TOP136 | cacccacataggcagcaccg | 20-40% |
| 88 | TOP137 | tgagggccagcacccacata | 20-40% |
| 89 | TOP138 | aagatcacgatgagggccag | 20-40% |
| 90 | TOP139 | gatggtgaggaagatcacga | <20% |
| 91 | TOP140 | ggagcacagcgatggtgagg | <20% |
| 92 | TOP141 | cggagggccaggagcacagc | <20% |
| 93 | TOP142 | gccacagaagcggagggcca | <20% |
| 94 | TOP143 | acccgtagatgccacagaag | >40% |
| 95 | TOP144 | cgcagcctgtacccgtagat | 20-40% |
| 96 | TOP145 | ccactttctgcgcagcctgt | >40% |
| 97 | TOP146 | tcttctcctcccactttctg | <20% |
| 98 | TOP147 | gggttggggatcttctcctc | <20% |
| 99 | TOP148 | gctcttgctggggttgggga | <20% |
| 100 | TOP149 | ggaacaggtggctcttgctg | <20% |
| 101 | TOP150 | ctcccgttctggaacaggtg | 20-40% |
| 102 | TOP151 | aagctctgcgctcccgttct | <20% |
| 103 | TOP152 | ctgggggccaaagctctgcg | <20% |
| 104 | TOP153 | gacatgctgcctgggggcca | 20-40% |
| 105 | TOP154 | agtgaaggccgacatgctgc | 20-40% |
| 106 | TOP155 | gactcccgctagtgaaggcc | >40% |
| 107 | TOP156 | tggtgtgggggactcccgct | <20% |
| 108 | TOP157 | ccacggcccctggtgtgggg | n.d. |
| 109 | TOP158 | agcggctgccccacggcccc | <20% |
| 110 | TOP159 | agctcagggaagcggctgcc | n.d. |
| 111 | TOP160 | cacccctccagctcaggga | 20-40% |
| 112 | TOP161 | ctacagggaacaccccctcc | n.d. |
| 113 | TOP162 | tccccgaatcctacagggaa | n.d. |
| 114 | TOP163 | cacctcgctgtccccgaatc | <20% |
| 115 | TOP164 | tgagaggtgacacctcgctg | 20-40% |
| 116 | TOP165 | atgcttggggccctctatgg | <20% |

TABLE 1a-continued

| Seq ID | AON ID | AON sequence (5'-3') | Activity |
|---|---|---|---|
| 117 | TOP166 | gatcacagacatgcttgggg | <20% |
| 118 | TOP167 | ccagatggtggatcacagac | 20-40% |
| 119 | TOP168 | cgtgtcaggcccagatggtg | <20% |
| 120 | TOP169 | agatctgaggcagctggagt | 20-40% |
| 121 | TOP170 | ctctgtgggtagatctgagg | <20% |
| 122 | TOP171 | tgggggctgctctgtgggt | <20% |
| 123 | TOP172 | ggctgggggctgggggctg | <20% |
| 124 | TOP173 | aggcgggcctggctggggc | <20% |
| 125 | TOP174 | gggaggcggcaggcgggcct | <20% |
| 126 | TOP175 | tcaggtgtgtgggaggcggc | <20% |
| 127 | TOP176 | agcctgtttctcaggtgtgt | <20% |
| 128 | TOP177 | caaagctggaagcctgtttc | >40% |
| 129 | TOP178 | ccattgaagtcaaagctgga | >40% |
| 130 | TOP179 | caggtagggcccattgaagt | <20% |
| 131 | TOP180 | ggggcggcccaggtagggc | <20% |
| 132 | TOP181 | gagcggctgtggggcggcc | <20% |
| 133 | TOP182 | gtcaggtagggagcggctgt | <20% |
| 134 | TOP183 | ggcccaggatgtcaggtagg | <20% |
| 135 | TOP184 | ggctccggctggcccaggat | 20-40% |
| 136 | TOP185 | ctcctgtgggggctccggct | <20% |
| 137 | TOP186 | ggctcccaccctcctgtggg | <20% |
| 138 | TOP187 | ggggacttctggctcccacc | <20% |
| 139 | TOP188 | ccctggaggtggggacttct | <20% |
| 140 | TOP189 | actccagggaccctggaggt | 20-40% |
| 141 | TOP190 | agacacaggtactccaggga | 20-40% |
| 142 | TOP191 | cccagcaggcagacacaggt | <20% |
| 143 | TOP192 | gcacctgccccccagcaggc | >40% |
| 144 | TOP193 | ctgggccagagggaccagtt | 20-40% |
| 145 | TOP194 | gtcccatcgcctgggccaga | <20% |
| 146 | TOP195 | gcctgtcccggtcccatcgc | 20-40% |
| 147 | TOP196 | ctggctcggccttctctc | 20-40% |
| 148 | TOP197 | ctgcagcccctggctc | <20% |
| 149 | TOP198 | agggagggactccctgcag | <20% |
| 150 | TOP199 | ggactccagggagggact | <20% |
| 151 | TOP200 | gcctccccggactcca | <20% |
| 152 | TOP201 | caggaggggcagggcctccc | <20% |
| 153 | TOP202 | ggcccaagagcaggaggggc | <20% |
| 154 | TOP203 | tcccacccttggcccaagag | 20-40% |
| 155 | TOP204 | ggtcctgtcctcccacccttt | <20% |
| 156 | TOP205 | ctgtccttttggtcctgtcc | 20-40% |
| 157 | TOP206 | atagccacagggctgtcctc | >40% |
| 158 | TOP207 | ctcatgggtatagccacagg | 20-40% |
| 159 | TOP208 | tccccagagctcatgggtat | 20-40% |
| 160 | TOP209 | cataaccagaggccactcc | 20-40% |
| 161 | TOP210 | ggagacataaccagaggcca | 20-40% |
| 162 | TOP211 | gcacaggagacataacc | 20-40% |
| 163 | TOP212 | ggtgaataccaggtctgc | 20-40% |
| 164 | TOP213 | ctgagtttggggtgaatacc | <20% |
| 165 | TOP214 | acagacgaggcccctgagtt | 20-40% |
| 166 | TOP215 | actagggagacagacgaggc | 20-40% |
| 167 | TOP216 | cagagagggaactagggaga | <20% |
| 168 | TOP217 | aggggaggcccagagaggga | <20% |
| 169 | TOP218 | gtctggtctgagggaggcc | <20% |
| 170 | TOP219 | taagctgggggtctggtctg | <20% |
| 171 | TOP220 | gcccaggacataagctgg | >40% |
| 172 | TOP221 | tccaggggtccactggcca | <20% |
| 173 | TOP222 | ggcctggggctccaggg | <20% |
| 174 | TOP223 | accctgacttcacagggcct | 20-40% |
| 175 | TOP224 | tcaaaccctgacttcacag | 20-40% |
| 176 | TOP225 | ccacatagccctcaaaccct | 20-40% |
| 177 | TOP226 | gccctcaattggagggagct | <20% |
| 178 | TOP227 | tgggggaccggccctcaat | n.d. |
| 179 | TOP228 | cttggtgacctgggggaccg | n.d. |
| 180 | TOP229 | ctcagggggacaggattgt | n.d. |
| 181 | TOP230 | cttttggcctcaggggggac | n.d. |
| 182 | TOP231 | aggacagggcttttggcctc | n.d. |
| 183 | TOP232 | ccctgggtccaggacagg | n.d. |
| 184 | TOP233 | gccgggcgttcccctgggtt | n.d. |
| 185 | TOP234 | ggacacatctgccgggcgtt | n.d. |
| 186 | TOP235 | ggatgttggggacacatct | n.d. |
| 187 | TOP236 | tcgggctgtggggatgttgg | n.d. |
| 188 | TOP237 | aggaggccctcgggctgcg | n.d. |
| 189 | TOP238 | gctgcaggacaaggaggcc | n.d. |
| 190 | TOP239 | tcgcccacttgctgcaggac | n.d. |
| 191 | TOP240 | gaagcaatagtcgcccactt | n.d. |
| 192 | TOP241 | ggccggggaggaagcaatag | n.d. |
| 193 | TOP242 | ccggggcccaggccggggag | n.d. |

TABLE 1a-continued

| Seq ID | AON ID | AON sequence (5'-3') | Activity |
|---|---|---|---|
| 194 | TOP243 | cgagagagggccgggcccca | n.d. |
| 195 | TOP244 | tactccggagcgagagagg | n.d. |
| 196 | TOP245 | gaagaaggtttactccgg | n.d. |
| 197 | TOP246 | ggtcccggggaagaaggtt | n.d. |
| 198 | TOP247 | tctcaggaccgggtccgg | n.d. |
| 199 | TOP248 | tgacttgaaaagcctggtct | n.d. |
| 200 | TOP249 | gggcttcttgacttgaa | n.d. |
| 201 | TOP250 | gcctggcctggggcttct | n.d. |
| 202 | TOP251 | acctggggcacagcctggcct | n.d. |
| 203 | TOP252 | tgacgggcacctggggcac | n.d. |
| 204 | TOP253 | agagctgaatgacgggcacc | n.d. |
| 205 | TOP254 | ctagggctttgaagagctga | n.d. |
| 206 | TOP255 | actgagacaactagggctt | n.d. |
| 207 | TOP256 | cacagacatcactgagacaa | n.d. |
| 208 | TOP257 | ctggaggtcccacagacatc | n.d. |
| 209 | TOP258 | tctcaagggactggaggtcc | n.d. |
| 210 | TOP259 | tgacgtggggtctcaaggga | n.d. |
| 211 | TOP260 | tcaggcttttgaagagctg | n.d. |
| 212 | TOP261 | tcctgctgcttcagggctt | n.d. |
| 213 | TOP262 | gacaggtagtcctgctgct | n.d. |
| 214 | TOP263 | agggggcagagacaggtag | n.d. |
| 215 | TOP264 | ttgacctcccaaggggcag | n.d. |
| 216 | TOP265 | ccaggcttgttgacctcc | n.d. |
| 217 | TOP266 | ctgaagccgcttgtagacc | n.d. |
| 218 | TOP267 | cgtcctcccaagagtcctg | n.d. |
| 219 | TOP268 | ttcgagaggaggatggct | n.d. |
| 220 | TOP269 | ctctggccccagggtggc | n.d. |
| 221 | TOP270 | tgctgggcatgaggtgctct | n.d. |
| 222 | TOP271 | gccgagaacctggggcca | n.d. |
| 223 | TOP272 | gtcccagcaaacctctg | n.d. |
| 224 | TOP273 | cctcatcccctggctgg | n.d. |
| 225 | TOP274 | actccaggttctggggctg | n.d. |
| 226 | TOP275 | ccgtcaaagaagcactc | n.d. |
| 227 | TOP276 | gcacggcggcccgtcaa | n.d. |
| 228 | TOP277 | gagcagctgagcacggcggc | n.d. |
| 229 | TOP278 | ctcacctcccaggagcagc | n.d. |
| 230 | TOP279 | aaggagaccgagctggc | n.d. |
| 231 | TOP280 | gaataggccaaaggagaccg | n.d. |
| 232 | TOP281 | ctgggcttgtagaataggcc | n.d. |
| 233 | TOP282 | tgcatctgggctgggcttgt | n.d. |
| 234 | TOP283 | cctcctcccctgcatctgg | n.d. |
| 235 | TOP284 | gggagcactcttcctcc | n.d. |
| 236 | TOP285 | ctcagcactggggagcactc | n.d. |
| 237 | TOP286 | cgagcccctccctcagcact | n.d. |
| 238 | TOP287 | tggaggctgccgagcccctc | n.d. |
| 239 | TOP288 | gtgcctggtgtggaggctgc | n.d. |
| 240 | TOP289 | tctggcagtggtgcctggtg | n.d. |
| 241 | TOP290 | ggcacgggaatctggcagtg | n.d. |
| 242 | TOP291 | cgcggggtcgggcacgggaa | n.d. |
| 243 | TOP292 | ggccgtgggtcgcggggtcg | n.d. |
| 244 | TOP293 | acgatgtattggccgtgg | n.d. |
| 245 | TOP294 | ctgaacagagacgatgtatt | n.d. |
| 246 | TOP295 | cctccttggctgaacagag | n.d. |
| 247 | TOP296 | ttctctgccctccctgg | n.d. |
| 248 | TOP297 | gctctttatgtgttctctg | n.d. |
| 249 | TOP298 | tgttcactgagctctttatg | n.d. |
| 250 | TOP299 | gccatctggatgttcactga | n.d. |
| 251 | TOP300 | ggatggaggggccatctgga | n.d. |
| 252 | TOP301 | tcacgttgagggatggagg | n.d. |
| 253 | TOP302 | tctccatccttggtcacgttg | n.d. |
| 254 | TOP303 | gcgcaggctgtagctgtctc | n.d. |
| 255 | TOP304 | attgtttcccagcgcaggct | n.d. |
| 256 | TOP305 | tcgcattttcattgtttccc | n.d. |
| 257 | TOP306 | tgtgttcgtatcgcatttc | n.d. |
| 258 | TOP307 | gtgtggtctatgtgttcgta | n.d. |
| 259 | TOP308 | gatctcaaatgtgtggtcta | n.d. |
| 260 | TOP309 | tcctgtactggatctcaa | n.d. |
| 261 | TOP310 | gccgtgtctttcctgtactg | n.d. |
| 262 | TOP311 | cttccacgtggccgtgtctt | n.d. |
| 263 | TOP312 | ggtctcggtcttgctgtc | n.d. |
| 264 | TOP313 | ggcgttctggagggtctcgg | n.d. |
| 265 | TOP314 | gccatgctgtgggcgttctgg | n.d. |
| 266 | TOP315 | gctggcagggccatgctgtg | n.d. |
| 267 | TOP316 | ggctccagggctggcagg | n.d. |
| 268 | TOP317 | acctggtggagggctccagg | n.d. |
| 269 | TOP318 | ctgggccagtacctggtgga | n.d. |
| 270 | TOP319 | gaccctcaccctggcccagt | n.d. |

TABLE 1a-continued

| Seq ID | AON ID | AON sequence (5'-3') | Activity |
|---|---|---|---|
| 271 | TOP320 | ggaggccctgaccctcacc | n.d. |
| 272 | TOP321 | tagccggtgcgggaggtcct | n.d. |
| 273 | TOP322 | gatcccgttgtagccggtgc | n.d. |
| 274 | TOP323 | actcgctccagatcccgttg | n.d. |
| 275 | TOP324 | tcaacacacctccccaggcttg | n.d. |
| 276 | TOP325 | tggggtctcaacacacctc | n.d. |
| 277 | TOP326 | tgtctaggcctggggtctc | n.d. |
| 278 | TOP327 | ttcttctggagcctctaggc | n.d. |
| 279 | TOP328 | agaccagtcttcttctggag | n.d. |
| 280 | TOP329 | gtggtgggagagaccagtct | n.d. |
| 281 | TOP330 | aggcctctgtgtggtgggag | n.d. |
| 282 | TOP331 | tgcctcctccaggcctctgt | n.d. |
| 283 | TOP332 | tcctggcctctgcctcctcc | n.d. |
| 284 | TOP333 | gacctctccctcctggcctc | n.d. |
| 285 | TOP334 | aggctctgggacctctcc | n.d. |
| 286 | TOP335 | ccatttcacaggctcttgg | n.d. |
| 287 | TOP336 | gccaggccagacccatttcac | n.d. |
| 288 | TOP337 | cagctgggagccaggccaga | n.d. |
| 289 | TOP338 | tgttcctgcccagctgggag | n.d. |
| 290 | TOP339 | tgaagtcctgtgttcctgcc | n.d. |
| 291 | TOP340 | cttagtgtcctgaagtcctg | n.d. |
| 292 | TOP341 | tgacagggtccttagtgtcc | n.d. |
| 293 | TOP342 | gccatgggcatgacagggtc | n.d. |
| 294 | TOP343 | gtgggtgctggccatgggca | n.d. |
| 295 | TOP344 | accagcactggtgggtgctg | n.d. |
| 296 | TOP345 | acaggcaggcaccagcactg | n.d. |
| 297 | TOP346 | tcagctctggacaggcaggc | n.d. |
| 298 | TOP347 | atacctctgtgtggtgggag | n.d. |
| 299 | TOP348 | ggccatacctctgtgtggt | n.d. |
| 300 | TOP349 | ctggacgccgggccatacctc | n.d. |
| 301 | TOP350 | ggcctgcagaaggagatgtc | n.d. |
| 302 | TOP351 | tcctccaggcctgcagaagg | n.d. |
| 303 | TOP352 | ctctgcctcctccaggcctg | n.d. |
| 304 | TOP353 | caccttctgcccctgccagg | n.d. |
| 305 | TOP354 | ccacgggactcaccttctgcc | n.d. |
| 306 | TOP355 | ggagccacgggactcacctt | n.d. |
| 307 | TOP356 | ttctgacaagaggggtaga | n.d. |
| 308 | TOP357 | ggatggtttctgacaagag | n.d. |
| 309 | TOP358 | ctgcagcgggatggtttctg | n.d. |
| 310 | TOP359 | cactcattcacccggcg | n.d. |
| 311 | TOP360 | gcatcactcactcattcacc | n.d. |
| 312 | TOP361 | ccagcatcactcactca | n.d. |
| 313 | TOP362 | tccctgttgggagaggacac | n.d. |
| 314 | TOP363 | caggaggtccctgttgggag | n.d. |
| 315 | TOP364 | ctggctccaggaggtccctg | n.d. |
| 316 | TOP365 | caccatgctgggtcagagtg | n.d. |
| 317 | TOP366 | cctcaccatgctgggtc | n.d. |
| 318 | TOP367 | ccccagcccctcaccat | n.d. |
| 319 | TOP368 | ggactggaggggaggaagtg | n.d. |
| 320 | TOP369 | ggaggctggactggagg | n.d. |
| 321 | TOP370 | ggctcaggaggctggactg | n.d. |
| 322 | TOP371 | tacctcccaagagtcctg | n.d. |
| 323 | TOP372 | cgtggttcctacctcccaag | n.d. |
| 324 | TOP373 | ctggccgtggttcctacctc | n.d. |
| 325 | TOP374 | gtcctgtcaggagacagtgg | n.d. |
| 326 | TOP375 | tggctgcgtcctgtcaggag | n.d. |
| 327 | TOP376 | caggacgcagccatcctcc | n.d. |
| 328 | TOP377 | tacctggctgggagtcc | n.d. |
| 329 | TOP378 | tggcaacattacctggctgg | n.d. |
| 330 | TOP379 | ggctctggcaacattacctg | n.d. |
| 331 | TOP380 | cccctgggttggagacaggt | n.d. |
| 332 | TOP381 | gcctcatcccctgggttgga | n.d. |
| 333 | TOP382 | ggctgggcctcatcccctg | n.d. |
| 334 | TOP383 | caccctgcatctgggctgg | n.d. |
| 335 | TOP384 | gatgctcaccctgcatctg | n.d. |
| 336 | TOP385 | aaaaagatgctcaccct | n.d. |
| 337 | TOP386 | tccctgaggagcacagcag | n.d. |
| 338 | TOP387 | ctcttcctccctgaggagc | n.d. |
| 339 | TOP388 | ggagcactcttcctccctg | n.d. |
| 340 | TOP389 | cactgttcactgagctctt | n.d. |
| 341 | TOP390 | aactcactgttcactgag | n.d. |
| 342 | TOP391 | gctaggagcaaactcactgt | n.d. |
| 343 | TOP392 | ggactggagggagggaagct | n.d. |
| 344 | TOP393 | gccatctggactggagggag | n.d. |
| 345 | TOP394 | tggagaggccatctggactg | n.d. |
| 346 | TOP395 | caccttccacgtggccgtgt | n.d. |
| 347 | TOP396 | cctcaccttccacgtgg | n.d. |

TABLE 1a-continued

| Seq ID | AON ID | AON sequence (5'-3') | Activity |
|---|---|---|---|
| 348 | TOP397 | ggcaaaggccctcacctt | n.d. |
| 349 | TOP398 | gtcctgtgggttggcactga | n.d. |
| 350 | TOP399 | tcttgctgtcctgtgggttg | n.d. |
| 351 | TOP400 | gtctcggtcttgctgtcctg | n.d. |
| 352 | TOP401 | tacccgactcggtgtcc | n.d. |
| 353 | TOP402 | gccttcacctacccgactcg | n.d. |
| 354 | TOP403 | ctccagccttcacctacccg | n.d. |
| 355 | TOP404 | gcacttccagcagccgg | n.d. |
| 356 | TOP405 | cataggcagcacttccagc | n.d. |
| 357 | TOP406 | ccacataggcagcactt | n.d. |
| 358 | TOP407 | cacctgtacccgtagatgcc | n.d. |
| 359 | TOP408 | gtccctcacctgtacccgt | n.d. |
| 360 | TOP409 | ccacagagtcccctcacctg | n.d. |
| 361 | TOP410 | agcctggaagacaccacgga | n.d. |
| 362 | TOP411 | ttctgcgcagcctggaagac | n.d. |
| 363 | TOP412 | ccactttctgcgcagcctg | n.d. |
| 364 | TOP413 | tacctggaacaggtggctct | n.d. |
| 365 | TOP414 | cagttcctacctggaacagg | n.d. |
| 366 | TOP415 | tcgcagccagttcctacctg | n.d. |
| 367 | TOP416 | gttctgcaagagcagagac | n.d. |
| 368 | TOP417 | gcgctcccgttctgcaagag | n.d. |
| 369 | TOP418 | gctctgcgctcccgttctg | n.d. |
| 370 | TOP419 | caccccctccagctcagg | n.d. |
| 371 | TOP420 | gagcccactcacccctccag | n.d. |
| 372 | TOP421 | tccacgagcccactcacccc | n.d. |
| 373 | TOP422 | accctgtgggaagaaatgg | n.d. |
| 374 | TOP423 | ggaacaccctgtgggaag | n.d. |
| 375 | TOP424 | tcctacagggaacaccctg | n.d. |
| 376 | TOP425 | gtctcaacacacctccc | n.d. |
| 377 | TOP426 | gcctgggggtctcaacacac | n.d. |
| 378 | TOP427 | gtctaggcctgggggtctca | n.d. |
| 379 | TOP428 | agccctgctcctggacgccgg | n.d. |
| 380 | TOP429 | ccaccctcagccctgctcc | n.d. |
| 381 | TOP430 | ctgctctgaccccaccccctc | n.d. |
| 382 | TOP431 | tgcccctccccttccacgtg | n.d. |
| 383 | TOP432 | gtcagcagtgagctcccctcc | n.d. |
| 384 | TOP433 | aggagatgtcagcagtgagc | n.d. |
| 385 | TOP434 | agtgggtgggagccacgg | n.d. |
| 386 | TOP435 | agggacagggaagtgggtgg | n.d. |
| 387 | TOP436 | gcagtgaggacagggacagg | n.d. |
| 388 | TOP437 | ctgcagggaccccttgtcacc | n.d. |
| 389 | TOP438 | ctctctttcctgcagggacc | n.d. |
| 390 | TOP439 | aggggtcacctctctttcc | n.d. |
| 391 | TOP440 | gaggggtagaaggggtcac | n.d. |
| 392 | TOP441 | gtggcccctgccccagcat | n.d. |
| 393 | TOP442 | gcccctgcccgtggcccctg | n.d. |
| 394 | TOP443 | ggacgtcgtagcccctgcc | n.d. |
| 395 | TOP444 | agggtgtatgggtatcactg | n.d. |
| 396 | TOP445 | ggcttagcccagggtgtatg | n.d. |
| 397 | TOP446 | gagaggacacggcttagcc | n.d. |
| 398 | TOP447 | ccgggcagggccccagc | n.d. |
| 399 | TOP448 | ggaaaccaagccccgggcag | n.d. |
| 400 | TOP449 | tgtccacacaggaaaccaag | n.d. |
| 401 | TOP450 | ccgctggggggcagtcagg | n.d. |
| 402 | TOP451 | aagggctggaccgctggg | n.d. |
| 403 | TOP452 | aagggcacctaagggctgga | n.d. |
| 404 | TOP453 | ggaggaagtgaagggcacct | n.d. |
| 405 | TOP454 | ggcagagctggccgtggt | n.d. |
| 406 | TOP455 | ccttcgggctggggcagagc | n.d. |
| 407 | TOP456 | gctgcccatcccttcgggct | n.d. |
| 408 | TOP457 | gtgctggaggaggggtgctg | n.d. |
| 409 | TOP458 | gagacagtgggtgctggagg | n.d. |
| 410 | TOP459 | gcatttcctggctctggca | n.d. |
| 411 | TOP460 | ccaccacggggcatttcctg | n.d. |
| 412 | TOP461 | gcctgccctcccaccacgg | n.d. |
| 413 | TOP462 | tccgtcattcatccctcccat | n.d. |
| 414 | TOP463 | cctcatgtactccgtcattc | n.d. |
| 415 | TOP464 | ggagacaggtcctcatgtac | n.d. |
| 416 | TOP465 | gaggggatggagaaaaaga | n.d. |
| 417 | TOP466 | aagaggagggagggatgg | n.d. |
| 418 | TOP467 | gagcaaggccaagaggagg | n.d. |
| 419 | TOP468 | ggaggggaggagagcttagg | n.d. |
| 420 | TOP469 | agggcacacggggagggagga | n.d. |
| 421 | TOP470 | agggagagggagggcacacg | n.d. |
| 422 | TOP471 | agctgagggcagggagagg | n.d. |
| 423 | TOP472 | agcacagcagagctgagggc | n.d. |
| 424 | TOP473 | ccacagcgggctaggagca | n.d. |

TABLE 1a-continued

| Seq ID | AON ID | AON sequence (5'-3') | Activity |
|---|---|---|---|
| 425 | TOP474 | cagaccatccccacagcgg | n.d. |
| 426 | TOP475 | gtgctggtcccagaccatcc | n.d. |
| 427 | TOP476 | gtcatcatacccaccctcca | n.d. |
| 428 | TOP477 | ttcaggagagtcatcatacc | n.d. |
| 429 | TOP478 | agggaagctttcaggagagt | n.d. |
| 430 | TOP479 | ctcccctccctgggcaaagg | n.d. |
| 431 | TOP480 | ccagtgtttctcccctcc | n.d. |
| 432 | TOP481 | tcccgccctcccagtgtt | n.d. |
| 433 | TOP482 | ccgtgggagcagctgcaaat | n.d. |
| 434 | TOP483 | tggcccggtgccgtgggag | n.d. |
| 435 | TOP484 | ggtgaggcctggcccggtg | n.d. |
| 436 | TOP485 | ttggcactgagggtgaggcc | n.d. |
| 437 | TOP486 | aagctctggactccagcctt | n.d. |
| 438 | TOP487 | tcctggccagaagctctgga | n.d. |
| 439 | TOP488 | tatgagctggtcctggccag | n.d. |
| 440 | TOP489 | gaaatcgacctcagggcagg | n.d. |
| 441 | TOP490 | atctgggcgggaaatcgacctc | n.d. |
| 442 | TOP491 | gaatgtcagcatctgggcgg | n.d. |
| 443 | TOP492 | ggagaaagaggaatgtcagc | n.d. |
| 444 | TOP493 | cagcagccggggagaaagag | n.d. |
| 445 | TOP494 | acctccagccccacagagtc | n.d. |
| 446 | TOP495 | ctcggctgccacctccagcc | n.d. |
| 447 | TOP496 | cctctggggtctcggctgcc | n.d. |
| 448 | TOP497 | atcagagacctcatggccag | n.d. |
| 449 | TOP498 | ggtgacagccatcagagacc | n.d. |
| 450 | TOP499 | acaccacggaggtgacagcc | n.d. |
| 451 | TOP500 | actccgccctcgcagccag | n.d. |
| 452 | TOP501 | agaagcccccactccgcc | n.d. |
| 453 | TOP502 | gcaggaacagagaagccccc | n.d. |
| 454 | TOP503 | gtgagcatcaggaggtccga | n.d. |
| 455 | TOP504 | atttggccggtgagcatca | n.d. |
| 456 | TOP505 | gagcagagacatttgggccg | n.d. |
| 457 | TOP506 | tcaggagtgatccacgagcc | n.d. |
| 458 | TOP507 | accccaaaggtcaggagtga | n.d. |
| 459 | TOP508 | ccgtatgaacccccaaagg | n.d. |
| 460 | TOP509 | gatccgggtcaggcacaag | n.d. |
| 461 | TOP510 | ctgggcagatgatccgggtca | n.d. |
| 462 | TOP511 | tgggaccaccctgggcagat | n.d. |
| 463 | TOP512 | gcagaagagttgggaccacc | n.d. |
| 464 | TOP513 | aagaaaatgggcagaagagt | n.d. |
| 465 | TOP514 | ccttgcctgtctaggcct | n.d. |
| 466 | TOP515 | cctctccatcccccttgcct | n.d. |
| 467 | TOP516 | ggaaggcaagccctctccat | n.d. |
| 468 | TOP517 | tccccttgcctgtctaggcc | n.d. |
| 469 | TOP518 | gccctctccatcccccttgcc | n.d. |
| 470 | TOP519 | ggaaggcaagccctctcca | n.d. |
| 471 | TOP520 | tcaggcgggagggaaggcaa | n.d. |
| 472 | TOP521 | ctgaggaaggtcaggcggga | n.d. |
| 473 | TOP522 | gcagaaatgactgaggaagg | n.d. |
| 474 | TOP523 | ccttggctttgcagaaatga | n.d. |
| 475 | TOP524 | ggaggctgccccttggctt | n.d. |
| 476 | TOP525 | taccttgacaggaggctgcc | n.d. |
| 477 | TOP526 | ggcctctagctaccttgaca | n.d. |
| 478 | TOP527 | tcctttcccaggcctctagc | n.d. |
| 479 | TOP528 | caaggctatctcctttccca | n.d. |
| 480 | TOP529 | ggccggagcaaggctatc | n.d. |
| 481 | TOP530 | gaaggtcaaggggccggag | n.d. |
| 482 | TOP531 | gtgatttgctgaaggtcaag | n.d. |
| 483 | TOP532 | agggagagaagtgatttgct | n.d. |
| 484 | TOP533 | gtgtgagcgcagggagagaa | n.d. |
| 485 | TOP534 | gtgtgtgtctgtgtgagcgc | n.d. |
| 486 | TOP535 | acgtgtgtgtgtgtgtgtct | n.d. |
| 487 | TOP536 | gtgtgcatgtacgtgtgtgt | n.d. |
| 488 | TOP537 | caggaaaaatgtgtgcatgt | n.d. |
| 489 | TOP538 | gttaacctgacaggaaaaat | n.d. |
| 490 | TOP539 | ctacaaataagttaacctga | n.d. |
| 491 | TOP540 | aatgcagaacctacaaataa | n.d. |
| 492 | TOP541 | aagttctaataatgcagaac | n.d. |
| 493 | TOP542 | tatatctagaaagttctaat | n.d. |
| 494 | TOP543 | atggaatgagtatatctaga | n.d. |
| 495 | TOP544 | tgaggggagatggaatgag | n.d. |
| 496 | TOP545 | attaaaaaaatgagggggag | n.d. |
| 497 | TOP546 | aggaaacctgattaaaaaaat | n.d. |
| 498 | TOP547 | ggcaaaagcaaggaaacctg | n.d. |
| 499 | TOP548 | gaagaaaatggcaaaagca | n.d. |
| 500 | TOP549 | gaaaaaagaaggaagaaaaatg | n.d. |
| 501 | TOP550 | taaatcagtgaaaaaagaag | n.d. |

TABLE 1a-continued

| Seq ID | AON ID | AON sequence (5'-3') | Activity |
|---|---|---|---|
| 502 | TOP551 | actctcataataaatcagtg | n.d. |
| 503 | TOP552 | cctcagccccactctcataa | n.d. |
| 504 | TOP553 | tcagctcagacctcagcc | n.d. |
| 505 | TOP554 | ctgataaggctcagctcaga | n.d. |
| 506 | TOP555 | gcatctcagtctgataaggc | n.d. |
| 507 | TOP556 | acaaccagccgcatctcagt | n.d. |
| 508 | TOP557 | agtcctcaacacaaccagcc | n.d. |
| 509 | TOP558 | agcccacacaagtcctcaac | n.d. |
| 510 | TOP559 | ggacaggcagcccacaca | n.d. |
| 511 | TOP560 | agcgactgccggggacaggc | n.d. |
| 512 | TOP561 | catgtgcatcagcgactgcc | n.d. |
| 513 | TOP562 | agaatcatgtcatgtgcatc | n.d. |
| 514 | TOP563 | cacccagatgagaatcatgt | n.d. |
| 515 | TOP564 | ccacctctgcacccagatg | n.d. |
| 516 | TOP565 | cctggtgcctcccacctctg | n.d. |
| 517 | TOP566 | cgggtgcccacctggtgcct | n.d. |
| 518 | TOP567 | ctaaccccacgggtgccca | n.d. |
| 519 | TOP568 | cttccaagccctaaccccca | n.d. |
| 520 | TOP569 | ctgtgccactcttccaagcc | n.d. |
| 521 | TOP570 | gtgcccagtcctgtgccact | n.d. |
| 522 | TOP571 | ctcactgagcgtgcccagtc | n.d. |
| 523 | TOP572 | ttccctgagcctcactgagc | n.d. |
| 524 | TOP573 | ctagtctgaattccctgagc | n.d. |
| 525 | TOP574 | acaatcgaggctagtctgaa | n.d. |
| 526 | TOP575 | tctcggagtgacaatcgagg | n.d. |
| 527 | TOP576 | catgcccatttctcggagtg | n.d. |
| 528 | TOP577 | ccaataccatgcccatt | n.d. |
| 529 | TOP578 | gcccccccgaccccaatac | n.d. |
| 530 | TOP579 | ccttgcaccgccccccga | n.d. |
| 531 | TOP580 | tcatgtgcgtcccttgcacc | n.d. |
| 532 | TOP581 | aacagtctctcatgtgcgt | n.d. |
| 533 | TOP582 | agaagctcccaaacagtctc | n.d. |
| 534 | TOP583 | agggctcccagaagctcc | n.d. |
| 535 | TOP584 | gacaactagcagggctcc | n.d. |
| 536 | TOP585 | acatcactgagacaactagc | n.d. |
| 537 | TOP586 | ggtcccacagacatcactga | n.d. |
| 538 | TOP587 | agggactggaggtcccacag | n.d. |
| 539 | TOP588 | tggggtctcaagggactgga | n.d. |
| 540 | TOP589 | ctacatgacgtggggtctca | n.d. |
| 541 | TOP590 | gttaacttctctacatgacg | n.d. |
| 542 | TOP591 | cacttgggccgttaacttct | n.d. |
| 543 | TOP592 | gcctgcccaccacttgggcc | n.d. |
| 544 | TOP593 | ggtcccgccagcctgcccac | n.d. |
| 545 | TOP594 | atgttccccaggtcccgcca | n.d. |
| 546 | TOP595 | tcctctcctgatgttcccca | n.d. |
| 547 | TOP596 | ggctctggactcctctcctg | n.d. |
| 548 | TOP597 | agtagacgtgggctctggac | n.d. |
| 549 | TOP598 | acttttccgcagtagacgtg | n.d. |
| 550 | TOP599 | gtttcccctgacttttccgc | n.d. |
| 551 | TOP600 | ttgtttggcagtttcccctg | n.d. |
| 552 | TOP601 | gcattttcctttgtttggca | n.d. |
| 553 | TOP602 | tgcctttggggcattttcct | n.d. |
| 554 | TOP603 | aagcatatatgcctttgg | n.d. |
| 555 | TOP604 | caaaggccctaaagcatata | n.d. |
| 556 | TOP605 | ccatttggaccaaaggccct | n.d. |
| 557 | TOP606 | gccacccgggccatttggac | n.d. |
| 558 | TOP607 | tggaagagtggccacccgg | n.d. |
| 559 | TOP608 | ctggtctatctggaagagtg | n.d. |
| 560 | TOP609 | ggagagttgcctggtctatc | n.d. |
| 561 | TOP610 | ccggtgggagggagagttgc | n.d. |
| 562 | TOP611 | tcatctgtggccggtgggag | n.d. |
| 563 | TOP612 | cagcagcccctcatctgtgg | n.d. |
| 564 | TOP613 | aggcatagatcagcagcc | n.d. |
| 565 | TOP614 | gtgcaggcccaggcatagat | n.d. |
| 566 | TOP615 | ataatccctggtgcaggcc | n.d. |
| 567 | TOP616 | taaaagaaccataatccctg | n.d. |
| 568 | TOP617 | aggcaaagatttaaaagaacc | n.d. |
| 569 | TOP618 | gtatctgaaaggcaaagatt | n.d. |
| 570 | TOP619 | tattttcctgtatctgaa | n.d. |
| 571 | TOP620 | ttaatgccattattttcct | n.d. |
| 572 | TOP621 | ttaaagcaatttaatgccat | n.d. |
| 573 | TOP622 | ataatgcaaattaaagcaat | n.d. |
| 574 | TOP623 | gataactaaaataatgcaa | n.d. |
| 575 | TOP624 | gtgcaaactggataactaa | n.d. |
| 576 | TOP625 | ataaaaatatgtgcaaactg | n.d. |
| 577 | TOP626 | taagatacctataaaaatat | n.d. |
| 578 | TOP627 | aatcgatgcctaagatacct | n.d. |

TABLE 1a-continued

| Seq ID | AON ID | AON sequence (5'-3') | Activity |
|---|---|---|---|
| 579 | TOP628 | aaaataccaatcgatgcc | n.d. |
| 580 | TOP629 | tggcccagttaaaaaatacc | n.d. |
| 581 | TOP630 | ttaatgggcttggcccagtt | n.d. |
| 582 | TOP631 | aagaaagaccttaatgggct | n.d. |
| 583 | TOP632 | cacccaacagaagaaagacc | n.d. |
| 584 | TOP633 | aatgatagcacccaacag | n.d. |
| 585 | TOP634 | acttaatcagaaaatgatag | n.d. |
| 586 | TOP635 | agtcaaaagacttaatcag | n.d. |
| 587 | TOP636 | gtatgtcaatagtcaaaaag | n.d. |
| 588 | TOP637 | gtgaaagactgtatgtcaat | n.d. |
| 589 | TOP638 | tccaccatctgtgaaagact | n.d. |
| 590 | TOP639 | ggaaaaacactccaccatct | n.d. |
| 591 | TOP640 | cagatttgggggaaaaacac | n.d. |
| 592 | TOP641 | agacaaacaacagatttgg | n.d. |
| 593 | TOP642 | caacattataagacaaacaa | n.d. |
| 594 | TOP643 | acctcatatacaacattata | n.d. |
| 595 | TOP644 | acaccataaaacctcatata | n.d. |
| 596 | TOP645 | tcatattcatacaccataa | n.d. |
| 597 | TOP646 | acagaagcattcatattcat | n.d. |
| 598 | TOP647 | gtttgacattacagaagcat | n.d. |
| 599 | TOP648 | ctagggatctgtttgacatt | n.d. |
| 600 | TOP649 | aaggagtttactagggatct | n.d. |
| 601 | TOP650 | aagtgaagaaggagttta | n.d. |
| 602 | TOP651 | atctgacagtaaaagtgaag | n.d. |
| 603 | TOP652 | acctttgtaaatctgacagt | n.d. |
| 604 | TOP653 | caatgggaggacctttgtaa | n.d. |
| 605 | TOP654 | cactgctttgcaatgggagg | n.d. |
| 606 | TOP655 | ttaggacaaacactgctttg | n.d. |
| 607 | TOP656 | aatatataaattaggacaa | n.d. |
| 608 | TOP657 | ctagaaaacaatatataa | n.d. |
| 609 | TOP658 | acaaaatgaactagaaaac | n.d. |
| 610 | TOP659 | agttggaaacacaaaatgaa | n.d. |
| 611 | TOP660 | ttacatgaaaagttggaaac | n.d. |
| 612 | TOP661 | aattaaaattttacatgaa | n.d. |
| 613 | TOP662 | attcaaaataattaaaatt | n.d. |
| 614 | TOP663 | acatccacacattcaaaaat | n.d. |
| 615 | TOP664 | cctcagtctcacatccacac | n.d. |
| 616 | TOP665 | ccaaaaggcacctcagtctc | n.d. |
| 617 | TOP666 | aatttcagtaccaaaaggca | n.d. |
| 618 | TOP667 | atggaaaaagaatttcagta | n.d. |
| 619 | TOP668 | cttcaggtacatggaaaaag | n.d. |
| 620 | TOP669 | aagtaacacttcaggtac | n.d. |
| 621 | TOP670 | cctatatcacaaaagtaaca | n.d. |
| 622 | TOP671 | acaaggatttcctatatcac | n.d. |
| 623 | TOP672 | aagtatatatacaaggatt | n.d. |
| 624 | TOP673 | ggaccaataaagtatatat | n.d. |
| 625 | TOP674 | aggaagcctagggaccaata | n.d. |
| 626 | TOP675 | gtaacaaaataggaagccta | n.d. |
| 627 | TOP676 | agaaagcaaggtaacaaaat | n.d. |
| 628 | TOP677 | gatgccatagagaaagcaag | n.d. |
| 629 | TOP678 | caaaatggtggatgccatag | n.d. |
| 630 | TOP679 | gtagaacaatcaaaatggtg | n.d. |
| 631 | TOP680 | tatcataaaagtagaacaat | n.d. |
| 632 | TOP681 | tatgaaaacatatcataa | n.d. |
| 633 | TOP682 | cttaaccacttatgaaaaca | n.d. |
| 634 | TOP683 | agaatacttgcttaaccact | n.d. |
| 635 | TOP684 | aagtaacgagaatacttg | n.d. |
| 636 | TOP685 | atttaagagcaaaagtaacg | n.d. |
| 637 | TOP686 | atgaatagggatttaagagc | n.d. |
| 638 | TOP687 | cattgctgtaatgaatagg | n.d. |
| 639 | TOP688 | tgaccaccaacattgctgta | n.d. |
| 640 | TOP689 | tcattttctttgaccaccaa | n.d. |
| 641 | TOP690 | aagttgtttatcattttctt | n.d. |
| 642 | TOP691 | ttgaacattcaagttgttta | n.d. |
| 643 | TOP692 | ttcaggaccattgaacattc | n.d. |
| 644 | TOP693 | tgttatgtatttcaggacca | n.d. |
| 645 | TOP694 | actaaaatgttgttatgtat | n.d. |
| 646 | TOP695 | ttacaatgtactaaaatgt | n.d. |
| 647 | TOP696 | aggattctactttacaatgt | n.d. |
| 648 | TOP697 | ttatgaacagaggattctac | n.d. |
| 649 | TOP698 | atcttgttcattatgaacag | n.d. |
| 650 | TOP699 | acattggttcatcttgttca | n.d. |
| 651 | TOP700 | ttctaatccacattggttc | n.d. |
| 652 | TOP701 | ctcggacttctttctaatcc | n.d. |
| 653 | TOP702 | attaatatctcggacttc | n.d. |
| 654 | TOP703 | ggatattttggaattaatat | n.d. |
| 655 | TOP704 | aacaatgtctggatattttg | n.d. |

TABLE 1a-continued

| Seq ID | AON ID | AON sequence (5'-3') | Activity |
|---|---|---|---|
| 656 | TOP705 | ttcccttaacaatgtct | n.d. |
| 657 | TOP706 | ttattgcaatttttcccctt | n.d. |
| 658 | TOP707 | acaaatattttattgcaatt | n.d. |
| 659 | TOP708 | ttttatgttacaaatattt | n.d. |
| 660 | TOP709 | gaccagttgcacctgccc | n.d. |
| 661 | TOP710 | ccacggcctgtcccggtc | n.d. |
| 662 | TOP711 | ggactccctgcagcccc | n.d. |
| 663 | TOP712 | aggggcagggcctccccc | n.d. |
| 664 | TOP713 | gccacagggctgtccttttg | n.d. |
| 665 | TOP714 | gccactccagggtcctcagtg | n.d. |
| 666 | TOP715 | accaggtctgcagaggag | n.d. |
| 667 | TOP716 | cgaggccctgagtttgg | n.d. |
| 668 | TOP717 | ccaggacataagctgggg | n.d. |
| 669 | TOP718 | gcctggggctccagggg | n.d. |
| 670 | TOP719 | ccacatagccctcaaacc | n.d. |
| 671 | TOP720 | ggacaggattgttccttg | n.d. |
| 672 | TOP721 | cgttcccctgggttcagg | n.d. |

Lower case letters = DNA
n.d. = not determined

TABLE 1B

| Seq ID number | Antisense ID | Sequence (5'-3') | CCR3 mRNA Inhibition |
|---|---|---|---|
| 673 | TOP020 | gtatctagtgaggttgtcat | <20% |
| 674 | TOP021 | ggtctcaactgtatctagtg | <20% |
| 675 | TOP022 | ccatcagtgctctggtatcagc | <20% |
| 676 | TOP023 | ggtacatcaccaccaccac | <20% |
| 677 | TOP024 | ggtcataattcggagcctcctg | <20% |
| 678 | TOP025 | gcttacacatgccatggcc | <20% |
| 679 | TOP026 | gctgctagcactgccagg | <20% |
| 680 | TOP027 | cctccagctatatactgtatcc | <20% |
| 681 | TOP028 | ggtccagatgcttgctcc | 20-40% |
| 682 | TOP029 | gcatgaccaggtccagatgc | 20-40% |
| 683 | TOP030 | cacctctgtcaccagcatg | >40% |
| 684 | TOP031 | gtacttccggaacctctctcc | >40% |
| 685 | TOP032 | ccacattgtagggtgtcca | >40% |
| 686 | TOP033 | agtgggagtaggcgatcacc | <20% |
| 687 | TOP034 | cgtagatcaccgggttcatg | 20-40% |
| 688 | TOP035 | ttccagcttctcactagga | >40% |
| 689 | TOP036 | tggtcattctcagagtgtgg | <20% |
| 690 | TOP037 | acagagctggttctttccag | >40% |
| 691 | TOP038 | gaatgggatgtatctgccca | >40% |
| 692 | TOP039 | ggatgtatctgcccaggtgc | 20-40% |
| 693 | TOP040 | caagtgcctgtggaagaagt | >40% |
| 694 | TOP041 | gcctgtggaagaagtggcgc | 20-40% |
| 695 | TOP042 | accaggtccagatgcttgct | >40% |
| 696 | TOP043 | attcaggaagagctgctagc | <20% |
| 697 | TOP044 | gtcgattgtcagcaggatta | <20% |
| 698 | TOP045 | atggaagggtgacgaggaag | <20% |

Lower case letters = DNA

TABLE 2a

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 699/700 | [1]siBc_1HP | CTCCTTTGGCCTATTCTACAA | UUGUAGAAUAGGCCAAAGGag | CUUUUGGCCUAUUCUACAAtt | >40% |
| 701/702 | [1]siBc_5HP | AAGCATGTCTGTGATCCACCA | UGGUGGAUCACAGACAUGCtt | GCAUGUCUGUGAUCCACCAtt | 20-40% |
| 703/704 | [1]siBc_6HP | AAGGACAGCCCTGTGGCTATA | UAUAGCCACAGGGCUGUCCtt | GGACAGCCCUGUGGCUAUAtt | 20-40% |
| 705/706 | [2]siBc_2281 | AAGGACAGCCCTGTGGCTATA | UAUAGCCACAGGGCUGUCCUUtt | AAGGACAGCCCUGUGGCUAUAtt | 20-40% |
| 707/708 | [2]siBc_1302 | AATGCGATACGAACACATAGA | UCUAUGUGUUCGUAUCGCAUUtt | AAUGCGAUACGAACACAUAGAtt | >40% |
| 709/710 | [2]siBc_1191 | AAGGAGGGCAGAGAAACACAT | AUGUGUUUCUCUGCCCUCCUUtt | AAGGAGGGCAGAGAAACACAUtt | >40% |
| 711/712 | TOP5217 | AACACAGGACTTCAGGACACTAA | AGUGUCCUGAAGUCCUGUGdTdT | CACAGGACUUCAGGACACUdTdT | n.d. |
| 713/714 | TOP5218 | TACAACGACTACACCAGCCACAT | GUGGCUGGUGUAGUCGUUGdTdT | CAACGACUACACCAGCCACdTdT | n.d. |
| 715/716 | TOP5219 | CAACGACTACACCAGCCACATCA | AUGUGGCUGGUGUAGUCGUdTdT | ACGACUACACCAGCCACAUdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 717/718 | TOP5220 | AACGACTACACCAGCCACATCAC | GAUGUGGCUGGUGUAGUCGdTdT | CGACUACACCAGCCACAUCdTdT | n.d. |
| 719/720 | TOP5221 | GACTACACCAGCCACATCACCTG | GGUGAUGUGGCUGGUGUAGdTdT | CUACACCAGCCACAUCACCdTdT | n.d. |
| 721/722 | TOP5222 | TACACCAGCCACATCACCTGCAG | GCAGGUGAUGUGGCUGGUGdTdT | CACCAGCCACAUCACCUGCdTdT | n d |
| 723/724 | TOP5223 | CACCAGCCACATCACCTGCAGGT | CUGCAGGUGAUGUGGCUGGdTdT | CCAGCCACAUCACCUGCAGdTdT | n.d. |
| 725/726 | TOP5224 | CAGCCACATCACCTGCAGGTGGG | CACCUGCAGGUGAUGUGGCdTdT | GCCACAUCACCUGCAGGUGdTdT | n.d. |
| 727/728 | TOP5225 | CACATCACCTGCAGGTGGGCAGA | UGCCCACCUGCAGGUGAUGdTdT | CAUCACCUGCAGGUGGGCAdTdT | n.d. |
| 729/730 | TOP5226 | CATCACCTGCAGGTGGGCAGACA | UCUGCCCACCUGCAGGUGAdTdT | UCACCUGCAGGUGGGCAGAdTdT | n.d. |
| 731/732 | TOP5227 | CACCTGCAGGTGGGCAGACACCC | GUGUCUGCCCACCUGCAGGdTdT | CCUGCAGGUGGGCAGACACdTdT | n.d. |
| 733/734 | TOP5228 | CAGGTGGGCAGACACCCAGGATG | UCCUGGGUGUCUGCCCACCdTdT | GGUGGGCAGACACCCAGGAdTdT | n.d. |
| 735/736 | TOP5229 | GGGCAGACACCCAGGATGC | GCAUCCUGGGUGUCUGCCCdtdt | GGGCAGACACCCAGGAUGCdtdt | n.d. |
| 737/738 | TOP5230 | CAGACACCCAGGATGCCCAGCGG | GCUGGGCAUCCUGGGUGUCdTdT | GACACCCAGGAUGCCCAGCdTdT | n.d. |
| 739/740 | TOP5231 | GATGCCCAGCGGCTCGTCAACGT | GUUGACGAGCCGCUGGGCAdTdT | UGCCCAGCGGCUCGUCAACdTdT | n.d. |
| 741/742 | TOP5232 | CAGCGGCTCGTCAACGTGACCCT | GGUCACGUUGACGAGCCGCdTdT | GCGGCUCGUCAACGUGACCdTdT | n.d. |
| 743/744 | TOP5233 | CAACGTGACCCTCATTCGCGGG | CGGCGAAUGAGGGUCACGUdTdT | ACGUGACCCUCAUUCGCCGdTdT | n.d. |
| 745/746 | TOP5234 | AACGTGACCCTCATTCGCGGGT | CCGGCGAAUGAGGGUCACGdTdT | CGUGACCCUCAUUCGCCGGdTdT | n.d. |
| 747/748 | TOP5235 | GACCCTCATTCGCCGGGTGAATG | UUCACCCGGCGAAUGAGGGdTdT | CCCUCAUUCGCCGGGUGAAdTdT | n.d. |
| 749/750 | TOP5236 | CCCTCATTCGCCGGGTGAA | UUCACCCGGCGAAUGAGGGdtdt | CCCUCAUUCGCCGGGUGAAdtdt | n.d. |
| 751/752 | TOP5237 | CATTCGCCGGGTGAATGAGGACC | UCCUCAUUCACCCGGCGAAdTdT | UUCGCCGGGUGAAUGAGGAdTdT | n.d |
| 753/754 | TOP5238 | GAATGAGGACCTCCTGGAGCCAG | GCUCCAGGAGGUCCUCAUdTdT | AUGAGGACCUCCUGGAGCCdTdT | n.d. |
| 755/756 | TOP5239 | AATGAGGACCTCCTGGAGCCAGT | UGGCUCCAGGAGGUCCUCAdTdT | UGAGGACCUCCUGGAGCCAdTdT | n.d. |
| 757/758 | TOP5240 | GAGGACCTCCTGGAGCCAGTGTC | CACUGGCUCCAGGAGGUCdTdT | GGACCUCCUGGAGCCAGUGdTdT | n.d. |
| 759/760 | TOP5241 | GGACCTCCTGGAGCCAGTG | CACUGGCUCCAGGAGGUCCdtdt | GGACCUCCUGGAGCCAGUGdtdt | n.d. |
| 761/762 | TOP5242 | GACCTCCTGGAGCCAGTGTCCTG | GGACACUGGCUCCAGGAGGdTdT | CCUCCUGGAGCCAGUGUCCdTdT | n.d. |
| 763/764 | TOP5243 | GAGCCAGTGTCCTGTGACCTCAG | GAGGUCACAGGACACUGGCdTdT | GCCAGUGUCCUGUGACCUCdTdT | n.d. |
| 765/766 | TOP5244 | CAGTGTCCTGTGACCTCAGTGAT | CACUGAGGUCACAGGACACdTdT | GUGUCCUGUGACCUCAGUGdTdT | n.d. |
| 767/768 | TOP5245 | GACCTCAGTGATGACATGCCCTG | GGGCAUGUCAUCACUGAGGdTdT | CCUCAGUGAUGACAUGCCCdTdT | n.d. |
| 769/770 | TOP5246 | CCTCAGTGATGACATGCCC | GGGCAUGUCAUCACUGAGGdtdt | CCUCAGUGAUGACAUGCCCdtdt | n.d. |
| 771/772 | TOP5247 | CAGTGATGACATGCCCTGGTCAG | GACCAGGGCAUGUCAUCACdTdT | GUGAUGACAUGCCCUGGUCdTdT | n.d. |
| 773/774 | TOP5248 | GATGACATGCCCTGGTCAGCCTG | GGCUGACCAGGGCAUGUCAdTdT | UGACAUGCCCUGGUCAGCCdTdT | n.d. |
| 775/776 | TOP5249 | GACATGCCCTGGTCAGCCTGCCC | GCAGGCUGACCAGGGCAUGdTdT | CAUGCCCUGGUCAGCCUGCdTdT | n.d. |
| 777/778 | TOP5250 | GCCCAGGAGATGTGTCATT | AAUGACACAUCUCCUGGGCdtdt | GCCCAGGAGAUGUGUCAUUdtdt | n.d. |
| 779/780 | TOP5251 | CAGGAGATGTGTCATTCCCTGCC | CAGGGAAUGACACAUCUCCdTdT | GGAGAUGUGUCAUUCCCUGdTdT | n.d. |
| 781/782 | TOP5252 | GAGATGTGTCATTCCCTGCCAGA | UGGCAGGGAAUGACACAUCdTdT | GAUGUGUCAUUCCCUGCCAdTdT | n.d. |
| 783/784 | TOP5253 | GATGTGTCATTCCCTGCCAGAGT | UCUGGCAGGGAAUGACACAdTdT | UGUGUCAUUCCCUGCCAGAdTdT | n.d. |
| 785/786 | TOP5254 | CATTCCCTGCCAGAGTTTTGTCG | ACAAAACUCUGGCAGGGAAdTdT | UUCCCUGCCAGAGUUUUGUdTdT | n.d. |
| 787/788 | TOP5255 | CAGAGTTTTGTCGTCACTGACGT | GUCAGUGACGACAAAACUCdTdT | GAGUUUUGUCGUCACUGACdTdT | n.d. |
| 789/790 | TOP5256 | GAGTTTTGTCGTCACTGACGTTG | ACGUCAGUGACGACAAAACdTdT | GUUUUGUCGUCACUGACGUdTdT | n.d. |
| 791/792 | TOP5257 | TCACTGACGTTGACTACTT | AAGUAGUCAACGUCAGUGAdtdt | UCACUGACGUUGACUACUUdtdt | n.d. |

TABLE 2a-continued

| SEQ ID Nos (antisense/ sense) | siRNA ID NUMBER | Target sequence (5'-3') | Antisense strand (5'-3') | Sense strand (5'-3') | β-chain mRNA Inhibition |
|---|---|---|---|---|---|
| 793/794 | TOP5258 | CACTGACGTTGACTACTTCTCAT | GAGAAGUAGUCAACGUCAGdTdT | CUGACGUUGACUACUUCUCdTdT | n.d. |
| 795/796 | TOP5259 | GACGTTGACTACTTCTCATTCCA | GAAUGAGAAGUAGUCAACGdTdT | CGUUGACUACUUCUCAUUCdTdT | n.d. |
| 797/798 | TOP5260 | GACTACTTCTCATTCCAACCAGA | UGGUUGGAAUGAGAAGUAGdTdT | CUACUUCUCAUUCCAACCAdTdT | n.d. |
| 799/800 | TOP5261 | TACTTCTCATTCCAACCAGACAG | CUUCUCAUUCCAACCAGACdTdT | CUUCUCAUUCCAACCAGACdTdT | n.d. |
| 801/802 | TOP5262 | CATTCCAACCAGACAGGCCTCTG | GAGGCCUGUCUGGUUGGAAdTdT | UUCCAACCAGACAGGCCUCdTdT | n.d. |
| 803/804 | TOP5263 | CAACCAGACAGGCCTCTGGGCAC | GCCCAGAGGCCUGUCUGGUdTdT | ACCAGACAGGCCUCUGGGCdTdT | n.d. |
| 805/806 | TOP5264 | AACCAGACAGGCCTCTGGGCACC | CCAGACAGGCCUCUGGGCAdTdT | CCAGACAGGCCUCUGGGCAdTdT | n.d. |
| 807/808 | TOP5265 | CACCCGGCTCACCGTCACTCTGA | AGAGUGACGGUGAGCCGGGdTdT | CCCGGCUCACCGUCACUCUdTdT | n.d. |
| 809/810 | TOP5266 | CACCGTCACTCTGACCCAGCATG | UGCUGGGUCAGAGUGACGGdTdT | CCGUCACUCUGACCCAGCAdTdT | n.d. |
| 811/812 | TOP5267 | CACTCTGACCCAGCATGTCCAGC | UGGACAUGCUGGGUCAGAGdTdT | CUCUGACCCAGCAUGUCCAdTdT | n.d. |
| 813/814 | TOP5268 | GACCCAGCATGTCCAGCCTCCTG | GGAGGCUGGACAUGCUGGGdTdT | CCCAGCAUGUCCAGCCUCCdTdT | n.d. |
| 815/816 | TOP5269 | CAGCATGTCCAGCCTCCTGAGCC | CUCAGGAGGCUGGACAUGCdTdT | GCAUGUCCAGCCUCCUGAGdTdT | n.d. |
| 817/818 | TOP5270 | CATGTCCAGCCTCCTGAGCCCAG | GGGCUCAGGAGGCUGGACAdTdT | UGUCCAGCCUCCUGAGCCCdTdT | n.d. |
| 819/820 | TOP5271 | GAGCCCAGGGACCTGCAGATCAG | GAUCUGCAGGUCCCUGGGCdTdT | GCCCAGGGACCUGCAGAUCdTdT | n.d. |
| 821/822 | TOP5272 | CAGGGACCTGCAGATCAGCACCG | GUGCUGAUCUGCAGGUCCCdTdT | GGGACCUGCAGAUCAGCACdTdT | n.d. |
| 823/824 | TOP5273 | GACCTGCAGATCAGCACCGACCA | GUCGGUGCUGAUCUGCAGGdTdT | CCUGCAGAUCAGCACCGACdTdT | n.d. |
| 825/826 | TOP5274 | CAGATCAGCACCGACCAGGACCA | GUCCUGGUCGGUGCUGAUCdTdT | GAUCAGCACCGACCAGGACdTdT | n.d. |
| 827/828 | TOP5275 | GATCAGCACCGACCAGGACCACT | UGGUCCUGGUCGGUGCUGAdTdT | UCAGCACCGACCAGGACCAdTdT | n.d. |
| 829/830 | TOP5276 | CAGCACCGACCAGGACCACTTCC | AAGUGGUCCUGGUCGGUGCdTdT | GCACCGACCAGGACCACUUdTdT | n.d. |
| 831/832 | TOP5277 | CACCGACCAGGACCACTTCCTGC | AGGAAGUGGUCCUGGUCGGdTdT | CCGACCAGGACCACUUCCUdTdT | n.d. |
| 833/834 | TOP5278 | GACCAGGACCACTTCCTGCTGAC | CAGCAGGAAGUGGUCCUGGdTdT | CCAGGACCACUUCCUGCUGdTdT | n.d. |
| 835/836 | TOP5279 | CAGGACCACTTCCTGCTGACCTG | GGUCAGCAGGAAGUGGUCCdTdT | GGACCACUUCCUGCUGACCdTdT | n.d. |
| 837/838 | TOP5280 | GACCACTTCCTGCTGACCTGGAG | CCAGGUCAGCAGGAAGUGGdTdT | CCACUUCCUGCUGACCUGGdTdT | n.d. |
| 839/840 | TOP5281 | CACTTCCTGCTGACCTGGAGTGT | ACUCCAGGUCAGCAGGAAGdTdT | CUUCCUGCUGACCUGGAGUdTdT | n.d. |
| 841/842 | TOP5282 | GACCTGGAGTGTGGCCCTTGGGA | CCAAGGGCCACACUCCAGGdTdT | CCUGGAGUGUGGCCCUUGGdTdT | n.d. |
| 843/844 | TOP5283 | GAGTGTGGCCCTTGGGAGTCCCC | GGACUCCCAAGGGCCACACdTdT | GUGUGGCCCUUGGGAGUCCdTdT | n.d. |
| 845/846 | TOP5284 | GAGTCCCCAGAGCCACTGGTTGT | AACCAGUGGCUCUGGGGACdTdT | GUCCCCAGAGCCACUGGUUdTdT | n.d. |
| 847/848 | TOP5285 | CAGAGCCACTGGTTGTCCCCAGG | UGGGGACAACCAGUGGCUCdTdT | GAGCCACUGGUUGUCCCCAdTdT | n.d. |
| 849/850 | TOP5286 | GCCACTGTTGTCCCCAGG | CCUGGGGACAACCAGUGGCdtdt | GCCACUGGUUGUCCCAGGdtdt | n.d. |
| 851/852 | TOP5287 | GATCTGGAGTTTGAGGTGGTCTA | GACCACCUCAAACUCCAGAdTdT | UCUGGAGUUUGAGGUGGUCdTdT | n.d. |
| 853/854 | TOP5288 | TGGAGTTTGAGGTGGTCTA | UAGACCACCUCAAACUCCAdtdt | UGGAGUUUGAGGUGGUCUAdtdt | n.d. |
| 855/856 | TOP5289 | GAGTTTGAGGTGGTCTACAAGCG | CUUGUAGACCACCUCAAACdTdT | GUUUGAGGUGGUCUACAAGdTdT | n.d. |
| 857/858 | TOP5290 | GAGGTGGTCTACAAGCGGCTTCA | AAGCCGCUUGUAGACCACCdTdT | GGUGGUCUACAAGCGGCUUdTdT | n.d. |
| 859/860 | TOP5291 | TACAAGCGGCTTCAGGACTCTTG | AGAGUCCUGAAGCCGCUUGdTdT | CAAGCGGCUUCAGGACUCUdTdT | n.d. |
| 861/862 | TOP5292 | CAAGCGGCTTCAGGACTCTTGGG | CAAGAGUCCUGAAGCCGCUdTdT | AGCGGCUUCAGGACUCUUGdTdT | n.d. |
| 863/864 | TOP5293 | AAGCGGCTTCAGGACTCTTGGGA | CCAAGAGUCCUGAAGCCGCdTdT | GCGGCUUCAGGACUCUUGGdTdT | n.d. |
| 865/866 | TOP5294 | CAGGACTCTTGGGAGGACGCAGC | UGCGUCCUCCCAAGAGUCCdTdT | GGACUCUUGGGAGGACGCAdTdT | n.d. |
| 867/868 | TOP5295 | GACTCTTGGGAGGACGCAGCCAT | GGCUGCGUCCUCCCAAGAGdTdT | CUCUUGGGAGGACGCAGCCdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 869/870 | TOP5296 | GAGGACGCAGCCATCCTCCTCTC | GAGGAGGAUGGCUGCGUCCdTdT | GGACGCAGCCAUCCUCCUCUCdTdT | n.d. |
| 871/872 | TOP5297 | GACGCAGCCATCCTCCTCTCCAA | GGAGAGGAGGAUGGCUGCGdTdT | CGCAGCCAUCCUCCUCUCCdTdT | n.d. |
| 873/874 | TOP5298 | CAGCCATCCTCCTCTCCAACACC | UGUUGGAGAGGAGGAUGGCdTdT | GCCAUCCUCCUCUCCAACAdTdT | n.d. |
| 875/876 | TOP5299 | CATCCTCCTCTCCAACACCTCCC | GAGGUGUUGGAGAGGAGGAdTdT | UCCUCCUCUCCAACACCUCdTdT | n.d. |
| 877/878 | TOP5300 | CAACACCTCCCAGGCCACCCTGG | AGGGUGGCCUGGGAGGUGUdTdT | ACACCUCCCAGGCCACCCUdTdT | n.d. |
| 879/880 | TOP5301 | AACACCTCCCAGGCCACCCTGGG | CAGGGUGGCCUGGGAGGUGdTdT | CACCUCCCAGGCCACCCUGdTdT | n.d. |
| 881/882 | TOP5302 | CAGAGCACCTCATGCCCAGCAGC | UGCUGGGCAUGAGGUGCUCdTdT | GAGCACCUCAUGCCCAGCAdTdT | n.d. |
| 883/884 | TOP5303 | GAGCACCTCATGCCCAGCAGCAC | GCUGCUGGGCAUGAGGUGCdTdT | GCACCUCAUGCCCAGCAGCdTdT | n.d. |
| 885/886 | TOP5304 | CACCTCATGCCCAGCAGCACCTA | GGUGCUGCUGGGCAUGAGGdTdT | CCUCAUGCCCAGCAGCACCUAdTdT | n.d. |
| 887/888 | TOP5305 | CATGCCCAGCAGCACCTACGTGG | ACGUAGGUGCUGCUGGGCAdTdT | UGCCCAGCAGCACCUACGUdTdT | n.d. |
| 889/890 | TOP5306 | CAGCACCTACGTGGCCCGAGTAC | ACUCGGGCCACGUAGGUGCdTdT | GCACCUACGUGGCCCGAGUdTdT | n.d. |
| 891/892 | TOP5307 | GCACCTACGTGGCCCGAGT | ACUCGGGCCACGUAGGUGCdtdt | GCACCUACGUGGCCCGAGUdtdt | n.d. |
| 893/894 | TOP5308 | CACCTACGTGGCCCGAGTACGGA | CGUACUCGGGCCACGUAGGdTdT | CCUACGUGGCCCGAGUACGdTdT | n.d. |
| 895/896 | TOP5309 | CAGGTTCTCGGCTCTCAGGACGT | GUCCUGAGAGCCGAGAACCdTdT | GGUUCUCGGCUCUCAGGACGUdTdT | n.d. |
| 897/898 | TOP5310 | CAGGACGTCCCAGCAAGTGGAGC | UCCACUUGCUGGGACGUCCdTdT | GGACGUCCCAGCAAGUGGAdTdT | n.d. |
| 899/900 | TOP5311 | GACGTCCCAGCAAGTGGAGCCCA | GGCUCCACUUGCUGGGACGdTdT | CGUCCCAGCAAGUGGAGCCdTdT | n.d. |
| 901/902 | TOP5312 | CAGCAAGTGGAGCCCAGAGGTTT | ACCUCUGGGCUCCACUUGCdTdT | GCAAGUGGAGCCCAGAGGUdTdT | n.d. |
| 903/904 | TOP5313 | CAAGTGGAGCCCAGAGGTTTGCT | CAAACCUCUGGGCUCCACUdTdT | AGUGGAGCCCAGAGGUUUGCUdTdT | n.d. |
| 905/906 | TOP5314 | CAAGTGGAGCCCAGAGGTT | AACCUCUGGGCUCCACUUGdtdt | CAAGUGGAGCCCAGAGGUUdtdt | n.d. |
| 907/908 | TOP5315 | AAGTGGAGCCCAGAGGTTTGCTG | GCAAACCUCUGGGCUCCACdTdT | GUGGAGCCCAGAGGUUUGCdTdT | n.d. |
| 909/910 | TOP5316 | GAGCCCAGAGGTTTGCTGGGACT | UCCCAGCAAACCUCUGGGCdTdT | GCCCAGAGGUUUGCUGGGAdTdT | n.d. |
| 911/912 | TOP5317 | CAGAGGTTTGCTGGGACTCCCAG | GGGAGUCCCAGCAAACCUCdTdT | GAGGUUUGCUGGGACUCCCdTdT | n.d. |
| 913/914 | TOP5318 | GAGGTTTGCTGGGACTCCCAGCC | CUGGGAGUCCCAGCAAACCdTdT | GGUUUGCUGGGACUCCCAGdTdT | n.d. |
| 915/916 | TOP5319 | GATGAGGCCCAGCCCCAGAACCT | GUUCUGGGGCUGGGCCUCAdTdT | UGAGGCCCAGCCCCAGAACdTdT | n.d. |
| 917/918 | TOP5320 | CAGCCCCAGAACCTGGAGTGCTT | GCACUCCAGGUUCUGGGGCdTdT | GCCCCAGAACCUGGAGUGCdTdT | n.d. |
| 919/920 | TOP5321 | CAGAACCTGGAGTGCTTCTTTGA | AAAGAAGCACUCCAGGUUCdTdT | GAACCUGGAGUGCUUCUUUdTdT | n.d. |
| 921/922 | TOP5322 | GAACCTGGAGTGCTTCTTTGACG | UCAAAGAAGCACUCCAGGUdTdT | ACCUGGAGUGCUUCUUUGAdTdT | n.d. |
| 923/924 | TOP5323 | AACCTGGAGTGCTTCTTTGACGG | GUCAAAGAAGCACUCCAGGdTdT | CCUGGAGUGCUUCUUUGACdTdT | n.d. |
| 925/926 | TOP5324 | CAGCTGCTCCTGGGAGGTGAGGA | CUCACCUCCCAGGAGCAGCdTdT | GCUGCUCCUGGGAGGUGAGdTdT | n.d. |
| 927/928 | TOP5325 | GAGGTGAGGAAGGAGGTGGCCAG | GGCCACCUCCUUCCUCACCdTdT | GGUGAGGAAGGAGGUGGCCdTdT | n.d. |
| 929/930 | TOP5326 | GAGGAAGGAGGTGGCCAGCTCGG | GAGCUGGCCACCUCCUUCCdTdT | GGAAGGAGGUGGCCAGCUCdTdT | n.d. |
| 931/932 | TOP5327 | GAAGGAGGTGGCCAGCTCGGTCT | ACCGAGCUGGCCACCUCCUdTdT | AGGAGGUGGCCAGCUCGGUdTdT | n.d. |
| 933/934 | TOP5328 | AAGGAGGTGGCCAGCTCGGTCTC | GACCGAGCUGGCCACCUCCdTdT | GGAGGUGGCCAGCUCGGUCdTdT | n.d. |
| 935/936 | TOP5329 | GAGGTGGCCAGCTCGGTCTCCTT | GGAGACCGAGCUGGCCACCdTdT | GGUGGCCAGCUCGGUCUCCdTdT | n.d. |
| 937/938 | TOP5330 | CAGCTCGGTCTCCTTTGGCTAT | AGGCCAAAGGAGACCGAGCdTdT | GCUCGGUCUCCUUUGGCCUdTdT | n.d. |
| 939/940 | TOP5330 | TATTCTACAAGCCCAGCCCAGAT | CUGGGCUGGGCUUGUAGAAdTdT | UUCUACAAGCCCAGCCCAGdTdT | n.d. |
| 941/942 | TOP5332 | TACAAGCCCAGCCCAGATGCAGG | USCAUCUGGGCUGGGCUUGdTdT | CAAGCCCAGCCCAGAUGCAdTdT | n.d. |
| 943/944 | TOP5333 | GAGGAAGAGTGCTCCCCAGTGCT | CACUGGGGAGCACUCUUCCdTdT | GGAAGAGUGCUCCCCAGUGdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 945/946 | TOP5334 | GAAGAGTGCTCCCCAGTGCTGAG | CAGCACUGGGGAGCACUCdTdT | AGAGUGCUCCCCAGUGCUGdTdT | n.d. |
| 947/948 | TOP5335 | AAGAGTGCTCCCCAGTGCTGAGG | UCAGCACUGGGGAGCACUCdTdT | GAGUGCUCCCCAGUGCUGAdTdT | n.d. |
| 949/950 | TOP5336 | GAGTGCTCCCCAGTGCTGAGGGA | CCUCAGCACUGGGGAGCACdTdT | GUGCUCCCCAGUGCUGAGGdTdT | n.d. |
| 951/952 | TOP5337 | CAGCCTCCACACCAGGCACCACT | UGGUGCCUGGUGUGGAGGCdTdT | GCCUCCACACCAGGCACCAdTdT | n.d. |
| 953/954 | TOP5338 | CACACCAGGCACCACTGCCAGAT | CUGGCAGUGGUGCCUGGUGdTdT | CACCAGGCACCACUGCCAGdTdT | n.d. |
| 955/956 | TOP5339 | CACCAGGCACCACTGCCAGATTC | AUCUGGCAGUGGUGCCUGGdTdT | CCAGGCACCACUGCCAGAUdTdT | n.d. |
| 957/958 | TOP5340 | CAGGCACCACTGCCAGATTCCCG | GGAAUCUGGCAGUGGUGCCdTdT | GGCACCACUGCCAGAUUCCdTdT | n.d. |
| 959/960 | TOP5341 | CACCACTGCCAGATTCCCGTGCC | CACGGGAAUCUGGCAGUGGdTdT | CCACUGCCAGAUUCCCGUGdTdT | n.d. |
| 961/962 | TOP5342 | CACTGCCAGATTCCCGTGCCCGA | CGCCACGGGAAUCUGGCAGdTdT | CUGCCAGAUUCCCGUGCCCdTdT | n.d. |
| 963/964 | TOP5343 | GACCCACGGCCAATACATCGTCT | ACGAUGUAUUGGCCGUGGGdTdT | CCCACGGCCAAUACAUCGUdTdT | n.d. |
| 965/966 | TOP5344 | CACGGCCAATACATCGTCTCTGT | AGAGACGAUGUAUUGGCCGdTdT | CGGCCAAUACAUCGUCUCUdTdT | n.d. |
| 967/968 | TOP5345 | CAATACATCGTCTCTGTTCAGCC | CUGAACAGAGACGAUGUAUdTdT | AUACAUCGUCUCUGUUCAGdTdT | n.d. |
| 969/970 | TOP5346 | AATACATCGTCTCTGTTCAGCCA | GCUGAACAGAGACGAUGUAdTdT | UACAUCGUCUCUGUUCAGCdTdT | n.d. |
| 971/972 | TOP5347 | TACATCGTCTCTGTTCAGCCAAG | UGGCUGAACAGAGACGAUGdTdT | CAUCGUCUCUGUUCAGCCAdTdT | n.d. |
| 973/974 | TOP5348 | CATCGTCTCTGTTCAGCCAAGGA | CUUGGCUGAACAGAGACGAdTdT | UCGUCUCUGUUCAGCCAAGdTdT | n.d. |
| 975/976 | TOP5101 | CAGCCAAGGAGGGCAGAGAAACA | UUUCUCUGCCCUCCUUGGCdTdT | GCCAAGGAGGGCAGAGAAAdTdT | <20% |
| 977/978 | TOP5114 | CAGCCAAGGAGGGCAGAGA | UCUCUGCCCUCCUUGGCUGdtdt | CAGCCAAGGAGGGCAGAGAdtdt | <20% |
| 979/980 | TOP5349 | CAAGGAGGGCAGAGAAACACATA | UGUGUUUCUCUGCCCUCCUdTdT | AGGAGGGCAGAGAAACACAdTdT | n.d. |
| 981/982 | TOP5350 | CAAGGAGGGCAGAGAAACA | UGUUUCUCUGCCCUCCUUGdtdt | CAAGGAGGGCAGAGAAACAdtdt | n.d. |
| 983/984 | TOP5351 | AAGGAGGGCAGAGAAACACATAPA | AUGUGUUUCUCUGCCCUCCdTdT | GGAGGGCAGAGAAACACAUdTdT | n.d. |
| 985/986 | TOP5100 | GAGGGCAGAGAAACACATAAAGA | UUUAUGUGUUUCUCUGCCCdTdT | GGGCAGAGAAACACAUAAAdTdT | >40% |
| 987/988 | TOP5102 | GCAGAGAAACACATAAAGA | UCUUDAUGUGUUUCUCUGCdtdt | GCAGAGAAACACAUAAAGAdtdt | >40% |
| 989/990 | TOP5352 | CAGAGAAACACATAAAGAGCTCA | AGCUCUUUAUGUGUUUCUCdTdT | GAGAAACACAUAAAGAGCUdTdT | n.d. |
| 991/992 | TOP5353 | GAGAAACACATAAAGAGCTCAGT | UGAGCUCUUUAUGUGUUUCdTdT | GAAACACAUAAAGAGCUCAdTdT | n.d. |
| 993/994 | TOP5109 | AGAAACACATAAAGAGCTC | CAGCUCUUUAUGUGUUUCUdtdt | AGAAACACAUAAAGAGCUCdtdt | <20% |
| 995/996 | TOP5354 | GAAACACATAAAGAGCTCAGTGA | ACUGAGCUCUUUAUGUGUUdTdT | AACACAUAAAGAGCUCAGUdTdT | n.d. |
| 997/996 | TOP5355 | AAACACATAAAGAGCTCAGTGAA | CACUGAGCUCUUUAUGUGUdTdT | ACACAUAAAGAGCUCAGUGdTdT | n.d. |
| 999/1000 | TOP5115 | AACACATAAAGAGCTCAGTGAAC | UCACUGAGCUCUUUAUGUCdTdT | CACAUAAAGAGCUCAGUGAdTdT | >40% |
| 1001/1002 | TOP5104 | CACATAAAGAGCTCAGTGAACAT | GUUCACUGAGCUCUUUAUGdTdT | CAUAAAGAGCUCAGUGAACdTdT | >40% |
| 1003/1004 | TOP5106 | ACATAAAGAGCTCAGTGAA | UUCACUGAGCUCUUUAUGUdtdt | ACAUAAAGAGCUCAGUGAAdtdt | 20-40% |
| 1005/1006 | TOP5110 | CATAAAGAGCTCAGTGAACATCC | AUGUUCACUGAGCUCUUUAdTdT | UAAAGAGCUCAGUGAACAUdTdT | 20-40% |
| 1007/1008 | TOP5108 | ATAAAGAGCTCAGTGAACA | UGUUCACUGAGCUCUUUAUdtdt | CGCAGAAAGUGGGAGGAGdtdt | 20-40% |
| 1009/1010 | TOP5356 | TAAAGAGCTCAGTGAACATCCAG | GGAUGUUCACUGACCUCUUdTdT | AAGAGCUCACUGAACAUCCdTdT | n.d. |
| 1011/1012 | TOP5357 | AAAGAGCTCAGTGAACATCCAGA | UGGAUGUUCACUGAGCUCUdTdT | AGAGCUCAGUGAACAUCCAdTdT | n.d. |
| 1013/1014 | TOP5358 | AAGAGCTCAGTGAACATCCAGAT | CUGGAUGUUCACUGAGCUCdTdT | GAGCUCAGUGAACAUCCAGdTdT | n.d. |
| 1015/1016 | TOP5359 | GAGCTCAGTGAACATCEAGATGG | AUCUGGAUGUUCACUGAGCdTdT | GCUCAGUGAACAUCCAGAUdTdT | n.d. |
| 1017/1018 | TOP5360 | CAGTGAACATCCAGATGGCCCCT | GGGGCCAUCUGGAUGUUCAdTdT | GUGAACAUCCAGAUGGCCCdTdT | n.d. |
| 1019/1020 | TOP5361 | GAACATCCAGATGGCCCCTCCAT | GGAGGGGCCAUCUGGAUGUdTdT | ACAUCCAGAUGGCCCCUCCdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 1021/1022 | TOP5362 | AACATCCAGATGGCCCCTCCATC | UGGAGGGGCCAUCUGGAUGdTdT | CAUCCAGAUGGCCCCUCCAdTdT | n.d. |
| 1023/1024 | TOP5363 | CATCCAGATGGCCCCTCCATCCC | GAUGGAGGGGCCAUCUGGAdTdT | UCCAGAUGGCCCCUCCAUCdTdT | n.d. |
| 1025/1026 | TOP5364 | CAGATGGCCCCTCCATCCCTCAA | GAGGGAUGGAGGGGCCAUCdTdT | GAUGGCCCCUCCAUCCCUCdTdT | n.d. |
| 1027/1028 | TOP5365 | GATGGCCCCTCCATCCCTCAACG | UUGAGGGAUGGAGGGGCCAdTdT | UGGCCCCUCCAUCCCUCAAdTdT | n.d. |
| 1029/1030 | TOP5366 | CATCCCTCAACGTGACCAAGGAT | CCUUGGUCACGUUGAGGGAdTdT | UCCCUCAACGUGACCAAGGdTdT | n.d. |
| 1031/1032 | TOP5367 | CAACGTGACCAAGGATGGAGACA | UCUCCAUCCUUGGUCACGUdTdT | ACGUGACCAAGGAUGGAGAdTdT | n.d. |
| 1033/1034 | TOP5368 | AACGTGACCAAGGATGGAGACAG | GUCUCCAUCCUUGGUCACGdTdT | CGUGACCAAGGAUGGAGACdTdT | n.d. |
| 1035/1036 | TOP5369 | GACCAAGGATGGAGACAGCTACA | UAGCUGUCUCCAUCCUUGGdTdT | CCAAGGAUGGAGACAGCUAdTdT | n.d. |
| 1037/1038 | TOP5370 | CAAGGATGGAGACAGCTACAGCC | CUGUAGCUGUCUCCAUCCUdTdT | AGGAUGGAGACAGCUACAGdTdT | n.d. |
| 1039/1040 | TOP5371 | AAGGATGGAGACAGCTACAGCCT | GCUGUAGCUGUCUCCAUCCdTdT | GGAUGGAGACAGCUACAGCdTdT | n.d. |
| 1041/1042 | TOP5372 | GATGGAGACAGCTACAGCCTGCG | CAGGCUGUAGCUGUCUCCAdTdT | UGGAGACAGCUACAGCCUGdTdT | n.d. |
| 1043/1044 | TOP5373 | GAGACAGCTACACCCTGCGCTGG | AGCGCAGGCUGUAGCUGUCdTdT | GACAGCUACAGCCUGCGCUdTdT | n.d. |
| 1045/1046 | TOP5374 | GACAGCTACAGCCTGCGCTGGGA | CCAGCGCAGGCUGUAGCUGdTdT | CAGCUACAGCCUGCGCUGGdTdT | n.d. |
| 1047/1048 | TOP5375 | CAGCTACAGCCTGCGCTGGGAAA | UCCCAGCGCAGGCUGUAGCdTdT | GCUACAGCCUGCGCUGGGAdTdT | n.d. |
| 1049/1050 | TOP5376 | TACAGCCTGCGCTGGGAAACAAT | UGUUUCCCAGCGCAGGCUGdTdT | CAGCCUGCGCUGGGAAACAdTdT | n.d. |
| 1051/1052 | TOP5377 | CAGCCTGCGCTGGGAAACAATGA | AUUGUUUCCCAGCGCAGGCdTdT | GCCUGCGCUGGGAAACAAUdTdT | n.d. |
| 1053/1054 | TOP5105 | GCGCTGGGAAACAATGAAA | UUUCAUUGUUUCCCAGCGCdtdt | GCGCUGGGAAACAAUGAAAdtdt | 20-40% |
| 1055/1056 | TOP5112 | GCTGGGAAACAATGAAAAT | AUUUUCAUUGUUUCCAGCdtdt | GCUGGGAAACAAUGAAAAUdtdt | 20-40% |
| 1057/1058 | TOP5378 | AAACAATGAAAATGCGATACGAA | CGUAUCGCAUUUUCAUUGUdTdT | ACAAUGAAAAUGCGAUACGdTdT | n.d. |
| 1059/1060 | TOP5379 | AACAATGAAAATGCGATACGAAC | UCGUAUCGCAUUUUCAUUGdTdT | CAAUGAAAAUGCGAUACGAdTdT | n.d. |
| 1061/1062 | TOP5380 | CAATGAAAATGCGATACGAACAC | GUUCGUAUCGCAUUUUCAUdTdT | AUGAAAAUGCGAUACGAACdTdT | n.d. |
| 1063/1064 | TOP5116 | AATGAAAATGCGATACGAACACA | UGUUCGUAUCGCAUUUUCAdTdT | UGAAAAUGCGAUACGAACAdTdT | <20% |
| 1065/1066 | TOP5381 | GAAAATGCGATACGAACACATAG | AUGUGUUCGUAUCGCAUUUdTdT | AAAUGCGAUACGAACACAUdTdT | n.d. |
| 1067/1068 | TOP5382 | AAAATGCGATACGAACACATAGA | UAUGUGUUCGUAUCGCAUUdTdT | AAUGCGAUACGAACACAUAdTdT | n.d. |
| 1069/1070 | TOP5383 | AAATGCGATACGAACACATAGAC | CUAUGUGUUCGUAUCGCAUdTdT | AUGCGAUACGAACACAUAGdTdT | n.d. |
| 1071/1072 | TOP5384 | AATGCGATACGAACACATAGACC | UCUAUGUGUUCGUAUCGCAdTdT | UGCGAUACGAACACAUAGAdTdT | n.d. |
| 1073/1074 | TOP5385 | CACATAGACCACACATTTGAGAT | CUCAAAUGUGUGGUCUAUGdTdT | CAUAGACCACACAUUUGAGdTdT | n.d. |
| 1075/1076 | TOP5386 | GATACGAACACATAGACCACACA | UGUGGUCUAUGUGUUCGUAdTdT | UACGAACACAUAGACCACAdTdT | n.d. |
| 1077/1078 | TOP5117 | GATACGAACACATAGACCA | UGGUCUAUGUGUUCGUAUCdtdt | GAUACGAACACAUAGACCAdtdt | >40% |
| 1079/1080 | TOP5387 | TACGAACACATAGACCACACATT | UGUGUGGUCUAUGUGUUCGdTdT | CGAACACAUAGACCACACAUdTdT | n.d. |
| 1081/1082 | TOP5107 | GAACACATAGACCACACATTTGA | AAAUGUGUGGUCUAUGUGUdTdT | ACACAUAGACCACACAUUUdTdT | >40% |
| 1083/1084 | TOP5388 | AACACATAGACCACACATTTGAG | CAAAUGUGUGGUCUAUGUGdTdT | CACAUAGACCACACAUUUGdTdT | n.d. |
| 1085/1086 | TOP5389 | CATAGACCACACATTTGAGATCC | AUCUCAAAUGUGUGGUCUAdTdT | UAGACCACACAUUUGAGAUdTdT | n.d. |
| 1087/1088 | TOP5390 | TAGACCACACATTTGAGATCCAG | GGAUCUCAAAUGUGUGGUCdTdT | GACCACACAUUUGAGAUCCdTdT | n.d. |
| 1089/1090 | TOP5391 | GACCACACATTTGAGATCCAGTA | CUGGAUCUCAAAUGUGUGGdTdT | CCACACAUUUGAGAUCCAGdTdT | n.d. |
| 1091/1092 | TOP5392 | CACACATTTGAGATCCAGTACAG | GUACUGGAUCUCAAAUGUGdTdT | CACAUUUGAGAUCCAGUACdTdT | n.d. |
| 1093/1094 | TOP5393 | CACATTTGAGATCCAGTACAGGA | CUGUACUGGAUCUCAAAUGdTdT | CAUUUGAGAUCCAGUACAGdTdT | n.d. |
| 1095/1096 | TOP5394 | CATTTGAGATCCAGTACAGGAAA | UCCUGUACUGGAUCUCAAAdTdT | UUUGAGAUCCAGUACAGGAdTdT | n.d. |

TABLE 2a-continued

| SEQ ID Nos (antisense/ sense) | siRNA ID NUMBER | Target sequence (5'-3') | Antisense strand (5'-3') | Sense strand (5'-3') | β-chain mRNA Inhibition |
|---|---|---|---|---|---|
| 1097/1098 | TOP5395 | GAGATCCAGTACAGGAAAGACAC | GUCUUUCCUGUACUGGAUCdTdT | GAUCCAGUACAGGAAAGACdTdT | n.d. |
| 1099/1100 | TOP5396 | GATCCAGTACAGGAAAGACACGG | GUGUCUUUCCUGUACUGGAdTdT | UCCAGUACAGGAAAGACACdTdT | n.d. |
| 1101/1102 | TOP5397 | CAGTACAGGAAAGACACGGCCAC | GGCCGUGUCUUUCCUGUACdTdT | GUACAGGAAAGACACGGCCdTdT | n.d. |
| 1103/1104 | TOP5398 | TACAGGAAAGACACGGCCACGTG | CGUGGCCGUGUCUUUCCUGdTdT | CAGGAAAGACACGGCCACGdTdT | n.d. |
| 1105/1106 | TOP5399 | CAGGAAAGACACGGCCACGTGGA | CACGUGGCCGUGUCUUUCCdTdT | GGAAAGACACGGCCACGUGdTdT | n.d. |
| 1107/1108 | TOP5400 | GAAAGACACGGCCACGTGGAAGG | UUCCACGUGGCCGUGUCUUdTdT | AAGACACGGCCACGUGGAAdTdT | n.d. |
| 1109/1110 | TOP5401 | AAAGACACGGCCACGTGGAAGGA | CUUCCACGUGGCCGUGUCUdTdT | AGACACGGCCACGUGGAAGdTdT | n.d. |
| 1111/1112 | TOP5402 | AAGACACGGCCACGTGGAAGGAC | CCUUCCACGUGGCCGUGUCdTdT | GACACGGCCACGUGGAAGGdTdT | n.d. |
| 1113/1114 | TOP5403 | GACACGGCCACGTGGAAGGACAG | GUCCUUCCACGUGGCCGUGdTdT | CACGGCCACGUGGAAGGACdTdT | n.d. |
| 1115/1116 | TOP5404 | CACGGCCACGTGGAAGGACAGCA | CUGUCCUUCCACGUGGCCGdTdT | CGGCCACGUGGAAGGACAGdTdT | n.d. |
| 1117/1118 | TOP5103 | CCACGTGGAAGGACAGCAA | UUGCUGUCCUUCCACGUGGdtdt | CCACGUGGAAGGACAGCAAdtdt | 20-40% |
| 1119/1120 | TOP5405 | CACGTGGAAGGACAGCAAGACCG | GUCUUGCUGUCCUUCCACGdTdT | CGUGGAAGGACAGCAAGACdTdT | n.d. |
| 1121/1122 | TOP5113 | ACGTGGAAGGACAGCAAGA | UCUUGCUGUCCUUCCACGUdtdt | ACGUGGAAGGACAGCAAGAdtdt | 20-40% |
| 1123/1124 | TOP5111 | GGAAGGACAGCAAGACCGA | UCGGUCUUGCUGUCCUUCCdtdt | GGAAGGACAGCAAGACCGAdtdt | 20-40% |
| 1125/1126 | TOP5406 | GAAGGACAGCAAGACCGAGACCC | GUCUCGGUCUUGCUGUCCUdTdT | AGGACAGCAAGACCGAGACdTdT | n.d. |
| 1127/1128 | TOP5407 | AAGGACAGCAAGACCGAGACCCT | GGUCUCGGUCUUGCUGUCCdTdT | GGACAGCAAGACCGAGACCdTdT | n.d. |
| 1129/1130 | TOP5118 | CAGGAGGGTGGGAGCCAGA | UCUGGCUCCCACCCUCCUGdtdt | CAGGAGGGUGGGAGCCAGAdtdt | <20% |
| 1131/1132 | TOP5408 | GACAGCAAGACCGAGACCCTCCA | GAGGGUCUCGGUCUUGCUGdTdT | CAGCAAGACCGAGACCCUCdTdT | n.d. |
| 1133/1134 | TOP5409 | CAGCAAGACCGAGACCCTCCAGA | UGGAGGGUCUCGGUCUUGCdTdT | GCAAGACCGAGACCCUCCAdTdT | n.d. |
| 1135/1136 | TOP5410 | CAAGACCGAGACCCTCCAGAACG | UUCUGGAGGGUCUCGGUCUdTdT | AGACCGAGACCCUCCAGAAdTdT | n.d. |
| 1137/1138 | TOP5411 | AAGACCGAGACCCTCCAGAACGC | GUUCUGGAGGGUCUCGGUCdTdT | GACCGAGACCCUCCAGAACdTdT | n.d. |
| 1139/1140 | TOP5412 | GACCGAGACCCTCCAGAACGCCC | GCGUUCUGGAGGGUCUCGGdTdT | CCGAGACCCUCCAGAACGCdTdT | n.d. |
| 1141/1142 | TOP5413 | GAGACCCTCCAGAACGCCCACAG | GUGGGCGUUCUGGAGGGUCdTdT | GACCCUCCAGAACGCCCACdTdT | n.d. |
| 1143/1144 | TOP5414 | GACCCTCCAGAACGCCCACAGCA | CUGUGGGCGUUCUGGAGGGdTdT | CCCUCCAGAACGCCCACAGdTdT | n.d. |
| 1145/1146 | TOP5415 | CAGAACGCCCACAGCATGGCCCT | GGCCAUGCUGUGGGCGUUCdTdT | GAACGCCCACAGCAUGGCCdTdT | n.d. |
| 1147/1148 | TOP5416 | GAACGCCCACAGCATGGCCCTGC | AGGGCCAUGCUGUGGGCGUdTdT | ACGCCCACAGCAUGGCCCUdTdT | n.d. |
| 1149/1150 | TOP5417 | AACGCCCACAGCATGGCCCTGCC | CAGGGCCAUGCUGUGGGCGdTdT | CGCCCACAGCAUGGCCCUGdTdT | n.d. |
| 1151/1152 | TOP5418 | CGCCCACAGCATGGCCCTG | CAGGGCCAUGCUGUGGGCGdtdt | CGCCCACAGCAUGGCCCUGdtdt | n.d. |
| 1153/1154 | TOP5419 | GAGCCCTCCACCAGGTACTGGGC | CCAGUACCUGGUGGAGGGCdTdT | GCCCUCCACCAGGUACUGGdTdT | n.d. |
| 1155/1156 | TOP5420 | CACCAGGTACTGGGCCAGGGTGA | ACCCUGGCCCAGUACCUGGdTdT | CCAGGUACUGGGCCAGGGUdTdT | n.d. |
| 1157/1158 | TOP5421 | CAGGTACTGGGCCAGGGTGAGGG | CUCACCCUGGCCCAGUACCdTdT | GGUACUGGGCCAGGGUGAGdTdT | n.d. |
| 1159/1160 | TOP5422 | CAGGGTGAGGGTCAGGACCTCCC | GAGGUCCUGACCCUCACCCdTdT | GGGUGAGGGUCAGGACCUCdTdT | n.d. |
| 1161/1162 | TOP5423 | GACCTCCCGCACCGGCTACAACG | UUGUAGCCGGUGCGGAGGdTdT | CCUCCCGCACCGGCUACAAdTdT | n.d. |
| 1163/1164 | TOP5424 | CACCGGCTACAACGGGATCTGGA | CAGAUCCCGUUGUAGCCGGdTdT | CCGGCUACAACGGGAUCUGdTdT | n.d. |
| 1165/1166 | TOP5425 | TACAACGGGATCTGGAGCGAGTG | CUCGCUCCAGAUCCCGUUGdTdT | CAACGGGAUCUGGAGCGAGdTdT | n.d. |
| 1167/1168 | TOP5426 | CAACGGGATCTGGAGCGAGTGGA | CACUCGCUCCAGAUCCCGUdTdT | ACGGGAUCUGGAGCGAGUGdTdT | n.d. |
| 1169/1170 | TOP5427 | AACGGGATCTGGAGCGAGTGGAG | CCACUCGCUCCAGAUCCCGdTdT | CGGGAUCUGGAGCGAGUGGdTdT | n.d. |
| 1171/1172 | TOP5428 | GATCTGGAGCGAGTGGAGTGAGG | UCACUCCACUCGCUCCAGAdTdT | UCUGGAGCGAGUGGAGUGAdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 1173/1174 | TOP5429 | GACACCGAGTCGGTGCTGCCTAT | AGGCAGCACCGACUCGGUGdTdT | CACCGAGUCGGUGCUGCCUdTdT | n.d. |
| 1175/1176 | TOP5430 | CACCGAGTCGGTGCTGCCTATGT | AUAGGCAGCACCGACUCGGdTdT | CCGAGUCGGUGCUGCCUAUdTdT | n.d. |
| 1177/1178 | TOP5431 | GAGTCGGTGCTGCCTATGTGGGT | CCACAUAGGCAGCACCGACdTdT | GUCGGUGCUGCCUAUGUGGdTdT | n.d. |
| 1179/1180 | TOP5432 | TATGTGGGTGCTGGCCCTCATCG | AUGAGGGCCAGCACCCACAdTdT | UGUGGGUGCUGGCCCUCAUdTdT | n.d. |
| 1181/1182 | TOP5433 | CATCGTGATCTTCCTCACCATCG | AUGGUGAGGAAGAUCACGAdTdT | UCGUGAUCUUCCUCACCAUdTdT | n.d. |
| 1183/1184 | TOP5434 | GATCTTCCTCACCATCGCTGTGC | ACAGCGAUGGUGAGGAAGAdTdT | UCUUCCUCACCAUCGCUGUdTdT | n.d. |
| 1185/1186 | TOP5435 | CACCATCGCTGTGCTCCTGGCCC | GCCAGGAGCACAGCGAUGGdTdT | CCAUCGCUGUGCUCCUGGCdTdT | n.d. |
| 1187/1188 | TOP5436 | CATCGCTGTGCTCCTGGCCCTCC | AGGGCCAGGAGCACAGCGAdTdT | UCGCUGUGCUCCUGGCCCUdTdT | n.d. |
| 1189/1190 | TOP5437 | CATCTACGGGTACAGGCTGCGCA | CGCAGCCUGUACCCGUAGAdTdT | UCUACGGGUACAGGCUGCGdTdT | n.d. |
| 1191/1192 | TOP5438 | TACGGGTACAGGCTGCGCAGAAA | UCUGCGCAGCCUGUACCCGdTdT | CGGGUACAGGCUGCGCAGAdTdT | n.d. |
| 1193/1194 | TOP5439 | GGGTACAGGCTGCGCAGAA | UUCUGCGCAGCCUGUACCCdtdt | GGGUACAGGCUGCGCAGAAdtdt | n.d. |
| 1195/1196 | TOP5440 | GGTACAGGCTGCGCAGAAA | UUUCUGCGCAGCCUGUACCdtdt | GGUACAGGCUGCGCAGAAAdtdt | n.d. |
| 1197/1198 | TOP5441 | TACAGGCTGCGCAGAAAGTGGGA | CCACUUUCUGCGCAGCCUGdTdT | CAGGCUGCGCAGAAAGUGGdTdT | n.d. |
| 1199/1200 | TOP5442 | CAGGCTGCGCAGAAAGTGGGAGG | UCCCACUUUCUGCGCAGCCdTdT | GGCUGCGCAGAAAGUGGGAdTdT | n.d. |
| 1201/1202 | TOP5443 | CGCAGAAAGTGGGAGGAGA | UCUCCUCCCACUUUCUGCGdtdt | CGCAGAAAGUGGGAGGAGAdtdt | n.d. |
| 1203/1204 | TOP5444 | GCAGAAAGTGGGAGGAGAA | UUCUCCUCCCACUUUCUGCdtdt | GCAGAAAGUGGGAGGAGAAdtdt | n.d. |
| 1205/1206 | TOP5445 | CAGAAAGTGGGAGGAGAAGATCC | AUCUUCUCCUCCCACUUUCdTdT | GAAAGUGGGAGGAGAAGAUdTdT | n.d. |
| 1207/1208 | TOP5446 | GAAAGTGGGAGGAGAAGATCCCC | GGAUCUUCUCCUCCCACUUdTdT | AAGUGGGAGGAGAAGAUCCdTdT | n.d. |
| 1209/1210 | TOP5447 | AAAGTGGGAGGAGAAGATCCCCA | GGGAUCUUCUCCUCCCACUdTdT | AGUGGGAGGAGAAGAUCCCdTdT | n.d. |
| 1211/1212 | TOP5448 | AAGTGGGAGGAGAAGATCCCCAA | GGGGAUCUUCUCCUCCCACdTdT | GUGGGAGGAGAAGAUCCCCdTdT | n.d. |
| 1213/1214 | TOP5449 | GAGGAGAAGATCCCCAACCCCAG | GGGGUUGGGGAUCUUCUCCdTdT | GGAGAAGAUCCCCAACCCCdTdT | n.d. |
| 1215/1216 | TOP5450 | GAGAAGATCCCCAACCCCAGCAA | GCUGGGGUUGGGGAUCUUCdTdT | GAAGAUCCCCAACCCCAGCdTdT | n.d. |
| 1217/1218 | TOP5451 | GAAGATCCCCAACCCCAGCAAGA | UUCCUGGGGUUGGGGAUCUdTdT | AGAUCCCCAACCCCAGCAAdTdT | n.d. |
| 1219/1220 | TOP5452 | AAGATCCCCAACCCCAGCAAGAG | CUUGCUGGGGUUGGGGAUCdTdT | GAUCCCCAACCCCAGCAAGdTdT | n.d. |
| 1221/1222 | TOP5453 | GATCCCCAACCCCAGCAAGAGCC | CUCUUGCUGGGGUUGGGGAdTdT | UCCCCAACCCCAGCAAGAGdTdT | n.d. |
| 1223/1224 | TOP5454 | CAACCCCAGCAAGAGCCACCTGT | AGGUGGCUCUUGCUGGGGUdTdT | ACCCCAGCAAGAGCCACCUdTdT | n.d. |
| 1225/1226 | TOP5455 | AACCCCAGCAAGAGCCACCTGTT | CAGGUGGCUCUUGCUGGGGdTdT | CCCCAGCAAGAGCCACCUGdTdT | n.d. |
| 1227/1228 | TOP5456 | CAGCAAGAGCCACCTGTTCCAGA | UGGAACAGGUGGCUCUUGCdTdT | GCAAGAGCCACCUGUUCCAdTdT | n.d. |
| 1229/1230 | TOP5457 | CAAGAGCCACCTGTTCCAGAACG | UUCUGGAACAGGUGGCUCUdTdT | AGAGCCACCUGUUCCAGAAdTdT | n.d. |
| 1231/1232 | TOP5458 | AAGAGCCACCTGTTCCAGAACGG | GUUCUGGAACAGGUGGCUCdTdT | GAGCCACCUGUUCCAGAACdTdT | n.d. |
| 1233/1234 | TOP5459 | GAGCCACCTGTTCCAGAACGGGA | CCGUUCUGGAACAGGUGGCdTdT | GCCACCUGUUCCAGAACGGdTdT | n.d. |
| 1235/1236 | TOP5460 | CACCTGTTCCAGAACGGGAGCGC | GCUCCCGUUCUGGAACAGGdTdT | CCUGUUCCAGAACGGGAGCdTdT | n.d. |
| 1237/1238 | TOP5461 | CAGAACGGGAGCGCAGAGCTTTG | AAGCUCUGCGCUCCCGUUCdTdT | GAACGGGAGCGCAGAGCUUdTdT | n.d. |
| 1239/1240 | TOP5462 | GAACGGGAGCGCAGAGCTTTGGC | CAAACCUCUGCCCUCCCGUdTdT | ACGGGAGCGCAGAGCUUUGdTdT | n.d. |
| 1241/1242 | TOP5463 | AACGGGAGCGCAGAGCTTTGGCC | CCAAAGCUCUGCGCUCCCGdTdT | CGGGAGCGCAGAGCUUUGGdTdT | n.d. |
| 1243/1244 | TOP5464 | CAGAGCTTTGGCCCCCAGGCAGC | UGCCUGGGGGCCAAAGCUCdTdT | GAGCUUUGGCCCCCAGGCAdTdT | n.d. |
| 1245/1246 | TOP5465 | CAGGCAGCATGTCGGCCTTCACT | UGAAGGCCGACAUGCUGCCdTdT | GGCAGCAUGUCGGCCUUCAdTdT | n.d. |
| 1247/1248 | TOP5466 | CAGCATGTCGGCCTTCACTAGCG | CUAGUGAAGGCCGACAUGCdTdT | GCAUGUCGGCCUUCACUAGdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 1249/1250 | TOP5467 | CATGTCGGCCTTCACTAGCGGGA | CCGCUAGUGAAGGCCGACAdTdT | UGUCGGCCUUCACUAGCGGAdTdT | n.d. |
| 1251/1252 | TOP5468 | CACTAGCGGGAGTCCCCCACACC | UGUGGGGGACUCCCGCUAGdTdT | CUAGCGGGAGUCCCCACACCdTdT | n.d |
| 1253/1254 | TOP5469 | GATCAAGAACCTAGACCAG | CUGGUCUAGGUUCUUGAUCdtdt | GAUCAAGAACCUAGACCAGdtdt | n.d. |
| 1255/1256 | TOP5470 | CAGCCGCTTCCCTGAGCTGGAGG | UCCAGCUCAGGGAAGCGGCdTdT | GCCGCUUCCCUGAGCUGGAdTdT | n.d. |
| 1257/1258 | TOP5471 | GGGTGTTCCCTGTAGGATT | AAUCCUAGAGGGAACACCCdtdt | GGGUGUUCCCUGUAGGAUUdtdt | n.d. |
| 1259/1260 | TOP5472 | GACAGCGAGGTGTCACCTCTCAC | GAGAGGUGACACCUCGCUGdTdT | CAGCGAGGUGUCACCUCUCdTdT | n.d. |
| 1261/1262 | TOP5473 | CAGCGAGGTGTCACCTCTCACCA | GUGAGAGGUGACACCUCGCdTdT | CCGAGGUGUCACCUCUCACdTdT | n.d. |
| 1263/1264 | TOP5474 | GAGGTGTCACCTCTCACCATAGA | UAUGGUGAGAGGUGACACCdTdT | GGUGUCACCUCUCACCAUAdTdT | n.d. |
| 1265/1266 | TOP5475 | CACCTCTCACCATAGAGGACCCC | GGUCCUCUAUGGUGAGAGGdTdT | CCUCUCACCAUAGAGGACCdTdT | n.d. |
| 1267/1268 | TOP5476 | CACCATAGAGGACCCCAAGCATG | UGCUUGGGGUCCUCUAUGGdTdT | CCAUAGAGGACCCCAAGCAdTdT | n.d. |
| 1269/1270 | TOP5477 | CATAGAGGACCCCAAGCATGTCT | ACAUGCUUGGGGUCCUCUAdTdT | UAGAGGACCCCAAGCAUGUdTdT | n.d. |
| 1271/1272 | TOP5478 | TAGAGGACCCCAAGCATGTCTGT | AGACAUGCUUGGGGUCCUCdTdT | GAGGACCCCAAGCAUGUCUdTdT | n.d. |
| 1273/1274 | TOP5479 | GAGGACCCCAAGCATGTCTGTGA | ACAGACAUGCUUGGGGUCCdTdT | GGACCCCAAGCAUGUCUGUdTdT | n.d. |
| 1275/1276 | TOP5480 | GACCCCAAGCATGTCTGTGATCC | AUCACAGACAUGCUUGGGGdTdT | CCCCAAGCAUGUCUGUGAUdTdT | n.d. |
| 1277/1278 | TOP5481 | CAAGCATGTCTGTGATCCACCAT | GGUGGAUCACAGACAUGCUdTdT | AGCAUGUCUGUGAUCCACCdTdT | n.d. |
| 1279/1280 | TOP5482 | AAGCATGTCTGTGATCCACCATC | UGGUGGAUCACAGACAUGCdTdT | GCAUGUCUGUGAUCCACCAdTdT | n.d. |
| 1281/1282 | TOP5483 | CATGTCTGTGATCCACCATCTGG | AGAUGGUGGAUCACAGACAdTdT | UGUCUGUGAUCCACCAUCUdTdT | n.d. |
| 1283/1284 | TOP5484 | GATCCACCATCTGGGCCTGACAC | CUCAGGCCCAGAUGGUGGAdTdT | UCCACCAUCUGGGCCUGACdTdT | n.d. |
| 1285/1286 | TOP5485 | CACCATCTGGGCCTGACACGACT | UCGUGUCAGGCCCAGAUGGdTdT | CCAUCUGGGCCUGACACGAdTdT | n.d. |
| 1287/1288 | TOP5486 | CATCTGGGCCTGACACGACTCCA | GAGUCGUGUCAGGCCCAGAdTdT | UCUGGGCCUGACACGACUCdTdT | n.d. |
| 1289/1290 | TOP5487 | GACACGACTCCAGCTGCCTCAGA | UGAGGCAGCUGGAGUCGUGdTdT | CACGACUCCAGCUGCCUCAdTdT | n.d. |
| 1291/1292 | TOP5488 | CACGACTCCAGCTGCCTCAGATC | UCUGAGGCAGCUGGAGUCGdTdT | CGACUCCAGCUGCCUCAGAdTdT | n.d. |
| 1293/1294 | TOP5489 | GACTCCAGCTGCCTCAGATCTAC | AGAUCUGAGGCAGCUGGAGdTdT | CUCCAGCUGCCUCAGAUCUdTdT | n.d. |
| 1295/1296 | TOP5490 | CAGCTGCCTCAGATCTACCCACA | UGGGUAGAUCUGAGGCAGCdTdT | GCUGCCUCAGAUCUACCCAdTdT | n.d. |
| 1297/1298 | TOP5491 | CCTCAGATCTACCCACAGA | UCUGUGGGUAGAUCUGAGGdtdt | CCUCAGAUCUACCCACAGAdtdt | n.d. |
| 1299/1300 | TOP5492 | CAGATCTACCCACAGAGCAGCCC | GCUGCUCUGUGGGUAGAUCdTdT | GAUCUACCCACAGAGCAGCdTdT | n.d. |
| 1301/1302 | TOP5493 | GATCTACCCACAGAGCAGCCCCC | GGGCUGCUCUGUGGGUAGAdTdT | UCUACCCACAGAGCAGCCCdTdT | n.d. |
| 1303/1304 | TOP5494 | CTCCCACACACCTGAGAAA | UUUCUCAGGUGUGUGGGAGdtdt | CUCCCACACCUGAGAAAdtdt | n.d. |
| 1305/1306 | TOP5495 | CCCACACACCTGAGAAACA | UGUUUCUCAGGUGUGUGGGdtdt | CCCACACACCUGAGAAACAdtdt | n.d. |
| 1307/1308 | TOP5496 | CACACACCTGAGAAACAGGCTTC | AGCCUGUUUCUCAGGUGUGdTdT | CACACCUGAGAAACAGGCUdTdT | n.d. |
| 1309/1310 | TOP5497 | CACACCTGAGAAACAGGCTTCCA | GAAGCCUGUUUCUCAGGUGdTdT | CACCUGAGAAACACGCUUCdTdT | n.d. |
| 1311/1312 | TOP5498 | CACCTGAGAAACAGGCTTCCAGC | UGGAAGCCUGUUUCUCAGGdTdT | CCUGAGAAACAGGCUUCCAdTdT | n.d. |
| 1313/1314 | TOP5499 | GAGAAACAGGCTTCCAGCTTTGA | AAAGCUGGAAGCCUGUUUCdTdT | GAAACAGGCUUCCAGCUUUdTdT | n.d. |
| 1315/1316 | TOP5500 | AGAAACAGGCTTCCAGCTT | AAGCUGGAAGCCUGUUUCUdtdt | AGAAACAGGCUUCCAGCUUdtdt | n.d. |
| 1317/1318 | TOP5501 | GAAACAGGCTTCCAGCTTTGACT | UCAAAGCUGGAAGCCUGUUdTdT | AACAGGCUUCCAGCUUUGAdTdT | n.d. |
| 1319/1320 | TOP5502 | AAACAGGCTTCCAGCTTTGACTT | GUCAAAGCUGGAAGCCUGUdTdT | ACAGGCUUCCAGCUUUGACdTdT | n.d. |
| 1321/1322 | TOP5503 | AACAGGCTTCCAGCTTTGACTTC | AGUCAAAGCUGGAAGCCUGdTdT | CAGCCUUCCACCUUUGACUdTdT | n.d. |
| 1323/1324 | TOP5504 | CAGGCTTCCAGCTTTGACTTCAA | GAAGUCAAAGCUGGAAGCCdTdT | GGCUUCCAGCUUUGACUUCdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 1325/1326 | TOP5505 | CAGCTTTGACTTCAATGGGCCCT | GGGCCCAUUGAAGUCAAAGCdTdT | GCUUUGACUUCAAUGGGCCCdTdT | n.d. |
| 1327/1328 | TOP5506 | GACTTCAATGGGCCCTACCTGGG | CAGGUAGGGCCCAUUGAAGdTdT | CUUCAAUGGGCCCUACCUGdTdT | n.d. |
| 1329/1330 | TOP5507 | CACAGCCGCTCCCTACCTGACAT | GUCAGGUAGGGAGCGGCUGdTdT | CAGCCGCUCCCUACCUGACdTdT | n.d. |
| 1331/1332 | TOP5508 | CAGCCGCTCCCTACCTGACATCC | AUGUCAGGUAGGGAGCGGCdTdT | GCCGCUCCCUACCUGACAUdTdT | n.d. |
| 1333/1334 | TOP5509 | TACCTGACATCCTGGGCCAGCCG | GCUGGCCCAGGAUGUCAGGdTdT | CCUGACAUCCUGGGCCAGCdTdT | n.d. |
| 1335/1336 | TOP5510 | CACAGGAGGGTGGGAGCCAGAAG | UCUGGCUCCCACCCUCCUGdTdT | CAGGAGGGUGGGAGCCAGAdTdT | n.d. |
| 1337/1338 | TOP5511 | CAGGAGGGTGGGAGCCAGAAGTC | CUUCUGGCUCCCACCCUCCdTdT | GGAGGGUGGGAGCCAGAAGdTdT | n.d. |
| 1339/1340 | TOP5512 | GAGGGTGGGAGCCAGAAGTCCCC | GGACUUCUGGCUCCCACCCdTdT | GGGUGGGAGCCAGAAGUCCdTdT | n.d. |
| 1341/1342 | TOP5513 | GAGCCAGAAGTCCCCACCTCCAG | GGAGGUGGGGACUUCUGGCdTdT | GCCAGAAGUCCCCACCUCCdTdT | n.d. |
| 1343/1344 | TOP5514 | CAGAAGTCCCCACCTCCAGGGTC | CCCUGGAGGUGGGGACUUCdTdT | GAAGUCCCCACCUCCAGGGdTdT | n.d. |
| 1345/1346 | TOP5515 | GAAGTCCCCACCTCCAGGGTCCC | GACCCUGGAGGUGGGGACUdTdT | AGUCCCCACCUCCAGGGUCdTdT | n.d. |
| 1347/1348 | TOP5516 | AAGTCCCCACCTCCAGGGTCCCT | GGACCCUGGAGGUGGGGACdTdT | GUCCCCACCUCCAGGGUCCdTdT | n.d. |
| 1349/1350 | TOP5517 | CACCTCCAGGGTCCCTGGAGTAC | ACUCCAGGGACCCUGGAGGdTdT | CCUCCAGGGUCCCUGGAGUdTdT | n.d. |
| 1351/1352 | TOP5518 | CAGGGTCCCTGGAGTACCTGTGT | ACAGGUACUCCAGGGACCCdTdT | GGGUCCCUGGAGUACCUGUdTdT | n.d. |
| 1353/1354 | TOP5519 | GAGTACCTGTGTCTGCCTGCTGG | AGCAGGCAGACACAGGUACdTdT | GUACCUGUGUCUGCCUGCUdTdT | n.d. |
| 1355/1356 | TOP5520 | GTACCTGTGTCTGCCTGCT | AGCAGGCAGACACAGGUACdtdt | GUACCUGUGUCUGCCUGCUdtdt | n.d. |
| 1357/1358 | TOP5521 | CAGGTGCAACTGGTCCCTCTGGC | CAGAGGGACCAGUUGCACCdTdT | GGUGCAACUGGUCCCUCUGdTdT | n.d. |
| 1359/1360 | TOP5522 | CAACTGGTCCCTCTGGCCCAGGC | CUGGGCCAGAGGGACCAGUdTdT | ACUGGUCCCUCUGGCCCAGdTdT | n.d. |
| 1361/1362 | TOP5523 | AACTGGTCCCTCTGGCCCAGGCG | CCUGGGCCAGAGGGACCAGdTdT | CUGGUCCCUCUGGCCCAGGdTdT | n.d. |
| 1363/1364 | TOP5524 | CAGGCGATGGGACCAGGACAGGC | CUGUCCUGGUCCCAUCGCCdTdT | GGCGAUGGGACCAGGACAGdTdT | n.d. |
| 1365/1366 | TOP5525 | GATGGGACCAGGACAGGCCGTGG | ACGGCCUGUCCUGGUCCCAdTdT | UGGGACCAGGACAGGCCGUdTdT | n.d. |
| 1367/1368 | TOP5526 | GACCAGGACAGGCCGTGGAAGTG | CUUCCACGGCCUGUCCUGGdTdT | CCAGGACAGGCCGUGGAAGdTdT | n.d. |
| 1369/1370 | TOP5527 | CAGGACAGGCCGTGGAAGTGGAG | CCACUUCCACGGCCUGUCCdTdT | GGACAGGCCGUGGAAGUGGdTdT | n.d. |
| 1371/1372 | TOP5528 | GACAGGCCGTGGAAGTGGAGAGA | UCUCCACUUCCACGGCCUGdTdT | CAGGCCGUGGAAGUGGAGAdTdT | n.d. |
| 1373/1374 | TOP5529 | CAGGCCGTGGAAGTGGAGAGAAG | UCUCUCCACUUCCACGGCCdTdT | GGCCGUGGAAGUGGAGAGAdTdT | n.d. |
| 1375/1376 | TOP5530 | GCCGTGGAAGTGGAGAGAA | UUCUCUCCACUUCCACGGCdtdt | GCCGUGGAAGUGGAGAGAAdtdt | n.d. |
| 1377/1378 | TOP5531 | GAAGTGGAGAGAAGGCCGAGCCA | GCUCGGCCUUCUCUCCACUdTdT | AGUGGAGAGAAGGCCGAGCdTdT | n.d. |
| 1379/1380 | TOP5532 | AAGTGGAGAGAAGGCCGAGCCAG | GGCUCGGCCUUCUCUCCACdTdT | GUGGAGAGAAGGCCGAGCCdTdT | n.d. |
| 1381/1382 | TOP5533 | CAGGGAGTCCCTCCCTGGAGTCC | ACUCCAGGGAGGGACUCCCdTdT | GGGAGUCCCUCCCUGGAGUdTdT | n.d. |
| 1383/1384 | TOP5534 | GGCCAAGGGTGGGAGGACA | UGUCCUCCCACCCUUGGCCdtdt | GGCCAAGGGUGGGAGGACAdtdt | n.d. |
| 1385/1386 | TOP5535 | CAAGGGTGGGAGGACAGGACCAA | GGUCCUGUCCUCCCACCCUdTdT | AGGGUGGGAGGACAGGACCdTdT | n.d. |
| 1387/1388 | TOP5536 | AAGGGTGGGAGGACAGGACCAAA | UGGUCCUGUCCUCCCACCCdTdT | GGGUGGGAGGACAGGACCAdTdT | n.d. |
| 1389/1390 | TOP5537 | GAGGACAGGACCAAAAGGACAGC | UGUCCUUUUGGUCCUGUCCdTdT | GGACAGGACCAAAAGGACAdTdT | n.d. |
| 1391/1392 | TOP5538 | GACAGGACCAAAAGGACAGCCCT | GGCUGUCCUUUUGGUCCUGdTdT | CAGGACCAAAAGGACAGCCdTdT | n.d. |
| 1393/1394 | TOP5539 | CAGGACCAAAAGGACAGCCCTGT | AGGGCUGUCCUUUUGGUCCdTdT | GGACCAAAAGGACAGCCCUdTdT | n.d. |
| 1395/1396 | TOP5540 | GACCAAAAGGACAGCCCTGTGGC | CACAGGGCUGUCCUUUUGGdTdT | CCAAAAGGACAGCCCUGUGdTdT | n.d. |
| 1397/1398 | TOP5541 | CAAAAGGACAGCCCTGTGGCTAT | AGCCACAGGGCUGUCCUUUdTdT | AAAGGACAGCCCUGUGGCUdTdT | n.d. |
| 1399/1400 | TOP5542 | AAAAGGACAGCCCTGTGGCTATA | UAGCCACAGGGCUGUCCUUdTdT | AAGGACAGCCCUGUGGCUAdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 1401/1402 | TOP5543 | AAAGGACAGCCCTGTGGCTATAC | AUAGCCACAGGGCUGUCCUdTdT | AGGACAGCCCUGUGGCUAUAdTdT | n.d. |
| 1403/1404 | TOP5544 | AAGGACAGCCCTGTGGCTATACC | UAUAGCCACAGGGCUGUCCdTdT | GGACAGCCCUGUGGCUAUAdTdT | n.d. |
| 1405/1406 | TOP5545 | GACAGCCCTGTGGCTATACCCAT | GGGUAUAGCCACAGGGCUGdTdT | CAGCCCUGUGGCUAUACCCdTdT | n.d. |
| 1407/1408 | TOP5546 | CAGCCCTGTGGCTATACCCATGA | AUGGGUAUAGCCACAGGGCdTdT | GCCCUGUGGCUAUACCCAUdTdT | n.d. |
| 1409/1410 | TOP5547 | GACACTGAGGACCCTGGAGTGGC | CACUCCAGGGUCCUCAGUGdTdT | CACUGAGGACCCUGGAGUGdTdT | n.d. |
| 1411/1412 | TOP5548 | CACTGAGGACCCTGGAGTGGCCT | GCCACUCCAGGGUCCUCAGdTdT | CUGAGGACCCUGGAGUGGCdTdT | n.d. |
| 1413/1414 | TOP5549 | GAGGACCCTGGAGTGGCCTCTGG | AGAGGCCACUCCAGGGUCCdTdT | GGACCCUGGAGUGGCCUCUdTdT | n.d. |
| 1415/1416 | TOP5550 | GACCCTGGAGTGGCCTCTGGTTA | ACCAGAGGCCACUCCAGGGdTdT | CCCUGGAGUGGCCUCUGGUdTdT | n.d. |
| 1417/1418 | TOP5551 | CTGGAGTGGCCTCTGGTTA | UAACCAGAGGCCACUCCAGdtdt | CUGGAGUGGCCUCUGGUUAdtdt | n.d. |
| 1419/1420 | TOP5552 | TGGACTGCCTCTGGTTAT | AUAACCAGAGGCCACUCCAdtdt | UGGAGUGGCCUCUGGUUAUdtdt | n.d. |
| 1421/1422 | TOP5553 | GAGTGGCCTCTGGTTATGTCTCC | AGACAUAACCAGAGGCCAdTdT | GUGGCCUCUGGUUAUGUCUdTdT | n.d. |
| 1423/1424 | TOP5554 | TATGTCTCCTCTGCAGACCTGGT | CAGGUCUGCAGAGGAGACAdTdT | UGUCUCCUCUGCAGACCUGdTdT | n.d. |
| 1425/1426 | TOP5555 | CAGACCTGGTATTCACCCCAAAC | UUGGGGUGAAUACCAGGUCdTdT | GACCUGGUAUUCACCCCAAdTdT | n.d. |
| 1427/1428 | TOP5556 | GACCTGGTATTCACCCCAAACTC | GUUUGGGGUGAAUACCAGGdTdT | CCUGGUAUUCACCCCAAACdTdT | n.d. |
| 1429/1430 | TOP5557 | TAGTTCCCTCTCTGGGCCTCCCC | GGAGGCCCAGAGAGGGAACdTdT | GUUCCCUCUCUGGGCCUCCdTdT | n.d. |
| 1431/1432 | TOP5558 | CAGACCAGACCCCCAGCTTATGT | AUAAGCUGGGGGUCUGGUCdTdT | GACCAGACCCCCAGCUUAUdTdT | n.d. |
| 1433/1434 | TOP5559 | GACCAGACCCCCAGCTTATGTCC | ACAUAAGCUGGGGGUCUGGdTdT | CCAGACCCCCAGCUUAUGUdTdT | n.d. |
| 1435/1436 | TOP5560 | CAGACCCCCAGCTTATGTCCTGG | AGGACAUAAGCUGGGGGUCdTdT | GACCCCCAGCUUAUGUCCUdTdT | n.d. |
| 1437/1438 | TOP5561 | GACCCCCAGCTTATGTCCTGGGC | CCAGGACAUAAGCUGGGGGdTdT | CCCCCAGCUUAUGUCCUGGdTdT | n.d. |
| 1439/1440 | TOP5562 | CAGCTTATGTCCTGGGCTGGCCA | GCCAGCCCAGGACAUAAGCdTdT | GCUUAUGUCCUGGGCUGGCdTdT | n.d. |
| 1441/1442 | TOP5563 | TATGTCCTGGGCTGGCCAGTGGA | CACUGGCCAGCCCAGGACAdTdT | UGUCCUGGGCUGGCCAGUGdTdT | n.d. |
| 1443/1444 | TOP5564 | GAGCCCCAGGCCCTGTGAAGTCA | ACUUCACAGGGCCUGGGGCdTdT | GCCCCAGGCCCUGUGAAGUdTdT | n.d. |
| 1445/1446 | TOP5565 | CAGGCCCTGTGAAGTCAGGGTTT | ACCCUGACUUCACAGGGCCdTdT | GGCCCUGUGAAGUCAGGGUdTdT | n.d. |
| 1447/1448 | TOP5566 | GAAGTCAGGGTTTGAGGGCTATG | UAGCCCUCAAACCCUGACUdTdT | AGUCAGGGUUUGAGGGCUAdTdT | n.d. |
| 1449/1450 | TOP5567 | AAGTCAGGGTTTGAGGGCTATGT | AUAGCCCUCAAACCCUGACdTdT | GUCAGGGUUUGAGGGCUAUdTdT | n.d. |
| 1451/1452 | TOP5568 | CAGGGTTTGAGGGCTATGTGGAG | CCACAUAGCCCUCAAACCCdTdT | GGGUUUGAGGGCUAUGUGGdTdT | n.d. |
| 1453/1454 | TOP5569 | GAGGGCTATGTGGAGCTCCCTCC | AGGGAGCUCCACAUAGCCCdTdT | GGGCUAUGUGGAGCUCCCUdTdT | n.d. |
| 1455/1456 | TOP5570 | TATGTGGAGCTCCCTCCAATTGA | AAUUGGAGGGAGCUCCACAdTdT | UGUGGAGCUCCCUCCAAUUdTdT | n.d. |
| 1457/1458 | TOP5571 | GAGCTCCCTCCAATTGAGGGCCG | GCCCUCAAUUGGAGGGAGCdTdT | GCUCCCUCCAAUUGAGGGCdTdT | n.d. |
| 1459/1460 | TOP5572 | CAATTGAGGGCCGGTCCCCCAGG | UGGGGGACCGGCCCUCAAUdTdT | AUUGAGGGCCGGUCCCCCAdTdT | n.d. |
| 1461/1462 | TOP5573 | AATTGAGGGCCGGTCCCCCAGGT | CUGGGGGACCGGCCCUCAAdTdT | UUGAGGGCCGGUCCCCCAGdTdT | n.d. |
| 1463/1464 | TOP5574 | CAGGTCACCAAGGAACAATCCTG | GGAUUGUUCCUUGGUGACCdTdT | GGUCACCAAGGAACAAUCCdTdT | n.d. |
| 1465/1466 | TOP5575 | CACCAAGGAACAATCCTGTCCCC | GGACAGGAUUGUUCCUUGGdTdT | CCAAGGAACAAUCCUGUCCdTdT | n.d. |
| 1467/1468 | TOP5576 | CAAGGAACAATCCTGTCCCCCCT | GGGGGACAGGAUUGUUCCUdTdT | AGGAACAAUCCUGUCCCCCdTdT | n.d. |
| 1469/1470 | TOP5577 | AAGGAACAATCCTGTCCCCCCTG | GGGGGGACAGGAUUGUUCCdTdT | GGAACAAUCCUGUCCCCCCdTdT | n.d. |
| 1471/1472 | TOP5578 | GAACAATCCTGTCCCCCCTGAGG | UCAGGGGGACAGGAUUGUdTdT | ACAAUCCUGUCCCCCCUGAdTdT | n.d. |
| 1473/1474 | TOP5579 | AACAATCCTGTCCCCCCTGAGGC | CUCAGGGGGACAGGAUUGUdTdT | CAAUCCUGUCCCCCCUGAGdTdT | n.d. |
| 1475/1476 | TOP5580 | CAATCCTGTCCCCCCTGAGGCCA | GCCUCAGGGGGACAGGAUdTdT | AUCCUGUCCCCCCUGAGGCdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 1477/1478 | TOP5581 | AATCCTGTCCCCCCTGAGGCCAA | GGCCUCAGGGGGGACAGGAdTdT | UCCUGUCCCCCCUGAGGCCdTdT | n.d. |
| 1479/1480 | TOP5582 | GAGGCCAAAAGCCCTGTCCTGAA | CAGGACAGGGCUUUUGGCCdTdT | GGCCAAAAGCCCUGUCCUGdTdT | n.d. |
| 1481/1482 | TOP5583 | CAAAAGCCCTGTCCTGAACCCAG | GGGUUCAGGACAGGGCUUUdTdT | AAAGCCCUGUCCUGAACCCdTdT | n.d. |
| 1483/1484 | TOP5584 | AAAAGCCCTGTCCTGAACCCAGG | UGGGUUCAGGACAGGGCUUdTdT | AAGCCCUGUCCUGAACCCAdTdT | n.d. |
| 1485/1486 | TOP5585 | AAAGCCCTGTCCTGAACCCAGGG | CUGGGUUCAGGACAGGGCUdTdT | AGCCCUGUCCUGAACCCAGdTdT | n.d. |
| 1487/1488 | TOP5586 | GAACGCCCGGCAGATGTGTCCCC | GGACACAUCUGCCGGGCGUdTdT | ACGCCCGGCAGAUGUGUCCdTdT | n.d. |
| 1489/1490 | TOP5587 | AACGCCCGGCAGATGTGTCCCCA | GGGACACAUCUGCCGGGCGdTdT | CGCCCGGCAGAUGUGUCCCdTdT | n.d. |
| 1491/1492 | TOP5588 | CAGATGTGTCCCCAACATCCCCA | GGGAUGUUGGGGACACAUCdTdT | GAUGUGUCCCCAACAUCCCdTdT | n.d. |
| 1493/1494 | TOP5589 | GATGTGTCCCCAACATCCCCACA | UGGGGAUGUUGGGGACACAdTdT | UGUGUCCCCAACAUCCCCAdTdT | n.d. |
| 1495/1496 | TOP5590 | CAACATCCCCACAGCCCGAGGGC | CCUCGGGCUGUGGGGAUGUdTdT | ACAUCCCCACAGCCCGAGGdTdT | n.d. |
| 1497/1498 | TOP5591 | AACATCCCCACAGCCCGAGGGCC | CCCUCGGGCUGUGGGGAUGdTdT | CAUCCCCACAGCCCGAGGGdTdT | n.d. |
| 1499/1500 | TOP5592 | GAGGGCCTCCTTGTCCTGCAGCA | CUGCAGGACAAGGAGGCCCdTdT | GGGCCUCCUUGUCCUGCAGdTdT | n.d. |
| 1501/1502 | TOP5593 | GCAGCAAGTGGGCGACTAT | AUAGUCGCCCACUUGCUGCdtdt | GCAGCAAGUGGGCGACUAUdtdt | n.d. |
| 1503/1504 | TOP5594 | CAGCAAGTGGGCGACTATTGCTT | GCAAUAGUCGCCCACUUGCdTdT | GCAAGUGGGCGACUAUUGCdTdT | n.d. |
| 1505/1506 | TOP5595 | CAAGTGGGCGACTATTGCTTCCT | GAAGCAAUAGUCGCCCACUdTdT | AGUGGGCGACUAUUGCUUCdTdT | n.d. |
| 1507/1508 | TOP5596 | AAGTGGGCGACTATTGCTTCCTC | GGAAGCAAUAGUCGCCCACdTdT | GUGGGCGACUAUUGCUUCCdTdT | n.d. |
| 1509/1510 | TOP5597 | GACTATTGCTTCCTCCCCGGCCT | GCCGGGGAGGAAGCAAUAGdTdT | CUAUUGCUUCCUCCCCGGCdTdT | n.d. |
| 1511/1512 | TOP5598 | TATTGCTTCCTCCCCGGCCTGGG | CAGGCCGGGGAGGAAGCAAdTdT | UUGCUUCCUCCCCGGCCUGdTdT | n.d. |
| 1513/1514 | TOP5599 | GAGTAAACCTTCTTCCCCGGGAC | CCCGGGGAAGAAGGUUUACdTdT | GUAAACCUUCUUCCCCGGdTdT | n.d. |
| 1515/1516 | TOP5600 | TAAACCTTCTTCCCCGGGACCCG | GGUCCCGGGGAAGAAGGUUdTdT | AACCUUCUUCCCCGGGACCdTdT | n.d. |
| 1517/1518 | TOP5601 | AAACCTTCTTCCCCGGGACCCGG | GGGUCCCGGGGAAGAAGGUdTdT | ACCUUCUUCCCCGGGACCCdTdT | n.d. |
| 1519/1520 | TOP5602 | AACCTTCTTCCCCGGGACCCGGT | CGGGUCCCGGGGAAGAAGGdTdT | CCUUCUUCCCCGGGACCCGdTdT | n.d. |
| 1521/1522 | TOP5603 | GACCCGGTCCTGAGATCAAGAAC | UCUUGAUCUCAGGACCGGGdTdT | CCCGGUCCUGAGAUCAAGAdTdT | n.d. |
| 1523/1524 | TOP5604 | GAGATCAAGAACCTAGACCAGGC | CUGGUCUAGGUUCUUGAUCdTdT | GAUCAAGAACCUAGACCAGdTdT | n.d. |
| 1525/1525 | TOP5605 | GATCAAGAACCTAGACCAGGCTT | GCCUGGUCUAGGUUCUUGAdTdT | UCAAGAACCUAGACCAGGCdTdT | n.d. |
| 1527/1528 | TOP5606 | CAAGAACCTAGACCAGGCTTTTC | AAAGCCUGGUCUAGGUUCUdTdT | AGAACCUAGACCAGGCUUUdTdT | n_d. |
| 1529/1530 | TOP5607 | AAGAACCTAGACCAGGCTTTTCA | AAAAGCCUGGUCUAGGUUCdTdT | GAACCUAGACCAGGCUUUUdTdT | n.d. |
| 1531/1532 | TOP5608 | GAACCTAGACCAGGCTTTTCAAG | UGAAAAGCCUGGUCUAGGUdTdT | ACCUAGACCAGGCUUUUCAdTdT | n.d. |
| 1533/1534 | TOP5609 | AACCTAGACCAGGCTTTTCAAGT | UUGAAAAGCCUGGUCUAGGdTdT | CCUAGACCAGGCUUUUCAAdTdT | n.d. |
| 1535/1536 | TOP5610 | TAGACCAGGCTTTTCAAGTCAAG | UGACUUGAAAAGCCUGGUCdTdT | GACCAGGCUUUUCAAGUCAdTdT | n.d. |
| 1537/1538 | TOP5611 | GACCAGGCTTTTCAAGTCAAGAA | CUUGACUUGAAAAGCCUGGdTdT | CCAGGCUUUUCAAGUCAAGdTdT | n.d. |
| 1539/1540 | TOP5612 | CAGGCTTTTCAAGTCAAGAAGCC | CUUCUUGACUUGAAAAGCCdTdT | GGCUUUUCAAGUCAAGAAGdTdT | n.d. |
| 1541/1542 | TOP5613 | CAAGTCAAGAAGCCCCCAGGCCA | GCCUGGGGGCUUCUUGACUdTdT | AGUCAAGAAGCCCCCAGGCdTdT | n.d. |
| 1543/1544 | TOP5614 | AAGTCAAGAAGCCCCCAGGCCAG | GGCUGGGGGCUUCUUGACUdTdT | GUCAAGAAGCCCCCAGGCCdTdT | n.d. |
| 1545/1546 | TOP5615 | AAGAAGCCCCCAGGCCAGGCTGT | AGCCUGGCCUGGGGGCUUCdTdT | GAAGCCCCCAGGCCAGGCUdTdT | n.d. |
| 1547/1548 | TOP5616 | CAGGTGCCCGTCATTCAGCTCTT | GAGCUGAAUGACGGGCACCdTdT | GGUGCCCGUCAUUCAGCUCdTdT | n.d. |
| 1549/1550 | TOP5617 | CCGTCATTCAGCTCTTCAA | UUGAAGAGCUGAAUGACGGdtdt | CCGUCAUUCAGCUCUUCAAdtdt | n.d. |
| 1551/1552 | TOP5618 | CATTCAGCTCTTCAAAGCCCTGA | AGGGCUUUGAAGAGCUGAAdTdT | UUCAGCUCUUCAAAGCCCUdTdT | n.d. |

TABLE 2a-continued

| SEQ ID Nos (antisense/sense) | siRNA ID NUMBER | Target sequence (5'-3') | Antisense strand (5'-3') | Sense strand (5'-3') | β-chain mRNA Inhibition |
|---|---|---|---|---|---|
| 1553/1554 | TOP5619 | CAGCTCTTCAAAGCCCTGAAGCA | CUUCAGGGCUUUGAAGAGCdTdT | GCUCUUCAAAGCCCUGAAGdTdT | n.d. |
| 1555/1556 | TOP5620 | CAAAGCCCTGAAGCAGCAGGACT | UCCUGCUGCUUCAGGGCUUdTdT | AAGCCCUGAAGCAGCAGGAdTdT | n.d. |
| 1557/1558 | TOP5621 | AAAGCCCTGAAGCAGCAGGACTA | GUCCUGCUGCUUCAGGGCUdTdT | AGCCCUGAAGCAGCAGGACdTdT | n.d. |
| 1559/1560 | TOP5622 | AAGCCCTGAAGCAGCAGGACTAC | AGUCCUGCUGCUUCAGGGCdTdT | GCCCUGAAGCAGCAGGACUdTdT | n.d. |
| 1561/1562 | TOP5623 | GAAGCAGCAGGACTACCTGTCTC | GACAGGUAGUCCUGCUGCUdTdT | AGCAGCAGGACUACCUGUCdTdT | n.d. |
| 1563/1564 | TOP5624 | AAGCAGCAGGACTACCTGTCTCT | AGACAGGUAGUCCUGCUGCdTdT | GCAGCAGGACUACCUGUCUdTdT | n.d. |
| 1565/1566 | TOP5625 | CAGCAGGACTACCTGTCTCTGCC | CAGAGACAGGUAGUCCUGCdTdT | GCAGGACUACCUGUCUCUGdTdT | n.d. |
| 1567/1568 | TOP5626 | CAGGACTACCTGTCTCTGCCCCC | GGGCAGAGACAGGUAGUCCdTdT | GGACUACCUGUCUCUGCCCdTdT | n.d. |
| 1569/1570 | TOP5627 | GACTACCTGTCTCTGCCCCCTTG | AGGGGGCAGAGACAGGUAGdTdT | CUACCUGUCUCUGCCCCCUdTdT | n.d. |
| 1571/1572 | TOP5628 | TACCTGTCTCTGCCCCCTTGGGA | CCAAGGGGGCAGAGACAGGdTdT | CCUGUCUCUGCCCCCUUGGdTdT | n.d. | n.d.: not-determined

TABLE 2b

| SEQ ID Nos (antisense/sense) | siRNA ID NUMBER | Target sequence (5'-3') | Antisense strand (5'-3') | Sense strand (5'-3') | CCR3 mRNA Inhibition |
|---|---|---|---|---|---|
| 1573/1574 | [1]siCCR3_1HP | CCGAATTATGACCAACATCTA | UAGAUGUUGGUCAUAAUUCgg | GAAUUAUGACCAACAUCUAtt | >40% |
| 1575/1576 | [2]siCCR3_1137 | AAGGCCATCCGGCTCATTTTT | AAAAAUGAGCCGGAUGGCCUUtt | AAGGCCAUCCGGCUCAUUUUUtt | 20-40% |
| 1577/1578 | [2]siCCR3_1320 | AACCCGGTGATCTACGCCTTT | AAAGGCGUAGAUCACCGGGUUtt | AACCCGGUGAUCUACGCCUUUtt | 20-40% |

RNA: UPPER CASE; dna: lower case
[1]Designed by Qiagen HP OnGuard siRNA Design (Genome Wide)
[2]Designed using Qiagen siRNA design tool (standard Tuschl-based design)
Thermo scientific Dharmacon RNAi Technologies siDESIGN Center (Custom siRNA Design Tool).

TABLE 3a

| Seq ID number | Antisense ID | Sequence (5'-3') | β-chain mRNA inhibition | β-chain protein inhibition | Relative stability in 50% FBS |
|---|---|---|---|---|---|
| 1579 | TOP057-F1 | PS-GAccgagctggccacCTCC | − | n.d. | n.d. |
| 1580 | TOP057-F2 | PS-GACcgagCTGgccaccTCC | − | n.d. | n.d. |
| 1581 | TOP062-F1 | PS-CTCTCCacttccacGGCCTG | − | n.d. | + |
| 1582 | TOP062-F2 | PS-CTctccacttccacggCCTG | = | = | + |
| 1583 | TOP062-F3 | PS-ctctccacttccacggCCTG | = | + | − |
| 1584 | TOP062-F4 | PS-CTCtccacttccacggcCTG | = | = | − |
| 1585 | TOP062-F5 | PS-CTctccaCTTccacggCCTG | = | n.d. | − |
| 1586 | TOP062-F6 | PS-CtCtCcacttccacgGcCtG | = | n.d. | + |
| 1587 | TOP062-F7 | PS-ctctccaCTTCCAcggcctg | = | = | + |
| 1588 | TOP062-F8 | PS-ctctcCACttccACGgcctg | = | − | + |
| 1589 | TOP062-F9 | ctctcCACttccACGgcctg | − | n.d. | − |
| 1590 | TOP062-F10 | CTCtccactt<u>cca</u>cggcCTG | − | n.d. | − |
| 1591 | TOP062-F11 | PS-cTcTcCaCtTcCaCgGcCtG | − | n.d. | + |
| 1592 | TOP062-F12 | PS-CTctCCacTTccACggCCTG | − | n.d. | − |

TABLE 3a-continued

| Seq ID number | Antisense ID | Sequence (5'-3') | β-chain mRNA inhibition | β-chain protein inhibition | Relative stability in 50% FBS |
|---|---|---|---|---|---|
| 1593 | TOP062-F13 | ctctcCActtccaCGgcctg | = | n.d. | n.d. |
| 1594 | TOP062-F14 | ct__ctc__CAC__ttcc__ACG__cc__tg | = | n.d. | n.d. |
| 1595 | TOP062-F15 | ctc__tc__CACttcc__ACG__cc__tg | = | n.d. | n.d. |
| 1596 | TOP062-F16 | ctc__tcca__CTTCCAc__gg__cctg | = | n.d. | n.d. |
| 1597 | TOP062-F17 | ctct__cca__CTTCCAc__gg__cctg | = | n.d. | n.d. |
| 1598 | TOP062-F18 | ctct__cca__CTTCCAc__gg__cctg | = | n.d. | n.d. |

Lower case letters = DNA; BOLD UPPERCASE LETTERS = 2'F-ANA
Phosphodiester linkage = underlined; All phosphorothioate linkages = prefix PS-
(+/-): efficacy or stability greater/lower than corresponding PS-DNA
(=): efficacy or stability equal to corresponding PS-DNA
n.d.: not-determined TABLE 3b

| Seq ID number | Antisense ID | Sequence (5'-3') | CCT3 mRNA inhibition | CCR3 protein inhibition | Relative stability in 50% FBS |
|---|---|---|---|---|---|
| 1599 | TOP030-F1 | PS-CACCTCtgtcaccAGCATG | = | = | + |
| 1600 | TOP030-F2 | PS-CACCTCTGtcaccagCATG | = | = | + |
| 1601 | TOP030-F3 | PS-CACCTgTGTCaccagcaTG | − | n.d. | + |
| 1602 | TOP030-F4 | PS-cacctctgtcaccagcATG | = | = | − |
| 1603 | TOP030-F5 | PS-CAcctctgtcaccagcATG | = | = | − |
| 1604 | TOP030-F6 | PS-CACCtctgtcaccagCATG | = | = | − |
| 1605 | TOP030-F7 | PS-CACCtctGTcaccagCATG | = | = | + |
| 1606 | TOP030-F8 | PS-CaCcTcTgTcAcCaGcAtG | − | n.d. | + |
| 1607 | TOP030-F9 | PS-CAccTCtgTCacCAgcATG | − | n.d. | − |
| 1608 | TOP030-F10 | CACC__TCTG__tcaccagCATG | − | n.d. | n.d. |
| 1609 | TOP030-F11 | CA__CCTCTG__tcaccagCATG | − | n.d. | n.d. |
| 1610 | TOP030-F12 | CACCTCTG__tc__accagCATG | = | + | n.d. |
| 1611 | TOP030-F13 | CACCTCTG__tcaccag__CATG | − | n.d. | n.d. |
| 1612 | TOP030-F14 | PS-CACCTCtgtcaccagCATG | = | = | n.d. |
| 1613 | TOP030-F15 | CACC__TCTG__tcaccagCATG | − | n.d. | n.d. |
| 1614 | TOP030-F16 | CA__CCTCTG__tcaccag__CATG__ | − | n.d. | n.d. |
| 1615 | TOP030-F17 | CACCTCTGtcdccdgCATG | − | − | n.d. |
| 1616 | TOP030-F18 | CACCTC__tgtcac__cagCATG | n.d. | n.d. | n.d. |
| 1617 | TOP038-F1 | PS-GAatgggatgtatctGCCCA | − | n.d. | n.d. |
| 1618 | TOP038-F2 | PS-GAatgggatgTAtctgcCCA | − | n.d. | n.d. |
| 1619 | TOP042-F1 | PS-ACcaggtccagatgcTTGCT | − | n.d. | n.d. |
| 1620 | TOP042-F2 | PS-ACcaggtcCAgatgcttGCT | − | n.d. | n.d. |

Lower case letters = DNA; BOLD UPPERCASE LETTERS = 2'F-ANA; d=DAP
Phosphodiester linkage = underlined; All phosphorothioate linkages = prefix PS-
(+/ −): efficacy or stability greater/ lower than corresponding PS-DNA
(=): efficacy or stability equal to corresponding PS-DNA;
n.d.: not-determined

TABLE 3c

| Seq ID | AON ID | AON sequence (5'-3') | β-chain mRNA Inhibition |
|---|---|---|---|
| 1621 | TOP062-DAP | ctctccdcttccdcggcctg | = |
| 1622 | TOP057-DAP | gdccgdgctggccdcctcc | = |
| 1623 | TOP073-DAP | tccdctggccdgcccdggdc | = |
| 1624 | TOP077-DAP | ddgdgtcctgddgccgcttgt | = |
| 1625 | TOP206-DAP | dtdgccdcdgggctgtcctt | n.d. |

Lower case letters = DNA
All phosphorothioate linkages
d = 2-amino-2'-deoxyadenosine
(=): efficacy equal to corresponding PS-DNA;
n.d.: not-determined

TABLE 4

| Target gene | Seq ID number | Antisense ID | Sequence (5'-3') |
|---|---|---|---|
| Rat β-chain | 1626 | TOP006 | tggcactttaggtggctg |
|  | 1627 | TOP006-F2 | TGgcactttaggtGGCTG |
| Rat CCR3 | 1628 | TOP007 | actcatattcataggtg |
|  | 1629 | TOP007-F8 | ACtcatattcatagGGTG |

All phosphorothioate linkages
Lower case letters = DNA;
BOLD UPPERCASE LETTERS = 2'F-ANA

TABLE 5

| | TPI ASM8 (mg/kg/day) | | | | | | TPI 1100 (mg/kg/day) | | | | | |
|---|---|---|---|---|---|---|---|---|---|---|---|---|
| | Main (Day 15) | | | | Recovery (Day 29) | | Main (Day 15) | | | | Recovery (Day 42) | |
| | 0 | 0.05 | 0.25 | 2.5 | 0 | 2.5 | 0 | 0.05 | 0.25 | 2.5 | 0 | 2.5 |
| Lung Accumulation of macrophages, foamy: | | | | | | | | | | | | |
| minimal | | | 3/6 | 2/6 | | 1/2 | | | | 3/6 | | |
| mild | | | | 4/6 | | | | | | 3/6 | | |
| Macrophage Accumulation, alveolar, non-foamy: | | | | | | | | | | | | |
| minimal | | | | | | | | | | 3/6 | | |
| mild | | | | | | | | | | 3/6 | | |
| Inflammation, intra-alveolar, granulocytic: minimal | | | | 2/6 | | | | | | | | |
| Metaplasia, bronchilar: minimal | | | | 1/6 | | | | | | | | |
| Haemorrhage, focal: | | | | | | | | | | | | |
| minimal | | | | 1/6 | | | | | | | | |
| mild | | | | 1/6 | | | | | | | | |
| Lymph node, bronchial | | | | | | | | | | | | |
| Accumulation of macrophages, foamy: minimal | | | | 6/6 | | 2/2 | | | | 1/6 | | |
| Histiocytosis, sinus: | | | | | | | | | | | | |
| minimal | | 1/6 | 1/6 | | | | | | | | 2/6 | 2/4 |
| mild | | | | | | | | | | | 4/6 | 1/4 |

Values represent number of animals in which change was observed per number of animals examined.

TABLE 6

| Name | Length | Target | Sequence 5'-3' | SEQ ID NO. |
|---|---|---|---|---|
| TPI ASM8 | | | | |
| TOP004 | 19 | Hu βc | GGGTCTGCDGCGGGDTGGT | 1630 |
| TOP005 | 21 | Hu CCR3 | GTTDCTDCTTCCDCCTGCCTG | 1631 |

TABLE 6-continued

TPI ASM8 and TPI 1100

| Name | Length | Target | Sequence 5'-3' | SEQ ID NO. |
|---|---|---|---|---|
| TPI 1100 |||||
| TOP1572 | 19 | Hu PDE4B/4D | GGTTGCTCAGI TCTGCACA | 1632 |
| TOP1731 | 21 | Hu PDE7A | TCATGAGTGGCAGCTGCAATT | 1633 |

All phosphorothioate linkages.
Uppercase letters = DNA;
Bold italic letters = FANA;
I = Inosine;
D = 2,amino-2'-deoxyadenosine

TABLE 7

| SEQ ID NOs 5p/3p strand | miRNA mimic | miRNA | 5p strand (5'-3') | 3p strand (5'-3') | β-chain inhibition |
|---|---|---|---|---|---|
| 1634/1635 | [1,2]TOP5119 | hsa-miR-493 | UUGUACAUGGUAGGCUUUCAUU | UGAAGGUCUACUGUGUGCCAGG | n.d. |
| 1636/1637 | [2,3]TOP5120 | hsa-miR-502 | AUCCUUGCUAUCUGGGUGCUA | AAUGCACCUGGGCAAGGAUUCA | >40% |
| 1638/1639 | [1,2,3]TOP5121 | hsa-miR-576 | AUUCUAAUUUCUCCACGUCUUU | AAGAUGUGGAAAAAUUGGAAUC | >40% |
| 1640/1641 | [2,3,4]TOP5122 | hsa-miR-548b | AAAAGUAAUUGUGGUUUUUGGCC | CAAGAACCUCAGUUGCUUUUGU | >40% |
| 1642/1643 | [1,2]TOP5123 | hsa-miR-136 | ACUCCAUUUGUUUUGAUGAUGGA | CAUCAUCGUCUCAAAUGAGUCU | >40% |
| 1644/1645 | [2]TOP5124 | hsa-miR-129 | CUUUUUGCGGUCUGGGCUUGC | AAGCCCUUACCCCAAAAAGCAU | >40% |
| 1646/1647 | [1,2]TOP5125 | hsa-miR-185 | UGGAGAGAAAGGCAGUUCCUGA | AGGGGCUGGCUUUCCUCUGGUC | n.d. |
| 1648/NA | [1,3]TOP5126 | hsa-miR-298 | AGCAGAAGCAGGGAGGUUCUCCCA | NA | n.d. |
| 1649/1650 | [1,2]TOP5127 | hsa-miR-324-3p | CGCAUCCCCUAGGGCAUUGGUGU | ACUGCCCCAGGUGCUGCUGG | n.d. |
| 1651/1652 | [1]TOP5128 | hsa-miR-339-3p | UCCCUGUCCUCCAGGAGCUCACG | UGAGCGCCUCGACGACAGAGCCG | n.d. |
| 1653/1654 | [1,2]TOP5129 | hsa-miR-485-5p | AGAGGCUGGCCCUGAUGAAUUC | GUCAUACACGGCUCUCCUCUCU | n.d. |
| 1655/1656 | [1]TOP5130 | hsa-miR-490-3p | CCAUGGAUCUCCAGGUGGGU | CAACCUGGAGGACUCCAUGCUG | n.d. |
| 1657/1658 | [1]TOP5131 | hsa-miR-628-5p | AUGCUGACAUAUUUACUAGAGG | UCUAGUAAGAGUGGCAGUCGA | n.d. |
| NA/1659 | [1,3]TOP5132 | hsa-miR-637 | NA | ACUGGGGGCUUUCGGGCUCUGCGU | n.d. |
| NA/1660 | [1]TOP5133 | hsa-miR-645 | NA | UCUAGGCUGGUACUGCUGA | n.d. |
| NA/1661 | [1]TOP5134 | hsa-miR-649 | NA | AAACCUGUGUUGUUCAAGAGUC | n.d. |
| NA/1662 | [1,3]TOP5135 | hsa-miR-661 | NA | UGCCUGGGUCUCUGGCCUGCGCGU | n.d. |
| 1663/NA | [1]TOP5136 | hsa-miR-1203 | CCCGGAGCCAGGAUGCAGCUC | NA | n.d. |
| 1664/NA | [1]TOP5137 | hsa-miR-1251 | ACUCUAGCUGCCAAAGGCGCU | NA | n.d. |
| 1665/NA | [1]TOP5138 | hsa-miR-1283 | UCUACAAAGGAAAGCGCUUUCU | NA | n.d. |
| 1666/1667 | [2]TOP5139 | hsa-miR-19a | AGUUUUGCAUAGUUGCACUACA | UGUGCAAAUCUAUGCAAAACUGA | n.d. |
| 1668/1669 | [2]TOP5140 | hsa-miR-20a | UAAAGUGCUUAUAGUGCAGGUAG | ACUGCAUUAUGAGCACUUAAAG | n.d. |
| 1670/1671 | [2]TOP5141 | hsa-miR-20b | CAAAGUGCUCAUAGUGCAGGUAG | ACUGUAGUAUGGGCACUUCCAG | n.d. |
| 1672/1673 | [2]TOP5142 | hsa-miR-27b | AGAGCUUAGCUGAUUGGUGAAC | UUCACAGUGGCUAAGUUCUGC | n.d. |
| 1674/1675 | [2]TOP5143 | hsa-miR-106b | UAAAGUGCUGACAGUGCAGAU | CCGCACUGUGGGUACUUGCUGC | n.d. |
| 1676/1677 | [2]TOP5144 | hsa-miR-127-5p | CUGAAGCUCAGAGGGCUCUGAU | UCGGAUCCGUCUGAGCUUGGCU | n.d. |
| 1678/NA | [2]TOP5145 | hsa-miR-134 | UGUGACUGGUUGACCAGAGGGG | NA | n.d. |
| 1679/1680 | [2]TOP5146 | hsa-miR-138-2 | AGCUGGUGUUGUGAAUCAGGCCG | GCUAUUUCACGACACCAGGGUU | n.d. |

TABLE 7-continued

| SEQ ID NOs 5p/3p strand | miRNA mimic | miRNA | 5p strand (5'-3') | 3p strand (5'-3') | β-chain inhibition |
|---|---|---|---|---|---|
| 1681/1682 | [2]TOP5147 | hsa-miR-148a | AAAGUUCUGAGACACUCCGACU | UCAGUGCACUACAGAACUUUGU | n.d. |
| 1683/1684 | [2]TOP5148 | hsa-miR-149 | UCUGGCUCCGUGUCUUCACUCCC | AGGGAGGGACGGGGGCUGUGC | n.d. |
| 1685/1686 | [2]TOP5149 | hsa-miR-154 | UAGGUUAUCCGUGUUGCCUUCG | AAUCAUACACGGUUGACCUAUU | n.d. |
| 1687/1688 | [2]TOP5150 | hsa-miR-155 | UUAAUGCUAAUCGUGAUAGGGGU | CUCCUACAUAUUAGCAUUAACA | n.d. |
| 1689/1690 | [2]TOP5151 | hsa-miR-182 | UUUGGCAAUGGUAGAACUCACACU | UGGUUCUAGACUUGCCAACUA | n.d. |
| 1691/1692 | [2]TOP5152 | hsa-miR-188-5p | CAUCCCUUGCAUGGUGGAGGG | CUCCCACAUGCAGGGUUUGCA | n.d. |
| 1693/NA | [2,3]TOP5153 | hsa-miR-204 | UUCCCUUUGUCAUCCUAUGCCU | NA | n.d. |
| 1694/NA | [2,3]TOP5154 | hsa-miR-211 | UUCCCUUUGUCAUCCUUCGCCU | NA | n.d. |
| 1695/1696 | [2]TOP5155 | hsa-miR-214 | UGCCUGUCUACACUUGCUGUGC | ACAGCAGGCACAGACAGGCAGU | n.d. |
| NA/1697 | [2]TOP5156 | hsa-miR-328 | NA | CUGGCCCUCUCUGCCCUUCCGU | n.d. |
| 1698/NA | [2]TOP5157 | hsa-miR-345 | GCUGACUCCUAGUCCAGGGCUC | NA | n.d. |
| 1699/1700 | [2]TOP5158 | hsa-miR-377 | AGAGGUUGCCCUUGGUGAAUUC | AUCACACAAAGGCAACUUUUGU | n.d. |
| NA/1701 | [2]TOP5159 | hsa-miR-453 | NA | AGGUUGUCCGUGGUGAGUUCGCA | n.d. |
| 1702/1703 | [2]TOP5160 | hsa-miR-483-5p | AAGACGGGAGGAAAGAAGGGAG | UCACUCCUCUCCUCCCGUCUU | n.d. |
| 1704/NA | [2]TOP5161 | hsa-miR-573 | CUGAAGUGAUGUGUAACUGAUCAG | NA | n.d. |
| NA/1705 | [2]TOP5162 | hsa-miR-600 | NA | ACUUACAGACAAGAGCCUUGCUC | n.d. |
| 1706/NA | [2]TOP5163 | hsa-miR-601 | UGGUCUAGGAUUGUUGGAGGAG | NA | n.d. |
| NA/1707 | [2]TOP5164 | hsa-miR-633 | NA | CUAAUAGUAUCUACCACAAUAAA | n.d. |
| 1708/NA | [2,3]TOP5165 | hsa-miR-650 | AGGAGGCAGCGCUCUCAGGAC | NA | n.d. |
| NA/1709 | [2]TOP5166 | hsa-miR-657 | NA | GGCAGGUUCUCACCCUCUCUAGG | n.d. |
| NA/1710 | [2,3]TOP5167 | hsa-miR-658 | NA | GGCGGAGGGAAGUAGGUCCGUUGGU | n.d. |
| 1711/NA | [2]TOP5168 | hsa-miR-663 | AGGCGGGGCGCCGCGGGACCGC | NA | n.d. |
| 1712/1713 | [2]TOP5169 | hsa-miR-877 | GUAGAGGAGAUGGCGCAGGG | UCCUCUUCUCCCUCCUCCCAG | n.d. |
| 1714/1715 | [2]TOP5170 | hsa-miR-886-5p | CGGGUCGGAGUUAGCUCAAGCGG | CGCGGGUGCUUACUGACCCUU | n.d. |
| NA/1716 | [2]TOP5171 | hsa-miR-940 | NA | AAGGCAGGGCCCCCGCUCCCC | n.d. |
| 1717/1718 | [3]TOP5172 | hsa-miR-32 | UAUUGCACAUUACUAAGUUGCA | CAAUUUAGUGUGUGUGAUAUUU | n.d. |
| NA/1719 | [3]TOP5173 | hsa-miR-137 | NA | UUAUUGCUUAAGAAUACGCGUAG | n.d. |
| 1720/1721 | [3]TOP5174 | hsa-miR-142-5p | CAUAAAGUAGAAAGCACUACU | UGUAGUGUUUCCUACUUUAUGGA | n.d. |
| 1722/1723 | [3]TOP5175 | hsa-miR-181a | AACAUUCAACGCUGUCGGUGAGU | ACCAUCGACCGUUGAUUGUACC | n.d. |
| NA/1724 | [3]TOP5176 | hsa-miR-181b | AACAUUCAUUGCUGUCGGUGGGU | NA | n.d. |
| 1725/1726 | [3,4]TOP5177 | hsa-miR-181c | AACAUUCAACCUGUCGGUGAGU | AACCAUCGACCGUUGAGUGGAC | n.d. |
| 1727/NA | [3]TOP5178 | hsa-miR-181d | AACAUUCAUUGUUGUCGGUGGGU | NA | n.d. |
| NA/1728 | [3]TOP5179 | hsa-miR-300 | NA | UAUACAAGGGCAGACUCUCUCU | n.d. |
| 1729/1730 | [3]TOP5180 | hsa-miR-335 | UCAAGAGCAAUAACGAAAAAUGU | UUUUUCAUUAUUGCUCCUGACC | n.d. |
| 1731/1732 | [3]TOP5181 | hsa-miR-337-3p | GAACGGCUUCAUACAGGAGUU | CUCCUAUGAUGCCUUUCUUC | n.d. |
| 1733/1734 | [3]TOP5182 | hsa-miR-376a | GUAGAUUCUCCUUCUAUGAGUA | AUCAUAGAGGAAAAUCCACGU | n.d. |
| NA/1735 | [3]TOP5183 | hsa-miR-376b | NA | AUCAUAGAGGAAAAUCCAUGUU | n.d. |
| NA/1736 | [3]TOP5184 | hsa-miR-381 | NA | UAUACAAGGGCAAGCUCUCUGU | n.d. |

TABLE 7-continued

| SEQ ID NOs 5p/3p strand | miRNA mimic | miRNA | 5p strand (5'-3') | 3p strand (5'-3') | β-chain inhibition |
|---|---|---|---|---|---|
| 1737/NA | ³TOP5185 | hsa-miR-382 | GAAGUUGUUCGUGGUGGAUUCG | NA | n.d. |
| 1738/1739 | ³TOP5186 | hsa-miR-409-3p | AGGUUACCCGAGCAACUUUGCAU | GAAUGUUGCUCGGUGAACCCCU | n.d. |
| 1740/1741 | ³TOP5187 | hsa-miR-450b-3p | UUUUGCAAUAUGUUCCUGAAUA | UUGGGAUCAUUUUGCAUCCAUA | n.d. |
| 1742/NA | ³TOP5188 | hsa-miR-513b | UUCACAAGGAGGUGUCAUUUAU | NA | n.d. |
| 1743/1744 | ³TOP5189 | hsa-miR-522 | CUCUAGAGGGAAGCGCUUUCUG | AAAAUGGUUCCCUUUAGAGUGU | n.d. |
| NA/1745 | ³TOP5190 | hsa-miR-543 | NA | AAACAUUCGCGGUGCACUUCUU | n.d. |
| 1746/1747 | ³TOP5191 | hsa-miR-548a-5p | AAAAGUAAUUGCGAGUUUUACC | CAAAACUGGCAAUUACUUUUGC | n.d. |
| 1748/1749 | ³TOP5192 | hsa-miR-548c-5p | AAAAGUAAUUGCGGUUUUUGCC | CAAAAUCUCAAUUACUUUUGC | n.d. |
| 1750/1751 | ³TOP5193 | hsa-miR-548d-5p | AAAAGUAAUUGUGGUUUUUGCC | CAAAAACCACAGUUUCUUUUGC | n.d. |
| 1752/NA | ³TOP5194 | hsa-miR-548h | AAAAGUAAUCGCGGUUUUUGUC | NA | n.d. |
| 1753/NA | ³TOP5195 | hsa-miR-548i | AAAAGUAAUUGCGGAUUUUGCC | NA | n.d. |
| 1754/NA | ³TOP5196 | hsa-miR-548j | AAAAGUAAUUGCGGUCUUUGGU | NA | n.d. |
| 1755/NA | ³TOP5197 | hsa-miR-548l | AAAAGUAAUUUGCGGGUUUUGUC | NA | n.d. |
| 1756/NA | ³TOP5198 | hsa-miR-548n | CAAAAGUAAUUGUGGAUUUUGU | NA | n.d. |
| NA/1757 | ³TOP5199 | hsa-miR-548p | NA | UAGCAAAAACUGCAGUUACUUU | n.d. |
| NA/1758 | ³TOP5200 | hsa-miR-570 | NA | CGAAAACAGCAAUUACCUUUGC | n.d. |
| 1759/NA | ³TOP5201 | hsa-miR-559 | UAAAGUAAAUAUGCACCAAAA | NA | n.d. |
| 1760/NA | ³TOP5202 | hsa-miR-641 | AAAGACAUAGGAUAGAGUCACCUC | NA | n.d. |
| 1761/1762 | ³TOP5203 | hsa-miR-654-3p | UGGUGGGCCGCAGAACAUGUGC | UAUGUCUGCUGACCAUCACCUU | n.d. |
| NA/1763 | ³TOP5204 | hsa-miR-659 | NA | CUUGGUUCAGGGAGGGUCCCCA | n.d. |
| 1764/1765 | ³TOP5205 | hsa-miR-671-5p | AGGAAGCCCUGGAGGGGCUGGAG | UCCGGUUCUCAGGGCUCCACC | n.d. |
| 1766/NA | ³TOP5206 | hsa-miR-802 | CAGUAACAAAGAUUCAUCCUUGU | NA | n.d. |
| 1767/1768 | ³TOP5207 | hsa-miR-876-5p | UGGAUUUCUUUGUGAAUCACCA | UGGUGGUUUACAAAGUAAUUCA | n.d. |
| NA/1769 | ³TOP5208 | hsa-miR-889 | NA | UUAAUAUCGGACAACCAUUGU | n.d. |
| 1770/NA | ³TOP5209 | hsa-miR-1231 | GUGUCUGGGCGGACAGCUGC | NA | n.d. |
| NA/1771 | ³TOP5210 | hsa-miR-1233 | NA | UGAGCCCUGUCCUCCCGCAG | n.d. |
| 1772/NA | ³TOP5211 | hsa-miR-1826 | AUUGAUCAUCGACACUUCGAACGCAAU | NA | n.d. |
| 1773/NA | ⁴TOP5212 | hsa-miR-383 | AGAUCAGAAGGUGAUUGUGGCU | NA | n.d. |
| 1774/1775 | ⁴TOP5213 | hsa-miR-500 | UAAUCCUUGCUACCUGGGUGAGA | AUGCACCUGGGCAAGGAUUCUG | n.d. |
| 1776/NA | ⁴TOP5214 | hsa-miR-596 | AAGCCUGCCCGGCUCCUCGGG | NA | n.d. |
| NA/1777 | ⁴TOP5215 | hsa-miR-622 | NA | ACAGUCUGCUGAGGUUGGAGC | n.d. |
| NA/1778 | ⁵TOP5216 | hsa-miR-147 | NA | GUGUGUGGAAAUGCUUCUGC | n.d. |

UPPER CASE LETTERS = RNA
NA = Not available
n.d. = not determined
[1] Predicted by TargetScan (Entrez gene symbol: CSF2RB)
[2] Predicted by miRBase (EnsEMBL identifier: ENSG00000100368)
[3] Predicted by miRANDA (target mRNA: CSF2RB)
[4] Predicted by miRGen (Ensembl Gene ID: ENSG00000100368)
[5] Predicted by DIANAmicroT (Ensembl Gene ID: ENSG00000100368)

TABLE 8

| Target gene | Seq ID number | Oligonucleotide ID | Sequence (5'-3') |
|---|---|---|---|
| Human β-chain | 1779 | TOP057s | ctggctcgaccggtggagg |
|  | 1780 | TOP062s | gagaggtgaaggtgccggac |
|  | 1781 | TOP063s | gtctccggtgaggtcccaggag |
| Human CCR3 | 1782 | TOP030s | gtggagacagtggtcgtac |
|  | 1783 | TOP031s | catgaaggccttggagagagg |
| Non-specific | 1784 | TOP4005 | atatccttgtcgtatccc |

---

The invention claimed is:

1. An isolated oligonucleotide consisting of (i) the base sequence SEQ ID NO:13 or (ii) the base sequence of SEQ ID NO:13 wherein at least one adenosine nucleotide of the oligonucleotide is substituted with 2-amino-2'-deoxyadenosine (DAP) or an analog thereof.

2. The oligonucleotide of claim 1, wherein at least one adenosine nucleotide of the oligonucleotide is substituted with 2-amino-2'-deoxyadenosine (DAP) or an analog thereof.

3. The oligonucleotide of claim 1, wherein at least one of the nucleotides of the oligonucleotide is an arabinose modified oligonucleotide.

4. The oligonucleotide of claim 3, wherein the arabinose modified nucleotide has a 2' substituent selected from the group consisting of fluorine, hydroxyl, amino, azido, alkyl, alkoxy, and alkoxyalkyl groups.

5. The oligonucleotide of claim 3, wherein the at least one arabinose modified nucleotide is 2'-deoxy-2'-fluoroarabinonucleotide (FANA).

6. The oligonucleotide of claim 5, wherein the at least one arabinose modified nucleotide is at the 5' end of the oligonucleotide.

7. The oligonucleotide of claim 5, wherein the at least one arabinose modified nucleotide is at the 3' end of the oligonucleotide.

8. The oligonucleotide of claim 5, having at least one arabinose modified nucleotide at both the 5' end and 3' end of the oligonucleotide.

9. The oligonucleotide of claim 5, having 1, 2, 3, 4, 5, 6, or 7 arabinose modified nucleotides independently at the 5' end and 3' end of the oligonucleotide.

10. The oligonucleotide of claim 5, having 1, 2, 3, 4, 5, or 6 arabinose modified nucleotides independently at the 5' end and 3' end of the oligonucleotide.

11. The oligonucleotide of claim 5, having 1, 2, 3, 4, or 5 arabinose modified nucleotides independently at the 5' end and 3' end of the oligonucleotide.

12. The oligonucleotide of claim 5, having 1, 2, 3, or 4 arabinose modified nucleotides independently at the 5' end and 3' end of the oligonucleotide.

13. The oligonucleotide of claim 5, having 1, 2, or 3 arabinose modified nucleotides independently at the 5' end and 3' end of the oligonucleotide.

14. The oligonucleotide of claim 1, containing at least one internucleotide linkage selected from the group consisting of phosphodiester, phosphotriester, phosphorothioate, methylphosphonate, boranophosphate and any combination thereof.

15. The oligonucleotide of claim 1, wherein the oligonucleotide is SEQ ID NO:13.

16. The isolated oligonucleotide of claim 1, wherein the oligonucleotide is an oligonucleotide selected from the group consisting of: SEQ ID NO: 1581, SEQ ID NO: 1582, SEQ ID NO: 1583, SEQ ID NO: 1584, SEQ ID NO: 1585, SEQ ID NO: 1586, SEQ ID NO: 1587, SEQ ID NO: 1588, SEQ ID NO: 1589, SEQ ID NO: 1590, SEQ ID NO: 1591, SEQ ID NO: 1592, SEQ ID NO: 1593, SEQ ID NO: 1594, SEQ ID NO: 1595, SEQ ID NO: 1596, SEQ ID NO: 1597, and SEQ ID NO: 1598.

17. A method of reducing the expression of the common β subunit of the interleukin-3/interleukin-5/granulocyte macrophage colony-stimulating factor receptor in a subject, said method comprising the step of administering to the subject a composition comprising an isolated oligonucleotide consisting of (i) the base sequence SEQ ID NO:13 or (ii) the base sequence of SEQ ID NO:13 wherein at least one adenosine nucleotide of the oligonucleotide is substituted with 2-amino-2'-deoxyadenosine (DAP) or an analog thereof.

18. A method of reducing the expression of the CCR3 receptor in a subject, said method comprising the step of administering to the subject a composition comprising an isolated oligonucleotide consisting of (i) the base sequence SEQ ID NO:13 or (ii) the base sequence of SEQ ID NO:13 wherein at least one adenosine nucleotide of the oligonucleotide is substituted with 2-amino-2'-deoxyadenosine (DAP) or an analog thereof.

* * * * *

SEQUENCE LISTING

<160> NUMBER OF SEQ ID NOS: 1785

<210> SEQ ID NO 1
<211> LENGTH: 22
<212> TYPE: DNA
<213> ORGANISM: Homo sapiens

<400> SEQUENCE: 1
gctggtgtag tcgttgtagc ag                                    22

<210> SEQ ID NO 2
<211> LENGTH: 22
<212> TYPE: DNA
<213> ORGANISM: Homo sapiens

<400> SEQUENCE: 2
gcaggtgatg tggctggtgt ag                                    22

<210> SEQ ID NO 3
<211> LENGTH: 21
<212> TYPE: DNA
<213> ORGANISM: Homo sapiens

<400> SEQUENCE: 3
ggctccagga ggtcctcatt c                                     21

<210> SEQ ID NO 4
<211> LENGTH: 21
<212> TYPE: DNA
<213> ORGANISM: Homo sapiens

<400> SEQUENCE: 4
ggctgaccag ggcatgtcat c                                     21

<210> SEQ ID NO 5
<211> LENGTH: 21
<212> TYPE: DNA
<213> ORGANISM: Homo sapiens

<400> SEQUENCE: 5
ctcaggaggc tggacatgct g                                     21

<210> SEQ ID NO 6
<211> LENGTH: 19
<212> TYPE: DNA
<213> ORGANISM: Homo sapiens

<400> SEQUENCE: 6
ggccacactc caggtcagc                                        19

```
<210> SEQ ID NO 7
<211> LENGTH: 19
<212> TYPE: DNA
<213> ORGANISM: Homo sapiens

<400> SEQUENCE: 7
ccacctcctt cctcacctc                                                    19

<210> SEQ ID NO 8
<211> LENGTH: 19
<212> TYPE: DNA
<213> ORGANISM: Homo sapiens

<400> SEQUENCE: 8
gaccgagctg gccacctcc                                                    19

<210> SEQ ID NO 9
<211> LENGTH: 20
<212> TYPE: DNA
<213> ORGANISM: Homo sapiens

<400> SEQUENCE: 9
ctgtctccat ccttggtcac                                                   20

<210> SEQ ID NO 10
<211> LENGTH: 22
<212> TYPE: DNA
<213> ORGANISM: Homo sapiens

<400> SEQUENCE: 10
gtcttgctgt ccttccacgt gg                                                22

<210> SEQ ID NO 11
<211> LENGTH: 22
<212> TYPE: DNA
<213> ORGANISM: Homo sapiens

<400> SEQUENCE: 11
ctcactccac tcgctccaga tc                                                22

<210> SEQ ID NO 12
<211> LENGTH: 21
<212> TYPE: DNA
<213> ORGANISM: Homo sapiens

<400> SEQUENCE: 12
tcctctatgg tgagaggtga c                                                 21

<210> SEQ ID NO 13
<211> LENGTH: 20
<212> TYPE: DNA
<213> ORGANISM: Homo sapiens

<400> SEQUENCE: 13
ctctccactt ccacggcctg                                                   20

<210> SEQ ID NO 14
<211> LENGTH: 22
<212> TYPE: DNA
<213> ORGANISM: Homo sapiens

<400> SEQUENCE: 14
cagaggccac tccagggtcc tc                                                22
```

<210> SEQ ID NO 15
<211> LENGTH: 20
<212> TYPE: DNA
<213> ORGANISM: Homo sapiens

<400> SEQUENCE: 15
ggttcttgat ctcaggaccg                                       20

<210> SEQ ID NO 16
<211> LENGTH: 20
<212> TYPE: DNA
<213> ORGANISM: Homo sapiens

<400> SEQUENCE: 16
agccgcttgt agaccacctc                                       20

<210> SEQ ID NO 17
<211> LENGTH: 20
<212> TYPE: DNA
<213> ORGANISM: Homo sapiens

<400> SEQUENCE: 17
tggcctggga ggtgttggag                                       20

<210> SEQ ID NO 18
<211> LENGTH: 20
<212> TYPE: DNA
<213> ORGANISM: Homo sapiens

<400> SEQUENCE: 18
tcctgagagc cgagaacctg                                       20

<210> SEQ ID NO 19
<211> LENGTH: 20
<212> TYPE: DNA
<213> ORGANISM: Homo sapiens

<400> SEQUENCE: 19
ctccacttgc tgggacgtcc                                       20

<210> SEQ ID NO 20
<211> LENGTH: 20
<212> TYPE: DNA
<213> ORGANISM: Homo sapiens

<400> SEQUENCE: 20
ctggagtcgt gtcaggccca                                       20

<210> SEQ ID NO 21
<211> LENGTH: 20
<212> TYPE: DNA
<213> ORGANISM: Homo sapiens

<400> SEQUENCE: 21
agagggacca gttgcacctg                                       20

<210> SEQ ID NO 22
<211> LENGTH: 20
<212> TYPE: DNA
<213> ORGANISM: Homo sapiens

<400> SEQUENCE: 22
cggccttctc tccacttcca                                       20

```
<210> SEQ ID NO 23
<211> LENGTH: 20
<212> TYPE: DNA
<213> ORGANISM: Homo sapiens

<400> SEQUENCE: 23
ctcagtgtcc ccagagctca                                        20

<210> SEQ ID NO 24
<211> LENGTH: 20
<212> TYPE: DNA
<213> ORGANISM: Homo sapiens

<400> SEQUENCE: 24
tccactggcc agcccaggac                                        20

<210> SEQ ID NO 25
<211> LENGTH: 20
<212> TYPE: DNA
<213> ORGANISM: Homo sapiens

<400> SEQUENCE: 25
ttggagggag ctccacatag                                        20

<210> SEQ ID NO 26
<211> LENGTH: 20
<212> TYPE: DNA
<213> ORGANISM: Homo sapiens

<400> SEQUENCE: 26
ggattgttcc ttggtgacct                                        20

<210> SEQ ID NO 27
<211> LENGTH: 20
<212> TYPE: DNA
<213> ORGANISM: Homo sapiens

<400> SEQUENCE: 27
tggtctaggt tcttgatctc                                        20

<210> SEQ ID NO 28
<211> LENGTH: 21
<212> TYPE: DNA
<213> ORGANISM: Homo sapiens

<400> SEQUENCE: 28
aagagtcctg aagccgcttg t                                      21

<210> SEQ ID NO 29
<211> LENGTH: 20
<212> TYPE: DNA
<213> ORGANISM: Homo sapiens

<400> SEQUENCE: 29
aggaggatgg ctgcgtcctc                                        20

<210> SEQ ID NO 30
<211> LENGTH: 18
<212> TYPE: DNA
<213> ORGANISM: Homo sapiens

<400> SEQUENCE: 30
gcatgaggtg ctctggcc                                          18
```

```
<210> SEQ ID NO 31
<211> LENGTH: 18
<212> TYPE: DNA
<213> ORGANISM: Homo sapiens

<400> SEQUENCE: 31
gccacgtagg tgctgctg                                                 18

<210> SEQ ID NO 32
<211> LENGTH: 19
<212> TYPE: DNA
<213> ORGANISM: Homo sapiens

<400> SEQUENCE: 32
gccaggcggg tccgtactc                                                19

<210> SEQ ID NO 33
<211> LENGTH: 18
<212> TYPE: DNA
<213> ORGANISM: Homo sapiens

<400> SEQUENCE: 33
tactcgggcc acgtaggt                                                 18

<210> SEQ ID NO 34
<211> LENGTH: 18
<212> TYPE: DNA
<213> ORGANISM: Homo sapiens

<400> SEQUENCE: 34
acctctgggc tccacttg                                                 18

<210> SEQ ID NO 35
<211> LENGTH: 21
<212> TYPE: DNA
<213> ORGANISM: Homo sapiens

<400> SEQUENCE: 35
cctggctggg agtcccagca a                                             21

<210> SEQ ID NO 36
<211> LENGTH: 17
<212> TYPE: DNA
<213> ORGANISM: Homo sapiens

<400> SEQUENCE: 36
gggctgggcc tcatccc                                                  17

<210> SEQ ID NO 37
<211> LENGTH: 18
<212> TYPE: DNA
<213> ORGANISM: Homo sapiens

<400> SEQUENCE: 37
gaagcactcc aggttctg                                                 18

<210> SEQ ID NO 38
<211> LENGTH: 20
<212> TYPE: DNA
<213> ORGANISM: Homo sapiens

<400> SEQUENCE: 38
catctccctg gtcagctctg                                               20
```

<210> SEQ ID NO 39
<211> LENGTH: 20
<212> TYPE: DNA
<213> ORGANISM: Homo sapiens

<400> SEQUENCE: 39
ggccagcacc atctccctgg                                                     20

<210> SEQ ID NO 40
<211> LENGTH: 20
<212> TYPE: DNA
<213> ORGANISM: Homo sapiens

<400> SEQUENCE: 40
gcagcccctg ggccagcacc                                                     20

<210> SEQ ID NO 41
<211> LENGTH: 20
<212> TYPE: DNA
<213> ORGANISM: Homo sapiens

<400> SEQUENCE: 41
gccatggaga gcagcccctg                                                     20

<210> SEQ ID NO 42
<211> LENGTH: 20
<212> TYPE: DNA
<213> ORGANISM: Homo sapiens

<400> SEQUENCE: 42
ggccagcagg gccatggaga                                                     20

<210> SEQ ID NO 43
<211> LENGTH: 20
<212> TYPE: DNA
<213> ORGANISM: Homo sapiens

<400> SEQUENCE: 43
cccagcacag ggccagcagg                                                     20

<210> SEQ ID NO 44
<211> LENGTH: 20
<212> TYPE: DNA
<213> ORGANISM: Homo sapiens

<400> SEQUENCE: 44
aggctgcgct cccagcacag                                                     20

<210> SEQ ID NO 45
<211> LENGTH: 20
<212> TYPE: DNA
<213> ORGANISM: Homo sapiens

<400> SEQUENCE: 45
tgcccctgcc aggctgcgct                                                     20

<210> SEQ ID NO 46
<211> LENGTH: 21
<212> TYPE: DNA
<213> ORGANISM: Homo sapiens

<400> SEQUENCE: 46
tggtttcttc tgcccctgcc a                                                   21

<210> SEQ ID NO 47
<211> LENGTH: 20
<212> TYPE: DNA
<213> ORGANISM: Homo sapiens

<400> SEQUENCE: 47
cgttgtagca gcgcagggtc                                               20

<210> SEQ ID NO 48
<211> LENGTH: 20
<212> TYPE: DNA
<213> ORGANISM: Homo sapiens

<400> SEQUENCE: 48
cccacctgca ggtgatgtgg                                               20

<210> SEQ ID NO 49
<211> LENGTH: 20
<212> TYPE: DNA
<213> ORGANISM: Homo sapiens

<400> SEQUENCE: 49
tgggtgtctg cccacctgca                                               20

<210> SEQ ID NO 50
<211> LENGTH: 20
<212> TYPE: DNA
<213> ORGANISM: Homo sapiens

<400> SEQUENCE: 50
ctgggcatcc tgggtgtctg                                               20

<210> SEQ ID NO 51
<211> LENGTH: 20
<212> TYPE: DNA
<213> ORGANISM: Homo sapiens

<400> SEQUENCE: 51
tgacgagccg ctgggcatcc                                               20

<210> SEQ ID NO 52
<211> LENGTH: 20
<212> TYPE: DNA
<213> ORGANISM: Homo sapiens

<400> SEQUENCE: 52
agggtcacgt tgacgagccg                                               20

<210> SEQ ID NO 53
<211> LENGTH: 20
<212> TYPE: DNA
<213> ORGANISM: Homo sapiens

<400> SEQUENCE: 53
ccggcgaatg agggtcacgt                                               20

<210> SEQ ID NO 54
<211> LENGTH: 20
<212> TYPE: DNA
<213> ORGANISM: Homo sapiens

<400> SEQUENCE: 54
cctcattcac ccggcgaatg                                               20

```
<210> SEQ ID NO 55
<211> LENGTH: 20
<212> TYPE: DNA
<213> ORGANISM: Homo sapiens

<400> SEQUENCE: 55
ggacactggc tccaggaggt                                               20

<210> SEQ ID NO 56
<211> LENGTH: 20
<212> TYPE: DNA
<213> ORGANISM: Homo sapiens

<400> SEQUENCE: 56
tgaggtcaca ggacactggc                                               20

<210> SEQ ID NO 57
<211> LENGTH: 20
<212> TYPE: DNA
<213> ORGANISM: Homo sapiens

<400> SEQUENCE: 57
atgtcatcac tgaggtcaca                                               20

<210> SEQ ID NO 58
<211> LENGTH: 20
<212> TYPE: DNA
<213> ORGANISM: Homo sapiens

<400> SEQUENCE: 58
gggggcaggc tgaccagggc                                               20

<210> SEQ ID NO 59
<211> LENGTH: 20
<212> TYPE: DNA
<213> ORGANISM: Homo sapiens

<400> SEQUENCE: 59
cagcggggat gggggcaggc                                               20

<210> SEQ ID NO 60
<211> LENGTH: 20
<212> TYPE: DNA
<213> ORGANISM: Homo sapiens

<400> SEQUENCE: 60
cctgggcacg cagcggggat                                               20

<210> SEQ ID NO 61
<211> LENGTH: 20
<212> TYPE: DNA
<213> ORGANISM: Homo sapiens

<400> SEQUENCE: 61
tgacacatct cctgggcacg                                               20

<210> SEQ ID NO 62
<211> LENGTH: 21
<212> TYPE: DNA
<213> ORGANISM: Homo sapiens

<400> SEQUENCE: 62
tggcagggaa tgacacatct c                                             21
```

```
<210> SEQ ID NO 63
<211> LENGTH: 20
<212> TYPE: DNA
<213> ORGANISM: Homo sapiens

<400> SEQUENCE: 63
gacaaaactc tggcagggaa                                                   20

<210> SEQ ID NO 64
<211> LENGTH: 21
<212> TYPE: DNA
<213> ORGANISM: Homo sapiens

<400> SEQUENCE: 64
cgtcagtgac gacaaaactc t                                                 21

<210> SEQ ID NO 65
<211> LENGTH: 20
<212> TYPE: DNA
<213> ORGANISM: Homo sapiens

<400> SEQUENCE: 65
aagtagtcaa cgtcagtgac                                                   20

<210> SEQ ID NO 66
<211> LENGTH: 20
<212> TYPE: DNA
<213> ORGANISM: Homo sapiens

<400> SEQUENCE: 66
ttggaatgag aagtagtcaa                                                   20

<210> SEQ ID NO 67
<211> LENGTH: 20
<212> TYPE: DNA
<213> ORGANISM: Homo sapiens

<400> SEQUENCE: 67
gcctgtctgg ttggaatgag                                                   20

<210> SEQ ID NO 68
<211> LENGTH: 20
<212> TYPE: DNA
<213> ORGANISM: Homo sapiens

<400> SEQUENCE: 68
gtgcccagag gcctgtctgg                                                   20

<210> SEQ ID NO 69
<211> LENGTH: 20
<212> TYPE: DNA
<213> ORGANISM: Homo sapiens

<400> SEQUENCE: 69
ggtgagccgg gtgcccagag                                                   20

<210> SEQ ID NO 70
<211> LENGTH: 20
<212> TYPE: DNA
<213> ORGANISM: Homo sapiens

<400> SEQUENCE: 70
tcagagtgac ggtgagccgg                                                   20
```

```
<210> SEQ ID NO 71
<211> LENGTH: 20
<212> TYPE: DNA
<213> ORGANISM: Homo sapiens

<400> SEQUENCE: 71
acatgctggg tcagagtgac                                               20

<210> SEQ ID NO 72
<211> LENGTH: 20
<212> TYPE: DNA
<213> ORGANISM: Homo sapiens

<400> SEQUENCE: 72
ccctgggctc aggaggctgg                                               20

<210> SEQ ID NO 73
<211> LENGTH: 21
<212> TYPE: DNA
<213> ORGANISM: Homo sapiens

<400> SEQUENCE: 73
atctgcaggt ccctgggctc a                                             21

<210> SEQ ID NO 74
<211> LENGTH: 20
<212> TYPE: DNA
<213> ORGANISM: Homo sapiens

<400> SEQUENCE: 74
gtcggtgctg atctgcaggt                                               20

<210> SEQ ID NO 75
<211> LENGTH: 20
<212> TYPE: DNA
<213> ORGANISM: Homo sapiens

<400> SEQUENCE: 75
agtggtcctg gtcggtgctg                                               20

<210> SEQ ID NO 76
<211> LENGTH: 20
<212> TYPE: DNA
<213> ORGANISM: Homo sapiens

<400> SEQUENCE: 76
gtcagcagga agtggtcctg                                               20

<210> SEQ ID NO 77
<211> LENGTH: 20
<212> TYPE: DNA
<213> ORGANISM: Homo sapiens

<400> SEQUENCE: 77
tcccaagggc cacactccag                                               20

<210> SEQ ID NO 78
<211> LENGTH: 22
<212> TYPE: DNA
<213> ORGANISM: Homo sapiens

<400> SEQUENCE: 78
ctctggggac tcccaagggc ca                                            22
```

```
<210> SEQ ID NO 79
<211> LENGTH: 20
<212> TYPE: DNA
<213> ORGANISM: Homo sapiens

<400> SEQUENCE: 79
caaccagtgg ctctggggac                                               20

<210> SEQ ID NO 80
<211> LENGTH: 18
<212> TYPE: DNA
<213> ORGANISM: Homo sapiens

<400> SEQUENCE: 80
cctggggaca accagtgg                                                 18

<210> SEQ ID NO 81
<211> LENGTH: 20
<212> TYPE: DNA
<213> ORGANISM: Homo sapiens

<400> SEQUENCE: 81
aactccagat cccctgggga                                               20

<210> SEQ ID NO 82
<211> LENGTH: 20
<212> TYPE: DNA
<213> ORGANISM: Homo sapiens

<400> SEQUENCE: 82
ccacctcaaa ctccagatcc                                               20

<210> SEQ ID NO 83
<211> LENGTH: 20
<212> TYPE: DNA
<213> ORGANISM: Homo sapiens

<400> SEQUENCE: 83
gcctcactcc actcgctcca                                               20

<210> SEQ ID NO 84
<211> LENGTH: 20
<212> TYPE: DNA
<213> ORGANISM: Homo sapiens

<400> SEQUENCE: 84
ccaggagcgc gcctcactcc                                               20

<210> SEQ ID NO 85
<211> LENGTH: 20
<212> TYPE: DNA
<213> ORGANISM: Homo sapiens

<400> SEQUENCE: 85
actcggtgtc ccaggagcgc                                               20

<210> SEQ ID NO 86
<211> LENGTH: 20
<212> TYPE: DNA
<213> ORGANISM: Homo sapiens

<400> SEQUENCE: 86
ggcagcaccg actcggtgtc                                               20
```

```
<210> SEQ ID NO 87
<211> LENGTH: 20
<212> TYPE: DNA
<213> ORGANISM: Homo sapiens

<400> SEQUENCE: 87
cacccacata ggcagcaccg                                               20

<210> SEQ ID NO 88
<211> LENGTH: 20
<212> TYPE: DNA
<213> ORGANISM: Homo sapiens

<400> SEQUENCE: 88
tgagggccag cacccacata                                               20

<210> SEQ ID NO 89
<211> LENGTH: 20
<212> TYPE: DNA
<213> ORGANISM: Homo sapiens

<400> SEQUENCE: 89
aagatcacga tgagggccag                                               20

<210> SEQ ID NO 90
<211> LENGTH: 20
<212> TYPE: DNA
<213> ORGANISM: Homo sapiens

<400> SEQUENCE: 90
gatggtgagg aagatcacga                                               20

<210> SEQ ID NO 91
<211> LENGTH: 20
<212> TYPE: DNA
<213> ORGANISM: Homo sapiens

<400> SEQUENCE: 91
ggagcacagc gatggtgagg                                               20

<210> SEQ ID NO 92
<211> LENGTH: 20
<212> TYPE: DNA
<213> ORGANISM: Homo sapiens

<400> SEQUENCE: 92
cggagggcca ggagcacagc                                               20

<210> SEQ ID NO 93
<211> LENGTH: 20
<212> TYPE: DNA
<213> ORGANISM: Homo sapiens

<400> SEQUENCE: 93
gccacagaag cggagggcca                                               20

<210> SEQ ID NO 94
<211> LENGTH: 20
<212> TYPE: DNA
<213> ORGANISM: Homo sapiens

<400> SEQUENCE: 94
acccgtagat gccacagaag                                               20
```

```
<210> SEQ ID NO 95
<211> LENGTH: 20
<212> TYPE: DNA
<213> ORGANISM: Homo sapiens

<400> SEQUENCE: 95
cgcagcctgt acccgtagat                                               20

<210> SEQ ID NO 96
<211> LENGTH: 20
<212> TYPE: DNA
<213> ORGANISM: Homo sapiens

<400> SEQUENCE: 96
ccactttctg cgcagcctgt                                               20

<210> SEQ ID NO 97
<211> LENGTH: 20
<212> TYPE: DNA
<213> ORGANISM: Homo sapiens

<400> SEQUENCE: 97
tcttctcctc ccactttctg                                               20

<210> SEQ ID NO 98
<211> LENGTH: 20
<212> TYPE: DNA
<213> ORGANISM: Homo sapiens

<400> SEQUENCE: 98
gggttgggga tcttctcctc                                               20

<210> SEQ ID NO 99
<211> LENGTH: 20
<212> TYPE: DNA
<213> ORGANISM: Homo sapiens

<400> SEQUENCE: 99
gctcttgctg gggttgggga                                               20

<210> SEQ ID NO 100
<211> LENGTH: 20
<212> TYPE: DNA
<213> ORGANISM: Homo sapiens

<400> SEQUENCE: 100
ggaacaggtg gctcttgctg                                               20

<210> SEQ ID NO 101
<211> LENGTH: 20
<212> TYPE: DNA
<213> ORGANISM: Homo sapiens

<400> SEQUENCE: 101
ctcccgttct ggaacaggtg                                               20

<210> SEQ ID NO 102
<211> LENGTH: 20
<212> TYPE: DNA
<213> ORGANISM: Homo sapiens

<400> SEQUENCE: 102
aagctctgcg ctcccgttct                                               20
```

```
<210> SEQ ID NO 103
<211> LENGTH: 20
<212> TYPE: DNA
<213> ORGANISM: Homo sapiens

<400> SEQUENCE: 103
ctgggggcca aagctctgcg                                               20

<210> SEQ ID NO 104
<211> LENGTH: 20
<212> TYPE: DNA
<213> ORGANISM: Homo sapiens

<400> SEQUENCE: 104
gacatgctgc ctgggggcca                                               20

<210> SEQ ID NO 105
<211> LENGTH: 20
<212> TYPE: DNA
<213> ORGANISM: Homo sapiens

<400> SEQUENCE: 105
agtgaaggcc gacatgctgc                                               20

<210> SEQ ID NO 106
<211> LENGTH: 20
<212> TYPE: DNA
<213> ORGANISM: Homo sapiens

<400> SEQUENCE: 106
gactcccgct agtgaaggcc                                               20

<210> SEQ ID NO 107
<211> LENGTH: 20
<212> TYPE: DNA
<213> ORGANISM: Homo sapiens

<400> SEQUENCE: 107
tggtgtgggg gactcccgct                                               20

<210> SEQ ID NO 108
<211> LENGTH: 20
<212> TYPE: DNA
<213> ORGANISM: Homo sapiens

<400> SEQUENCE: 108
ccacggcccc tggtgtgggg                                               20

<210> SEQ ID NO 109
<211> LENGTH: 20
<212> TYPE: DNA
<213> ORGANISM: Homo sapiens

<400> SEQUENCE: 109
agcggctgcc ccacggcccc                                               20

<210> SEQ ID NO 110
<211> LENGTH: 20
<212> TYPE: DNA
<213> ORGANISM: Homo sapiens

<400> SEQUENCE: 110
agctcaggga agcggctgcc                                               20
```

```
<210> SEQ ID NO 111
<211> LENGTH: 20
<212> TYPE: DNA
<213> ORGANISM: Homo sapiens

<400> SEQUENCE: 111 cacccctcc agctcaggga                                                    20

<210> SEQ ID NO 112
<211> LENGTH: 20
<212> TYPE: DNA
<213> ORGANISM: Homo sapiens

<400> SEQUENCE: 112
ctacagggaa cacccctcc                                                    20

<210> SEQ ID NO 113
<211> LENGTH: 20
<212> TYPE: DNA
<213> ORGANISM: Homo sapiens

<400> SEQUENCE: 113
tccccgaatc ctacagggaa                                                   20

<210> SEQ ID NO 114
<211> LENGTH: 20
<212> TYPE: DNA
<213> ORGANISM: Homo sapiens

<400> SEQUENCE: 114
cacctcgctg tccccgaatc                                                   20

<210> SEQ ID NO 115
<211> LENGTH: 20
<212> TYPE: DNA
<213> ORGANISM: Homo sapiens

<400> SEQUENCE: 115
tgagaggtga cacctcgctg                                                   20

<210> SEQ ID NO 116
<211> LENGTH: 20
<212> TYPE: DNA
<213> ORGANISM: Homo sapiens

<400> SEQUENCE: 116
atgcttgggg tcctctatgg                                                   20

<210> SEQ ID NO 117
<211> LENGTH: 20
<212> TYPE: DNA
<213> ORGANISM: Homo sapiens

<400> SEQUENCE: 117
gatcacagac atgcttgggg                                                   20

<210> SEQ ID NO 118
<211> LENGTH: 20
<212> TYPE: DNA
<213> ORGANISM: Homo sapiens

<400> SEQUENCE: 118
ccagatggtg gatcacagac                                                   20
```

<210> SEQ ID NO 119
<211> LENGTH: 20
<212> TYPE: DNA
<213> ORGANISM: Homo sapiens

<400> SEQUENCE: 119
cgtgtcaggc ccagatggtg                                            20

<210> SEQ ID NO 120
<211> LENGTH: 20
<212> TYPE: DNA
<213> ORGANISM: Homo sapiens

<400> SEQUENCE: 120
agatctgagg cagctggagt                                            20

<210> SEQ ID NO 121
<211> LENGTH: 20
<212> TYPE: DNA
<213> ORGANISM: Homo sapiens

<400> SEQUENCE: 121
ctctgtgggt agatctgagg                                            20

<210> SEQ ID NO 122
<211> LENGTH: 20
<212> TYPE: DNA
<213> ORGANISM: Homo sapiens

<400> SEQUENCE: 122 tgggggctg ctctgtgggt                                             20

<210> SEQ ID NO 123
<211> LENGTH: 20
<212> TYPE: DNA
<213> ORGANISM: Homo sapiens

<400> SEQUENCE: 123
ggctgggggc tgggggctg                                             20

<210> SEQ ID NO 124
<211> LENGTH: 20
<212> TYPE: DNA
<213> ORGANISM: Homo sapiens

<400> SEQUENCE: 124
aggcgggcct ggctgggggc                                            20

<210> SEQ ID NO 125
<211> LENGTH: 20
<212> TYPE: DNA
<213> ORGANISM: Homo sapiens

<400> SEQUENCE: 125
gggaggcggc aggcgggcct                                            20

<210> SEQ ID NO 126
<211> LENGTH: 20
<212> TYPE: DNA
<213> ORGANISM: Homo sapiens

<400> SEQUENCE: 126
tcaggtgtgt gggaggcggc                                            20

```
<210> SEQ ID NO 127
<211> LENGTH: 20
<212> TYPE: DNA
<213> ORGANISM: Homo sapiens

<400> SEQUENCE: 127
agcctgtttc tcaggtgtgt                                               20

<210> SEQ ID NO 128
<211> LENGTH: 20
<212> TYPE: DNA
<213> ORGANISM: Homo sapiens

<400> SEQUENCE: 128
caaagctgga agcctgtttc                                               20

<210> SEQ ID NO 129
<211> LENGTH: 20
<212> TYPE: DNA
<213> ORGANISM: Homo sapiens

<400> SEQUENCE: 129
ccattgaagt caaagctgga                                               20

<210> SEQ ID NO 130
<211> LENGTH: 20
<212> TYPE: DNA
<213> ORGANISM: Homo sapiens

<400> SEQUENCE: 130
caggtagggc ccattgaagt                                               20

<210> SEQ ID NO 131
<211> LENGTH: 20
<212> TYPE: DNA
<213> ORGANISM: Homo sapiens

<400> SEQUENCE: 131
ggggcggccc caggtagggc                                               20

<210> SEQ ID NO 132
<211> LENGTH: 20
<212> TYPE: DNA
<213> ORGANISM: Homo sapiens

<400> SEQUENCE: 132
gagcggctgt ggggcggccc                                               20

<210> SEQ ID NO 133
<211> LENGTH: 20
<212> TYPE: DNA
<213> ORGANISM: Homo sapiens

<400> SEQUENCE: 133
gtcaggtagg gagcggctgt                                               20

<210> SEQ ID NO 134
<211> LENGTH: 20
<212> TYPE: DNA
<213> ORGANISM: Homo sapiens

<400> SEQUENCE: 134
ggcccaggat gtcaggtagg                                               20
```

-continued

<210> SEQ ID NO 135
<211> LENGTH: 20
<212> TYPE: DNA
<213> ORGANISM: Homo sapiens

<400> SEQUENCE: 135
ggctccggct ggcccaggat                                               20

<210> SEQ ID NO 136
<211> LENGTH: 20
<212> TYPE: DNA
<213> ORGANISM: Homo sapiens

<400> SEQUENCE: 136
ctcctgtggg ggctccggct                                               20

<210> SEQ ID NO 137
<211> LENGTH: 20
<212> TYPE: DNA
<213> ORGANISM: Homo sapiens

<400> SEQUENCE: 137
ggctcccacc ctcctgtggg                                               20

<210> SEQ ID NO 138
<211> LENGTH: 20
<212> TYPE: DNA
<213> ORGANISM: Homo sapiens

<400> SEQUENCE: 138
ggggacttct ggctcccacc                                               20

<210> SEQ ID NO 139
<211> LENGTH: 20
<212> TYPE: DNA
<213> ORGANISM: Homo sapiens

<400> SEQUENCE: 139
ccctggaggt ggggacttct                                               20

<210> SEQ ID NO 140
<211> LENGTH: 20
<212> TYPE: DNA
<213> ORGANISM: Homo sapiens

<400> SEQUENCE: 140
actccaggga ccctggaggt                                               20

<210> SEQ ID NO 141
<211> LENGTH: 20
<212> TYPE: DNA
<213> ORGANISM: Homo sapiens

<400> SEQUENCE: 141
agacacaggt actccaggga                                               20

<210> SEQ ID NO 142
<211> LENGTH: 20
<212> TYPE: DNA
<213> ORGANISM: Homo sapiens

<400> SEQUENCE: 142
cccagcaggc agacacaggt                                               20

```
<210> SEQ ID NO 143
<211> LENGTH: 20
<212> TYPE: DNA
<213> ORGANISM: Homo sapiens

<400> SEQUENCE: 143
gcacctgccc cccagcaggc                                              20

<210> SEQ ID NO 144
<211> LENGTH: 20
<212> TYPE: DNA
<213> ORGANISM: Homo sapiens

<400> SEQUENCE: 144
ctgggccaga gggaccagtt                                              20

<210> SEQ ID NO 145
<211> LENGTH: 20
<212> TYPE: DNA
<213> ORGANISM: Homo sapiens

<400> SEQUENCE: 145
gtcccatcgc ctgggccaga                                              20

<210> SEQ ID NO 146
<211> LENGTH: 20
<212> TYPE: DNA
<213> ORGANISM: Homo sapiens

<400> SEQUENCE: 146
gcctgtcccg gtcccatcgc                                              20

<210> SEQ ID NO 147
<211> LENGTH: 18
<212> TYPE: DNA
<213> ORGANISM: Homo sapiens

<400> SEQUENCE: 147
ctggctcggc cttctctc                                                18

<210> SEQ ID NO 148
<211> LENGTH: 17
<212> TYPE: DNA
<213> ORGANISM: Homo sapiens

<400> SEQUENCE: 148
ctgcagcccc ctggctc                                                 17

<210> SEQ ID NO 149
<211> LENGTH: 19
<212> TYPE: DNA
<213> ORGANISM: Homo sapiens

<400> SEQUENCE: 149
agggagggac tccctgcag                                               19

<210> SEQ ID NO 150
<211> LENGTH: 18
<212> TYPE: DNA
<213> ORGANISM: Homo sapiens

<400> SEQUENCE: 150
ggactccagg gagggact                                                18
```

```
<210> SEQ ID NO 151
<211> LENGTH: 17
<212> TYPE: DNA
<213> ORGANISM: Homo sapiens

<400> SEQUENCE: 151
gcctcccccg gactcca                                                    17

<210> SEQ ID NO 152
<211> LENGTH: 20
<212> TYPE: DNA
<213> ORGANISM: Homo sapiens

<400> SEQUENCE: 152
caggaggggc agggcctccc                                                 20

<210> SEQ ID NO 153
<211> LENGTH: 20
<212> TYPE: DNA
<213> ORGANISM: Homo sapiens

<400> SEQUENCE: 153
ggcccaagag caggaggggc                                                 20

<210> SEQ ID NO 154
<211> LENGTH: 20
<212> TYPE: DNA
<213> ORGANISM: Homo sapiens

<400> SEQUENCE: 154
tcccacccTt ggcccaagag                                                 20

<210> SEQ ID NO 155
<211> LENGTH: 20
<212> TYPE: DNA
<213> ORGANISM: Homo sapiens

<400> SEQUENCE: 155
ggtcctgtcc tcccaccctt                                                 20

<210> SEQ ID NO 156
<211> LENGTH: 20
<212> TYPE: DNA
<213> ORGANISM: Homo sapiens

<400> SEQUENCE: 156
ctgtcctttt ggtcctgtcc                                                 20

<210> SEQ ID NO 157
<211> LENGTH: 20
<212> TYPE: DNA
<213> ORGANISM: Homo sapiens

<400> SEQUENCE: 157
atagccacag ggctgtcctt                                                 20

<210> SEQ ID NO 158
<211> LENGTH: 20
<212> TYPE: DNA
<213> ORGANISM: Homo sapiens

<400> SEQUENCE: 158
ctcatgggta tagccacagg                                                 20
```

<210> SEQ ID NO 159
<211> LENGTH: 20
<212> TYPE: DNA
<213> ORGANISM: Homo sapiens

<400> SEQUENCE: 159
tccccagagc tcatgggtat                                                    20

<210> SEQ ID NO 160
<211> LENGTH: 19
<212> TYPE: DNA
<213> ORGANISM: Homo sapiens

<400> SEQUENCE: 160
cataaccaga ggccactcc                                                     19

<210> SEQ ID NO 161
<211> LENGTH: 20
<212> TYPE: DNA
<213> ORGANISM: Homo sapiens

<400> SEQUENCE: 161
ggagacataa ccagaggcca                                                    20

<210> SEQ ID NO 162
<211> LENGTH: 17
<212> TYPE: DNA
<213> ORGANISM: Homo sapiens

<400> SEQUENCE: 162
gcagaggaga cataacc                                                       17

<210> SEQ ID NO 163
<211> LENGTH: 18
<212> TYPE: DNA
<213> ORGANISM: Homo sapiens

<400> SEQUENCE: 163
ggtgaatacc aggtctgc                                                      18

<210> SEQ ID NO 164
<211> LENGTH: 20
<212> TYPE: DNA
<213> ORGANISM: Homo sapiens

<400> SEQUENCE: 164
ctgagtttgg ggtgaatacc                                                    20

<210> SEQ ID NO 165
<211> LENGTH: 20
<212> TYPE: DNA
<213> ORGANISM: Homo sapiens

<400> SEQUENCE: 165
acagacgagg cccctgagtt                                                    20

<210> SEQ ID NO 166
<211> LENGTH: 20
<212> TYPE: DNA
<213> ORGANISM: Homo sapiens

<400> SEQUENCE: 166
actagggaga cagacgaggc                                                    20

-continued

<210> SEQ ID NO 167
<211> LENGTH: 20
<212> TYPE: DNA
<213> ORGANISM: Homo sapiens

<400> SEQUENCE: 167
cagagaggga actagggaga					20

<210> SEQ ID NO 168
<211> LENGTH: 20
<212> TYPE: DNA
<213> ORGANISM: Homo sapiens

<400> SEQUENCE: 168
aggggaggcc cagagaggga					20

<210> SEQ ID NO 169
<211> LENGTH: 20
<212> TYPE: DNA
<213> ORGANISM: Homo sapiens

<400> SEQUENCE: 169
gtctggtctg aggggaggcc					20

<210> SEQ ID NO 170
<211> LENGTH: 20
<212> TYPE: DNA
<213> ORGANISM: Homo sapiens

<400> SEQUENCE: 170
taagctgggg gtctggtctg					20

<210> SEQ ID NO 171
<211> LENGTH: 18
<212> TYPE: DNA
<213> ORGANISM: Homo sapiens

<400> SEQUENCE: 171
gcccaggaca taagctgg					18

<210> SEQ ID NO 172
<211> LENGTH: 20
<212> TYPE: DNA
<213> ORGANISM: Homo sapiens

<400> SEQUENCE: 172
tccagggggt ccactggcca					20

<210> SEQ ID NO 173
<211> LENGTH: 17
<212> TYPE: DNA
<213> ORGANISM: Homo sapiens

<400> SEQUENCE: 173
ggcctggggc tccaggg					17

<210> SEQ ID NO 174
<211> LENGTH: 20
<212> TYPE: DNA
<213> ORGANISM: Homo sapiens

<400> SEQUENCE: 174
accctgactt cacagggcct					20

```
<210> SEQ ID NO 175
<211> LENGTH: 19
<212> TYPE: DNA
<213> ORGANISM: Homo sapiens

<400> SEQUENCE: 175
tcaaaccctg acttcacag                                                   19

<210> SEQ ID NO 176
<211> LENGTH: 20
<212> TYPE: DNA
<213> ORGANISM: Homo sapiens

<400> SEQUENCE: 176
ccacatagcc ctcaaaccct                                                  20

<210> SEQ ID NO 177
<211> LENGTH: 20
<212> TYPE: DNA
<213> ORGANISM: Homo sapiens

<400> SEQUENCE: 177
gccctcaatt ggagggagct                                                  20

<210> SEQ ID NO 178
<211> LENGTH: 19
<212> TYPE: DNA
<213> ORGANISM: Homo sapiens

<400> SEQUENCE: 178
tgggggaccg gccctcaat                                                   19

<210> SEQ ID NO 179
<211> LENGTH: 20
<212> TYPE: DNA
<213> ORGANISM: Homo sapiens

<400> SEQUENCE: 179
cttggtgacc tggggaccg                                                   20

<210> SEQ ID NO 180
<211> LENGTH: 20
<212> TYPE: DNA
<213> ORGANISM: Homo sapiens

<400> SEQUENCE: 180
ctcagggggg acaggattgt                                                  20

<210> SEQ ID NO 181
<211> LENGTH: 20
<212> TYPE: DNA
<213> ORGANISM: Homo sapiens

<400> SEQUENCE: 181
cttttggcct caggggggac                                                  20

<210> SEQ ID NO 182
<211> LENGTH: 20
<212> TYPE: DNA
<213> ORGANISM: Homo sapiens

<400> SEQUENCE: 182
aggacagggc ttttggcctc                                                  20
```

```
<210> SEQ ID NO 183
<211> LENGTH: 18
<212> TYPE: DNA
<213> ORGANISM: Homo sapiens

<400> SEQUENCE: 183
ccctgggttc aggacagg                                                 18

<210> SEQ ID NO 184
<211> LENGTH: 20
<212> TYPE: DNA
<213> ORGANISM: Homo sapiens

<400> SEQUENCE: 184
gccgggcgtt ccctgggtt                                                20

<210> SEQ ID NO 185
<211> LENGTH: 20
<212> TYPE: DNA
<213> ORGANISM: Homo sapiens

<400> SEQUENCE: 185
ggacacatct gccgggcgtt                                               20

<210> SEQ ID NO 186
<211> LENGTH: 19
<212> TYPE: DNA
<213> ORGANISM: Homo sapiens

<400> SEQUENCE: 186
ggatgttggg gacacatct                                                19

<210> SEQ ID NO 187
<211> LENGTH: 20
<212> TYPE: DNA
<213> ORGANISM: Homo sapiens

<400> SEQUENCE: 187
tcgggctgtg gggatgttgg                                               20

<210> SEQ ID NO 188
<211> LENGTH: 19
<212> TYPE: DNA
<213> ORGANISM: Homo sapiens

<400> SEQUENCE: 188
aggaggccct cgggctgtg                                                19

<210> SEQ ID NO 189
<211> LENGTH: 19
<212> TYPE: DNA
<213> ORGANISM: Homo sapiens

<400> SEQUENCE: 189
gctgcaggac aaggaggcc                                                19

<210> SEQ ID NO 190
<211> LENGTH: 20
<212> TYPE: DNA
<213> ORGANISM: Homo sapiens

<400> SEQUENCE: 190
tcgcccactt gctgcaggac                                               20
```

```
<210> SEQ ID NO 191
<211> LENGTH: 20
<212> TYPE: DNA
<213> ORGANISM: Homo sapiens

<400> SEQUENCE: 191
gaagcaatag tcgcccactt                                               20

<210> SEQ ID NO 192
<211> LENGTH: 20
<212> TYPE: DNA
<213> ORGANISM: Homo sapiens

<400> SEQUENCE: 192
ggccggggag gaagcaatag                                               20

<210> SEQ ID NO 193
<211> LENGTH: 20
<212> TYPE: DNA
<213> ORGANISM: Homo sapiens

<400> SEQUENCE: 193
ccgggcccca ggccggggag                                               20

<210> SEQ ID NO 194
<211> LENGTH: 20
<212> TYPE: DNA
<213> ORGANISM: Homo sapiens

<400> SEQUENCE: 194
cgagagaggg ccgggcccca                                               20

<210> SEQ ID NO 195
<211> LENGTH: 19
<212> TYPE: DNA
<213> ORGANISM: Homo sapiens

<400> SEQUENCE: 195
tactccggag cgagagagg                                                19

<210> SEQ ID NO 196
<211> LENGTH: 18
<212> TYPE: DNA
<213> ORGANISM: Homo sapiens

<400> SEQUENCE: 196
gaagaaggtt tactccgg                                                 18

<210> SEQ ID NO 197
<211> LENGTH: 19
<212> TYPE: DNA
<213> ORGANISM: Homo sapiens

<400> SEQUENCE: 197
ggtcccgggg aagaaggtt                                                19

<210> SEQ ID NO 198
<211> LENGTH: 19
<212> TYPE: DNA
<213> ORGANISM: Homo sapiens

<400> SEQUENCE: 198
ggtcccgggg aagaaggtt                                                19
```

```
<210> SEQ ID NO 199
<211> LENGTH: 20
<212> TYPE: DNA
<213> ORGANISM: Homo sapiens

<400> SEQUENCE: 199
tgacttgaaa agcctggtct                                              20

<210> SEQ ID NO 200
<211> LENGTH: 17
<212> TYPE: DNA
<213> ORGANISM: Homo sapiens

<400> SEQUENCE: 200
gggcttcttg acttgaa                                                 17

<210> SEQ ID NO 201
<211> LENGTH: 19
<212> TYPE: DNA
<213> ORGANISM: Homo sapiens

<400> SEQUENCE: 201
gcctggcctg ggggcttct                                               19

<210> SEQ ID NO 202
<211> LENGTH: 21
<212> TYPE: DNA
<213> ORGANISM: Homo sapiens

<400> SEQUENCE: 202
acctggggca cagcctggcc t                                            21

<210> SEQ ID NO 203
<211> LENGTH: 19
<212> TYPE: DNA
<213> ORGANISM: Homo sapiens

<400> SEQUENCE: 203
tgacgggcac ctggggcac                                               19

<210> SEQ ID NO 204
<211> LENGTH: 20
<212> TYPE: DNA
<213> ORGANISM: Homo sapiens

<400> SEQUENCE: 204
agagctgaat gacgggcacc                                              20

<210> SEQ ID NO 205
<211> LENGTH: 20
<212> TYPE: DNA
<213> ORGANISM: Homo sapiens

<400> SEQUENCE: 205
ctagggcttt gaagagctga                                              20

<210> SEQ ID NO 206
<211> LENGTH: 19
<212> TYPE: DNA
<213> ORGANISM: Homo sapiens

<400> SEQUENCE: 206
actgagacaa ctagggctt                                               19
```

```
<210> SEQ ID NO 207
<211> LENGTH: 20
<212> TYPE: DNA
<213> ORGANISM: Homo sapiens

<400> SEQUENCE: 207
cacagacatc actgagacaa                                                  20

<210> SEQ ID NO 208
<211> LENGTH: 20
<212> TYPE: DNA
<213> ORGANISM: Homo sapiens

<400> SEQUENCE: 208
ctggaggtcc cacagacatc                                                  20

<210> SEQ ID NO 209
<211> LENGTH: 20
<212> TYPE: DNA
<213> ORGANISM: Homo sapiens

<400> SEQUENCE: 209
tctcaaggga ctggaggtcc                                                  20

<210> SEQ ID NO 210
<211> LENGTH: 20
<212> TYPE: DNA
<213> ORGANISM: Homo sapiens

<400> SEQUENCE: 210
tgacgtgggg tctcaaggga                                                  20

<210> SEQ ID NO 211
<211> LENGTH: 19
<212> TYPE: DNA
<213> ORGANISM: Homo sapiens

<400> SEQUENCE: 211
tcagggcttt gaagagctg                                                   19

<210> SEQ ID NO 212
<211> LENGTH: 19
<212> TYPE: DNA
<213> ORGANISM: Homo sapiens

<400> SEQUENCE: 212
tcctgctgct tcagggctt                                                   19

<210> SEQ ID NO 213
<211> LENGTH: 19
<212> TYPE: DNA
<213> ORGANISM: Homo sapiens

<400> SEQUENCE: 213
gacaggtagt cctgctgct                                                   19

<210> SEQ ID NO 214
<211> LENGTH: 19
<212> TYPE: DNA
<213> ORGANISM: Homo sapiens

<400> SEQUENCE: 214 aggggggcaga gacaggtag                                                  19
```

```
<210> SEQ ID NO 215
<211> LENGTH: 20
<212> TYPE: DNA
<213> ORGANISM: Homo sapiens

<400> SEQUENCE: 215
ttgacctccc aaggggggcag                                          20

<210> SEQ ID NO 216
<211> LENGTH: 20
<212> TYPE: DNA
<213> ORGANISM: Homo sapiens

<400> SEQUENCE: 216
ttgacctccc aaggggggcag                                          20

<210> SEQ ID NO 217
<211> LENGTH: 19
<212> TYPE: DNA
<213> ORGANISM: Homo sapiens

<400> SEQUENCE: 217
ctgaagccgc ttgtagacc                                            19

<210> SEQ ID NO 218
<211> LENGTH: 19
<212> TYPE: DNA
<213> ORGANISM: Homo sapiens

<400> SEQUENCE: 218
cgtcctccca agagtcctg                                            19

<210> SEQ ID NO 219
<211> LENGTH: 18
<212> TYPE: DNA
<213> ORGANISM: Homo sapiens

<400> SEQUENCE: 219
ttggagagga ggatggct                                             18

<210> SEQ ID NO 220
<211> LENGTH: 18
<212> TYPE: DNA
<213> ORGANISM: Homo sapiens

<400> SEQUENCE: 220
ctctggcccc agggtggc                                             18

<210> SEQ ID NO 221
<211> LENGTH: 20
<212> TYPE: DNA
<213> ORGANISM: Homo sapiens

<400> SEQUENCE: 221
tgctgggcat gaggtgctct                                           20

<210> SEQ ID NO 222
<211> LENGTH: 18
<212> TYPE: DNA
<213> ORGANISM: Homo sapiens

<400> SEQUENCE: 222
gccgagaacc tggggcca                                             18
```

```
<210> SEQ ID NO 223
<211> LENGTH: 17
<212> TYPE: DNA
<213> ORGANISM: Homo sapiens

<400> SEQUENCE: 223
gtcccagcaa acctctg                                                  17

<210> SEQ ID NO 224
<211> LENGTH: 17
<212> TYPE: DNA
<213> ORGANISM: Homo sapiens

<400> SEQUENCE: 224
cctcatcccc tggctgg                                                  17

<210> SEQ ID NO 225
<211> LENGTH: 17
<212> TYPE: DNA
<213> ORGANISM: Homo sapiens

<400> SEQUENCE: 225
cctcatcccc tggctgg                                                  17

<210> SEQ ID NO 226
<211> LENGTH: 17
<212> TYPE: DNA
<213> ORGANISM: Homo sapiens

<400> SEQUENCE: 226
ccgtcaaaga agcactc                                                  17

<210> SEQ ID NO 227
<211> LENGTH: 18
<212> TYPE: DNA
<213> ORGANISM: Homo sapiens

<400> SEQUENCE: 227
gcacggcggc cccgtcaa                                                 18

<210> SEQ ID NO 228
<211> LENGTH: 20
<212> TYPE: DNA
<213> ORGANISM: Homo sapiens

<400> SEQUENCE: 228
gagcagctga gcacggcggc                                               20

<210> SEQ ID NO 229
<211> LENGTH: 19
<212> TYPE: DNA
<213> ORGANISM: Homo sapiens

<400> SEQUENCE: 229
ctcacctccc aggagcagc                                                19

<210> SEQ ID NO 230
<211> LENGTH: 17
<212> TYPE: DNA
<213> ORGANISM: Homo sapiens

<400> SEQUENCE: 230
aaggagaccg agctggc                                                  17
```

<210> SEQ ID NO 231
<211> LENGTH: 20
<212> TYPE: DNA
<213> ORGANISM: Homo sapiens

<400> SEQUENCE: 231
gaataggcca aaggagaccg                                                   20

<210> SEQ ID NO 232
<211> LENGTH: 20
<212> TYPE: DNA
<213> ORGANISM: Homo sapiens

<400> SEQUENCE: 232
ctgggcttgt agaataggcc                                                   20

<210> SEQ ID NO 233
<211> LENGTH: 20
<212> TYPE: DNA
<213> ORGANISM: Homo sapiens

<400> SEQUENCE: 233
tgcatctggg ctgggcttgt                                                   20

<210> SEQ ID NO 234
<211> LENGTH: 19
<212> TYPE: DNA
<213> ORGANISM: Homo sapiens

<400> SEQUENCE: 234
cttcctcccc tgcatctgg                                                    19

<210> SEQ ID NO 235
<211> LENGTH: 17
<212> TYPE: DNA
<213> ORGANISM: Homo sapiens

<400> SEQUENCE: 235
gggagcactc ttcctcc                                                      17

<210> SEQ ID NO 236
<211> LENGTH: 20
<212> TYPE: DNA
<213> ORGANISM: Homo sapiens

<400> SEQUENCE: 236
ctcagcactg gggagcactc                                                   20

<210> SEQ ID NO 237
<211> LENGTH: 20
<212> TYPE: DNA
<213> ORGANISM: Homo sapiens

<400> SEQUENCE: 237
cgagcccctc cctcagcact                                                   20

<210> SEQ ID NO 238
<211> LENGTH: 20
<212> TYPE: DNA
<213> ORGANISM: Homo sapiens

<400> SEQUENCE: 238
tggaggctgc cgagcccctc                                                   20

```
<210> SEQ ID NO 239
<211> LENGTH: 20
<212> TYPE: DNA
<213> ORGANISM: Homo sapiens

<400> SEQUENCE: 239
gtgcctggtg tggaggctgc                                              20

<210> SEQ ID NO 240
<211> LENGTH: 20
<212> TYPE: DNA
<213> ORGANISM: Homo sapiens

<400> SEQUENCE: 240
tctggcagtg gtgcctggtg                                              20

<210> SEQ ID NO 241
<211> LENGTH: 20
<212> TYPE: DNA
<213> ORGANISM: Homo sapiens

<400> SEQUENCE: 241
ggcacgggaa tctggcagtg                                              20

<210> SEQ ID NO 242
<211> LENGTH: 20
<212> TYPE: DNA
<213> ORGANISM: Homo sapiens

<400> SEQUENCE: 242
cgcggggtcg ggcacgggaa                                              20

<210> SEQ ID NO 243
<211> LENGTH: 20
<212> TYPE: DNA
<213> ORGANISM: Homo sapiens

<400> SEQUENCE: 243
ggccgtgggt cgcggggtcg                                              20

<210> SEQ ID NO 244
<211> LENGTH: 18
<212> TYPE: DNA
<213> ORGANISM: Homo sapiens

<400> SEQUENCE: 244
acgatgtatt ggccgtgg                                                18

<210> SEQ ID NO 245
<211> LENGTH: 20
<212> TYPE: DNA
<213> ORGANISM: Homo sapiens

<400> SEQUENCE: 245
ctgaacagag acgatgtatt                                              20

<210> SEQ ID NO 246
<211> LENGTH: 19
<212> TYPE: DNA
<213> ORGANISM: Homo sapiens

<400> SEQUENCE: 246
cctccttggc tgaacagag                                               19
```

<210> SEQ ID NO 247
<211> LENGTH: 17
<212> TYPE: DNA
<213> ORGANISM: Homo sapiens

<400> SEQUENCE: 247
ttctctgccc tccttgg                                                      17

<210> SEQ ID NO 248
<211> LENGTH: 20
<212> TYPE: DNA
<213> ORGANISM: Homo sapiens

<400> SEQUENCE: 248
gctctttatg tgtttctctg                                                   20

<210> SEQ ID NO 249
<211> LENGTH: 20
<212> TYPE: DNA
<213> ORGANISM: Homo sapiens

<400> SEQUENCE: 249
tgttcactga gctctttatg                                                   20

<210> SEQ ID NO 250
<211> LENGTH: 20
<212> TYPE: DNA
<213> ORGANISM: Homo sapiens

<400> SEQUENCE: 250
gccatctgga tgttcactga                                                   20

<210> SEQ ID NO 251
<211> LENGTH: 20
<212> TYPE: DNA
<213> ORGANISM: Homo sapiens

<400> SEQUENCE: 251
ggatggaggg gccatctgga                                                   20

<210> SEQ ID NO 252
<211> LENGTH: 19
<212> TYPE: DNA
<213> ORGANISM: Homo sapiens

<400> SEQUENCE: 252
tcacgttgag ggatggagg                                                    19

<210> SEQ ID NO 253
<211> LENGTH: 21
<212> TYPE: DNA
<213> ORGANISM: Homo sapiens

<400> SEQUENCE: 253
tctccatcct tggtcacgtt g                                                 21

<210> SEQ ID NO 254
<211> LENGTH: 19
<212> TYPE: DNA
<213> ORGANISM: Homo sapiens

<400> SEQUENCE: 254
gcgcaggctg tagctgtct                                                    19

<210> SEQ ID NO 255
<211> LENGTH: 20
<212> TYPE: DNA
<213> ORGANISM: Homo sapiens

<400> SEQUENCE: 255
attgtttccc agcgcaggct                                               20

<210> SEQ ID NO 256
<211> LENGTH: 20
<212> TYPE: DNA
<213> ORGANISM: Homo sapiens

<400> SEQUENCE: 256
tcgcattttc attgtttccc                                               20

<210> SEQ ID NO 257
<211> LENGTH: 20
<212> TYPE: DNA
<213> ORGANISM: Homo sapiens

<400> SEQUENCE: 257
tgtgttcgta tcgcattttc                                               20

<210> SEQ ID NO 258
<211> LENGTH: 20
<212> TYPE: DNA
<213> ORGANISM: Homo sapiens

<400> SEQUENCE: 258
gtgtggtcta tgtgttcgta                                               20

<210> SEQ ID NO 259
<211> LENGTH: 20
<212> TYPE: DNA
<213> ORGANISM: Homo sapiens

<400> SEQUENCE: 259
gatctcaaat gtgtggtcta                                               20

<210> SEQ ID NO 260
<211> LENGTH: 18
<212> TYPE: DNA
<213> ORGANISM: Homo sapiens

<400> SEQUENCE: 260
tcctgtactg gatctcaa                                                 18

<210> SEQ ID NO 261
<211> LENGTH: 20
<212> TYPE: DNA
<213> ORGANISM: Homo sapiens

<400> SEQUENCE: 261
gccgtgtctt tcctgtactg                                               20

<210> SEQ ID NO 262
<211> LENGTH: 20
<212> TYPE: DNA
<213> ORGANISM: Homo sapiens

<400> SEQUENCE: 262
gccgtgtctt tcctgtactg                                               20

```
<210> SEQ ID NO 263
<211> LENGTH: 18
<212> TYPE: DNA
<213> ORGANISM: Homo sapiens

<400> SEQUENCE: 263
ggtctcggtc ttgctgtc                                                 18

<210> SEQ ID NO 264
<211> LENGTH: 20
<212> TYPE: DNA
<213> ORGANISM: Homo sapiens

<400> SEQUENCE: 264
ggcgttctgg agggtctcgg                                               20

<210> SEQ ID NO 265
<211> LENGTH: 21
<212> TYPE: DNA
<213> ORGANISM: Homo sapiens

<400> SEQUENCE: 265
gccatgctgt gggcgttctg g                                             21

<210> SEQ ID NO 266
<211> LENGTH: 20
<212> TYPE: DNA
<213> ORGANISM: Homo sapiens

<400> SEQUENCE: 266
gctggcaggg ccatgctgtg                                               20

<210> SEQ ID NO 267
<211> LENGTH: 18
<212> TYPE: DNA
<213> ORGANISM: Homo sapiens

<400> SEQUENCE: 267
ggctccaggg ctggcagg                                                 18

<210> SEQ ID NO 268
<211> LENGTH: 20
<212> TYPE: DNA
<213> ORGANISM: Homo sapiens

<400> SEQUENCE: 268
acctggtgga gggctccagg                                               20

<210> SEQ ID NO 269
<211> LENGTH: 20
<212> TYPE: DNA
<213> ORGANISM: Homo sapiens

<400> SEQUENCE: 269
ctggcccagt acctggtgga                                               20

<210> SEQ ID NO 270
<211> LENGTH: 20
<212> TYPE: DNA
<213> ORGANISM: Homo sapiens

<400> SEQUENCE: 270
gaccctcacc ctggcccagt                                               20
```

```
<210> SEQ ID NO 271
<211> LENGTH: 20
<212> TYPE: DNA
<213> ORGANISM: Homo sapiens

<400> SEQUENCE: 271
gaccctcacc ctggcccagt                                               20

<210> SEQ ID NO 272
<211> LENGTH: 20
<212> TYPE: DNA
<213> ORGANISM: Homo sapiens

<400> SEQUENCE: 272
tagccggtgc gggaggtcct                                               20

<210> SEQ ID NO 273
<211> LENGTH: 20
<212> TYPE: DNA
<213> ORGANISM: Homo sapiens

<400> SEQUENCE: 273
gatcccgttg tagccggtgc                                               20

<210> SEQ ID NO 274
<211> LENGTH: 20
<212> TYPE: DNA
<213> ORGANISM: Homo sapiens

<400> SEQUENCE: 274
actcgctcca gatcccgttg                                               20

<210> SEQ ID NO 275
<211> LENGTH: 22
<212> TYPE: DNA
<213> ORGANISM: Homo sapiens

<400> SEQUENCE: 275
tcaacacacc tccccaggct tg                                            22

<210> SEQ ID NO 276
<211> LENGTH: 20
<212> TYPE: DNA
<213> ORGANISM: Homo sapiens

<400> SEQUENCE: 276
tgggggtctc aacacacctc                                               20

<210> SEQ ID NO 277
<211> LENGTH: 20
<212> TYPE: DNA
<213> ORGANISM: Homo sapiens

<400> SEQUENCE: 277
tgtctaggcc tgggggtctc                                               20

<210> SEQ ID NO 278
<211> LENGTH: 20
<212> TYPE: DNA
<213> ORGANISM: Homo sapiens

<400> SEQUENCE: 278
ttcttctgga gcctctaggc                                               20
```

<210> SEQ ID NO 279
<211> LENGTH: 20
<212> TYPE: DNA
<213> ORGANISM: Homo sapiens

<400> SEQUENCE: 279
agaccagtct tcttctggag                                          20

<210> SEQ ID NO 280
<211> LENGTH: 20
<212> TYPE: DNA
<213> ORGANISM: Homo sapiens

<400> SEQUENCE: 280
gtggtgggag agaccagtct                                          20

<210> SEQ ID NO 281
<211> LENGTH: 20
<212> TYPE: DNA
<213> ORGANISM: Homo sapiens

<400> SEQUENCE: 281
aggcctctgt gtggtgggag                                          20

<210> SEQ ID NO 282
<211> LENGTH: 20
<212> TYPE: DNA
<213> ORGANISM: Homo sapiens

<400> SEQUENCE: 282
tgcctcctcc aggcctctgt                                          20

<210> SEQ ID NO 283
<211> LENGTH: 20
<212> TYPE: DNA
<213> ORGANISM: Homo sapiens

<400> SEQUENCE: 283
tcctggcctc tgcctcctcc                                          20

<210> SEQ ID NO 284
<211> LENGTH: 20
<212> TYPE: DNA
<213> ORGANISM: Homo sapiens

<400> SEQUENCE: 284
gacctctccc tcctggcctc                                          20

<210> SEQ ID NO 285
<211> LENGTH: 19
<212> TYPE: DNA
<213> ORGANISM: Homo sapiens

<400> SEQUENCE: 285
aggctcttgg gacctctcc                                           19

<210> SEQ ID NO 286
<211> LENGTH: 19
<212> TYPE: DNA
<213> ORGANISM: Homo sapiens

<400> SEQUENCE: 286
ccatttcaca ggctcttgg                                           19

<210> SEQ ID NO 287
<211> LENGTH: 21
<212> TYPE: DNA
<213> ORGANISM: Homo sapiens

<400> SEQUENCE: 287
gccaggccag acccatttca c                                    21

<210> SEQ ID NO 288
<211> LENGTH: 20
<212> TYPE: DNA
<213> ORGANISM: Homo sapiens

<400> SEQUENCE: 288
cagctgggag ccaggccaga                                       20

<210> SEQ ID NO 289
<211> LENGTH: 20
<212> TYPE: DNA
<213> ORGANISM: Homo sapiens

<400> SEQUENCE: 289
tgttcctgcc cagctgggag                                       20

<210> SEQ ID NO 290
<211> LENGTH: 20
<212> TYPE: DNA
<213> ORGANISM: Homo sapiens

<400> SEQUENCE: 290
tgaagtcctg tgttcctgcc                                       20

<210> SEQ ID NO 291
<211> LENGTH: 20
<212> TYPE: DNA
<213> ORGANISM: Homo sapiens

<400> SEQUENCE: 291
cttagtgtcc tgaagtcctg                                       20

<210> SEQ ID NO 292
<211> LENGTH: 20
<212> TYPE: DNA
<213> ORGANISM: Homo sapiens

<400> SEQUENCE: 292
tgacagggtc cttagtgtcc                                       20

<210> SEQ ID NO 293
<211> LENGTH: 20
<212> TYPE: DNA
<213> ORGANISM: Homo sapiens

<400> SEQUENCE: 293
gccatgggca tgacagggtc                                       20

<210> SEQ ID NO 294
<211> LENGTH: 20
<212> TYPE: DNA
<213> ORGANISM: Homo sapiens

<400> SEQUENCE: 294
gtgggtgctg gccatgggca                                       20

```
<210> SEQ ID NO 295
<211> LENGTH: 20
<212> TYPE: DNA
<213> ORGANISM: Homo sapiens

<400> SEQUENCE: 295
accagcactg gtgggtgctg                                               20

<210> SEQ ID NO 296
<211> LENGTH: 20
<212> TYPE: DNA
<213> ORGANISM: Homo sapiens

<400> SEQUENCE: 296
acaggcaggc accagcactg                                               20

<210> SEQ ID NO 297
<211> LENGTH: 20
<212> TYPE: DNA
<213> ORGANISM: Homo sapiens

<400> SEQUENCE: 297
tcagctctgg acaggcaggc                                               20

<210> SEQ ID NO 298
<211> LENGTH: 20
<212> TYPE: DNA
<213> ORGANISM: Homo sapiens

<400> SEQUENCE: 298
atacctctgt gtggtgggag                                               20

<210> SEQ ID NO 299
<211> LENGTH: 19
<212> TYPE: DNA
<213> ORGANISM: Homo sapiens

<400> SEQUENCE: 299
ggccatacct ctgtgtggt                                                19

<210> SEQ ID NO 300
<211> LENGTH: 21
<212> TYPE: DNA
<213> ORGANISM: Homo sapiens

<400> SEQUENCE: 300
ctggacgccg ggccatacct c                                             21

<210> SEQ ID NO 301
<211> LENGTH: 20
<212> TYPE: DNA
<213> ORGANISM: Homo sapiens

<400> SEQUENCE: 301
ggcctgcaga aggagatgtc                                               20

<210> SEQ ID NO 302
<211> LENGTH: 20
<212> TYPE: DNA
<213> ORGANISM: Homo sapiens

<400> SEQUENCE: 302
tcctccaggc ctgcagaagg                                               20
```

```
<210> SEQ ID NO 303
<211> LENGTH: 20
<212> TYPE: DNA
<213> ORGANISM: Homo sapiens

<400> SEQUENCE: 303
ctctgcctcc tccaggcctg                                               20

<210> SEQ ID NO 304
<211> LENGTH: 20
<212> TYPE: DNA
<213> ORGANISM: Homo sapiens

<400> SEQUENCE: 304
caccttctgc ccctgccagg                                               20

<210> SEQ ID NO 305
<211> LENGTH: 21
<212> TYPE: DNA
<213> ORGANISM: Homo sapiens

<400> SEQUENCE: 305
ccacgggact caccttctgc c                                             21

<210> SEQ ID NO 306
<211> LENGTH: 20
<212> TYPE: DNA
<213> ORGANISM: Homo sapiens

<400> SEQUENCE: 306
ggagccacgg gactcacctt                                               20

<210> SEQ ID NO 307
<211> LENGTH: 19
<212> TYPE: DNA
<213> ORGANISM: Homo sapiens

<400> SEQUENCE: 307
ttctgacaag aggggtaga                                                19

<210> SEQ ID NO 308
<211> LENGTH: 19
<212> TYPE: DNA
<213> ORGANISM: Homo sapiens

<400> SEQUENCE: 308
ggatggtttc tgacaagag                                                19

<210> SEQ ID NO 309
<211> LENGTH: 20
<212> TYPE: DNA
<213> ORGANISM: Homo sapiens

<400> SEQUENCE: 309
ctgcagcggg atggtttctg                                               20

<210> SEQ ID NO 310
<211> LENGTH: 17
<212> TYPE: DNA
<213> ORGANISM: Homo sapiens

<400> SEQUENCE: 310
cactcattca cccggcg                                                  17
```

```
<210> SEQ ID NO 311
<211> LENGTH: 20
<212> TYPE: DNA
<213> ORGANISM: Homo sapiens

<400> SEQUENCE: 311
gcatcactca ctcattcacc                                                 20

<210> SEQ ID NO 312
<211> LENGTH: 17
<212> TYPE: DNA
<213> ORGANISM: Homo sapiens

<400> SEQUENCE: 312
ccagcatcac tcactca                                                    17

<210> SEQ ID NO 313
<211> LENGTH: 20
<212> TYPE: DNA
<213> ORGANISM: Homo sapiens

<400> SEQUENCE: 313
tccctgttgg gagaggacac                                                 20

<210> SEQ ID NO 314
<211> LENGTH: 20
<212> TYPE: DNA
<213> ORGANISM: Homo sapiens

<400> SEQUENCE: 314
caggaggtcc ctgttgggag                                                 20

<210> SEQ ID NO 315
<211> LENGTH: 20
<212> TYPE: DNA
<213> ORGANISM: Homo sapiens

<400> SEQUENCE: 315
ctggctccag gaggtccctg                                                 20

<210> SEQ ID NO 316
<211> LENGTH: 20
<212> TYPE: DNA
<213> ORGANISM: Homo sapiens

<400> SEQUENCE: 316
caccatgctg ggtcagagtg                                                 20

<210> SEQ ID NO 317
<211> LENGTH: 17
<212> TYPE: DNA
<213> ORGANISM: Homo sapiens

<400> SEQUENCE: 317
cctcaccatg ctgggtc                                                    17

<210> SEQ ID NO 318
<211> LENGTH: 17
<212> TYPE: DNA
<213> ORGANISM: Homo sapiens

<400> SEQUENCE: 318
ccccagcccc tcaccat                                                    17
```

```
<210> SEQ ID NO 319
<211> LENGTH: 20
<212> TYPE: DNA
<213> ORGANISM: Homo sapiens

<400> SEQUENCE: 319
ggactggagg ggaggaagtg                                          20

<210> SEQ ID NO 320
<211> LENGTH: 17
<212> TYPE: DNA
<213> ORGANISM: Homo sapiens

<400> SEQUENCE: 320
ggaggctgga ctggagg                                             17

<210> SEQ ID NO 321
<211> LENGTH: 19
<212> TYPE: DNA
<213> ORGANISM: Homo sapiens

<400> SEQUENCE: 321
ggctcaggag gctggactg                                           19

<210> SEQ ID NO 322
<211> LENGTH: 18
<212> TYPE: DNA
<213> ORGANISM: Homo sapiens

<400> SEQUENCE: 322
tacctcccaa gagtcctg                                            18

<210> SEQ ID NO 323
<211> LENGTH: 20
<212> TYPE: DNA
<213> ORGANISM: Homo sapiens

<400> SEQUENCE: 323
cgtggttcct acctcccaag                                          20

<210> SEQ ID NO 324
<211> LENGTH: 20
<212> TYPE: DNA
<213> ORGANISM: Homo sapiens

<400> SEQUENCE: 324
ctggccgtgg ttcctacctc                                          20

<210> SEQ ID NO 325
<211> LENGTH: 20
<212> TYPE: DNA
<213> ORGANISM: Homo sapiens

<400> SEQUENCE: 325
gtcctgtcag gagacagtgg                                          20

<210> SEQ ID NO 326
<211> LENGTH: 20
<212> TYPE: DNA
<213> ORGANISM: Homo sapiens

<400> SEQUENCE: 326
tggctgcgtc ctgtcaggag                                          20
```

```
<210> SEQ ID NO 327
<211> LENGTH: 19
<212> TYPE: DNA
<213> ORGANISM: Homo sapiens

<400> SEQUENCE: 327
caggacgcag ccatcctcc                                               19

<210> SEQ ID NO 328
<211> LENGTH: 17
<212> TYPE: DNA
<213> ORGANISM: Homo sapiens

<400> SEQUENCE: 328
tacctggctg ggagtcc                                                 17

<210> SEQ ID NO 329
<211> LENGTH: 20
<212> TYPE: DNA
<213> ORGANISM: Homo sapiens

<400> SEQUENCE: 329
tggcaacatt acctggctgg                                              20

<210> SEQ ID NO 330
<211> LENGTH: 20
<212> TYPE: DNA
<213> ORGANISM: Homo sapiens

<400> SEQUENCE: 330
ggctctggca acattacctg                                              20

<210> SEQ ID NO 331
<211> LENGTH: 20
<212> TYPE: DNA
<213> ORGANISM: Homo sapiens

<400> SEQUENCE: 331
cccctgggtt ggagacaggt                                              20

<210> SEQ ID NO 332
<211> LENGTH: 20
<212> TYPE: DNA
<213> ORGANISM: Homo sapiens

<400> SEQUENCE: 332
gcctcatccc ctgggttgga                                              20

<210> SEQ ID NO 333
<211> LENGTH: 19
<212> TYPE: DNA
<213> ORGANISM: Homo sapiens

<400> SEQUENCE: 333
ggctgggcct catcccctg                                               19

<210> SEQ ID NO 334
<211> LENGTH: 19
<212> TYPE: DNA
<213> ORGANISM: Homo sapiens

<400> SEQUENCE: 334
caccctgcat ctgggctgg                                               19
```

```
<210> SEQ ID NO 335
<211> LENGTH: 19
<212> TYPE: DNA
<213> ORGANISM: Homo sapiens

<400> SEQUENCE: 335
gatgctcacc ctgcatctg                                                19

<210> SEQ ID NO 336
<211> LENGTH: 17
<212> TYPE: DNA
<213> ORGANISM: Homo sapiens

<400> SEQUENCE: 336
aaaaagatgc tcaccct                                                  17

<210> SEQ ID NO 337
<211> LENGTH: 19
<212> TYPE: DNA
<213> ORGANISM: Homo sapiens

<400> SEQUENCE: 337
tccctgagga gcacagcag                                                19

<210> SEQ ID NO 338
<211> LENGTH: 19
<212> TYPE: DNA
<213> ORGANISM: Homo sapiens

<400> SEQUENCE: 338
ctcttcctcc ctgaggagc                                                19

<210> SEQ ID NO 339
<211> LENGTH: 19
<212> TYPE: DNA
<213> ORGANISM: Homo sapiens

<400> SEQUENCE: 339
ggagcactct tcctccctg                                                19

<210> SEQ ID NO 340
<211> LENGTH: 19
<212> TYPE: DNA
<213> ORGANISM: Homo sapiens

<400> SEQUENCE: 340
cactgttcac tgagctctt                                                19

<210> SEQ ID NO 341
<211> LENGTH: 18
<212> TYPE: DNA
<213> ORGANISM: Homo sapiens

<400> SEQUENCE: 341
aactcactgt tcactgag                                                 18

<210> SEQ ID NO 342
<211> LENGTH: 20
<212> TYPE: DNA
<213> ORGANISM: Homo sapiens

<400> SEQUENCE: 342
gctaggagca aactcactgt                                               20
```

<210> SEQ ID NO 343
<211> LENGTH: 20
<212> TYPE: DNA
<213> ORGANISM: Homo sapiens

<400> SEQUENCE: 343
ggactggagg gagggaagct                                                    20

<210> SEQ ID NO 344
<211> LENGTH: 20
<212> TYPE: DNA
<213> ORGANISM: Homo sapiens

<400> SEQUENCE: 344
gccatctgga ctggagggag                                                    20

<210> SEQ ID NO 345
<211> LENGTH: 20
<212> TYPE: DNA
<213> ORGANISM: Homo sapiens

<400> SEQUENCE: 345
tggaggggcc atctggactg                                                    20

<210> SEQ ID NO 346
<211> LENGTH: 20
<212> TYPE: DNA
<213> ORGANISM: Homo sapiens

<400> SEQUENCE: 346
caccttccac gtggccgtgt                                                    20

<210> SEQ ID NO 347
<211> LENGTH: 17
<212> TYPE: DNA
<213> ORGANISM: Homo sapiens

<400> SEQUENCE: 347
cctcaccttc cacgtgg                                                       17

<210> SEQ ID NO 348
<211> LENGTH: 18
<212> TYPE: DNA
<213> ORGANISM: Homo sapiens

<400> SEQUENCE: 348
ggcaaaggcc ctcacctt                                                      18

<210> SEQ ID NO 349
<211> LENGTH: 20
<212> TYPE: DNA
<213> ORGANISM: Homo sapiens

<400> SEQUENCE: 349
gtcctgtggg ttggcactga                                                    20

<210> SEQ ID NO 350
<211> LENGTH: 20
<212> TYPE: DNA
<213> ORGANISM: Homo sapiens

<400> SEQUENCE: 350
tcttgctgtc ctgtgggttg                                                    20

```
<210> SEQ ID NO 351
<211> LENGTH: 20
<212> TYPE: DNA
<213> ORGANISM: Homo sapiens

<400> SEQUENCE: 351
gtctcggtct tgctgtcctg                                               20

<210> SEQ ID NO 352
<211> LENGTH: 17
<212> TYPE: DNA
<213> ORGANISM: Homo sapiens

<400> SEQUENCE: 352
tacccgactc ggtgtcc                                                  17

<210> SEQ ID NO 353
<211> LENGTH: 20
<212> TYPE: DNA
<213> ORGANISM: Homo sapiens

<400> SEQUENCE: 353
gccttcacct acccgactcg                                               20

<210> SEQ ID NO 354
<211> LENGTH: 20
<212> TYPE: DNA
<213> ORGANISM: Homo sapiens

<400> SEQUENCE: 354
ctccagcctt cacctacccg                                               20

<210> SEQ ID NO 355
<211> LENGTH: 17
<212> TYPE: DNA
<213> ORGANISM: Homo sapiens

<400> SEQUENCE: 355
gcacttccag cagccgg                                                  17

<210> SEQ ID NO 356
<211> LENGTH: 19
<212> TYPE: DNA
<213> ORGANISM: Homo sapiens

<400> SEQUENCE: 356
cataggcagc acttccagc                                                19

<210> SEQ ID NO 357
<211> LENGTH: 17
<212> TYPE: DNA
<213> ORGANISM: Homo sapiens

<400> SEQUENCE: 357
ccacataggc agcactt                                                  17

<210> SEQ ID NO 358
<211> LENGTH: 20
<212> TYPE: DNA
<213> ORGANISM: Homo sapiens

<400> SEQUENCE: 358
cacctgtacc cgtagatgcc                                               20
```

<210> SEQ ID NO 359
<211> LENGTH: 20
<212> TYPE: DNA
<213> ORGANISM: Homo sapiens

<400> SEQUENCE: 359
gtcccctcac ctgtacccgt                                          20

<210> SEQ ID NO 360
<211> LENGTH: 20
<212> TYPE: DNA
<213> ORGANISM: Homo sapiens

<400> SEQUENCE: 360
ccacagagtc ccctcacctg                                          20

<210> SEQ ID NO 361
<211> LENGTH: 20
<212> TYPE: DNA
<213> ORGANISM: Homo sapiens

<400> SEQUENCE: 361
agcctggaag acaccacgga                                          20

<210> SEQ ID NO 362
<211> LENGTH: 20
<212> TYPE: DNA
<213> ORGANISM: Homo sapiens

<400> SEQUENCE: 362
ttctgcgcag cctggaagac                                          20

<210> SEQ ID NO 363
<211> LENGTH: 19
<212> TYPE: DNA
<213> ORGANISM: Homo sapiens

<400> SEQUENCE: 363
ccactttctg cgcagcctg                                           19

<210> SEQ ID NO 364
<211> LENGTH: 20
<212> TYPE: DNA
<213> ORGANISM: Homo sapiens

<400> SEQUENCE: 364
tacctggaac aggtggctct                                          20

<210> SEQ ID NO 365
<211> LENGTH: 20
<212> TYPE: DNA
<213> ORGANISM: Homo sapiens

<400> SEQUENCE: 365
cagttcctac ctggaacagg                                          20

<210> SEQ ID NO 366
<211> LENGTH: 20
<212> TYPE: DNA
<213> ORGANISM: Homo sapiens

<400> SEQUENCE: 366
tcgcagccag ttcctacctg                                          20

<210> SEQ ID NO 367
<211> LENGTH: 19
<212> TYPE: DNA
<213> ORGANISM: Homo sapiens

<400> SEQUENCE: 367
gttctgcaag agcagagac                                                    19

<210> SEQ ID NO 368
<211> LENGTH: 20
<212> TYPE: DNA
<213> ORGANISM: Homo sapiens

<400> SEQUENCE: 368
gcgctcccgt tctgcaagag                                                   20

<210> SEQ ID NO 369
<211> LENGTH: 19
<212> TYPE: DNA
<213> ORGANISM: Homo sapiens

<400> SEQUENCE: 369
gctctgcgct cccgttctg                                                    19

<210> SEQ ID NO 370
<211> LENGTH: 17
<212> TYPE: DNA
<213> ORGANISM: Homo sapiens

<400> SEQUENCE: 370
cacccctcca gctcagg                                                      17

<210> SEQ ID NO 371
<211> LENGTH: 20
<212> TYPE: DNA
<213> ORGANISM: Homo sapiens

<400> SEQUENCE: 371
gagcccactc acccctccag                                                   20

<210> SEQ ID NO 372
<211> LENGTH: 20
<212> TYPE: DNA
<213> ORGANISM: Homo sapiens

<400> SEQUENCE: 372
tccacgagcc cactcacccc                                                   20

<210> SEQ ID NO 373
<211> LENGTH: 20
<212> TYPE: DNA
<213> ORGANISM: Homo sapiens

<400> SEQUENCE: 373
accctgtggg aagaaaatgg                                                   20

<210> SEQ ID NO 374
<211> LENGTH: 18
<212> TYPE: DNA
<213> ORGANISM: Homo sapiens

<400> SEQUENCE: 374
ggaacaccct gtgggaag                                                     18

```
<210> SEQ ID NO 375
<211> LENGTH: 19
<212> TYPE: DNA
<213> ORGANISM: Homo sapiens

<400> SEQUENCE: 375
tcctacaggg aacaccctg                                                19

<210> SEQ ID NO 376
<211> LENGTH: 17
<212> TYPE: DNA
<213> ORGANISM: Homo sapiens

<400> SEQUENCE: 376
gtctcaacac acctccc                                                  17

<210> SEQ ID NO 377
<211> LENGTH: 20
<212> TYPE: DNA
<213> ORGANISM: Homo sapiens

<400> SEQUENCE: 377
gcctgggggt ctcaacacac                                               20

<210> SEQ ID NO 378
<211> LENGTH: 20
<212> TYPE: DNA
<213> ORGANISM: Homo sapiens

<400> SEQUENCE: 378
gtctaggcct gggggtctca                                               20

<210> SEQ ID NO 379
<211> LENGTH: 21
<212> TYPE: DNA
<213> ORGANISM: Homo sapiens

<400> SEQUENCE: 379
agccctgctc ctggacgccg g                                             21

<210> SEQ ID NO 380
<211> LENGTH: 20
<212> TYPE: DNA
<213> ORGANISM: Homo sapiens

<400> SEQUENCE: 380
ccacccctca gccctgctcc                                               20

<210> SEQ ID NO 381
<211> LENGTH: 20
<212> TYPE: DNA
<213> ORGANISM: Homo sapiens

<400> SEQUENCE: 381
ctgctctgac cccaccccctc                                              20

<210> SEQ ID NO 382
<211> LENGTH: 20
<212> TYPE: DNA
<213> ORGANISM: Homo sapiens

<400> SEQUENCE: 382
tgcccctccc cttccacgtg                                               20
```

```
<210> SEQ ID NO 383
<211> LENGTH: 22
<212> TYPE: DNA
<213> ORGANISM: Homo sapiens

<400> SEQUENCE: 383
gtcagcagtg agctgcccct cc                                              22

<210> SEQ ID NO 384
<211> LENGTH: 20
<212> TYPE: DNA
<213> ORGANISM: Homo sapiens

<400> SEQUENCE: 384
aggagatgtc agcagtgagc                                                 20

<210> SEQ ID NO 385
<211> LENGTH: 18
<212> TYPE: DNA
<213> ORGANISM: Homo sapiens

<400> SEQUENCE: 385
agtgggtggg agccacgg                                                   18

<210> SEQ ID NO 386
<211> LENGTH: 20
<212> TYPE: DNA
<213> ORGANISM: Homo sapiens

<400> SEQUENCE: 386
agggacaggg aagtgggtgg                                                 20

<210> SEQ ID NO 387
<211> LENGTH: 20
<212> TYPE: DNA
<213> ORGANISM: Homo sapiens

<400> SEQUENCE: 387
gcagtgagga cagggacagg                                                 20

<210> SEQ ID NO 388
<211> LENGTH: 20
<212> TYPE: DNA
<213> ORGANISM: Homo sapiens

<400> SEQUENCE: 388
ctgcagggac ccttgtcacc                                                 20

<210> SEQ ID NO 389
<211> LENGTH: 20
<212> TYPE: DNA
<213> ORGANISM: Homo sapiens

<400> SEQUENCE: 389
ctctctttcc tgcagggacc                                                 20

<210> SEQ ID NO 390
<211> LENGTH: 20
<212> TYPE: DNA
<213> ORGANISM: Homo sapiens

<400> SEQUENCE: 390 aggggggtcac ctctctttcc                                                20
```

<210> SEQ ID NO 391
<211> LENGTH: 20
<212> TYPE: DNA
<213> ORGANISM: Homo sapiens

<400> SEQUENCE: 391
gaggggtaga aggggtcac                                              20

<210> SEQ ID NO 392
<211> LENGTH: 20
<212> TYPE: DNA
<213> ORGANISM: Homo sapiens

<400> SEQUENCE: 392
gtggcccctg cccccagcat                                             20

<210> SEQ ID NO 393
<211> LENGTH: 20
<212> TYPE: DNA
<213> ORGANISM: Homo sapiens

<400> SEQUENCE: 393 gccccctgccc gtggcccctg                                            20

<210> SEQ ID NO 394
<211> LENGTH: 19
<212> TYPE: DNA
<213> ORGANISM: Homo sapiens

<400> SEQUENCE: 394
ggacgtcgta gccctgcc                                               19

<210> SEQ ID NO 395
<211> LENGTH: 20
<212> TYPE: DNA
<213> ORGANISM: Homo sapiens

<400> SEQUENCE: 395
agggtgtatg ggtatcactg                                             20

<210> SEQ ID NO 396
<211> LENGTH: 20
<212> TYPE: DNA
<213> ORGANISM: Homo sapiens

<400> SEQUENCE: 396
ggcttagccc agggtgtatg                                             20

<210> SEQ ID NO 397
<211> LENGTH: 19
<212> TYPE: DNA
<213> ORGANISM: Homo sapiens

<400> SEQUENCE: 397
gagaggacac ggcttagcc                                              19

<210> SEQ ID NO 398
<211> LENGTH: 18
<212> TYPE: DNA
<213> ORGANISM: Homo sapiens

<400> SEQUENCE: 398
ccgggcaggg cccccagc                                               18

<210> SEQ ID NO 399
<211> LENGTH: 20
<212> TYPE: DNA
<213> ORGANISM: Homo sapiens

<400> SEQUENCE: 399
ggaaaccaag ccccgggcag                                               20

<210> SEQ ID NO 400
<211> LENGTH: 20
<212> TYPE: DNA
<213> ORGANISM: Homo sapiens

<400> SEQUENCE: 400
tgtccacaca ggaaaccaag                                               20

<210> SEQ ID NO 401
<211> LENGTH: 19
<212> TYPE: DNA
<213> ORGANISM: Homo sapiens

<400> SEQUENCE: 401
ccgctggggg gcagtcagg                                                19

<210> SEQ ID NO 402
<211> LENGTH: 18
<212> TYPE: DNA
<213> ORGANISM: Homo sapiens

<400> SEQUENCE: 402
aagggctgga ccgctggg                                                 18

<210> SEQ ID NO 403
<211> LENGTH: 20
<212> TYPE: DNA
<213> ORGANISM: Homo sapiens

<400> SEQUENCE: 403
aagggcacct aagggctgga                                               20

<210> SEQ ID NO 404
<211> LENGTH: 20
<212> TYPE: DNA
<213> ORGANISM: Homo sapiens

<400> SEQUENCE: 404
ggaggaagtg aagggcacct                                               20

<210> SEQ ID NO 405
<211> LENGTH: 18
<212> TYPE: DNA
<213> ORGANISM: Homo sapiens

<400> SEQUENCE: 405
ggcagagctg gccgtggt                                                 18

<210> SEQ ID NO 406
<211> LENGTH: 20
<212> TYPE: DNA
<213> ORGANISM: Homo sapiens

<400> SEQUENCE: 406
ccttcgggct ggggcagagc                                               20

<210> SEQ ID NO 407
<211> LENGTH: 20
<212> TYPE: DNA
<213> ORGANISM: Homo sapiens

<400> SEQUENCE: 407
gctgcccatc ccttcgggct                                         20

<210> SEQ ID NO 408
<211> LENGTH: 20
<212> TYPE: DNA
<213> ORGANISM: Homo sapiens

<400> SEQUENCE: 408
gtgctggagg aggggtgctg                                         20

<210> SEQ ID NO 409
<211> LENGTH: 20
<212> TYPE: DNA
<213> ORGANISM: Homo sapiens

<400> SEQUENCE: 409
gagacagtgg gtgctggagg                                         20

<210> SEQ ID NO 410
<211> LENGTH: 20
<212> TYPE: DNA
<213> ORGANISM: Homo sapiens

<400> SEQUENCE: 410
gcatttcctg ggctctggca                                         20

<210> SEQ ID NO 411
<211> LENGTH: 20
<212> TYPE: DNA
<213> ORGANISM: Homo sapiens

<400> SEQUENCE: 411
ccaccacggg gcatttcctg                                         20

<210> SEQ ID NO 412
<211> LENGTH: 19
<212> TYPE: DNA
<213> ORGANISM: Homo sapiens

<400> SEQUENCE: 412
gcctgccctc ccaccacgg                                          19

<210> SEQ ID NO 413
<211> LENGTH: 21
<212> TYPE: DNA
<213> ORGANISM: Homo sapiens

<400> SEQUENCE: 413
tccgtcattc atccctccca t                                       21

<210> SEQ ID NO 414
<211> LENGTH: 20
<212> TYPE: DNA
<213> ORGANISM: Homo sapiens

<400> SEQUENCE: 414
cctcatgtac tccgtcattc                                         20

```
<210> SEQ ID NO 415
<211> LENGTH: 20
<212> TYPE: DNA
<213> ORGANISM: Homo sapiens

<400> SEQUENCE: 415
ggagacaggt cctcatgtac                                               20

<210> SEQ ID NO 416
<211> LENGTH: 20
<212> TYPE: DNA
<213> ORGANISM: Homo sapiens

<400> SEQUENCE: 416
gaggggatgg agaaaaaaga                                               20

<210> SEQ ID NO 417
<211> LENGTH: 20
<212> TYPE: DNA
<213> ORGANISM: Homo sapiens

<400> SEQUENCE: 417
aagaggaggg gaggggatgg                                               20

<210> SEQ ID NO 418
<211> LENGTH: 19
<212> TYPE: DNA
<213> ORGANISM: Homo sapiens

<400> SEQUENCE: 418
gagcaaggcc aagaggagg                                                19

<210> SEQ ID NO 419
<211> LENGTH: 19
<212> TYPE: DNA
<213> ORGANISM: Homo sapiens

<400> SEQUENCE: 419
ggagggagga gagcttagg                                                19

<210> SEQ ID NO 420
<211> LENGTH: 20
<212> TYPE: DNA
<213> ORGANISM: Homo sapiens

<400> SEQUENCE: 420
agggcacacg ggagggagga                                               20

<210> SEQ ID NO 421
<211> LENGTH: 20
<212> TYPE: DNA
<213> ORGANISM: Homo sapiens

<400> SEQUENCE: 421
agggagaggg agggcacacg                                               20

<210> SEQ ID NO 422
<211> LENGTH: 19
<212> TYPE: DNA
<213> ORGANISM: Homo sapiens

<400> SEQUENCE: 422
agctgagggc agggagagg                                                19
```

<210> SEQ ID NO 423
<211> LENGTH: 20
<212> TYPE: DNA
<213> ORGANISM: Homo sapiens

<400> SEQUENCE: 423
agcacagcag agctgagggc                                               20

<210> SEQ ID NO 424
<211> LENGTH: 19
<212> TYPE: DNA
<213> ORGANISM: Homo sapiens

<400> SEQUENCE: 424
ccacagcggg ctaggagca                                                19

<210> SEQ ID NO 425
<211> LENGTH: 19
<212> TYPE: DNA
<213> ORGANISM: Homo sapiens

<400> SEQUENCE: 425
cagaccatcc ccacagcgg                                                19

<210> SEQ ID NO 426
<211> LENGTH: 20
<212> TYPE: DNA
<213> ORGANISM: Homo sapiens

<400> SEQUENCE: 426
gtgctggtcc cagaccatcc                                               20

<210> SEQ ID NO 427
<211> LENGTH: 20
<212> TYPE: DNA
<213> ORGANISM: Homo sapiens

<400> SEQUENCE: 427
gtcatcatac ccaccctcca                                               20

<210> SEQ ID NO 428
<211> LENGTH: 20
<212> TYPE: DNA
<213> ORGANISM: Homo sapiens

<400> SEQUENCE: 428
ttcaggagag tcatcatacc                                               20

<210> SEQ ID NO 429
<211> LENGTH: 20
<212> TYPE: DNA
<213> ORGANISM: Homo sapiens

<400> SEQUENCE: 429
agggaagctt tcaggagagt                                               20

<210> SEQ ID NO 430
<211> LENGTH: 20
<212> TYPE: DNA
<213> ORGANISM: Homo sapiens

<400> SEQUENCE: 430
ctcccctccc tgggcaaagg                                               20

<210> SEQ ID NO 431
<211> LENGTH: 18
<212> TYPE: DNA
<213> ORGANISM: Homo sapiens

<400> SEQUENCE: 431
ccagtgtttc tccctcc                                                  18

<210> SEQ ID NO 432
<211> LENGTH: 19
<212> TYPE: DNA
<213> ORGANISM: Homo sapiens

<400> SEQUENCE: 432
tcccgccctc cccagtgtt                                                19

<210> SEQ ID NO 433
<211> LENGTH: 20
<212> TYPE: DNA
<213> ORGANISM: Homo sapiens

<400> SEQUENCE: 433
ccgtgggagc agctgcaaat                                               20

<210> SEQ ID NO 434
<211> LENGTH: 20
<212> TYPE: DNA
<213> ORGANISM: Homo sapiens

<400> SEQUENCE: 434
tggcccggtg cccgtgggag                                               20

<210> SEQ ID NO 435
<211> LENGTH: 19
<212> TYPE: DNA
<213> ORGANISM: Homo sapiens

<400> SEQUENCE: 435
ggtgaggcct ggcccggtg                                                19

<210> SEQ ID NO 436
<211> LENGTH: 20
<212> TYPE: DNA
<213> ORGANISM: Homo sapiens

<400> SEQUENCE: 436
ttggcactga gggtgaggcc                                               20

<210> SEQ ID NO 437
<211> LENGTH: 20
<212> TYPE: DNA
<213> ORGANISM: Homo sapiens

<400> SEQUENCE: 437
aagctctgga ctccagcctt                                               20

<210> SEQ ID NO 438
<211> LENGTH: 20
<212> TYPE: DNA
<213> ORGANISM: Homo sapiens

<400> SEQUENCE: 438
tcctggccag aagctctgga                                               20

<210> SEQ ID NO 439
<211> LENGTH: 20
<212> TYPE: DNA
<213> ORGANISM: Homo sapiens

<400> SEQUENCE: 439
tatgagctgg tcctggccag          20

<210> SEQ ID NO 440
<211> LENGTH: 20
<212> TYPE: DNA
<213> ORGANISM: Homo sapiens

<400> SEQUENCE: 440
gaaatcgacc tcagggcagg          20

<210> SEQ ID NO 441
<211> LENGTH: 22
<212> TYPE: DNA
<213> ORGANISM: Homo sapiens

<400> SEQUENCE: 441
atctgggcgg gaaatcgacc tc          22

<210> SEQ ID NO 442
<211> LENGTH: 20
<212> TYPE: DNA
<213> ORGANISM: Homo sapiens

<400> SEQUENCE: 442
gaatgtcagc atctgggcgg          20

<210> SEQ ID NO 443
<211> LENGTH: 20
<212> TYPE: DNA
<213> ORGANISM: Homo sapiens

<400> SEQUENCE: 443
ggagaaagag gaatgtcagc          20

<210> SEQ ID NO 444
<211> LENGTH: 20
<212> TYPE: DNA
<213> ORGANISM: Homo sapiens

<400> SEQUENCE: 444
cagcagccgg ggagaaagag          20

<210> SEQ ID NO 445
<211> LENGTH: 20
<212> TYPE: DNA
<213> ORGANISM: Homo sapiens

<400> SEQUENCE: 445
acctccagcc ccacagagtc          20

<210> SEQ ID NO 446
<211> LENGTH: 20
<212> TYPE: DNA
<213> ORGANISM: Homo sapiens

<400> SEQUENCE: 446
acctccagcc ccacagagtc          20

```
<210> SEQ ID NO 447
<211> LENGTH: 20
<212> TYPE: DNA
<213> ORGANISM: Homo sapiens

<400> SEQUENCE: 447
cctctggggt ctcggctgcc                                               20

<210> SEQ ID NO 448
<211> LENGTH: 20
<212> TYPE: DNA
<213> ORGANISM: Homo sapiens

<400> SEQUENCE: 448
atcagagacc tcatggccag                                               20

<210> SEQ ID NO 449
<211> LENGTH: 20
<212> TYPE: DNA
<213> ORGANISM: Homo sapiens

<400> SEQUENCE: 449
ggtgacagcc atcagagacc                                               20

<210> SEQ ID NO 450
<211> LENGTH: 20
<212> TYPE: DNA
<213> ORGANISM: Homo sapiens

<400> SEQUENCE: 450
acaccacgga ggtgacagcc                                               20

<210> SEQ ID NO 451
<211> LENGTH: 20
<212> TYPE: DNA
<213> ORGANISM: Homo sapiens

<400> SEQUENCE: 451
actccgcccc tcgcagccag                                               20

<210> SEQ ID NO 452
<211> LENGTH: 18
<212> TYPE: DNA
<213> ORGANISM: Homo sapiens

<400> SEQUENCE: 452
agaagccccc actccgcc                                                 18

<210> SEQ ID NO 453
<211> LENGTH: 20
<212> TYPE: DNA
<213> ORGANISM: Homo sapiens

<400> SEQUENCE: 453
gcaggaacag agaagccccc                                               20

<210> SEQ ID NO 454
<211> LENGTH: 20
<212> TYPE: DNA
<213> ORGANISM: Homo sapiens

<400> SEQUENCE: 454
gtgagcatca ggaggtccga                                               20
```

```
<210> SEQ ID NO 455
<211> LENGTH: 20
<212> TYPE: DNA
<213> ORGANISM: Homo sapiens

<400> SEQUENCE: 455
atttgggccg gtgagcatca                                              20

<210> SEQ ID NO 456
<211> LENGTH: 20
<212> TYPE: DNA
<213> ORGANISM: Homo sapiens

<400> SEQUENCE: 456
gagcagagac atttgggccg                                              20

<210> SEQ ID NO 457
<211> LENGTH: 20
<212> TYPE: DNA
<213> ORGANISM: Homo sapiens

<400> SEQUENCE: 457
tcaggagtga tccacgagcc                                              20

<210> SEQ ID NO 458
<211> LENGTH: 20
<212> TYPE: DNA
<213> ORGANISM: Homo sapiens

<400> SEQUENCE: 458
accccaaagg tcaggagtga                                              20

<210> SEQ ID NO 459
<211> LENGTH: 18
<212> TYPE: DNA
<213> ORGANISM: Homo sapiens

<400> SEQUENCE: 459
ccgtatgaac cccaaagg                                                18

<210> SEQ ID NO 460
<211> LENGTH: 19
<212> TYPE: DNA
<213> ORGANISM: Homo sapiens

<400> SEQUENCE: 460
gatccgggtc aggcacaag                                               19

<210> SEQ ID NO 461
<211> LENGTH: 21
<212> TYPE: DNA
<213> ORGANISM: Homo sapiens

<400> SEQUENCE: 461
ctgggcagat gatccgggtc a                                            21

<210> SEQ ID NO 462
<211> LENGTH: 20
<212> TYPE: DNA
<213> ORGANISM: Homo sapiens

<400> SEQUENCE: 462
tgggaccacc ctgggcagat                                              20
```

<210> SEQ ID NO 463
<211> LENGTH: 20
<212> TYPE: DNA
<213> ORGANISM: Homo sapiens

<400> SEQUENCE: 463
gcagaagagt tgggaccacc                                               20

<210> SEQ ID NO 464
<211> LENGTH: 20
<212> TYPE: DNA
<213> ORGANISM: Homo sapiens

<400> SEQUENCE: 464
aagaaaatgg gcagaagagt                                               20

<210> SEQ ID NO 465
<211> LENGTH: 18
<212> TYPE: DNA
<213> ORGANISM: Homo sapiens

<400> SEQUENCE: 465
ccttgcctgt ctaggcct                                                 18

<210> SEQ ID NO 466
<211> LENGTH: 19
<212> TYPE: DNA
<213> ORGANISM: Homo sapiens

<400> SEQUENCE: 466
cctctccatc cccttgcct                                                19

<210> SEQ ID NO 467
<211> LENGTH: 20
<212> TYPE: DNA
<213> ORGANISM: Homo sapiens

<400> SEQUENCE: 467
ggaaggcaag ccctctccat                                               20

<210> SEQ ID NO 468
<211> LENGTH: 20
<212> TYPE: DNA
<213> ORGANISM: Homo sapiens

<400> SEQUENCE: 468
tccccttgcc tgtctaggcc                                               20

<210> SEQ ID NO 469
<211> LENGTH: 20
<212> TYPE: DNA
<213> ORGANISM: Homo sapiens

<400> SEQUENCE: 469
gccctctcca tccccttgcc                                               20

<210> SEQ ID NO 470
<211> LENGTH: 19
<212> TYPE: DNA
<213> ORGANISM: Homo sapiens

<400> SEQUENCE: 470
ggaaggcaag ccctctcca                                                19

<210> SEQ ID NO 471
<211> LENGTH: 20
<212> TYPE: DNA
<213> ORGANISM: Homo sapiens

<400> SEQUENCE: 471
tcaggcggga gggaaggcaa                                               20

<210> SEQ ID NO 472
<211> LENGTH: 20
<212> TYPE: DNA
<213> ORGANISM: Homo sapiens

<400> SEQUENCE: 472
ctgaggaagg tcaggcggga                                               20

<210> SEQ ID NO 473
<211> LENGTH: 20
<212> TYPE: DNA
<213> ORGANISM: Homo sapiens

<400> SEQUENCE: 473
gcagaaatga ctgaggaagg                                               20

<210> SEQ ID NO 474
<211> LENGTH: 20
<212> TYPE: DNA
<213> ORGANISM: Homo sapiens

<400> SEQUENCE: 474
ccttggcttt gcagaaatga                                               20

<210> SEQ ID NO 475
<211> LENGTH: 19
<212> TYPE: DNA
<213> ORGANISM: Homo sapiens

<400> SEQUENCE: 475
ggaggctgcc ccttggctt                                                19

<210> SEQ ID NO 476
<211> LENGTH: 20
<212> TYPE: DNA
<213> ORGANISM: Homo sapiens

<400> SEQUENCE: 476
taccttgaca ggaggctgcc                                               20

<210> SEQ ID NO 477
<211> LENGTH: 20
<212> TYPE: DNA
<213> ORGANISM: Homo sapiens

<400> SEQUENCE: 477
ggcctctagc taccttgaca                                               20

<210> SEQ ID NO 478
<211> LENGTH: 20
<212> TYPE: DNA
<213> ORGANISM: Homo sapiens

<400> SEQUENCE: 478
tcctttccca ggcctctagc                                               20

<210> SEQ ID NO 479
<211> LENGTH: 20
<212> TYPE: DNA
<213> ORGANISM: Homo sapiens

<400> SEQUENCE: 479
caaggctatc tcctttccca                                               20

<210> SEQ ID NO 480
<211> LENGTH: 18
<212> TYPE: DNA
<213> ORGANISM: Homo sapiens

<400> SEQUENCE: 480
ggccggagca aggctatc                                                 18

<210> SEQ ID NO 481
<211> LENGTH: 20
<212> TYPE: DNA
<213> ORGANISM: Homo sapiens

<400> SEQUENCE: 481
gaaggtcaag ggggccggag                                               20

<210> SEQ ID NO 482
<211> LENGTH: 20
<212> TYPE: DNA
<213> ORGANISM: Homo sapiens

<400> SEQUENCE: 482
gtgatttgct gaaggtcaag                                               20

<210> SEQ ID NO 483
<211> LENGTH: 20
<212> TYPE: DNA
<213> ORGANISM: Homo sapiens

<400> SEQUENCE: 483
agggagagaa gtgatttgct                                               20

<210> SEQ ID NO 484
<211> LENGTH: 20
<212> TYPE: DNA
<213> ORGANISM: Homo sapiens

<400> SEQUENCE: 484
gtgtgagcgc agggagagaa                                               20

<210> SEQ ID NO 485
<211> LENGTH: 20
<212> TYPE: DNA
<213> ORGANISM: Homo sapiens

<400> SEQUENCE: 485
gtgtgtgtct gtgtgagcgc                                               20

<210> SEQ ID NO 486
<211> LENGTH: 20
<212> TYPE: DNA
<213> ORGANISM: Homo sapiens

<400> SEQUENCE: 486
acgtgtgtgt gtgtgtgtct                                               20

```
<210> SEQ ID NO 487
<211> LENGTH: 20
<212> TYPE: DNA
<213> ORGANISM: Homo sapiens

<400> SEQUENCE: 487
gtgtgcatgt acgtgtgtgt                                                   20

<210> SEQ ID NO 488
<211> LENGTH: 20
<212> TYPE: DNA
<213> ORGANISM: Homo sapiens

<400> SEQUENCE: 488
caggaaaaat gtgtgcatgt                                                   20

<210> SEQ ID NO 489
<211> LENGTH: 20
<212> TYPE: DNA
<213> ORGANISM: Homo sapiens

<400> SEQUENCE: 489
gttaacctga caggaaaaat                                                   20

<210> SEQ ID NO 490
<211> LENGTH: 20
<212> TYPE: DNA
<213> ORGANISM: Homo sapiens

<400> SEQUENCE: 490
ctacaaataa gttaacctga                                                   20

<210> SEQ ID NO 491
<211> LENGTH: 20
<212> TYPE: DNA
<213> ORGANISM: Homo sapiens

<400> SEQUENCE: 491
aatgcagaac ctacaaataa                                                   20

<210> SEQ ID NO 492
<211> LENGTH: 20
<212> TYPE: DNA
<213> ORGANISM: Homo sapiens

<400> SEQUENCE: 492
aagttctaat aatgcagaac                                                   20

<210> SEQ ID NO 493
<211> LENGTH: 20
<212> TYPE: DNA
<213> ORGANISM: Homo sapiens

<400> SEQUENCE: 493
tatatctaga aagttctaat                                                   20

<210> SEQ ID NO 494
<211> LENGTH: 20
<212> TYPE: DNA
<213> ORGANISM: Homo sapiens

<400> SEQUENCE: 494
atggaatgag tatatctaga                                                   20
```

<210> SEQ ID NO 495
<211> LENGTH: 20
<212> TYPE: DNA
<213> ORGANISM: Homo sapiens

<400> SEQUENCE: 495
tgagggggag atggaatgag                                                    20

<210> SEQ ID NO 496
<211> LENGTH: 20
<212> TYPE: DNA
<213> ORGANISM: Homo sapiens

<400> SEQUENCE: 496
attaaaaaaa tgagggggag                                                    20

<210> SEQ ID NO 497
<211> LENGTH: 21
<212> TYPE: DNA
<213> ORGANISM: Homo sapiens

<400> SEQUENCE: 497
aggaaacctg attaaaaaaa t                                                  21

<210> SEQ ID NO 498
<211> LENGTH: 20
<212> TYPE: DNA
<213> ORGANISM: Homo sapiens

<400> SEQUENCE: 498
ggcaaaagca aggaaacctg                                                    20

<210> SEQ ID NO 499
<211> LENGTH: 20
<212> TYPE: DNA
<213> ORGANISM: Homo sapiens

<400> SEQUENCE: 499
gaagaaaaat ggcaaaagca                                                    20

<210> SEQ ID NO 500
<211> LENGTH: 22
<212> TYPE: DNA
<213> ORGANISM: Homo sapiens

<400> SEQUENCE: 500 gaaaaagaa ggaagaaaaa tg                                                  22

<210> SEQ ID NO 501
<211> LENGTH: 20
<212> TYPE: DNA
<213> ORGANISM: Homo sapiens

<400> SEQUENCE: 501
taaatcagtg aaaaagaag                                                     20

<210> SEQ ID NO 502
<211> LENGTH: 20
<212> TYPE: DNA
<213> ORGANISM: Homo sapiens

<400> SEQUENCE: 502
actctcataa taaatcagtg                                                    20

```
<210> SEQ ID NO 503
<211> LENGTH: 20
<212> TYPE: DNA
<213> ORGANISM: Homo sapiens

<400> SEQUENCE: 503
cctcagcccc actctcataa                                               20

<210> SEQ ID NO 504
<211> LENGTH: 18
<212> TYPE: DNA
<213> ORGANISM: Homo sapiens

<400> SEQUENCE: 504
tcagctcaga cctcagcc                                                 18

<210> SEQ ID NO 505
<211> LENGTH: 20
<212> TYPE: DNA
<213> ORGANISM: Homo sapiens

<400> SEQUENCE: 505
ctgataaggc tcagctcaga                                               20

<210> SEQ ID NO 506
<211> LENGTH: 20
<212> TYPE: DNA
<213> ORGANISM: Homo sapiens

<400> SEQUENCE: 506
gcatctcagt ctgataaggc                                               20

<210> SEQ ID NO 507
<211> LENGTH: 20
<212> TYPE: DNA
<213> ORGANISM: Homo sapiens

<400> SEQUENCE: 507
acaaccagcc gcatctcagt                                               20

<210> SEQ ID NO 508
<211> LENGTH: 20
<212> TYPE: DNA
<213> ORGANISM: Homo sapiens

<400> SEQUENCE: 508
agtcctcaac acaaccagcc                                               20

<210> SEQ ID NO 509
<211> LENGTH: 20
<212> TYPE: DNA
<213> ORGANISM: Homo sapiens

<400> SEQUENCE: 509
agcccacaca agtcctcaac                                               20

<210> SEQ ID NO 510
<211> LENGTH: 18
<212> TYPE: DNA
<213> ORGANISM: Homo sapiens

<400> SEQUENCE: 510
ggacaggcag cccacaca                                                 18
```

```
<210> SEQ ID NO 511
<211> LENGTH: 20
<212> TYPE: DNA
<213> ORGANISM: Homo sapiens

<400> SEQUENCE: 511
agcgactgcc ggggacaggc                                               20

<210> SEQ ID NO 512
<211> LENGTH: 20
<212> TYPE: DNA
<213> ORGANISM: Homo sapiens

<400> SEQUENCE: 512
catgtgcatc agcgactgcc                                               20

<210> SEQ ID NO 513
<211> LENGTH: 20
<212> TYPE: DNA
<213> ORGANISM: Homo sapiens

<400> SEQUENCE: 513
agaatcatgt catgtgcatc                                               20

<210> SEQ ID NO 514
<211> LENGTH: 20
<212> TYPE: DNA
<213> ORGANISM: Homo sapiens

<400> SEQUENCE: 514
cacccagatg agaatcatgt                                               20

<210> SEQ ID NO 515
<211> LENGTH: 19
<212> TYPE: DNA
<213> ORGANISM: Homo sapiens

<400> SEQUENCE: 515
ccacctctgc acccagatg                                                19

<210> SEQ ID NO 516
<211> LENGTH: 20
<212> TYPE: DNA
<213> ORGANISM: Homo sapiens

<400> SEQUENCE: 516
cctggtgcct cccacctctg                                               20

<210> SEQ ID NO 517
<211> LENGTH: 20
<212> TYPE: DNA
<213> ORGANISM: Homo sapiens

<400> SEQUENCE: 517
cgggtgccca cctggtgcct                                               20

<210> SEQ ID NO 518
<211> LENGTH: 20
<212> TYPE: DNA
<213> ORGANISM: Homo sapiens

<400> SEQUENCE: 518
ctaaccccca cgggtgccca                                               20
```

<210> SEQ ID NO 519
<211> LENGTH: 20
<212> TYPE: DNA
<213> ORGANISM: Homo sapiens

<400> SEQUENCE: 519
cttccaagcc ctaaccccca                                                  20

<210> SEQ ID NO 520
<211> LENGTH: 20
<212> TYPE: DNA
<213> ORGANISM: Homo sapiens

<400> SEQUENCE: 520
ctgtgccact cttccaagcc                                                  20

<210> SEQ ID NO 521
<211> LENGTH: 20
<212> TYPE: DNA
<213> ORGANISM: Homo sapiens

<400> SEQUENCE: 521
gtgcccagtc ctgtgccact                                                  20

<210> SEQ ID NO 522
<211> LENGTH: 20
<212> TYPE: DNA
<213> ORGANISM: Homo sapiens

<400> SEQUENCE: 522
ctcactgagc gtgcccagtc                                                  20

<210> SEQ ID NO 523
<211> LENGTH: 20
<212> TYPE: DNA
<213> ORGANISM: Homo sapiens

<400> SEQUENCE: 523
ttccctgagc ctcactgagc                                                  20

<210> SEQ ID NO 524
<211> LENGTH: 20
<212> TYPE: DNA
<213> ORGANISM: Homo sapiens

<400> SEQUENCE: 524
ctagtctgaa ttccctgagc                                                  20

<210> SEQ ID NO 525
<211> LENGTH: 20
<212> TYPE: DNA
<213> ORGANISM: Homo sapiens

<400> SEQUENCE: 525
acaatcgagg ctagtctgaa                                                  20

<210> SEQ ID NO 526
<211> LENGTH: 20
<212> TYPE: DNA
<213> ORGANISM: Homo sapiens

<400> SEQUENCE: 526
tctcggagtg acaatcgagg                                                  20

```
<210> SEQ ID NO 527
<211> LENGTH: 20
<212> TYPE: DNA
<213> ORGANISM: Homo sapiens

<400> SEQUENCE: 527
catgcccatt tctcggagtg                                               20

<210> SEQ ID NO 528
<211> LENGTH: 17
<212> TYPE: DNA
<213> ORGANISM: Homo sapiens

<400> SEQUENCE: 528
ccaataccat gcccatt                                                  17

<210> SEQ ID NO 529
<211> LENGTH: 20
<212> TYPE: DNA
<213> ORGANISM: Homo sapiens

<400> SEQUENCE: 529
gcccccccga ccccaatac                                                20

<210> SEQ ID NO 530
<211> LENGTH: 19
<212> TYPE: DNA
<213> ORGANISM: Homo sapiens

<400> SEQUENCE: 530
ccttgcaccg ccccccga                                                 19

<210> SEQ ID NO 531
<211> LENGTH: 20
<212> TYPE: DNA
<213> ORGANISM: Homo sapiens

<400> SEQUENCE: 531
tcatgtgcgt cccttgcacc                                               20

<210> SEQ ID NO 532
<211> LENGTH: 19
<212> TYPE: DNA
<213> ORGANISM: Homo sapiens

<400> SEQUENCE: 532
aacagtctct catgtgcgt                                                19

<210> SEQ ID NO 533
<211> LENGTH: 20
<212> TYPE: DNA
<213> ORGANISM: Homo sapiens

<400> SEQUENCE: 533
agaagctccc aaacagtctc                                               20

<210> SEQ ID NO 534
<211> LENGTH: 19
<212> TYPE: DNA
<213> ORGANISM: Homo sapiens

<400> SEQUENCE: 534
agggctcccc agaagctcc                                                19
```

<210> SEQ ID NO 535
<211> LENGTH: 18
<212> TYPE: DNA
<213> ORGANISM: Homo sapiens

<400> SEQUENCE: 535
gacaactagc agggctcc                                                 18

<210> SEQ ID NO 536
<211> LENGTH: 20
<212> TYPE: DNA
<213> ORGANISM: Homo sapiens

<400> SEQUENCE: 536
acatcactga gacaactagc                                               20

<210> SEQ ID NO 537
<211> LENGTH: 20
<212> TYPE: DNA
<213> ORGANISM: Homo sapiens

<400> SEQUENCE: 537
ggtcccacag acatcactga                                               20

<210> SEQ ID NO 538
<211> LENGTH: 20
<212> TYPE: DNA
<213> ORGANISM: Homo sapiens

<400> SEQUENCE: 538
agggactgga ggtcccacag                                               20

<210> SEQ ID NO 539
<211> LENGTH: 20
<212> TYPE: DNA
<213> ORGANISM: Homo sapiens

<400> SEQUENCE: 539
tggggtctca agggactgga                                               20

<210> SEQ ID NO 540
<211> LENGTH: 20
<212> TYPE: DNA
<213> ORGANISM: Homo sapiens

<400> SEQUENCE: 540
ctacatgacg tggggtctca                                               20

<210> SEQ ID NO 541
<211> LENGTH: 20
<212> TYPE: DNA
<213> ORGANISM: Homo sapiens

<400> SEQUENCE: 541
gttaacttct ctacatgacg                                               20

<210> SEQ ID NO 542
<211> LENGTH: 20
<212> TYPE: DNA
<213> ORGANISM: Homo sapiens

<400> SEQUENCE: 542
cacttgggcc gttaacttct                                               20

<210> SEQ ID NO 543
<211> LENGTH: 20
<212> TYPE: DNA
<213> ORGANISM: Homo sapiens

<400> SEQUENCE: 543
gcctgcccac cacttgggcc        20

<210> SEQ ID NO 544
<211> LENGTH: 20
<212> TYPE: DNA
<213> ORGANISM: Homo sapiens

<400> SEQUENCE: 544
ggtcccgcca gcctgcccac        20

<210> SEQ ID NO 545
<211> LENGTH: 20
<212> TYPE: DNA
<213> ORGANISM: Homo sapiens

<400> SEQUENCE: 545
atgttcccca ggtcccgcca        20

<210> SEQ ID NO 546
<211> LENGTH: 20
<212> TYPE: DNA
<213> ORGANISM: Homo sapiens

<400> SEQUENCE: 546
tcctctcctg atgttcccca        20

<210> SEQ ID NO 547
<211> LENGTH: 20
<212> TYPE: DNA
<213> ORGANISM: Homo sapiens

<400> SEQUENCE: 547
ggctctggac tcctctcctg        20

<210> SEQ ID NO 548
<211> LENGTH: 20
<212> TYPE: DNA
<213> ORGANISM: Homo sapiens

<400> SEQUENCE: 548
agtagacgtg ggctctggac        20

<210> SEQ ID NO 549
<211> LENGTH: 20
<212> TYPE: DNA
<213> ORGANISM: Homo sapiens

<400> SEQUENCE: 549
acttttccgc agtagacgtg        20

<210> SEQ ID NO 550
<211> LENGTH: 20
<212> TYPE: DNA
<213> ORGANISM: Homo sapiens

<400> SEQUENCE: 550
gtttcccctg acttttccgc        20

```
<210> SEQ ID NO 551
<211> LENGTH: 20
<212> TYPE: DNA
<213> ORGANISM: Homo sapiens

<400> SEQUENCE: 551
ttgtttggca gtttcccctg                                               20

<210> SEQ ID NO 552
<211> LENGTH: 20
<212> TYPE: DNA
<213> ORGANISM: Homo sapiens

<400> SEQUENCE: 552 gcatttcct ttgtttggca                                                20

<210> SEQ ID NO 553
<211> LENGTH: 20
<212> TYPE: DNA
<213> ORGANISM: Homo sapiens

<400> SEQUENCE: 553
tgcctttggg gcatttcct                                                20

<210> SEQ ID NO 554
<211> LENGTH: 18
<212> TYPE: DNA
<213> ORGANISM: Homo sapiens

<400> SEQUENCE: 554
aagcatatat gcctttgg                                                 18

<210> SEQ ID NO 555
<211> LENGTH: 20
<212> TYPE: DNA
<213> ORGANISM: Homo sapiens

<400> SEQUENCE: 555
caaaggccct aaagcatata                                               20

<210> SEQ ID NO 556
<211> LENGTH: 20
<212> TYPE: DNA
<213> ORGANISM: Homo sapiens

<400> SEQUENCE: 556
ccatttggac caaaggccct                                               20

<210> SEQ ID NO 557
<211> LENGTH: 20
<212> TYPE: DNA
<213> ORGANISM: Homo sapiens

<400> SEQUENCE: 557
ccatttggac caaaggccct                                               20

<210> SEQ ID NO 558
<211> LENGTH: 19
<212> TYPE: DNA
<213> ORGANISM: Homo sapiens

<400> SEQUENCE: 558
tggaagagtg gccacccgg                                                19
```

<210> SEQ ID NO 559
<211> LENGTH: 20
<212> TYPE: DNA
<213> ORGANISM: Homo sapiens

<400> SEQUENCE: 559
ctggtctatc tggaagagtg                                               20

<210> SEQ ID NO 560
<211> LENGTH: 20
<212> TYPE: DNA
<213> ORGANISM: Homo sapiens

<400> SEQUENCE: 560
ggagagttgc ctggtctatc                                               20

<210> SEQ ID NO 561
<211> LENGTH: 20
<212> TYPE: DNA
<213> ORGANISM: Homo sapiens

<400> SEQUENCE: 561
ccggtgggag ggagagttgc                                               20

<210> SEQ ID NO 562
<211> LENGTH: 20
<212> TYPE: DNA
<213> ORGANISM: Homo sapiens

<400> SEQUENCE: 562
tcatctgtgg ccggtgggag                                               20

<210> SEQ ID NO 563
<211> LENGTH: 20
<212> TYPE: DNA
<213> ORGANISM: Homo sapiens

<400> SEQUENCE: 563
cagcagcccc tcatctgtgg                                               20

<210> SEQ ID NO 564
<211> LENGTH: 18
<212> TYPE: DNA
<213> ORGANISM: Homo sapiens

<400> SEQUENCE: 564
aggcatagat cagcagcc                                                 18

<210> SEQ ID NO 565
<211> LENGTH: 20
<212> TYPE: DNA
<213> ORGANISM: Homo sapiens

<400> SEQUENCE: 565
gtgcaggccc aggcatagat                                               20

<210> SEQ ID NO 566
<211> LENGTH: 19
<212> TYPE: DNA
<213> ORGANISM: Homo sapiens

<400> SEQUENCE: 566
ataatccctg gtgcaggcc                                                19

```
<210> SEQ ID NO 567
<211> LENGTH: 20
<212> TYPE: DNA
<213> ORGANISM: Homo sapiens

<400> SEQUENCE: 567
taaaagaacc ataatccctg                                               20

<210> SEQ ID NO 568
<211> LENGTH: 21
<212> TYPE: DNA
<213> ORGANISM: Homo sapiens

<400> SEQUENCE: 568
aggcaaagat ttaaaagaac c                                             21

<210> SEQ ID NO 569
<211> LENGTH: 19
<212> TYPE: DNA
<213> ORGANISM: Homo sapiens

<400> SEQUENCE: 569
gtatctgaaa ggcaaagat                                                19

<210> SEQ ID NO 570
<211> LENGTH: 19
<212> TYPE: DNA
<213> ORGANISM: Homo sapiens

<400> SEQUENCE: 570
tatttttcct gtatctgaa                                                19

<210> SEQ ID NO 571
<211> LENGTH: 20
<212> TYPE: DNA
<213> ORGANISM: Homo sapiens

<400> SEQUENCE: 571
ttaatgccat tatttttcct                                               20

<210> SEQ ID NO 572
<211> LENGTH: 20
<212> TYPE: DNA
<213> ORGANISM: Homo sapiens

<400> SEQUENCE: 572
ttaaagcaat ttaatgccat                                               20

<210> SEQ ID NO 573
<211> LENGTH: 20
<212> TYPE: DNA
<213> ORGANISM: Homo sapiens

<400> SEQUENCE: 573
ataatgcaaa ttaaagcaat                                               20

<210> SEQ ID NO 574
<211> LENGTH: 19
<212> TYPE: DNA
<213> ORGANISM: Homo sapiens

<400> SEQUENCE: 574
gataactaaa ataatgcaa                                                19
```

<210> SEQ ID NO 575
<211> LENGTH: 19
<212> TYPE: DNA
<213> ORGANISM: Homo sapiens

<400> SEQUENCE: 575
gtgcaaactg gataactaa                                              19

<210> SEQ ID NO 576
<211> LENGTH: 20
<212> TYPE: DNA
<213> ORGANISM: Homo sapiens

<400> SEQUENCE: 576
ataaaaatat gtgcaaactg                                             20

<210> SEQ ID NO 577
<211> LENGTH: 20
<212> TYPE: DNA
<213> ORGANISM: Homo sapiens

<400> SEQUENCE: 577
taagatacct ataaaaatat                                             20

<210> SEQ ID NO 578
<211> LENGTH: 20
<212> TYPE: DNA
<213> ORGANISM: Homo sapiens

<400> SEQUENCE: 578
aatcgatgcc taagatacct                                             20

<210> SEQ ID NO 579
<211> LENGTH: 18
<212> TYPE: DNA
<213> ORGANISM: Homo sapiens

<400> SEQUENCE: 579
aaaataccaa tcgatgcc                                               18

<210> SEQ ID NO 580
<211> LENGTH: 20
<212> TYPE: DNA
<213> ORGANISM: Homo sapiens

<400> SEQUENCE: 580
tggcccagtt aaaaatacc                                              20

<210> SEQ ID NO 581
<211> LENGTH: 20
<212> TYPE: DNA
<213> ORGANISM: Homo sapiens

<400> SEQUENCE: 581
ttaatgggct tggcccagtt                                             20

<210> SEQ ID NO 582
<211> LENGTH: 20
<212> TYPE: DNA
<213> ORGANISM: Homo sapiens

<400> SEQUENCE: 582
aagaaagacc ttaatgggct                                             20

<210> SEQ ID NO 583
<211> LENGTH: 20
<212> TYPE: DNA
<213> ORGANISM: Homo sapiens

<400> SEQUENCE: 583
cacccaacag aagaaagacc                                                     20

<210> SEQ ID NO 584
<211> LENGTH: 18
<212> TYPE: DNA
<213> ORGANISM: Homo sapiens

<400> SEQUENCE: 584
aatgatagca cccaacag                                                       18

<210> SEQ ID NO 585
<211> LENGTH: 20
<212> TYPE: DNA
<213> ORGANISM: Homo sapiens

<400> SEQUENCE: 585
acttaatcag aaaatgatag                                                     20

<210> SEQ ID NO 586
<211> LENGTH: 20
<212> TYPE: DNA
<213> ORGANISM: Homo sapiens

<400> SEQUENCE: 586
agtcaaaaag acttaatcag                                                     20

<210> SEQ ID NO 587
<211> LENGTH: 20
<212> TYPE: DNA
<213> ORGANISM: Homo sapiens

<400> SEQUENCE: 587
gtatgtcaat agtcaaaaag                                                     20

<210> SEQ ID NO 588
<211> LENGTH: 20
<212> TYPE: DNA
<213> ORGANISM: Homo sapiens

<400> SEQUENCE: 588
gtgaaagact gtatgtcaat                                                     20

<210> SEQ ID NO 589
<211> LENGTH: 20
<212> TYPE: DNA
<213> ORGANISM: Homo sapiens

<400> SEQUENCE: 589
tccaccatct gtgaaagact                                                     20

<210> SEQ ID NO 590
<211> LENGTH: 20
<212> TYPE: DNA
<213> ORGANISM: Homo sapiens

<400> SEQUENCE: 590
ggaaaaacac tccaccatct                                                     20

<210> SEQ ID NO 591
<211> LENGTH: 20
<212> TYPE: DNA
<213> ORGANISM: Homo sapiens

<400> SEQUENCE: 591
cagatttggg ggaaaaacac                                               20

<210> SEQ ID NO 592
<211> LENGTH: 19
<212> TYPE: DNA
<213> ORGANISM: Homo sapiens

<400> SEQUENCE: 592
agacaaacaa cagatttgg                                                19

<210> SEQ ID NO 593
<211> LENGTH: 20
<212> TYPE: DNA
<213> ORGANISM: Homo sapiens

<400> SEQUENCE: 593
caacattata agacaaacaa                                               20

<210> SEQ ID NO 594
<211> LENGTH: 20
<212> TYPE: DNA
<213> ORGANISM: Homo sapiens

<400> SEQUENCE: 594
acctcatata caacattata                                               20

<210> SEQ ID NO 595
<211> LENGTH: 20
<212> TYPE: DNA
<213> ORGANISM: Homo sapiens

<400> SEQUENCE: 595
acaccataaa acctcatata                                               20

<210> SEQ ID NO 596
<211> LENGTH: 19
<212> TYPE: DNA
<213> ORGANISM: Homo sapiens

<400> SEQUENCE: 596
tcatattcat acaccataa                                                19

<210> SEQ ID NO 597
<211> LENGTH: 20
<212> TYPE: DNA
<213> ORGANISM: Homo sapiens

<400> SEQUENCE: 597
acagaagcat tcatattcat                                               20

<210> SEQ ID NO 598
<211> LENGTH: 20
<212> TYPE: DNA
<213> ORGANISM: Homo sapiens

<400> SEQUENCE: 598
gtttgacatt acagaagcat                                               20

<210> SEQ ID NO 599
<211> LENGTH: 20
<212> TYPE: DNA
<213> ORGANISM: Homo sapiens

<400> SEQUENCE: 599
ctagggatct gtttgacatt                                               20

<210> SEQ ID NO 600
<211> LENGTH: 20
<212> TYPE: DNA
<213> ORGANISM: Homo sapiens

<400> SEQUENCE: 600
aaggagttta ctagggatct                                               20

<210> SEQ ID NO 601
<211> LENGTH: 18
<212> TYPE: DNA
<213> ORGANISM: Homo sapiens

<400> SEQUENCE: 601
aagtgaagaa ggagttta                                                 18

<210> SEQ ID NO 602
<211> LENGTH: 18
<212> TYPE: DNA
<213> ORGANISM: Homo sapiens

<400> SEQUENCE: 602
aagtgaagaa ggagttta                                                 18

<210> SEQ ID NO 603
<211> LENGTH: 20
<212> TYPE: DNA
<213> ORGANISM: Homo sapiens

<400> SEQUENCE: 603
acctttgtaa atctgacagt                                               20

<210> SEQ ID NO 604
<211> LENGTH: 20
<212> TYPE: DNA
<213> ORGANISM: Homo sapiens

<400> SEQUENCE: 604
caatgggagg acctttgtaa                                               20

<210> SEQ ID NO 605
<211> LENGTH: 20
<212> TYPE: DNA
<213> ORGANISM: Homo sapiens

<400> SEQUENCE: 605
cactgctttg caatgggagg                                               20

<210> SEQ ID NO 606
<211> LENGTH: 20
<212> TYPE: DNA
<213> ORGANISM: Homo sapiens

<400> SEQUENCE: 606
ttaggacaaa cactgctttg                                               20

<210> SEQ ID NO 607
<211> LENGTH: 19
<212> TYPE: DNA
<213> ORGANISM: Homo sapiens

<400> SEQUENCE: 607
aatatataaa ttaggacaa                                                19

<210> SEQ ID NO 608
<211> LENGTH: 19
<212> TYPE: DNA
<213> ORGANISM: Homo sapiens

<400> SEQUENCE: 608
ctagaaaaac aatatataa                                                19

<210> SEQ ID NO 609
<211> LENGTH: 20
<212> TYPE: DNA
<213> ORGANISM: Homo sapiens

<400> SEQUENCE: 609
acaaaatgaa ctagaaaaac                                               20

<210> SEQ ID NO 610
<211> LENGTH: 20
<212> TYPE: DNA
<213> ORGANISM: Homo sapiens

<400> SEQUENCE: 610
agttggaaac acaaaatgaa                                               20

<210> SEQ ID NO 611
<211> LENGTH: 20
<212> TYPE: DNA
<213> ORGANISM: Homo sapiens

<400> SEQUENCE: 611
ttacatgaaa agttggaaac                                               20

<210> SEQ ID NO 612
<211> LENGTH: 19
<212> TYPE: DNA
<213> ORGANISM: Homo sapiens

<400> SEQUENCE: 612
aattaaaatt ttacatgaa                                                19

<210> SEQ ID NO 613
<211> LENGTH: 20
<212> TYPE: DNA
<213> ORGANISM: Homo sapiens

<400> SEQUENCE: 613
attcaaaaat aattaaaatt                                               20

<210> SEQ ID NO 614
<211> LENGTH: 20
<212> TYPE: DNA
<213> ORGANISM: Homo sapiens

<400> SEQUENCE: 614
acatccacac attcaaaaat                                               20

<210> SEQ ID NO 615
<211> LENGTH: 20
<212> TYPE: DNA
<213> ORGANISM: Homo sapiens

<400> SEQUENCE: 615
cctcagtctc acatccacac                                               20

<210> SEQ ID NO 616
<211> LENGTH: 20
<212> TYPE: DNA
<213> ORGANISM: Homo sapiens

<400> SEQUENCE: 616
ccaaaaggca cctcagtctc                                               20

<210> SEQ ID NO 617
<211> LENGTH: 20
<212> TYPE: DNA
<213> ORGANISM: Homo sapiens

<400> SEQUENCE: 617
aatttcagta ccaaaaggca                                               20

<210> SEQ ID NO 618
<211> LENGTH: 20
<212> TYPE: DNA
<213> ORGANISM: Homo sapiens

<400> SEQUENCE: 618
atggaaaaag aatttcagta                                               20

<210> SEQ ID NO 619
<211> LENGTH: 20
<212> TYPE: DNA
<213> ORGANISM: Homo sapiens

<400> SEQUENCE: 619
cttcaggtac atggaaaaag                                               20

<210> SEQ ID NO 620
<211> LENGTH: 18
<212> TYPE: DNA
<213> ORGANISM: Homo sapiens

<400> SEQUENCE: 620
aagtaacact tcaggtac                                                 18

<210> SEQ ID NO 621
<211> LENGTH: 20
<212> TYPE: DNA
<213> ORGANISM: Homo sapiens

<400> SEQUENCE: 621
cctatatcac aaaagtaaca                                               20

<210> SEQ ID NO 622
<211> LENGTH: 20
<212> TYPE: DNA
<213> ORGANISM: Homo sapiens

<400> SEQUENCE: 622
acaaggattt cctatatcac                                               20

<210> SEQ ID NO 623
<211> LENGTH: 19
<212> TYPE: DNA
<213> ORGANISM: Homo sapiens

<400> SEQUENCE: 623
aagtatatat acaaggatt                                                  19

<210> SEQ ID NO 624
<211> LENGTH: 19
<212> TYPE: DNA
<213> ORGANISM: Homo sapiens

<400> SEQUENCE: 624
ggaccaataa agtatatat                                                  19

<210> SEQ ID NO 625
<211> LENGTH: 20
<212> TYPE: DNA
<213> ORGANISM: Homo sapiens

<400> SEQUENCE: 625
aggaagccta gggaccaata                                                 20

<210> SEQ ID NO 626
<211> LENGTH: 20
<212> TYPE: DNA
<213> ORGANISM: Homo sapiens

<400> SEQUENCE: 626
gtaacaaaat aggaagccta                                                 20

<210> SEQ ID NO 627
<211> LENGTH: 20
<212> TYPE: DNA
<213> ORGANISM: Homo sapiens

<400> SEQUENCE: 627
agaaagcaag gtaacaaaat                                                 20

<210> SEQ ID NO 628
<211> LENGTH: 20
<212> TYPE: DNA
<213> ORGANISM: Homo sapiens

<400> SEQUENCE: 628
gatgccatag agaaagcaag                                                 20

<210> SEQ ID NO 629
<211> LENGTH: 20
<212> TYPE: DNA
<213> ORGANISM: Homo sapiens

<400> SEQUENCE: 629
caaaatggtg gatgccatag                                                 20

<210> SEQ ID NO 630
<211> LENGTH: 20
<212> TYPE: DNA
<213> ORGANISM: Homo sapiens

<400> SEQUENCE: 630
gtagaacaat caaaatggtg                                                 20

```
<210> SEQ ID NO 631
<211> LENGTH: 20
<212> TYPE: DNA
<213> ORGANISM: Homo sapiens

<400> SEQUENCE: 631
tatcataaaa gtagaacaat                                                    20

<210> SEQ ID NO 632
<211> LENGTH: 18
<212> TYPE: DNA
<213> ORGANISM: Homo sapiens

<400> SEQUENCE: 632
tatgaaaaca tatcataa                                                      18

<210> SEQ ID NO 633
<211> LENGTH: 20
<212> TYPE: DNA
<213> ORGANISM: Homo sapiens

<400> SEQUENCE: 633
cttaaccact tatgaaaaca                                                    20

<210> SEQ ID NO 634
<211> LENGTH: 20
<212> TYPE: DNA
<213> ORGANISM: Homo sapiens

<400> SEQUENCE: 634
agaatacttg cttaaccact                                                    20

<210> SEQ ID NO 635
<211> LENGTH: 18
<212> TYPE: DNA
<213> ORGANISM: Homo sapiens

<400> SEQUENCE: 635
aagtaacgag aatacttg                                                      18

<210> SEQ ID NO 636
<211> LENGTH: 20
<212> TYPE: DNA
<213> ORGANISM: Homo sapiens

<400> SEQUENCE: 636
atttaagagc aaaagtaacg                                                    20

<210> SEQ ID NO 637
<211> LENGTH: 20
<212> TYPE: DNA
<213> ORGANISM: Homo sapiens

<400> SEQUENCE: 637
atgaataggg atttaagagc                                                    20

<210> SEQ ID NO 638
<211> LENGTH: 19
<212> TYPE: DNA
<213> ORGANISM: Homo sapiens

<400> SEQUENCE: 638
cattgctgta atgaatagg                                                     19
```

```
<210> SEQ ID NO 639
<211> LENGTH: 20
<212> TYPE: DNA
<213> ORGANISM: Homo sapiens

<400> SEQUENCE: 639
tgaccaccaa cattgctgta                                                  20

<210> SEQ ID NO 640
<211> LENGTH: 20
<212> TYPE: DNA
<213> ORGANISM: Homo sapiens

<400> SEQUENCE: 640
tcattttctt tgaccaccaa                                                  20

<210> SEQ ID NO 641
<211> LENGTH: 20
<212> TYPE: DNA
<213> ORGANISM: Homo sapiens

<400> SEQUENCE: 641
aagttgttta tcattttctt                                                  20

<210> SEQ ID NO 642
<211> LENGTH: 20
<212> TYPE: DNA
<213> ORGANISM: Homo sapiens

<400> SEQUENCE: 642
ttgaacattc aagttgttta                                                  20

<210> SEQ ID NO 643
<211> LENGTH: 20
<212> TYPE: DNA
<213> ORGANISM: Homo sapiens

<400> SEQUENCE: 643
ttcaggacca ttgaacattc                                                  20

<210> SEQ ID NO 644
<211> LENGTH: 20
<212> TYPE: DNA
<213> ORGANISM: Homo sapiens

<400> SEQUENCE: 644
tgttatgtat ttcaggacca                                                  20

<210> SEQ ID NO 645
<211> LENGTH: 20
<212> TYPE: DNA
<213> ORGANISM: Homo sapiens

<400> SEQUENCE: 645
actaaaatgt tgttatgtat                                                  20

<210> SEQ ID NO 646
<211> LENGTH: 19
<212> TYPE: DNA
<213> ORGANISM: Homo sapiens

<400> SEQUENCE: 646
ttacaatgta ctaaaatgt                                                   19
```

<210> SEQ ID NO 647
<211> LENGTH: 20
<212> TYPE: DNA
<213> ORGANISM: Homo sapiens

<400> SEQUENCE: 647
aggattctac tttacaatgt                                            20

<210> SEQ ID NO 648
<211> LENGTH: 20
<212> TYPE: DNA
<213> ORGANISM: Homo sapiens

<400> SEQUENCE: 648
ttatgaacag aggattctac                                            20

<210> SEQ ID NO 649
<211> LENGTH: 20
<212> TYPE: DNA
<213> ORGANISM: Homo sapiens

<400> SEQUENCE: 649
atcttgttca ttatgaacag                                            20

<210> SEQ ID NO 650
<211> LENGTH: 20
<212> TYPE: DNA
<213> ORGANISM: Homo sapiens

<400> SEQUENCE: 650
acattggttc atcttgttca                                            20

<210> SEQ ID NO 651
<211> LENGTH: 19
<212> TYPE: DNA
<213> ORGANISM: Homo sapiens

<400> SEQUENCE: 651
ttctaatcca cattggttc                                             19

<210> SEQ ID NO 652
<211> LENGTH: 20
<212> TYPE: DNA
<213> ORGANISM: Homo sapiens

<400> SEQUENCE: 652
ctcggacttc tttctaatcc                                            20

<210> SEQ ID NO 653
<211> LENGTH: 18
<212> TYPE: DNA
<213> ORGANISM: Homo sapiens

<400> SEQUENCE: 653
attaatatct cggacttc                                              18

<210> SEQ ID NO 654
<211> LENGTH: 20
<212> TYPE: DNA
<213> ORGANISM: Homo sapiens

<400> SEQUENCE: 654
ggatattttg gaattaatat                                            20

<210> SEQ ID NO 655
<211> LENGTH: 20
<212> TYPE: DNA
<213> ORGANISM: Homo sapiens

<400> SEQUENCE: 655
aacaatgtct ggatattttg                                              20

<210> SEQ ID NO 656
<211> LENGTH: 18
<212> TYPE: DNA
<213> ORGANISM: Homo sapiens

<400> SEQUENCE: 656
ttccctttaa caatgtct                                                18

<210> SEQ ID NO 657
<211> LENGTH: 20
<212> TYPE: DNA
<213> ORGANISM: Homo sapiens

<400> SEQUENCE: 657
ttattgcaat ttttcccctt                                              20

<210> SEQ ID NO 658
<211> LENGTH: 20
<212> TYPE: DNA
<213> ORGANISM: Homo sapiens

<400> SEQUENCE: 658
acaaatattt tattgcaatt                                              20

<210> SEQ ID NO 659
<211> LENGTH: 19
<212> TYPE: DNA
<213> ORGANISM: Homo sapiens

<400> SEQUENCE: 659
ttttatgtta caaatattt                                               19

<210> SEQ ID NO 660
<211> LENGTH: 18
<212> TYPE: DNA
<213> ORGANISM: Homo sapiens

<400> SEQUENCE: 660
gaccagttgc acctgccc                                                18

<210> SEQ ID NO 661
<211> LENGTH: 18
<212> TYPE: DNA
<213> ORGANISM: Homo sapiens

<400> SEQUENCE: 661
ccacggcctg tcccggtc                                                18

<210> SEQ ID NO 662
<211> LENGTH: 17
<212> TYPE: DNA
<213> ORGANISM: Homo sapiens

<400> SEQUENCE: 662
ggactccctg cagcccc                                                 17

```
<210> SEQ ID NO 663
<211> LENGTH: 18
<212> TYPE: DNA
<213> ORGANISM: Homo sapiens

<400> SEQUENCE: 663
aggggcaggg cctccccc                                              18

<210> SEQ ID NO 664
<211> LENGTH: 20
<212> TYPE: DNA
<213> ORGANISM: Homo sapiens

<400> SEQUENCE: 664
gccacagggc tgtccttttg                                            20

<210> SEQ ID NO 665
<211> LENGTH: 21
<212> TYPE: DNA
<213> ORGANISM: Homo sapiens

<400> SEQUENCE: 665
gccactccag ggtcctcagt g                                          21

<210> SEQ ID NO 666
<211> LENGTH: 18
<212> TYPE: DNA
<213> ORGANISM: Homo sapiens

<400> SEQUENCE: 666
accaggtctg cagaggag                                              18

<210> SEQ ID NO 667
<211> LENGTH: 18
<212> TYPE: DNA
<213> ORGANISM: Homo sapiens

<400> SEQUENCE: 667
cgaggcccct gagtttgg                                              18

<210> SEQ ID NO 668
<211> LENGTH: 18
<212> TYPE: DNA
<213> ORGANISM: Homo sapiens

<400> SEQUENCE: 668
ccaggacata agctgggg                                              18

<210> SEQ ID NO 669
<211> LENGTH: 18
<212> TYPE: DNA
<213> ORGANISM: Homo sapiens

<400> SEQUENCE: 669
gcctggggct ccaggggg                                              18

<210> SEQ ID NO 670
<211> LENGTH: 18
<212> TYPE: DNA
<213> ORGANISM: Homo sapiens

<400> SEQUENCE: 670
ccacatagcc ctcaaacc                                              18
```

<210> SEQ ID NO 671
<211> LENGTH: 18
<212> TYPE: DNA
<213> ORGANISM: Homo sapiens

<400> SEQUENCE: 671
ggacaggatt gttccttg                                                       18

<210> SEQ ID NO 672
<211> LENGTH: 18
<212> TYPE: DNA
<213> ORGANISM: Homo sapiens

<400> SEQUENCE: 672
cgttcccctg ggttcagg                                                       18

<210> SEQ ID NO 673
<211> LENGTH: 20
<212> TYPE: DNA
<213> ORGANISM: Homo sapiens

<400> SEQUENCE: 673
gtatctagtg aggttgtcat                                                     20

<210> SEQ ID NO 674
<211> LENGTH: 20
<212> TYPE: DNA
<213> ORGANISM: Homo sapiens

<400> SEQUENCE: 674
ggtctcaact gtatctagtg                                                     20

<210> SEQ ID NO 675
<211> LENGTH: 22
<212> TYPE: DNA
<213> ORGANISM: Homo sapiens

<400> SEQUENCE: 675
ccatcagtgc tctggtatca gc                                                  22

<210> SEQ ID NO 676
<211> LENGTH: 19
<212> TYPE: DNA
<213> ORGANISM: Homo sapiens

<400> SEQUENCE: 676
ggtacatcac caccaccac                                                      19

<210> SEQ ID NO 677
<211> LENGTH: 22
<212> TYPE: DNA
<213> ORGANISM: Homo sapiens

<400> SEQUENCE: 677
ggtcataatt cggagcctcc tg                                                  22

<210> SEQ ID NO 678
<211> LENGTH: 19
<212> TYPE: DNA
<213> ORGANISM: Homo sapiens

<400> SEQUENCE: 678
gcttacacat gccatggcc                                                      19

<210> SEQ ID NO 679
<211> LENGTH: 18
<212> TYPE: DNA
<213> ORGANISM: Homo sapiens

<400> SEQUENCE: 679
gctgctagca ctgccagg                                                    18

<210> SEQ ID NO 680
<211> LENGTH: 22
<212> TYPE: DNA
<213> ORGANISM: Homo sapiens

<400> SEQUENCE: 680
cctccagcta tatactgtat cc                                               22

<210> SEQ ID NO 681
<211> LENGTH: 18
<212> TYPE: DNA
<213> ORGANISM: Homo sapiens

<400> SEQUENCE: 681
ggtccagatg cttgctcc                                                    18

<210> SEQ ID NO 682
<211> LENGTH: 20
<212> TYPE: DNA
<213> ORGANISM: Homo sapiens

<400> SEQUENCE: 682
gcatgaccag gtccagatgc                                                  20

<210> SEQ ID NO 683
<211> LENGTH: 19
<212> TYPE: DNA
<213> ORGANISM: Homo sapiens

<400> SEQUENCE: 683
cacctctgtc accagcatg                                                   19

<210> SEQ ID NO 684
<211> LENGTH: 21
<212> TYPE: DNA
<213> ORGANISM: Homo sapiens

<400> SEQUENCE: 684
gtacttccgg aacctctctc c                                                21

<210> SEQ ID NO 685
<211> LENGTH: 19
<212> TYPE: DNA
<213> ORGANISM: Homo sapiens

<400> SEQUENCE: 685
ccacattgta gggtgtcca                                                   19

<210> SEQ ID NO 686
<211> LENGTH: 20
<212> TYPE: DNA
<213> ORGANISM: Homo sapiens

<400> SEQUENCE: 686
agtgggagta ggcgatcacc                                                  20

<210> SEQ ID NO 687
<211> LENGTH: 20
<212> TYPE: DNA
<213> ORGANISM: Homo sapiens

<400> SEQUENCE: 687
cgtagatcac cgggttcatg                                               20

<210> SEQ ID NO 688
<211> LENGTH: 19
<212> TYPE: DNA
<213> ORGANISM: Homo sapiens

<400> SEQUENCE: 688
ttccagcttc tcactagga                                                19

<210> SEQ ID NO 689
<211> LENGTH: 20
<212> TYPE: DNA
<213> ORGANISM: Homo sapiens

<400> SEQUENCE: 689
tggtcattct cagagtgtgg                                               20

<210> SEQ ID NO 690
<211> LENGTH: 20
<212> TYPE: DNA
<213> ORGANISM: Homo sapiens

<400> SEQUENCE: 690
acagagctgg ttctttccag                                               20

<210> SEQ ID NO 691
<211> LENGTH: 20
<212> TYPE: DNA
<213> ORGANISM: Homo sapiens

<400> SEQUENCE: 691
gaatgggatg tatctgccca                                               20

<210> SEQ ID NO 692
<211> LENGTH: 20
<212> TYPE: DNA
<213> ORGANISM: Homo sapiens

<400> SEQUENCE: 692
ggatgtatct gcccaggtgc                                               20

<210> SEQ ID NO 693
<211> LENGTH: 20
<212> TYPE: DNA
<213> ORGANISM: Homo sapiens

<400> SEQUENCE: 693
caagtgcctg tggaagaagt                                               20

<210> SEQ ID NO 694
<211> LENGTH: 20
<212> TYPE: DNA
<213> ORGANISM: Homo sapiens

<400> SEQUENCE: 694
gcctgtggaa gaagtggcgc                                               20

<210> SEQ ID NO 695
<211> LENGTH: 20
<212> TYPE: DNA
<213> ORGANISM: Homo sapiens

<400> SEQUENCE: 695
accaggtcca gatgcttgct                                          20

<210> SEQ ID NO 696
<211> LENGTH: 20
<212> TYPE: DNA
<213> ORGANISM: Homo sapiens

<400> SEQUENCE: 696
attcaggaag agctgctagc                                          20

<210> SEQ ID NO 697
<211> LENGTH: 20
<212> TYPE: DNA
<213> ORGANISM: Homo sapiens

<400> SEQUENCE: 697
gtcgattgtc agcaggatta                                          20

<210> SEQ ID NO 698
<211> LENGTH: 20
<212> TYPE: DNA
<213> ORGANISM: Homo sapiens

<400> SEQUENCE: 698
atggaagggt gacgaggaag                                          20

<210> SEQ ID NO 699
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (21)..(22)
<223> OTHER INFORMATION: DNA

<400> SEQUENCE: 699
uuguagaaua ggccaaagga g                                        21

<210> SEQ ID NO 700
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 700
cuuuuggccu auucuacaat t                                        21

<210> SEQ ID NO 701
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 701
ugguggauca cagacaugct t                                              21

<210> SEQ ID NO 702
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 702
gcaugucugu gauccaccat t                                              21

<210> SEQ ID NO 703
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 703
uauagccaca gggcugucct t                                              21

<210> SEQ ID NO 704
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 704
ggacagcccu guggcuauat t                                              21

<210> SEQ ID NO 705
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
```

```
<222> LOCATION: (22)..(23)
<223> OTHER INFORMATION: DNA

<400> SEQUENCE: 705
uauagccaca gggcuguccu utt                                           23

<210> SEQ ID NO 706
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 706
aaggacagcc cuguggcuau att                                           23

<210> SEQ ID NO 707
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 707 ucuauuguu cguaucgcau utt                                            23

<210> SEQ ID NO 708
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 708
aaugcgauac gaacacauag att                                           23

<210> SEQ ID NO 709
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 709 auuguuucu cugcccuccu utt                                            23
```

```
<210> SEQ ID NO 710
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 710
aaggagggca gagaaacaca utt                                              23

<210> SEQ ID NO 711
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 711
aguguccuga aguccugugt t                                                21

<210> SEQ ID NO 712
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 712
cacaggacuu caggacacut t                                                21

<210> SEQ ID NO 713
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 713
guggcuggug uagucguugt t                                                21

<210> SEQ ID NO 714
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 714
caacgacuac accagccact t                                              21

<210> SEQ ID NO 715
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 715
auguggcugg uguagucgut t                                              21

<210> SEQ ID NO 716
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 716
acgacuacac cagccacaut t                                              21

<210> SEQ ID NO 717
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 717
gauguggcug guguagucgt t                                              21

<210> SEQ ID NO 718
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 718
cgacuacacc agccacauct t                                              21
```

<210> SEQ ID NO 719
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 719
ggugaugugg cugguguagt t                                              21

<210> SEQ ID NO 720
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 720
cuacaccagc cacaucacct t                                              21

<210> SEQ ID NO 721
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 721
gcaggugaug uggcuggugt t                                              21

<210> SEQ ID NO 722
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 722
caccagccac aucaccugct t                                              21

<210> SEQ ID NO 723
<211> LENGTH: 21
<212> TYPE: DNA
<213> ORGANISM: Homo sapiens
<220> FEATURE:
<221> NAME/KEY: misc_feature

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 723
cugcagguga uguggcuggt t                                              21

<210> SEQ ID NO 724
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 724
ccagccacau caccugcagt t                                              21

<210> SEQ ID NO 725
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 725
caccugcagg ugauguggct t                                              21

<210> SEQ ID NO 726
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 726
gccacaucac cugcaggugt t                                              21

<210> SEQ ID NO 727
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 727
```
ugcccaccug caggugaugt t                                    21

<210> SEQ ID NO 728
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 728
caucaccugc agguggcat t                                     21

<210> SEQ ID NO 729
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 729
ucugcccacc ugcaggugat t                                    21

<210> SEQ ID NO 730
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 730
ucaccugcag gugggcagat t                                    21

<210> SEQ ID NO 731
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 731
gugucugccc accugcaggt t                                    21

<210> SEQ ID NO 732
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 732
ccugcaggug ggcagacact t                                              21

<210> SEQ ID NO 733
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 733
uccugggugu cugcccacct t                                              21

<210> SEQ ID NO 734
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 734
uccugggugu cugcccacct t                                              21

<210> SEQ ID NO 735
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 735
gcauccuggg ugucugccct t                                              21

<210> SEQ ID NO 736
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 736
gggcagacac ccaggaugct t                                              21

<210> SEQ ID NO 737
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 737
gcugggcauc cugggugct t                                               21

<210> SEQ ID NO 738
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 738
gacacccagg augcccagct t                                              21

<210> SEQ ID NO 739
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 739
guugacgagc cgcugggcat t                                              21

<210> SEQ ID NO 740
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 740
ugcccagcgg cucgucaact t                                              21

<210> SEQ ID NO 741
<211> LENGTH: 21

<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 741
ggucacguug acgagccgct t                                              21

<210> SEQ ID NO 742
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 742
gcggcucguc aacgugacct t                                              21

<210> SEQ ID NO 743
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 743
cggcgaauga gggucacgut t                                              21

<210> SEQ ID NO 744
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 744
acgugacccu cauucgccgt t                                              21

<210> SEQ ID NO 745
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature

```
<222> LOCATION: (20)..(21)
<223> OTHER INFORMATION: DNA

<400> SEQUENCE: 745
ccggcgaaug agggucacgt t                                               21

<210> SEQ ID NO 746
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 746
cgugacccuc auucgccggt t                                               21

<210> SEQ ID NO 747
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 747
cgugacccuc auucgccggt t                                               21

<210> SEQ ID NO 748
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 748
cccucauucg ccgggugaat t                                               21

<210> SEQ ID NO 749
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 749
uucacccggc gaaugagggt t                                               21
```

```
<210> SEQ ID NO 750
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 750
cccucauucg ccgggugaat t                                              21

<210> SEQ ID NO 751
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 751
uccucauuca cccggcgaat t                                              21

<210> SEQ ID NO 752
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 752
uucgccgggu gaaugaggat t                                              21

<210> SEQ ID NO 753
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 753
ggcuccagga gguccucaut t                                              21

<210> SEQ ID NO 754
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 754
augaggaccu ccuggagcct t                                      21

<210> SEQ ID NO 755
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 755
uggcuccagg agguccucat t                                      21

<210> SEQ ID NO 756
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 756
ugaggaccuc cuggagccat t                                      21

<210> SEQ ID NO 757
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 757
cacuggcucc aggaggucct t                                      21

<210> SEQ ID NO 758
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 758
ggaccuccug gagccagugt t                                      21
```

<210> SEQ ID NO 759
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 759
cacuggcucc aggaggucct t                                              21

<210> SEQ ID NO 760
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 760
ggaccuccug gagccagugt t                                              21

<210> SEQ ID NO 761
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 761
ggacacuggc uccaggaggt t                                              21

<210> SEQ ID NO 762
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 762
ccuccuggag ccagugucct t                                              21

<210> SEQ ID NO 763
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 763
gaggucacag gacacuggct t                                              21

<210> SEQ ID NO 764
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 764
gccagugucc ugugaccuct t                                              21

<210> SEQ ID NO 765
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 765
cacugagguc acaggacact t                                              21

<210> SEQ ID NO 766
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 766
guguccugug accucagugt t                                              21

<210> SEQ ID NO 767
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 767

```
gggcauguca ucacugaggt t                                              21

<210> SEQ ID NO 768
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 768
ccucagugau gacaugcccu t                                              21

<210> SEQ ID NO 769
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 769
gggcauguca ucacugaggt t                                              21

<210> SEQ ID NO 770
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 770
ccucagugau gacaugcccu t                                              21

<210> SEQ ID NO 771
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 771
gaccagggca ugucaucact t                                              21

<210> SEQ ID NO 772
<211> LENGTH: 21
<212> TYPE: DNA
<213> ORGANISM: Homo sapiens
```

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: RNA

<400> SEQUENCE: 772
gugaugacau gcccugguct t                                              21

<210> SEQ ID NO 773
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 773
ggcugaccag ggcaugucat t                                              21

<210> SEQ ID NO 774
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 774
ugacaugccc uggucagcct t                                              21

<210> SEQ ID NO 775
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 775
gcaggcugac cagggcaugt t                                              21

<210> SEQ ID NO 776
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

-continued

<400> SEQUENCE: 776
caugcccugg ucagccugct t                                              21

<210> SEQ ID NO 777
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 777
aaugacacau cuccugggct t                                              21

<210> SEQ ID NO 778
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 778
gcccaggaga ugugucauut t                                              21

<210> SEQ ID NO 779
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 779
cagggaauga cacaucucct t                                              21

<210> SEQ ID NO 780
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 780
ggagaugugu cauucccugt t                                              21

<210> SEQ ID NO 781
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 781
uggcagggaa ugacacauct t                                              21

<210> SEQ ID NO 782
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 782
gaugugucau ucccugccat t                                              21

<210> SEQ ID NO 783
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 783
ucuggcaggg aaugacacat t                                              21

<210> SEQ ID NO 784
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 784
ugugucauuc ccugccagat t                                              21

<210> SEQ ID NO 785
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 785
acaaaacucu ggcagggaat t                                              21

<210> SEQ ID NO 786
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 786
uucccugcca gaguuuugut t                                              21

<210> SEQ ID NO 787
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 787
gucagugacg acaaaacuct t                                              21

<210> SEQ ID NO 788
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 788
gaguuuuguc gucacugact t                                              21

<210> SEQ ID NO 789
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 789
acgucaguga cgacaaaact t                                              21
```

```
<210> SEQ ID NO 790
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 790
acgucaguga cgacaaaact t                                              21

<210> SEQ ID NO 791
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 791
aaguagucaa cgucagugat t                                              21

<210> SEQ ID NO 792
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 792
ucacugacgu ugactacuut t                                              21

<210> SEQ ID NO 793
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 793
gagaaguagu caacgucagt t                                              21

<210> SEQ ID NO 794
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
-continued

<220> FEATURE:
<221> NAME/KEY: misc_feature
<222> LOCATION: (20)..(21)
<223> OTHER INFORMATION: DNA

<400> SEQUENCE: 794
cugacguuga cuacuucuct t                                              21

<210> SEQ ID NO 795
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 795
gaaugagaag uagucaacgt t                                              21

<210> SEQ ID NO 796
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 796
cguugacuac uucucauuct t                                              21

<210> SEQ ID NO 797
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 797
ugguuggaau gagaaguagt t                                              21

<210> SEQ ID NO 798
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 798
cuacuucuca uuccaaccat t                                              21
```

<210> SEQ ID NO 799
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 799
cuucucauuc caaccagact t                                              21

<210> SEQ ID NO 800
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 800
cuucucauuc caaccagact t                                              21

<210> SEQ ID NO 801
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 801
gaggccuguc ugguuggaat t                                              21

<210> SEQ ID NO 802
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 802
uuccaaccag acaggccuct t                                              21

<210> SEQ ID NO 803
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 803
gcccagaggc cugucuggut t                                              21

<210> SEQ ID NO 804
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 804
accagacagg ccucugggct t                                              21

<210> SEQ ID NO 805
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 805
ccagacaggc cucugggcat t                                              21

<210> SEQ ID NO 806
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 806
ccagacaggc cucugggcat t                                              21

<210> SEQ ID NO 807
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 807
agagugacgg ugagccgggt t                                       21

<210> SEQ ID NO 808
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 808
cccggcucac cgucacucut t                                       21

<210> SEQ ID NO 809
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 809
ugcuggguca gagugacggt t                                       21

<210> SEQ ID NO 810
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 810
ccgucacucu gacccagcat t                                       21

<210> SEQ ID NO 811
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 811
uggacaugcu gggucagagt t                                       21

<210> SEQ ID NO 812
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 812
cucugaccca gcauguccat t                                               21

<210> SEQ ID NO 813
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 813
ggaggcugga caugcugggt t                                               21

<210> SEQ ID NO 814
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 814
cccagcaugu ccagccucct t                                               21

<210> SEQ ID NO 815
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 815
cucaggaggc uggacaugct t                                               21

<210> SEQ ID NO 816
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 816
gcauguccag ccuccugagt t                                          21

<210> SEQ ID NO 817
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 817
gggcucagga ggcuggacat t                                          21

<210> SEQ ID NO 818
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 818
gggcucagga ggcuggacat t                                          21

<210> SEQ ID NO 819
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 819
gaucugcagg ucccugggct t                                          21

<210> SEQ ID NO 820
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 820
gcccagggac cugcagauct t                                          21

<210> SEQ ID NO 821
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 821
gugcugaucu gcagguccct t                                              21

<210> SEQ ID NO 822
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 822
gggaccugca gaucagcact t                                              21

<210> SEQ ID NO 823
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 823
gucggugcug aucugcaggt t                                              21

<210> SEQ ID NO 824
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 824
ccugcagauc agcaccgact t                                              21

<210> SEQ ID NO 825
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

-continued

<222> LOCATION: (20)..(21)
<223> OTHER INFORMATION: DNA

<400> SEQUENCE: 825
guccuggucg gugcugauct t                                              21

<210> SEQ ID NO 826
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 826
gaucagcacc gaccaggact t                                              21

<210> SEQ ID NO 827
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 827
ugguccuggu cggugcugat t                                              21

<210> SEQ ID NO 828
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 828
ucagcaccga ccaggaccat t                                              21

<210> SEQ ID NO 829
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 829
aagugguccu ggucggugct t                                              21

```
<210> SEQ ID NO 830
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 830
gcaccgacca ggaccacuut t                                              21

<210> SEQ ID NO 831
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 831
aggaaguggu ccuggucggt t                                              21

<210> SEQ ID NO 832
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 832
ccgaccagga ccacuuccut t                                              21

<210> SEQ ID NO 833
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 833
cagcaggaag ugguccuggt t                                              21

<210> SEQ ID NO 834
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

<220> FEATURE:
<221> NAME/KEY: misc_feature
<222> LOCATION: (20)..(21)
<223> OTHER INFORMATION: DNA

<400> SEQUENCE: 834
ccaggaccac uuccugcugt t    21

<210> SEQ ID NO 835
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 835
ggucagcagg aaguggucct t    21

<210> SEQ ID NO 836
<211> LENGTH: 21
<212> TYPE: DNA
<213> ORGANISM: Homo sapiens
<220> FEATURE:
<221> NAME/KEY: misc_feature
<222> LOCATION: (0)..(21)
<223> OTHER INFORMATION: DNA
<220> FEATURE:
<221> NAME/KEY: misc_feature
<222> LOCATION: (1)..(19)
<223> OTHER INFORMATION: RNA

<400> SEQUENCE: 836
ggaccacuuc cugcugacct t    21

<210> SEQ ID NO 837
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 837
ccaggucagc aggaaguggt t    21

<210> SEQ ID NO 838
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 838
ccacuuccug cugaccuggt t    21

```
<210> SEQ ID NO 839
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 839
acuccagguc agcaggaagt t                                              21

<210> SEQ ID NO 840
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 840
cuuccugcug accuggagut t                                              21

<210> SEQ ID NO 841
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 841
ccaagggcca cacuccaggt t                                              21

<210> SEQ ID NO 842
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 842
ccuggagugu ggcccuuggt t                                              21

<210> SEQ ID NO 843
<211> LENGTH: 21
<212> TYPE: DNA
<213> ORGANISM: Homo sapiens
<220> FEATURE:
<221> NAME/KEY: misc_feature
```

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 843
ggacucccaa gggccacact t                                              21

<210> SEQ ID NO 844
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 844
guguggcccu ugggagucct t                                              21

<210> SEQ ID NO 845
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 845
aaccaguggc ucugggact t                                               21

<210> SEQ ID NO 846
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 846
guccccagag ccacugguut t                                              21

<210> SEQ ID NO 847
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 847
``` ugggggacaac caguggcuct t                                              21

<210> SEQ ID NO 848
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 848
gagccacugg uuguccccat t                                               21

<210> SEQ ID NO 849
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 849
ccuggggaca accaguggct t                                               21

<210> SEQ ID NO 850
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 850
gccacugguu gucccaggt t                                                21

<210> SEQ ID NO 851
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 851
gaccaccuca aacuccagat t                                               21

<210> SEQ ID NO 852
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 852
ucuggaguuu gaggugguct t                                              21

<210> SEQ ID NO 853
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 853
uagaccaccu caaacuccat t                                              21

<210> SEQ ID NO 854
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 854
uggaguuuga gguggucuat t                                              21

<210> SEQ ID NO 855
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 855
cuuguagacc accucaaact t                                              21

<210> SEQ ID NO 856
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 856
guuugaggug gucuacaagt t                                              21

<210> SEQ ID NO 857
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 857
aagccgcuug uagaccacct t                                              21

<210> SEQ ID NO 858
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 858
gguggucuac aagcggcuut t                                              21

<210> SEQ ID NO 859
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 859
agaguccuga agccgcuugt t                                              21

<210> SEQ ID NO 860
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 860
caagcggcuu caggacucut t                                              21

<210> SEQ ID NO 861
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 861
caagaguccu gaagccgcut t                                              21

<210> SEQ ID NO 862
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 862
agcggcuuca ggacucuugt t                                              21

<210> SEQ ID NO 863
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 863
ccaagagucc ugaagccgct t                                              21

<210> SEQ ID NO 864
<211> LENGTH: 21
<212> TYPE: DNA
<213> ORGANISM: Homo sapiens

<400> SEQUENCE: 864
gcggcuucag gacucuuggt t                                              21

<210> SEQ ID NO 865
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 865
ugcguccucc caagagucct t                                              21
```

```
<210> SEQ ID NO 866
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 866
ggacucuugg gaggacgcat t                                              21

<210> SEQ ID NO 867
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 867
ggcugcgucc ucccaagagt t                                              21

<210> SEQ ID NO 868
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 868
cucuugggag gacgcagcct t                                              21

<210> SEQ ID NO 869
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 869
gaggaggaug gcugcgucct t                                              21

<210> SEQ ID NO 870
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 870
ggacgcagcc auccuccuct t                                              21

<210> SEQ ID NO 871
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 871
ggagaggagg auggcugcgt t                                              21

<210> SEQ ID NO 872
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 872
cgcagccauc cuccucucct t                                              21

<210> SEQ ID NO 873
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 873
uguuggagag gaggauggct t                                              21

<210> SEQ ID NO 874
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 874
gccauccucc ucuccaacat t                                              21
```

```
<210> SEQ ID NO 875
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 875
gagguguugg agaggaggat t                                              21

<210> SEQ ID NO 876
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 876
uccuccucuc caacaccuct t                                              21

<210> SEQ ID NO 877
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 877
aggguggccu gggaggugut t                                              21

<210> SEQ ID NO 878
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 878
acaccuccca ggccacccut t                                              21

<210> SEQ ID NO 879
<211> LENGTH: 21
<212> TYPE: DNA
<213> ORGANISM: Homo sapiens
<220> FEATURE:
<221> NAME/KEY: misc_feature
```

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 879
caggguggcc ugggaggugt t                                              21

<210> SEQ ID NO 880
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 880
caccucccag gccacccugt t                                              21

<210> SEQ ID NO 881
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 881
ugcugggcau gaggugcuct t                                              21

<210> SEQ ID NO 882
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 882
gagcaccuca ugcccagcat t                                              21

<210> SEQ ID NO 883
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 883
```

```
gcugcugggc augaggugct t                                              21

<210> SEQ ID NO 884
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 884
gcaccucaug cccagcagct t                                              21

<210> SEQ ID NO 885
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 885
ggugcugcug ggcaugaggt t                                              21

<210> SEQ ID NO 886
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 886
ccucaugccc agcagcacct t                                              21

<210> SEQ ID NO 887
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 887
acguaggugc ugcugggcat t                                              21

<210> SEQ ID NO 888
<211> LENGTH: 21
<212> TYPE: DNA
<213> ORGANISM: Homo sapiens
```

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 888
ugcccagcag caccuacgut t                                              21

<210> SEQ ID NO 889
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 889
acucgggcca cguaggugct t                                              21

<210> SEQ ID NO 890
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 890
gcaccuacgu ggcccgagut t                                              21

<210> SEQ ID NO 891
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 891
acucgggcca cguaggugct t                                              21

<210> SEQ ID NO 892
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

```
<400> SEQUENCE: 892
gcaccuacgu ggcccgagut t                                      21

<210> SEQ ID NO 893
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 893
cguacucggg ccacguaggt t                                      21

<210> SEQ ID NO 894
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 894
ccuacguggc ccgaguacgt t                                      21

<210> SEQ ID NO 895
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 895
guccugagag ccgagaacct t                                      21

<210> SEQ ID NO 896
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 896
gguucucggc ucucaggact t                                      21

<210> SEQ ID NO 897
<211> LENGTH: 21
```

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 897
uccacuugcu gggacgucct t                                              21

<210> SEQ ID NO 898
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 898
ggacguccca gcaaguggat t                                              21

<210> SEQ ID NO 899
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 899
ggcuccacuu gcugggacgt t                                              21

<210> SEQ ID NO 900
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 900
cgucccagca aguggagcct t                                              21

<210> SEQ ID NO 901
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 901
accucugggc uccacuugct t                                              21

<210> SEQ ID NO 902
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 902
gcaaguggag cccagaggut t                                              21

<210> SEQ ID NO 903
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 903
caaaccucug ggcuccacut t                                              21

<210> SEQ ID NO 904
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 904
aguggagccc agagguuugt t                                              21

<210> SEQ ID NO 905
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 905
aaccucuggg cuccacuugt t                                              21
```

```
<210> SEQ ID NO 906
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 906
caaguggagc ccagagguut t                                      21

<210> SEQ ID NO 907
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 907
gcaaaccucu gggcuccact t                                      21

<210> SEQ ID NO 908
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 908
guggagccca gagguuugct t                                      21

<210> SEQ ID NO 909
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 909
ucccagcaaa ccucugggct t                                      21

<210> SEQ ID NO 910
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 910
gcccagaggu uugcugggat t                                              21

<210> SEQ ID NO 911
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 911
gggaguccca gcaaaccuct t                                              21

<210> SEQ ID NO 912
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 912
gagguuugcu gggacuccct t                                              21

<210> SEQ ID NO 913
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 913
cugggagucc cagcaaacct t                                              21

<210> SEQ ID NO 914
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 914
gguuugcugg gacucccagt t                                              21
```

```
<210> SEQ ID NO 915
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 915
guucuggggc ugggccucat t                                              21

<210> SEQ ID NO 916
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 916
ugaggcccag ccccagaact t                                              21

<210> SEQ ID NO 917
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 917
gcacuccagg uucuggggct t                                              21

<210> SEQ ID NO 918
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 918
gccccagaac cuggagugct t                                              21

<210> SEQ ID NO 919
<211> LENGTH: 21
<212> TYPE: DNA
<213> ORGANISM: Homo sapiens
<220> FEATURE:
<221> NAME/KEY: misc_feature
```

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 919
aaagaagcac uccagguuct t                                              21

<210> SEQ ID NO 920
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 920
gaaccuggag ugcuucuuut t                                              21

<210> SEQ ID NO 921
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 921
ucaaagaagc acuccaggut t                                              21

<210> SEQ ID NO 922
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 922
accuggagug cuucuuugat t                                              21

<210> SEQ ID NO 923
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 923
```
gucaaagaag cacuccaggt t          21

<210> SEQ ID NO 924
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 924
ccuggagugc uucuuugact t          21

<210> SEQ ID NO 925
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 925
cucaccuccc aggagcagct t          21

<210> SEQ ID NO 926
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 926
gcugcuccug ggaggugagt t          21

<210> SEQ ID NO 927
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 927
ggccaccucc uuccucacct t          21

<210> SEQ ID NO 928
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 928
ggugaggaag gagguggcct t                                              21

<210> SEQ ID NO 929
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 929
gagcuggcca ccuccuucct t                                              21

<210> SEQ ID NO 930
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 930
ggaaggaggu ggccagcuct t                                              21

<210> SEQ ID NO 931
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 931
accgagcugg ccaccuccut t                                              21

<210> SEQ ID NO 932
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 932
aggagguggc cagcucggut t					21

<210> SEQ ID NO 933
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 933
gaccgagcug gccaccucct t					21

<210> SEQ ID NO 934
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 934
ggagguggcc agcucgguct t					21

<210> SEQ ID NO 935
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 935
ggagaccgag cuggccacct t					21

<210> SEQ ID NO 936
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 936
gguggccagc ucggucucct t					21

<210> SEQ ID NO 937
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 937
aggccaaagg agaccgagct t                                              21

<210> SEQ ID NO 938
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 938
gcucggucuc cuuuggccut t                                              21

<210> SEQ ID NO 939
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 939
cugggcuggg cuuguagaat t                                              21

<210> SEQ ID NO 940
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 940
uucuacaagc ccagcccagt t                                              21

<210> SEQ ID NO 941
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 941
ugcaucuggg cugggcuugt t                                              21

<210> SEQ ID NO 942
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 942
caagcccagc ccagaugcat t                                              21

<210> SEQ ID NO 943
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 943
cacuggggag cacucuucct t                                              21

<210> SEQ ID NO 944
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 944
ggaagagugc uccccagugt t                                              21

<210> SEQ ID NO 945
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 945
cagcacuggg gagcacucut t                                              21
```

```
<210> SEQ ID NO 946
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 946
agagugcucc ccagugcugt t                                              21

<210> SEQ ID NO 947
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 947
ucagcacugg ggagcacuct t                                              21

<210> SEQ ID NO 948
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 948
gagugcuccc cagugcugat t                                              21

<210> SEQ ID NO 949
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 949
ccucagcacu ggggagcact t                                              21

<210> SEQ ID NO 950
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 950
gugcucccca gugcugaggt t                                              21

<210> SEQ ID NO 951
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 951
uggugccugg uguggaggct t                                              21

<210> SEQ ID NO 952
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 952
gccuccacac caggcaccat t                                              21

<210> SEQ ID NO 953
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 953
cuggcagugg ugccuggugt t                                              21

<210> SEQ ID NO 954
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 954
caccaggcac cacugccagt t                                              21
```

```
<210> SEQ ID NO 955
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 955
aucuggcagu ggugccuggt t                                              21

<210> SEQ ID NO 956
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 956
ccaggcacca cugccagaut t                                              21

<210> SEQ ID NO 957
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 957
ggaaucuggc aguggugcct t                                              21

<210> SEQ ID NO 958
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 958
ggcaccacug ccagauucct t                                              21

<210> SEQ ID NO 959
<211> LENGTH: 21
<212> TYPE: DNA
<213> ORGANISM: Homo sapiens
<220> FEATURE:
<221> NAME/KEY: misc_feature
```

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 959
cacgggaauc uggcaguggt t                                        21

<210> SEQ ID NO 960
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 960
ccacugccag auucccgugt t                                        21

<210> SEQ ID NO 961
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 961
gggcacggga aucuggcagt t                                        21

<210> SEQ ID NO 962
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 962
cugccagauu cccgugccct t                                        21

<210> SEQ ID NO 963
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 963
```
acgauguauu ggccgugggt t                                           21

<210> SEQ ID NO 964
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 964
cccacggcca auacaucgut t                                           21

<210> SEQ ID NO 965
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 965
agagacgaug uauuggccgt t                                           21

<210> SEQ ID NO 966
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 966
cggccaauac aucgucucut t                                           21

<210> SEQ ID NO 967
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 967
cugaacagag acgauguaut t                                           21

<210> SEQ ID NO 968
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 968
auacaucguc ucuguucagt t                                              21

<210> SEQ ID NO 969
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 969
gcugaacaga gacgauguat t                                              21

<210> SEQ ID NO 970
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 970
uacaucgucu cuguucagct t                                              21

<210> SEQ ID NO 971
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 971
uggcugaaca gagacgaugt t                                              21

<210> SEQ ID NO 972
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 972
caucgucucu guucagccat t					21

<210> SEQ ID NO 973
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 973
cuuggcugaa cagagacgat t					21

<210> SEQ ID NO 974
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 974
ucgucucugu ucagccaagt t					21

<210> SEQ ID NO 975
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 975
uuucucugcc cuccuuggct t					21

<210> SEQ ID NO 976
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 976
gccaaggagg gcagagaaat t					21

<210> SEQ ID NO 977
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 977
ucucugcccu ccuuggcugt t                                              21

<210> SEQ ID NO 978
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 978
cagccaagga gggcagagat t                                              21

<210> SEQ ID NO 979
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 979
uguguuucuc ugcccuccut t                                              21

<210> SEQ ID NO 980
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 980
aggagggcag agaaacacat t                                              21

<210> SEQ ID NO 981
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 981
uguuucucug cccuccuugt t                                              21

<210> SEQ ID NO 982
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 982
caaggagggc agagaaacat t                                              21

<210> SEQ ID NO 983
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 983
auguguuucu cugcccucct t                                              21

<210> SEQ ID NO 984
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 984
ggagggcaga gaaacacaut t                                              21

<210> SEQ ID NO 985
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 985
uuuauguguu ucucugccct t                                              21
```

```
<210> SEQ ID NO 986
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 986
gggcagagaa acacauaaat t                                          21

<210> SEQ ID NO 987
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 987
ucuuuaugug uuucucugct t                                          21

<210> SEQ ID NO 988
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 988
gcagagaaac acauaaagat t                                          21

<210> SEQ ID NO 989
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 989
agcucuuuau guguuucuct t                                          21

<210> SEQ ID NO 990
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

-continued

```
<220> FEATURE:
<221> NAME/KEY: misc_feature
<222> LOCATION: (20)..(21)
<223> OTHER INFORMATION: DNA

<400> SEQUENCE: 990
gagaaacaca uaaagagcut t                                      21

<210> SEQ ID NO 991
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 991
ugagcucuuu auguguuuct t                                      21

<210> SEQ ID NO 992
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 992
gaaacacaua aagagcucat t                                      21

<210> SEQ ID NO 993
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 993
gagcucuuua uguguuucut t                                      21

<210> SEQ ID NO 994
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 994
agaaacacau aaagagcuct t                                      21
```

<210> SEQ ID NO 995
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 995
acugagcucu uuauguguut t                                              21

<210> SEQ ID NO 996
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 996
aacacauaaa gagcucagut t                                              21

<210> SEQ ID NO 997
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 997
cacugagcuc uuuaugugut t                                              21

<210> SEQ ID NO 998
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 998
acacauaaag agcucagugt t                                              21

<210> SEQ ID NO 999
<211> LENGTH: 21
<212> TYPE: DNA
<213> ORGANISM: Homo sapiens
<220> FEATURE:
<221> NAME/KEY: misc_feature

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 999
ucacugagcu cuuuaugugt t                                              21

<210> SEQ ID NO 1000
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1000
cacauaaaga gcucagugat t                                              21

<210> SEQ ID NO 1001
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1001
guucacugag cucuuuaugt t                                              21

<210> SEQ ID NO 1002
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1002
cauaaagagc ucagugaact t                                              21

<210> SEQ ID NO 1003
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1003
```
uucacugagc ucuuuaugut t                                              21

<210> SEQ ID NO 1004
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1004
acauaaagag cucagugaat t                                              21

<210> SEQ ID NO 1005
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1005
auguucacug agcucuuuat t                                              21

<210> SEQ ID NO 1006
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1006
uaaagagcuc agugaacaut t                                              21

<210> SEQ ID NO 1007
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1007
uguucacuga gcucuuuaut t                                              21

<210> SEQ ID NO 1008
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1008
cgcagaaagu gggaggagat t                                              21

<210> SEQ ID NO 1009
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1009
ggauguucac ugagcucuut t                                              21

<210> SEQ ID NO 1010
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1010
aagagcucag ugaacaucct t                                              21

<210> SEQ ID NO 1011
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1011
uggauguuca cugagcucut t                                              21

<210> SEQ ID NO 1012
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1012
agagcucagu gaacauccat t				21

<210> SEQ ID NO 1013
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1013
cuggauguuc acugagcuct t				21

<210> SEQ ID NO 1014
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1014
gagcucagug aacauccagt t				21

<210> SEQ ID NO 1015
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1015
aucuggaugu ucacugagct t				21

<210> SEQ ID NO 1016
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1016
gcucagugaa cauccagaut t				21

<210> SEQ ID NO 1017
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1017
gggccaucug gauguucact t                                              21

<210> SEQ ID NO 1018
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1018
gugaacaucc agauggcccu t                                              21

<210> SEQ ID NO 1019
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1019
ggaggggcca ucuggaugut t                                              21

<210> SEQ ID NO 1020
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1020
acauccagau ggccccucct t                                              21

<210> SEQ ID NO 1021
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1021
uggaggggcc aucuggaugt t                                              21

<210> SEQ ID NO 1022
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1022
cauccagaug gccccuccat t                                              21

<210> SEQ ID NO 1023
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1023
gauggagggg ccaucuggat t                                              21

<210> SEQ ID NO 1024
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1024
uccagauggc cccuccauct t                                              21

<210> SEQ ID NO 1025
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1025
gagggaugga ggggccauct t                                              21
```

```
<210> SEQ ID NO 1026
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1026
gauggcsccu ccaucccuct t                                              21

<210> SEQ ID NO 1027
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1027
uugagggaug gagggaccat t                                              21

<210> SEQ ID NO 1028
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1028
uggccccucc aucccucaat t                                              21

<210> SEQ ID NO 1029
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1029
ccuuggucac guugagggat t                                              21

<210> SEQ ID NO 1030
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1030
ucccucaacg ugaccaaggt t                                              21

<210> SEQ ID NO 1031
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1031
ucuccauccu uggucacgut t                                              21

<210> SEQ ID NO 1032
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1032
acgugaccaa ggauggagat t                                              21

<210> SEQ ID NO 1033
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1033
gucuccaucc uuggucacgt t                                              21

<210> SEQ ID NO 1034
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1034
cgugaccaag gauggagact t                                              21
```

<210> SEQ ID NO 1035
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1035
uagcugucuc cauccuuggt t                                              21

<210> SEQ ID NO 1036
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1036
ccaaggaugg agacagcuat t                                              21

<210> SEQ ID NO 1037
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1037
cuguagcugu cuccauccut t                                              21

<210> SEQ ID NO 1038
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1038
aggauggaga cagcuacagt t                                              21

<210> SEQ ID NO 1039
<211> LENGTH: 21
<212> TYPE: DNA
<213> ORGANISM: Homo sapiens
<220> FEATURE:
<221> NAME/KEY: misc_feature

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1039
gcuguagcug ucuccaucct t                                              21

<210> SEQ ID NO 1040
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1040
ggauggagac agcuacagct t                                              21

<210> SEQ ID NO 1041
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1041
caggcuguag cugucuccat t                                              21

<210> SEQ ID NO 1042
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1042
uggagacagc uacagccugt t                                              21

<210> SEQ ID NO 1043
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1043
```
agcgcaggcu guagcuguct t                                               21

<210> SEQ ID NO 1044
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1044
gacagcuaca gccugcgcut t                                               21

<210> SEQ ID NO 1045
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1045
ccagcgcagg cuguagcugt t                                               21

<210> SEQ ID NO 1046
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1046
cagcuacagc cugcgcuggt t                                               21

<210> SEQ ID NO 1047
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1047
ucccagcgca ggcuguagct t                                               21

<210> SEQ ID NO 1048
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1048
gcuacagccu gcgcugggat t                                              21

<210> SEQ ID NO 1049
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1049 uguuuccag cgcaggcugt t                                               21

<210> SEQ ID NO 1050
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1050
cagccugcgc ugggaaacat t                                              21

<210> SEQ ID NO 1051
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1051
auuguuuccc agcgcaggct t                                              21

<210> SEQ ID NO 1052
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1052
gccugcgcug ggaaacaaut t                                              21

<210> SEQ ID NO 1053
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1053
uuucauuguu ucccagcgct t                                              21

<210> SEQ ID NO 1054
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1054
gcgcugggaa acaaugaaat t                                              21

<210> SEQ ID NO 1055
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1055
auuuucauug uucccagct t                                               21

<210> SEQ ID NO 1056
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1056
gcugggaaac aaugaaaaut t                                              21

<210> SEQ ID NO 1057
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1057
cguaucgcau uuucauugut t                                              21

<210> SEQ ID NO 1058
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1058
acaaugaaaa ugcgauacgt t                                              21

<210> SEQ ID NO 1059
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1059
ucguaucgca uuuucauugt t                                              21

<210> SEQ ID NO 1060
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1060
caaugaaaau gcgauacgat t                                              21

<210> SEQ ID NO 1061
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1061
guucguaucg cauuuucaut t                                              21

<210> SEQ ID NO 1062
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1062
augaaaaugc gauacgaact t                                              21

<210> SEQ ID NO 1063
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1063
uguucguauc gcauuuucat t                                              21

<210> SEQ ID NO 1064
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1064
ugaaaaugcg auacgaacat t                                              21

<210> SEQ ID NO 1065
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1065
auguguucgu aucgcauuut t                                              21
```

```
<210> SEQ ID NO 1066
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1066
aaaugcgaua cgaacacaut t                                              21

<210> SEQ ID NO 1067
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1067
uauguguucg uaucgcauut t                                              21

<210> SEQ ID NO 1068
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1068
aaugcgauac gaacacauat t                                              21

<210> SEQ ID NO 1069
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1069
cuauguguuc guaucgcaut t                                              21

<210> SEQ ID NO 1070
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1070
augcgauacg aacacauagt t                                              21

<210> SEQ ID NO 1071
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1071
ucuauguguu cguaucgcat t                                              21

<210> SEQ ID NO 1072
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1072
ugcgauacga acacauagat t                                              21

<210> SEQ ID NO 1073
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1073
cucaaaugug uggucuaugt t                                              21

<210> SEQ ID NO 1074
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1074
cauagaccac acauuugagt t                                              21
```

<210> SEQ ID NO 1075
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1075
uguggucuau guguucguat t                                              21

<210> SEQ ID NO 1076
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1076
uacgaacaca uagaccacat t                                              21

<210> SEQ ID NO 1077
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1077
uggucuaugu guucguauct t                                              21

<210> SEQ ID NO 1078
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1078
gauacgaaca cauagaccat t                                              21

<210> SEQ ID NO 1079
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1079
uguguggucu auguguucgt t                                              21

<210> SEQ ID NO 1080
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1080
cgaacacaua gaccacacat t                                              21

<210> SEQ ID NO 1081
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1081
aaaugugugg ucuaugugut t                                              21

<210> SEQ ID NO 1082
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1082
acacauagac cacacauuut t                                              21

<210> SEQ ID NO 1083
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1083
caaaugugug gucuaugugt t                                                 21

<210> SEQ ID NO 1084
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1084
cacauagacc acacauuugt t                                                 21

<210> SEQ ID NO 1085
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1085
aucucaaaug uguggucuat t                                                 21

<210> SEQ ID NO 1086
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1086
uagaccacac auuugagaut t                                                 21

<210> SEQ ID NO 1087
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1087
ggaucucaaa ugugugguct t                                                 21

<210> SEQ ID NO 1088
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1088
gaccacacau uugagaucct t                                             21

<210> SEQ ID NO 1089
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1089
cuggaucuca aaugaguggt t                                             21

<210> SEQ ID NO 1090
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1090
ccacacauuu gagauccagt t                                             21

<210> SEQ ID NO 1091
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1091
guacuggauc ucaaaugugt t                                             21

<210> SEQ ID NO 1092
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

```
<400> SEQUENCE: 1092
cacauuugag auccaguact t                                         21

<210> SEQ ID NO 1093
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1093
cuguacugga ucucaaaugt t                                         21

<210> SEQ ID NO 1094
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1094
cauuugagau ccaguacagt t                                         21

<210> SEQ ID NO 1095
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1095
uccuguacug gaucucaaat t                                         21

<210> SEQ ID NO 1096
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1096
uuugagaucc aguacaggat t                                         21

<210> SEQ ID NO 1097
<211> LENGTH: 21
```

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1097
gucuuuccug uacuggauct t                                              21

<210> SEQ ID NO 1098
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1098
gauccaguac aggaaagact t                                              21

<210> SEQ ID NO 1099
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1099
gugucuuucc uguacuggat t                                              21

<210> SEQ ID NO 1100
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1100
uccaguacag gaaagacact t                                              21

<210> SEQ ID NO 1101
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1101
ggccgugucu uuccuguact t                                              21

<210> SEQ ID NO 1102
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1102
guacaggaaa gacacggcct t                                              21

<210> SEQ ID NO 1103
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1103
cguggccgug ucuuuccugt t                                              21

<210> SEQ ID NO 1104
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1104
caggaaagac acggccacgt t                                              21

<210> SEQ ID NO 1105
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1105
cacguggccg ugucuuucct t                                              21
```

```
<210> SEQ ID NO 1106
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1106
ggaaagacac ggccacgugt t                                              21

<210> SEQ ID NO 1107
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1107
uuccacgugg ccgugucuut t                                              21

<210> SEQ ID NO 1108
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1108
aagacacggc cacguggaat t                                              21

<210> SEQ ID NO 1109
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1109
cuuccacgug gccgugucut t                                              21

<210> SEQ ID NO 1110
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1110
agacacggcc acguggaagt t                                              21

<210> SEQ ID NO 1111
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1111
ccuuccacgu ggccguguct t                                              21

<210> SEQ ID NO 1112
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1112
gacacggcca cguggaaggt t                                              21

<210> SEQ ID NO 1113
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1113
guccuuccac guggccgugt t                                              21

<210> SEQ ID NO 1114
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1114
cacggccacg uggaaggact t                                              21
```

<210> SEQ ID NO 1115
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1115
cuguccuucc acguggccgt t                                            21

<210> SEQ ID NO 1116
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1116
cggccacgug gaaggacagt t                                            21

<210> SEQ ID NO 1117
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1117
uugcuguccu uccacguggt t                                            21

<210> SEQ ID NO 1118
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1118
ccacguggaa ggacagcaat t                                            21

<210> SEQ ID NO 1119
<211> LENGTH: 21
<212> TYPE: DNA
<213> ORGANISM: Homo sapiens
<220> FEATURE:
<221> NAME/KEY: misc_feature

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1119
gucuugcugu ccuuccacgt t                                              21

<210> SEQ ID NO 1120
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1120
cguggaagga cagcaagact t                                              21

<210> SEQ ID NO 1121
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1121
ucuugcuguc cuuccacgut t                                              21

<210> SEQ ID NO 1122
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1122
acguggaagg acagcaagat t                                              21

<210> SEQ ID NO 1123
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1123
```
ucggucuugc uguccuucct t                                              21

<210> SEQ ID NO 1124
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1124
ggaaggacag caagaccgat t                                              21

<210> SEQ ID NO 1125
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1125
gucucggucu ugcuguccut t                                              21

<210> SEQ ID NO 1126
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1126
aggacagcaa gaccgagact t                                              21

<210> SEQ ID NO 1127
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1127
ggucucgguc uugcuguect t                                              21

<210> SEQ ID NO 1128
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1128
ggacagcaag accgagacct t                                              21

<210> SEQ ID NO 1129
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1129
ucuggcuccc acccuccugt t                                              21

<210> SEQ ID NO 1130
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1130
caggagggug ggagccagat t                                              21

<210> SEQ ID NO 1131
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1131
gagggucucg gucuugcugt t                                              21

<210> SEQ ID NO 1132
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1132
cagcaagacc gagacccuct t                                              21

<210> SEQ ID NO 1133
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1133
uggagggucu cggucuugct t                                              21

<210> SEQ ID NO 1134
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1134
gcaagaccga gacccuccat t                                              21

<210> SEQ ID NO 1135
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1135
uucuggaggg ucucggucut t                                              21

<210> SEQ ID NO 1136
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1136
agaccgagac ccuccagaat t                                              21

<210> SEQ ID NO 1137
<211> LENGTH: 21

-continued

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1137
guucuggagg gucucgguct t                                              21

<210> SEQ ID NO 1138
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1138
gaccgagacc cuccagaact t                                              21

<210> SEQ ID NO 1139
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1139
gcguucugga gggucucggt t                                              21

<210> SEQ ID NO 1140
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1140
ccgagacccu ccagaacgct t                                              21

<210> SEQ ID NO 1141
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1141
gugggcguuc uggagggguct t                                              21

<210> SEQ ID NO 1142
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1142
gacccuccag aacgcccact t                                               21

<210> SEQ ID NO 1143
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1143
cugugggcgu ucuggagggt t                                               21

<210> SEQ ID NO 1144
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1144
cccuccagaa cgcccacagt t                                               21

<210> SEQ ID NO 1145
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1145
ggccaugcug ugggcguuct t                                               21
```

```
<210> SEQ ID NO 1146
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1146
gaacgcccac agcauggcct t                                              21

<210> SEQ ID NO 1147
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1147
agggccaugc ugugggcgut t                                              21

<210> SEQ ID NO 1148
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1148
acgcccacag cauggcccut t                                              21

<210> SEQ ID NO 1149
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1149
cagggccaug cugugggcgt t                                              21

<210> SEQ ID NO 1150
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1150
cgcccacagc auggcccugt t                                              21

<210> SEQ ID NO 1151
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1151
cagggccaug cugugggcgt t                                              21

<210> SEQ ID NO 1152
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1152
cgcccacagc auggcccugt t                                              21

<210> SEQ ID NO 1153
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1153
ccaguaccug guggagggct t                                              21

<210> SEQ ID NO 1154
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1154
gcccuccacc agguacuggt t                                              21
```

<210> SEQ ID NO 1155
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1155
acccuggccc aguaccuggt t                                    21

<210> SEQ ID NO 1156
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1156
ccagguacug ggccagggut t                                    21

<210> SEQ ID NO 1157
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1157
cucacccugg cccaguacct t                                    21

<210> SEQ ID NO 1158
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1158
gguacugggc cagggugagt t                                    21

<210> SEQ ID NO 1159
<211> LENGTH: 21
<212> TYPE: DNA
<213> ORGANISM: Homo sapiens
<220> FEATURE:
<221> NAME/KEY: misc_feature

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1159
gagguccuga cccucaccct t                                              21

<210> SEQ ID NO 1160
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1160
gggugagggu caggaccuct t                                              21

<210> SEQ ID NO 1161
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1161
uuguagccgg ugcgggaggt t                                              21

<210> SEQ ID NO 1162
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1162
ccucccgcac cggcuacaat t                                              21

<210> SEQ ID NO 1163
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1163
```
cagaucccgu uguagccggt t                                        21

<210> SEQ ID NO 1164
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1164
ccggcuacaa cgggaucugt t                                        21

<210> SEQ ID NO 1165
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1165
cucgcuccag aucccguugt t                                        21

<210> SEQ ID NO 1166
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1166
caacgggauc uggagcgagt t                                        21

<210> SEQ ID NO 1167
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1167
cacucgcucc agaucccgut t                                        21

<210> SEQ ID NO 1168
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1168
acgggaucug gagcgagugt t                                              21

<210> SEQ ID NO 1169
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1169
ccacucgcuc cagaucccgt t                                              21

<210> SEQ ID NO 1170
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1170
cgggaucugg agcgaguggt t                                              21

<210> SEQ ID NO 1171
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1171
ucacuccacu cgcuccagat t                                              21

<210> SEQ ID NO 1172
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1172
ucuggagcga guggagugat t                                              21

<210> SEQ ID NO 1173
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1173
aggcagcacc gacucggugt t                                              21

<210> SEQ ID NO 1174
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1174
caccgagucg gugcugccut t                                              21

<210> SEQ ID NO 1175
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1175
auaggcagca ccgacucggt t                                              21

<210> SEQ ID NO 1176
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1176
ccgagucggu gcugccuaut t                                              21

<210> SEQ ID NO 1177
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1177
ccacauaggc agcaccgact t                                          21

<210> SEQ ID NO 1178
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1178
gucggugcug ccuauguggt t                                          21

<210> SEQ ID NO 1179
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (19)..(21)
<223> OTHER INFORMATION: DNA
<220> FEATURE:
<221> NAME/KEY: misc_feature
<222> LOCATION: (20)..(21)
<223> OTHER INFORMATION: DNA

<400> SEQUENCE: 1179
augagggcca gcacccacat t                                          21

<210> SEQ ID NO 1180
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1180
ugugggugcu ggcccucaut t                                          21

<210> SEQ ID NO 1181
<211> LENGTH: 21
<212> TYPE: DNA
<213> ORGANISM: Homo sapiens
<220> FEATURE:
<221> NAME/KEY: misc_feature
```

<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1181
auggugagga agaucacgat t                                             21

<210> SEQ ID NO 1182
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1182
ucgugaucuu ccucaccaut t                                             21

<210> SEQ ID NO 1183
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1183
acagcgaugg ugaggaagat t                                             21

<210> SEQ ID NO 1184
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1184
ucuuccucac caucgcugut t                                             21

<210> SEQ ID NO 1185
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1185

```
gccaggagca cagcgauggt t                                               21

<210> SEQ ID NO 1186
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1186
ccaucgcugu gcuccuggct t                                               21

<210> SEQ ID NO 1187
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1187
agggccagga gcacagcgat t                                               21

<210> SEQ ID NO 1188
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1188
ucgcugugcu ccuggcccut t                                               21

<210> SEQ ID NO 1189
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1189
cgcagccugu acccguagat t                                               21

<210> SEQ ID NO 1190
<211> LENGTH: 21
<212> TYPE: DNA
<213> ORGANISM: Homo sapiens
```

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1190
ucuacgggua caggcugcgt t                                          21

<210> SEQ ID NO 1191
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1191
ucugcgcagc cuguacccgt t                                          21

<210> SEQ ID NO 1192
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1192
cggguacagg cugcgcagat t                                          21

<210> SEQ ID NO 1193
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1193
uucugcgcag ccuguaccct t                                          21

<210> SEQ ID NO 1194
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

```
<400> SEQUENCE: 1194
ggguacaggc ugcgcagaat t                                              21

<210> SEQ ID NO 1195
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1195
uuucugcgca gccuguacct t                                              21

<210> SEQ ID NO 1196
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1196
gguacaggcu gcgcagaaat t                                              21

<210> SEQ ID NO 1197
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1197
ccacuuucug cgcagccugt t                                              21

<210> SEQ ID NO 1198
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1198
caggcugcgc agaaaguggt t                                              21

<210> SEQ ID NO 1199
<211> LENGTH: 21
```

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1199
ucccacuuuc ugcgcagcct t                                              21

<210> SEQ ID NO 1200
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1200
ggcugcgcag aaagugggat t                                              21

<210> SEQ ID NO 1201
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1201
ucuccuccca cuuucugcgt t                                              21

<210> SEQ ID NO 1202
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1202
cgcagaaagu gggaggagat t                                              21

<210> SEQ ID NO 1203
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1203
uucuccuccc acuuucugct t                                          21

<210> SEQ ID NO 1204
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1204
gcagaaagug ggaggagaat t                                          21

<210> SEQ ID NO 1205
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(32)
<223> OTHER INFORMATION: DNA

<400> SEQUENCE: 1205
aucuucuccu cccacuuuct t                                          21

<210> SEQ ID NO 1206
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1206
gaaaguggga ggagaagaut t                                          21

<210> SEQ ID NO 1207
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1207
ggaucuucuc cucccacuut t                                          21
```

```
<210> SEQ ID NO 1208
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1208
aagugggagg agaagaucct t                                              21

<210> SEQ ID NO 1209
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1209
gggaucuucu ccucccacut t                                              21

<210> SEQ ID NO 1210
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1210
agugggagga gaagauccct t                                              21

<210> SEQ ID NO 1211
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1211
ggggaucuuc uccucccact t                                              21

<210> SEQ ID NO 1212
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1212
gugggaggag aagauccccu t                                              21

<210> SEQ ID NO 1213
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1213 gggguuggg aucuucuccu t                                               21

<210> SEQ ID NO 1214
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1214
ggagaagauc cccaacccct t                                              21

<210> SEQ ID NO 1215
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1215 gcuggguug gggaucuucu t                                               21

<210> SEQ ID NO 1216
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1216
gaagaucccc aacccagcu t                                               21
```

```
<210> SEQ ID NO 1217
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1217
uugcuggggu ugggaucut t                                              21

<210> SEQ ID NO 1218
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1218 agaucccaa ccccagcaat t                                              21

<210> SEQ ID NO 1219
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1219 cuugcuggggg uugggauct t                                             21

<210> SEQ ID NO 1220
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1220
gauccccaac cccagcaagt t                                             21

<210> SEQ ID NO 1221
<211> LENGTH: 21
<212> TYPE: DNA
<213> ORGANISM: Homo sapiens
<220> FEATURE:
<221> NAME/KEY: misc_feature
```

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1221
cucuugcugg gguuggggat t                                              21

<210> SEQ ID NO 1222
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1222
uccccaaccc cagcaagagt t                                              21

<210> SEQ ID NO 1223
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1223
agguggcucu ugcuggggut t                                              21

<210> SEQ ID NO 1224
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1224
accccagcaa gagccaccut t                                              21

<210> SEQ ID NO 1225
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1225
``` caggguggcuc uugcuggggt t                                          21

<210> SEQ ID NO 1226
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1226
ccccagcaag agccaccugt t                                           21

<210> SEQ ID NO 1227
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1227
uggaacaggu ggcucuugct t                                           21

<210> SEQ ID NO 1228
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1228
gcaagagcca ccuguuccat t                                           21

<210> SEQ ID NO 1229
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1229
uucuggaaca gguggcucut t                                           21

<210> SEQ ID NO 1230
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1230
agagccaccu guuccagaat t                                              21

<210> SEQ ID NO 1231
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1231
guucuggaac agguggcuct t                                              21

<210> SEQ ID NO 1232
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1232
gagccaccug uuccagaact t                                              21

<210> SEQ ID NO 1233
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1233
ccguucugga acagguggct t                                              21

<210> SEQ ID NO 1234
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1234
gccaccuguu ccagaacggt t                                             21

<210> SEQ ID NO 1235
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1235
gcucccguuc uggaacaggt t                                             21

<210> SEQ ID NO 1236
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1236
ccuguuccag aacgggagct t                                             21

<210> SEQ ID NO 1237
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1237
aagcucugcg cucccguuct t                                             21

<210> SEQ ID NO 1238
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1238
gaacgggagc gcagagcuut t                                             21

<210> SEQ ID NO 1239
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1239
caaagcucug cgcucccgut t                                              21

<210> SEQ ID NO 1240
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1240
acgggagcgc agagcuuugt t                                              21

<210> SEQ ID NO 1241
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1241
ccaaagcucu gcgcucccgt t                                              21

<210> SEQ ID NO 1242
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1242
cgggagcgca gagcuuuggt t                                              21

<210> SEQ ID NO 1243
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1243
ugccuggggg ccaaagcuct t                                              21

<210> SEQ ID NO 1244
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1244
gagcuuuggc ccccaggcat t                                              21

<210> SEQ ID NO 1245
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1245
ugaaggccga caugcugcct t                                              21

<210> SEQ ID NO 1246
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1246
ggcagcaugu cggccuucat t                                              21

<210> SEQ ID NO 1247
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1247
cuagugaagg ccgacaugct t                                              21
```

<210> SEQ ID NO 1248
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1248
gcaugucggc cuucacuagt t                                              21

<210> SEQ ID NO 1249
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1249
ccgcuaguga aggccgacat t                                              21

<210> SEQ ID NO 1250
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1250
ugucggccuu cacuagcggt t                                              21

<210> SEQ ID NO 1251
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1251 uguggggac ucccgcuagt t                                               21

<210> SEQ ID NO 1252
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA

```
<220> FEATURE:
<221> NAME/KEY: misc_feature
<222> LOCATION: (20)..(21)
<223> OTHER INFORMATION: DNA

<400> SEQUENCE: 1252
cuagcgggag uccccacat t                                               21

<210> SEQ ID NO 1253
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1253
cuggucuagg uucuugauct t                                              21

<210> SEQ ID NO 1254
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1254
gaucaagaac cuagaccagt t                                              21

<210> SEQ ID NO 1255
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1255
uccagcucag ggaagcggct t                                              21

<210> SEQ ID NO 1256
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1256
gccgcuuccc ugagcuggat t                                              21
```

```
<210> SEQ ID NO 1257
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1257
aauccuagag ggaacaccct t                                             21

<210> SEQ ID NO 1258
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1258
ggguguuccc uguaggauut t                                             21

<210> SEQ ID NO 1259
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1259
gagaggugac accucgcugt t                                             21

<210> SEQ ID NO 1260
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1260
cagcgaggug ucaccucuct t                                             21

<210> SEQ ID NO 1261
<211> LENGTH: 21
<212> TYPE: DNA
<213> ORGANISM: Homo sapiens
<220> FEATURE:
<221> NAME/KEY: misc_feature
```

<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1261
gugagaggug acaccucgct t                                              21

<210> SEQ ID NO 1262
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1262
gcgagguguc accucucact t                                              21

<210> SEQ ID NO 1263
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1263
uauggugaga ggugacacct t                                              21

<210> SEQ ID NO 1264
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1264
ggugucaccu cucaccauat t                                              21

<210> SEQ ID NO 1265
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1265
gguccucuau ggugagaggt t                                              21

<210> SEQ ID NO 1266
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1266
ccucucacca uagaggacct t                                              21

<210> SEQ ID NO 1267
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1267
ugcuuggggu ccucuauggt t                                              21

<210> SEQ ID NO 1268
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1268
ccauagagga ccccaagcat t                                              21

<210> SEQ ID NO 1269
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1269
acaugcuugg gguccucuat t                                              21

<210> SEQ ID NO 1270
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1270
uagaggaccc caagcaugut t                                              21

<210> SEQ ID NO 1271
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1271
agacaugcuu gggguccuct t                                              21

<210> SEQ ID NO 1272
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1272
gaggacccca agcaugucut t                                              21

<210> SEQ ID NO 1273
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1273
acagacaugc uuggggucct t                                              21

<210> SEQ ID NO 1274
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1274
ggaccccaag caugucugut t                                              21

<210> SEQ ID NO 1275
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1275
aucacagaca ugcuuggggt t                                              21

<210> SEQ ID NO 1276
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1276
ccccaagcau gucugugaut t                                              21

<210> SEQ ID NO 1277
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1277
gguggaucac agacaugcut t                                              21

<210> SEQ ID NO 1278
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1278
agcaugucug ugauccacct t                                              21

<210> SEQ ID NO 1279
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1279
ugguggauca cagacaugct t                                              21

<210> SEQ ID NO 1280
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1280
gcaugucugu gauccaccat t                                              21

<210> SEQ ID NO 1281
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1281
agauggugga ucacagacat t                                              21

<210> SEQ ID NO 1282
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1282
ugucugugau ccaccaucut t                                              21

<210> SEQ ID NO 1283
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1283
gucaggccca gaugguggat t                                              21

<210> SEQ ID NO 1284
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1284
uccaccaucu gggccugact t                                              21

<210> SEQ ID NO 1285
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1285
ucgugucagg cccagauggt t                                              21

<210> SEQ ID NO 1286
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1286
ccaucugggc cugacacgat t                                              21

<210> SEQ ID NO 1287
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1287
gagucguguc aggcccagat t                                              21
```

```
<210> SEQ ID NO 1288
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1288
ucugggccug acacgacuct t                                              21

<210> SEQ ID NO 1289
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1289
ugaggcagcu ggagucgugt t                                              21

<210> SEQ ID NO 1290
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1290
cacgacucca gcugccucat t                                              21

<210> SEQ ID NO 1291
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1291
ucugaggcag cuggagucgt t                                              21

<210> SEQ ID NO 1292
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1292
cgacuccagc ugccucagat t                                              21

<210> SEQ ID NO 1293
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1293
agaucugagg cagcuggagt t                                              21

<210> SEQ ID NO 1294
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1294
cuccagcugc cucagaucut t                                              21

<210> SEQ ID NO 1295
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1295
uggguagauc ugaggcagct t                                              21

<210> SEQ ID NO 1296
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1296
gcugccucag aucuacccat t                                              21
```

<210> SEQ ID NO 1297
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1297
ucugugggua gaucugaggt t                                              21

<210> SEQ ID NO 1298
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1298
ccucagaucu acccacagat t                                              21

<210> SEQ ID NO 1299
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1299
gcugcucugu ggguagauct t                                              21

<210> SEQ ID NO 1300
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1300
gaucuaccca cagagcagct t                                              21

<210> SEQ ID NO 1301
<211> LENGTH: 21
<212> TYPE: DNA
<213> ORGANISM: Homo sapiens
<220> FEATURE:
<221> NAME/KEY: misc_feature

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1301
gggcugcucu gugguagat t                                               21

<210> SEQ ID NO 1302
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1302
ucuacccaca gagcagccct t                                              21

<210> SEQ ID NO 1303
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1303
uuucucaggu guguggagt t                                               21

<210> SEQ ID NO 1304
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1304
cucccacaca ccugagaaat t                                              21

<210> SEQ ID NO 1305
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1305
```

```
uguuucucag gugugugggt t                                              21

<210> SEQ ID NO 1306
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1306
cccacacacc ugagaaacat t                                              21

<210> SEQ ID NO 1307
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1307
agccuguuuc ucaggugugt t                                              21

<210> SEQ ID NO 1308
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1308
cacaccugag aaacaggcut t                                              21

<210> SEQ ID NO 1309
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1309
gaagccuguu ucucaggugt t                                              21

<210> SEQ ID NO 1310
<211> LENGTH: 21
<212> TYPE: DNA
<213> ORGANISM: Homo sapiens
```

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1310
caccugagaa acaggcuuct t                                              21

<210> SEQ ID NO 1311
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1311
uggaagccug uuucucaggt t                                              21

<210> SEQ ID NO 1312
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1312
ccugagaaac aggcuuccat t                                              21

<210> SEQ ID NO 1313
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1313
aaagcuggaa gccuguuuct t                                              21

<210> SEQ ID NO 1314
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1314
gaaacaggcu uccagcuuut t                                              21

<210> SEQ ID NO 1315
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1315
aagcuggaag ccuguuucut t                                              21

<210> SEQ ID NO 1316
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1316
agaaacaggc uuccagcuut t                                              21

<210> SEQ ID NO 1317
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1317
ucaaagcugg aagccuguut t                                              21

<210> SEQ ID NO 1318
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1318
aacaggcuuc cagcuuugat t                                              21

<210> SEQ ID NO 1319
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1319
gucaaagcug gaagccugut t                                              21

<210> SEQ ID NO 1320
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1320
acaggcuucc agcuuugact t                                              21

<210> SEQ ID NO 1321
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1321
agucaaagcu ggaagccugt t                                              21

<210> SEQ ID NO 1322
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1322
caggcuucca gcuuugacut t                                              21

<210> SEQ ID NO 1323
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

-continued

```
<222> LOCATION: (20)..(21)
<223> OTHER INFORMATION: DNA

<400> SEQUENCE: 1323
gaagucaaag cuggaagcct t                                              21

<210> SEQ ID NO 1324
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1324
ggcuuccagc uuugacuuct t                                              21

<210> SEQ ID NO 1325
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1325
ggcccauuga agucaaagct t                                              21

<210> SEQ ID NO 1326
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1326
gcuuugacuu caaugggcct t                                              21

<210> SEQ ID NO 1327
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1327
cagguagggc ccauugaagt t                                              21
```

```
<210> SEQ ID NO 1328
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1328
cuucaauggg cccuaccugt t                                              21

<210> SEQ ID NO 1329
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1329
gucagguagg gagcggcugt t                                              21

<210> SEQ ID NO 1330
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1330
cagccgcucc cuaccugact t                                              21

<210> SEQ ID NO 1331
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1331
augucaggua gggagcggct t                                              21

<210> SEQ ID NO 1332
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1332 gccgcuccu accugacaut t                                               21

<210> SEQ ID NO 1333
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1333
gcuggcccag gaugucaggt t                                              21

<210> SEQ ID NO 1334
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1334
ccugacaucc ugggccagct t                                              21

<210> SEQ ID NO 1335
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1335
ucuggcuccc acccuccugt t                                              21

<210> SEQ ID NO 1336
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1336
caggagggug ggagccagat t                                              21
```

```
<210> SEQ ID NO 1337
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1337
cuucuggcuc ccacccucct t                                              21

<210> SEQ ID NO 1338
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1338
ggaggguggg agccagaagt t                                              21

<210> SEQ ID NO 1339
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1339
ggacuucugg cucccaccct t                                              21

<210> SEQ ID NO 1340
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1340 ggguggagc cagaagucct t                                               21

<210> SEQ ID NO 1341
<211> LENGTH: 21
<212> TYPE: DNA
<213> ORGANISM: Homo sapiens
<220> FEATURE:
<221> NAME/KEY: misc_feature
```

<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1341
ggaggugggg acuucuggct t                                              21

<210> SEQ ID NO 1342
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1342
gccagaaguc cccaccucct t                                              21

<210> SEQ ID NO 1343
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1343
cccuggaggu ggggacuuct t                                              21

<210> SEQ ID NO 1344
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1344 gaaguccca ccuccagggt t                                               21

<210> SEQ ID NO 1345
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1345

```
gacccuggag gugggggacut t                                             21

<210> SEQ ID NO 1346
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1346 agucccacc uccagggucu t                                               21

<210> SEQ ID NO 1347
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1347
ggacccugga ggugggact t                                               21

<210> SEQ ID NO 1348
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1348 gucccaccu ccagggucct t                                               21

<210> SEQ ID NO 1349
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1349
acuccaggga cccuggaggt t                                              21

<210> SEQ ID NO 1350
<211> LENGTH: 21
<212> TYPE: DNA
<213> ORGANISM: Homo sapiens
```

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1350
ccuccagggu cccuggagut t                                              21

<210> SEQ ID NO 1351
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1351
acagguacuc cagggaccct t                                              21

<210> SEQ ID NO 1352
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1352
gggucccugg aguaccugut t                                              21

<210> SEQ ID NO 1353
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1353
agcaggcaga cacagguact t                                              21

<210> SEQ ID NO 1354
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

```
<400> SEQUENCE: 1354
guaccugugu cugccugcut t                                          21

<210> SEQ ID NO 1355
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1355
agcaggcaga cacagguact t                                          21

<210> SEQ ID NO 1356
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1356
guaccugugu cugccugcut t                                          21

<210> SEQ ID NO 1357
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1357
cagagggacc aguugcacct t                                          21

<210> SEQ ID NO 1358
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1358
ggugcaacug gucccucugt t                                          21

<210> SEQ ID NO 1359
<211> LENGTH: 21
```

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1359
cugggccaga gggaccagut t                                              21

<210> SEQ ID NO 1360
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1360 acugguccu cuggcccagt t                                               21

<210> SEQ ID NO 1361
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1361
ccugggccag agggaccagt t                                              21

<210> SEQ ID NO 1362
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1362
cuggucccuc uggcccaggt t                                              21

<210> SEQ ID NO 1363
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1363
cuguccuggu cccaucgcct t                                              21

<210> SEQ ID NO 1364
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1364
ggcgauggga ccaggacagt t                                              21

<210> SEQ ID NO 1365
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1365
acggccuguc cugguccat t                                               21

<210> SEQ ID NO 1366
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1366
ugggaccagg acaggccgut t                                              21

<210> SEQ ID NO 1367
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1367
cuuccacggc cuguccuggt t                                              21
```

```
<210> SEQ ID NO 1368
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1368
ccaggacagg ccguggaagt t                                              21

<210> SEQ ID NO 1369
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1369
ccacuuccac ggccugucct t                                              21

<210> SEQ ID NO 1370
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1370
ggacaggccg uggaaguggt t                                              21

<210> SEQ ID NO 1371
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1371
ucuccacuuc cacggccugt t                                              21

<210> SEQ ID NO 1372
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1372
caggccgugg aaguggagat t                                              21

<210> SEQ ID NO 1373
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1373
ucucuccacu uccacggcct t                                              21

<210> SEQ ID NO 1374
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1374
ggccguggaa guggagagat t                                              21

<210> SEQ ID NO 1375
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1375
uucucuccac uuccacggct t                                              21

<210> SEQ ID NO 1376
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1376
gccguggaag uggagagaat t                                              21
```

```
<210> SEQ ID NO 1377
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1377
gcucggccuu cucuccacut t                                         21

<210> SEQ ID NO 1378
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1378
aguggagaga aggccgagct t                                         21

<210> SEQ ID NO 1379
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1379
ggcucggccu ucucuccact t                                         21

<210> SEQ ID NO 1380
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1380
guggagagaa ggccgagcct t                                         21

<210> SEQ ID NO 1381
<211> LENGTH: 21
<212> TYPE: DNA
<213> ORGANISM: Homo sapiens
<220> FEATURE:
<221> NAME/KEY: misc_feature
```

<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1381
acuccaggga gggacuccct t                                              21

<210> SEQ ID NO 1382
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1382
gggagucccu cccuggagut t                                              21

<210> SEQ ID NO 1383
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1383
uguccuccca cccuuggcct t                                              21

<210> SEQ ID NO 1384
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1384
ggccaagggu gggaggacat t                                              21

<210> SEQ ID NO 1385
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1385

```
gguccugucc ucccaccccut t                                              21

<210> SEQ ID NO 1386
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1386
agggugggag gacaggaccct t                                              21

<210> SEQ ID NO 1387
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1387
ugguccuguc cucccaccct t                                               21

<210> SEQ ID NO 1388
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1388
gggugggagg acaggaccat t                                               21

<210> SEQ ID NO 1389
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1389
uguccuuuug guccugucct t                                               21

<210> SEQ ID NO 1390
<211> LENGTH: 21
<212> TYPE: DNA
<213> ORGANISM: Homo sapiens
```

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1390
ggacaggacc aaaaggacat t                                              21

<210> SEQ ID NO 1391
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1391
ggcuguccuu uugguccugt t                                              21

<210> SEQ ID NO 1392
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1392
caggaccaaa aggacagcct t                                              21

<210> SEQ ID NO 1393
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1393
agggcugucc uuuuggucct t                                              21

<210> SEQ ID NO 1394
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

```
<400> SEQUENCE: 1394
ggaccaaaag gacagcccut t                                        21

<210> SEQ ID NO 1395
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1395
cacagggcug uccuuuggt t                                         21

<210> SEQ ID NO 1396
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1396
ccaaaaggac agcccugugt t                                        21

<210> SEQ ID NO 1397
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1397
agccacaggg cuguccuuut t                                        21

<210> SEQ ID NO 1398
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1398
aaaggacagc ccuguggcut t                                        21

<210> SEQ ID NO 1399
<211> LENGTH: 21
```

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1399
uagccacagg gcuguccuut t                                              21

<210> SEQ ID NO 1400
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1400
aaggacagcc cuguggcuat t                                              21

<210> SEQ ID NO 1401
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1401
auagccacag ggcuguccut t                                              21

<210> SEQ ID NO 1402
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1402
aggacagccc uguggcuaut t                                              21

<210> SEQ ID NO 1403
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1403
uauagccaca gggcugucct t                                              21

<210> SEQ ID NO 1404
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1404
ggacagcccu guggcuauat t                                              21

<210> SEQ ID NO 1405
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1405
ggguauagcc acagggcugt t                                              21

<210> SEQ ID NO 1406
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1406
cagcccugug gcuauaccct t                                              21

<210> SEQ ID NO 1407
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1407
auggguauag ccacagggct t                                              21
```

```
<210> SEQ ID NO 1408
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1408
gcccuguggc uauacccaut t                                              21

<210> SEQ ID NO 1409
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1409
cacuccaggg uccucagugt t                                              21

<210> SEQ ID NO 1410
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1410
cacugaggac ccuggagugt t                                              21

<210> SEQ ID NO 1411
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1411
gccacuccag gguccucagt t                                              21

<210> SEQ ID NO 1412
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1412
cugaggaccc uggaguggct t                                              21

<210> SEQ ID NO 1413
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1413
agaggccacu ccagguccct t                                              21

<210> SEQ ID NO 1414
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1414
ggacccugga guggccucut t                                              21

<210> SEQ ID NO 1415
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1415
accagaggcc acuccagggt t                                              21

<210> SEQ ID NO 1416
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1416
cccuggagug gccucuggut t                                              21
```

<210> SEQ ID NO 1417
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1417
uaaccagagg ccacuccagt t                                              21

<210> SEQ ID NO 1418
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1418
cuggaguggc cucugguuat t                                              21

<210> SEQ ID NO 1419
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1419
auaaccagag gccacuccat t                                              21

<210> SEQ ID NO 1420
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1420
uggaguggcc ucugguuaut t                                              21

<210> SEQ ID NO 1421
<211> LENGTH: 21
<212> TYPE: DNA
<213> ORGANISM: Homo sapiens
<220> FEATURE:
<221> NAME/KEY: misc_feature -continued
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1421
agacauaacc agaggccact t                                              21

<210> SEQ ID NO 1422
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1422
guggccucug guuaugucut t                                              21

<210> SEQ ID NO 1423
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1423
caggucugca gaggagacat t                                              21

<210> SEQ ID NO 1424
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1424
ugucuccucu gcagaccugt t                                              21

<210> SEQ ID NO 1425
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1425
uuggggugaa uaccagguct t             21

<210> SEQ ID NO 1426
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1426
gaccugguau ucaccccaat t             21

<210> SEQ ID NO 1427
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1427 guuggggug aauaccaggt t             21

<210> SEQ ID NO 1428
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1428
ccugguauuc accccaaact t             21

<210> SEQ ID NO 1429
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1429
ggaggcccag agagggaact t             21

<210> SEQ ID NO 1430
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1430
guucccucuc ugggccucct t                                          21

<210> SEQ ID NO 1431
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1431
auaagcuggg ggucuggguct t                                         21

<210> SEQ ID NO 1432
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1432
gaccagaccc ccagcuuaut t                                          21

<210> SEQ ID NO 1433
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1433
acauaagcug ggggucuggt t                                          21

<210> SEQ ID NO 1434
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1434
ccagaccccc agcuuaugut t                                              21

<210> SEQ ID NO 1435
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1435
aggacauaag cuggggguct t                                              21

<210> SEQ ID NO 1436
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1436 gaccccagc uuauguccut t                                               21

<210> SEQ ID NO 1437
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1437
ccaggacaua agcuggggt t                                               21

<210> SEQ ID NO 1438
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1438
cccccagcuu auguccuggt t                                              21

<210> SEQ ID NO 1439
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1439
gccagcccag gacauaagct t                                              21

<210> SEQ ID NO 1440
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1440
gcuuaugucc ugggcuggct t                                              21

<210> SEQ ID NO 1441
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1441
cacuggccag cccaggacat t                                              21

<210> SEQ ID NO 1442
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1442
uguccugggc uggccagugt t                                              21

<210> SEQ ID NO 1443
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1443
acuucacagg gccugggct t                                              21

<210> SEQ ID NO 1444
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1444
gccccaggcc cugugaagut t                                             21

<210> SEQ ID NO 1445
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1445
acccugacuu cacagggcct t                                             21

<210> SEQ ID NO 1446
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1446
ggcccuguga agucagggut t                                             21

<210> SEQ ID NO 1447
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1447
uagcccucaa acccugacut t                                             21
```

```
<210> SEQ ID NO 1448
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1448
agucaggguu ugagggcuat t                                              21

<210> SEQ ID NO 1449
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1449
auagcccuca aacccugact t                                              21

<210> SEQ ID NO 1450
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1450
gucaggguuu gagggcuaut t                                              21

<210> SEQ ID NO 1451
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1451
ccacauagcc cucaaaccct t                                              21

<210> SEQ ID NO 1452
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1452
ggguuugagg gcuauguggt t                                              21

<210> SEQ ID NO 1453
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1453
agggagcucc acauagccct t                                              21

<210> SEQ ID NO 1454
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1454
gggcuaugug gagcuccut t                                               21

<210> SEQ ID NO 1455
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1455
aauuggaggg agcuccacat t                                              21

<210> SEQ ID NO 1456
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1456
uguggagcuc ccuccaauut t                                              21
```

<210> SEQ ID NO 1457
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1457
gcccucaauu ggagggagct t                                     21

<210> SEQ ID NO 1458
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1458
gcucccucca auugagggct t                                     21

<210> SEQ ID NO 1459
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1459 uggggggaccg gcccucaaut t                                    21

<210> SEQ ID NO 1460
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1460
auugagggcc gguccccat t                                      21

<210> SEQ ID NO 1461
<211> LENGTH: 21
<212> TYPE: DNA
<213> ORGANISM: Homo sapiens
<220> FEATURE:
<221> NAME/KEY: misc_feature

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1461 cuggggggacc ggcccucaat t                                             21

<210> SEQ ID NO 1462
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1462
uugagggccg guccccagt t                                               21

<210> SEQ ID NO 1463
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1463
ggauuguucc uuggugacct t                                              21

<210> SEQ ID NO 1464
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1464
ggucaccaag gaacaaucct t                                              21

<210> SEQ ID NO 1465
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1465
```
ggacaggauu guuccuuggt t                       21

<210> SEQ ID NO 1466
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1466
ccaaggaaca auccugucct t                       21

<210> SEQ ID NO 1467
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1467
gggggacagg auuguuccut t                       21

<210> SEQ ID NO 1468
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1468
aggaacaauc cugucccct t                        21

<210> SEQ ID NO 1469
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1469 gggggggacag gauuguucct t                      21

<210> SEQ ID NO 1470
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1470
ggaacaaucc ugucccccct t                                              21

<210> SEQ ID NO 1471
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1471
ucagggggga caggauugut t                                              21

<210> SEQ ID NO 1472
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1472
acaauccugu cccccugat t                                               21

<210> SEQ ID NO 1473
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1473 cucaggggg acaggauugt t                                               21

<210> SEQ ID NO 1474
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

```
<400> SEQUENCE: 1474
caauccuguc ccccugagt t                                              21

<210> SEQ ID NO 1475
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1475
gccucagggg ggacaggaut t                                             21

<210> SEQ ID NO 1476
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1476
auccugcccc cccugaggct t                                             21

<210> SEQ ID NO 1477
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1477
ggccucaggg gggacaggat t                                             21

<210> SEQ ID NO 1478
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1478 uccuguccc ccugaggcct t                                              21

<210> SEQ ID NO 1479
<211> LENGTH: 21
```

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1479
caggacaggg cuuuuggcct t                                              21

<210> SEQ ID NO 1480
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1480
ggccaaaagc ccguccugt t                                               21

<210> SEQ ID NO 1481
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1481
ggguucagga cagggcuuut t                                              21

<210> SEQ ID NO 1482
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1482
aaagcccugu ccugaaccct t                                              21

<210> SEQ ID NO 1483
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1483
uggguucagg acagggcuut t                                              21

<210> SEQ ID NO 1484
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1484
aagcccuguc cugaacccat t                                              21

<210> SEQ ID NO 1485
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1485 cugguucag gacagggcut t                                               21

<210> SEQ ID NO 1486
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1486
agcccugucc ugaacccagt t                                              21

<210> SEQ ID NO 1487
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1487
ggacacaucu gccgggcgut t                                              21
```

```
<210> SEQ ID NO 1488
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1488
acgcccggca gaugugucct t                                              21

<210> SEQ ID NO 1489
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1489
gggacacauc ugccgggcgt t                                              21

<210> SEQ ID NO 1490
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1490
cgcccggcag auguguccct t                                              21

<210> SEQ ID NO 1491
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1491
gggauguugg ggacacauct t                                              21

<210> SEQ ID NO 1492
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1492
gauguguccc caacauccct t                                              21

<210> SEQ ID NO 1493
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1493 ugggauguu ggggacacat t                                               21

<210> SEQ ID NO 1494
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1494 uguguccca acaucccat t                                                21

<210> SEQ ID NO 1495
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1495
ccucgggcug uggggaugut t                                              21

<210> SEQ ID NO 1496
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1496 acaucccccac agcccgaggt t                                             21
```

```
<210> SEQ ID NO 1497
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1497
cccucgggcu gugggaugt t                                          21

<210> SEQ ID NO 1498
<211> LENGTH: 20
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1498
cauccccaca gcccgaggtt                                           20

<210> SEQ ID NO 1499
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1499
cugcaggaca aggaggccct t                                         21

<210> SEQ ID NO 1500
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1500
gggccuccuu guccugcagt t                                         21

<210> SEQ ID NO 1501
<211> LENGTH: 21
<212> TYPE: DNA
<213> ORGANISM: Homo sapiens
<220> FEATURE:
<221> NAME/KEY: misc_feature
```

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1501
auagucgccc acuugcugct t                                              21

<210> SEQ ID NO 1502
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1502
gcagcaagug ggcgacuaut t                                              21

<210> SEQ ID NO 1503
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1503
gcaauagucg cccacuugct t                                              21

<210> SEQ ID NO 1504
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1504
gcaagugggc gacuauugct t                                              21

<210> SEQ ID NO 1505
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1505
```

```
gaagcaauag ucgcccacut t                                          21
```

<210> SEQ ID NO 1506
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1506

```
agugggcgac uauugcuuct t                                          21
```

<210> SEQ ID NO 1507
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1507

```
ggaagcaaua gucgcccact t                                          21
```

<210> SEQ ID NO 1508
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1508

```
gugggcgacu auugcuucct t                                          21
```

<210> SEQ ID NO 1509
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1509

```
gccggggagg aagcaauagt t                                          21
```

<210> SEQ ID NO 1510
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1510
cuauugcuuc cucccggct t                                               21

<210> SEQ ID NO 1511
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1511
caggccgggg aggaagcaat t                                              21

<210> SEQ ID NO 1512
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1512
uugcuuccuc cccggccugt t                                              21

<210> SEQ ID NO 1513
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1513
cccggggaag aagguuuact t                                              21

<210> SEQ ID NO 1514
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

<400> SEQUENCE: 1514
guaaaccuuc uucccgggt t                                        21

<210> SEQ ID NO 1515
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1515
ggucccgggg aagaagguut t                                       21

<210> SEQ ID NO 1516
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1516
aaccuucuuc cccgggacct t                                       21

<210> SEQ ID NO 1517
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1517
gggucccggg gaagaaggut t                                       21

<210> SEQ ID NO 1518
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1518
accuucuucc ccgggaccct t                                       21

<210> SEQ ID NO 1519
<211> LENGTH: 21

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1519
cgggucccgg ggaagaaggt t                                              21

<210> SEQ ID NO 1520
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1520
ccuucuuccc cgggacccgt t                                              21

<210> SEQ ID NO 1521
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1521
ucuugaucuc aggaccgggt t                                              21

<210> SEQ ID NO 1522
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1522
cccgguccug agaucaagat t                                              21

<210> SEQ ID NO 1523
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

```
<222> LOCATION: (20)..(21)
<223> OTHER INFORMATION: DNA

<400> SEQUENCE: 1523
cuggucuagg uucuugauct t                                              21

<210> SEQ ID NO 1524
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1524
gaucaagaac cuagaccagt t                                              21

<210> SEQ ID NO 1525
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1525
gccuggucua gguucuugat t                                              21

<210> SEQ ID NO 1526
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1526
ucaagaaccu agaccaggct t                                              21

<210> SEQ ID NO 1527
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1527
aaagccuggu cugguucut t                                               21
```

```
<210> SEQ ID NO 1528
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1528
agaaccuaga ccaggcuuut t                                              21

<210> SEQ ID NO 1529
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1529
aaaagccugg ucuagguuct t                                              21

<210> SEQ ID NO 1530
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1530
gaaccuagac caggcuuuut t                                              21

<210> SEQ ID NO 1531
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1531
ugaaaagccu ggucuaggut t                                              21

<210> SEQ ID NO 1532
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1532
accuagacca ggcuuuucat t                                              21

<210> SEQ ID NO 1533
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1533
uugaaaagcc uggucuaggt t                                              21

<210> SEQ ID NO 1534
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1534
ccuagaccag gcuuuucaat t                                              21

<210> SEQ ID NO 1535
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1535
ugacuugaaa agccugguct t                                              21

<210> SEQ ID NO 1536
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1536
gaccaggcuu uucaagucat t                                              21
```

<210> SEQ ID NO 1537
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1537
cuugacuuga aaagccuggt t                                              21

<210> SEQ ID NO 1538
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1538
ccaggcuuuu caagucaagt t                                              21

<210> SEQ ID NO 1539
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1539
cuucuugacu ugaaaagcct t                                              21

<210> SEQ ID NO 1540
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1540
ggcuuuucaa gucaagaagt t                                              21

<210> SEQ ID NO 1541
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1541 gccuggggc uucuugacut t                                            21

<210> SEQ ID NO 1542
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1542
agucaagaag cccccaggct t                                           21

<210> SEQ ID NO 1543
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1543
ggccuggggg cuucuugact t                                           21

<210> SEQ ID NO 1544
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1544
gucaagaagc ccccaggcct t                                           21

<210> SEQ ID NO 1545
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1545
agccuggccu gggggcuuct t                                              21

<210> SEQ ID NO 1546
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1546 gaagcccccca ggccaggcut t                                             21

<210> SEQ ID NO 1547
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1547
gagcugaaug acgggcacct t                                              21

<210> SEQ ID NO 1548
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1548
ggugcccguc auucagcuct t                                              21

<210> SEQ ID NO 1549
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1549
uugaagagcu gaaugacggt t                                              21

<210> SEQ ID NO 1550
<211> LENGTH: 21
<212> TYPE: DNA
<213> ORGANISM: Homo sapiens

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1550
ccgucauuca gcucuucaat t                                              21

<210> SEQ ID NO 1551
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1551
agggcuuuga agagcugaat t                                              21

<210> SEQ ID NO 1552
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1552
uucagcucuu caaagcccut t                                              21

<210> SEQ ID NO 1553
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1553
cuucagggcu uugaagagct t                                              21

<210> SEQ ID NO 1554
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA
```

```
<400> SEQUENCE: 1554
gcucuucaaa gcccugaagt t                                              21

<210> SEQ ID NO 1555
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1555
uccugcugcu ucagggcuut t                                              21

<210> SEQ ID NO 1556
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1556
aagcccugaa gcagcaggat t                                              21

<210> SEQ ID NO 1557
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1557
guccugcugc uucagggcut t                                              21

<210> SEQ ID NO 1558
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1558
agcccugaag cagcaggact t                                              21

<210> SEQ ID NO 1559
<211> LENGTH: 21
```

```
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1559
aguccugcug cuucagggct t                                              21

<210> SEQ ID NO 1560
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1560
gcccugaagc agcaggacut t                                              21

<210> SEQ ID NO 1561
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1561
gacagguagu ccugcugcut t                                              21

<210> SEQ ID NO 1562
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1562
agcagcagga cuaccuguct t                                              21

<210> SEQ ID NO 1563
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
```

<222> LOCATION: (20)..(21)
<223> OTHER INFORMATION: DNA

<400> SEQUENCE: 1563
agacagguag uccugcugct t                                              21

<210> SEQ ID NO 1564
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1564
gcagcaggac uaccugucut t                                              21

<210> SEQ ID NO 1565
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1565
cagagacagg uaguccugct t                                              21

<210> SEQ ID NO 1566
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1566
gcaggacuac cugucucugt t                                              21

<210> SEQ ID NO 1567
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1567
gggcagagac agguaguccu t                                              21

```
<210> SEQ ID NO 1568
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1568
ggacuaccug ucucugccct t                                      21

<210> SEQ ID NO 1569
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1569 aggggggcaga gacagguagt t                                     21

<210> SEQ ID NO 1570
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1570
cuaccugucu cugcccccut t                                      21

<210> SEQ ID NO 1571
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1571 ccaaggggc agagacaggt t                                       21

<210> SEQ ID NO 1572
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
```

```
<220> FEATURE:
<221> NAME/KEY: misc_feature
<222> LOCATION: (20)..(21)
<223> OTHER INFORMATION: DNA

<400> SEQUENCE: 1572
ccugucucug cccccuuggt t                                              21

<210> SEQ ID NO 1573
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1573
uagauguugg ucauaauucg g                                              21

<210> SEQ ID NO 1574
<211> LENGTH: 21
<212> TYPE: DNA
<213> ORGANISM: Homo sapiens
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1574
gaauuaugac caacaucuat t                                              21

<210> SEQ ID NO 1575
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 1575
aaaaaugagc cggauggccu utt                                            23

<210> SEQ ID NO 1576
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 1576
aaggccaucc ggcucauuuu utt                                            23
```

```
<210> SEQ ID NO 1577
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 1577
aaaggcguag aucaccgggu utt                                              23

<210> SEQ ID NO 1578
<211> LENGTH: 23
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 1578
aacccgguga ucuacgccuu utt                                              23

<210> SEQ ID NO 1579
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides at positions 1, 2, 16, 17, 18 and
      19 are 2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1579
gaccgagctg gccacctcc                                                   19

<210> SEQ ID NO 1580
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides at positions 1-3, 8-10, and 17-19
      are 2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1580
gaccgagctg gccacctcc                                                   19

<210> SEQ ID NO 1581
<211> LENGTH: 20
<212> TYPE: DNA
<213> ORGANISM: Homo sapiens
<220> FEATURE:
<221> NAME/KEY: misc_feature
```

<223> OTHER INFORMATION: Nucleotides at positions 1, 2, 3, 4, 5, 6, 15,
      16, 17, 18, 19 and 20 are 2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1581
ctctccactt ccacggcctg                                                 20

<210> SEQ ID NO 1582
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides 1, 2, and 17-20 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1582
ctctccactt ccacggcctg                                                 20

<210> SEQ ID NO 1583
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 17-20 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1583
ctctccactt ccacggcctg                                                 20

<210> SEQ ID NO 1584
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 1-3 and 18-20 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1584
ctctccactt ccacggcctg                                                 20

<210> SEQ ID NO 1585
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 1, 2, 8-10, and 17-20
      are 2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1585

-continued ctctccactt ccacggcctg                                              20

<210> SEQ ID NO 1586
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 1, 3, 5, 16, 18, and
      20 are 2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1586
ctctccactt ccacggcctg                                              20

<210> SEQ ID NO 1587
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 8-13 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1587
ctctccactt ccacggcctg                                              20

<210> SEQ ID NO 1588
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 6-8 and 13-15 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1588
ctctccactt ccacggcctg                                              20

<210> SEQ ID NO 1589
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 6-8 and 13-15 are
      2'-deoxy-2'fluoro-arabinonucleotides
<220> FEATURE:
<221> NAME/KEY: misc_feature
<223> OTHER INFORMATION: Nucleotides at positions 1-5, 9-12, and 16-20
      are linked by phosphorothioate linkages

<400> SEQUENCE: 1589
ctctccactt ccacggcctg                                              20

<210> SEQ ID NO 1590
<211> LENGTH: 20
<212> TYPE: DNA
<213> ORGANISM: Homo sapiens

```
<220> FEATURE:
<221> NAME/KEY: misc_feature
<223> OTHER INFORMATION: Nucleotides at positions 1-3 and 18-20 are
      2'-deoxy-2'fluoro-arabinonucleotides
<220> FEATURE:
<221> NAME/KEY: misc_feature
<223> OTHER INFORMATION: Nucleotides at positions 1-3, 7-10 and 14-20
      are linked by phosphorothioate linkages

<400> SEQUENCE: 1590
ctctccactt ccacggcctg                                                   20

<210> SEQ ID NO 1591
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions, 2, 4, 6, 8, 10, 12,
      14, 16, 18 ad 20 are 2'-deoxy-2'fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1591
ctctccactt ccacggcctg                                                   20

<210> SEQ ID NO 1592
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 1, 2, 5, 6, 9, 10, 13,
      14, and 17-20 are 2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1592
ctctccactt ccacggcctg                                                   20

<210> SEQ ID NO 1593
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 6, 7, 14, and 15 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1593
ctctccactt ccacggcctg                                                   20

<210> SEQ ID NO 1594
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 6-8 and 13-15 are
      2'-deoxy-2'-fluoro-arabinonucleotides
<220> FEATURE:
<221> NAME/KEY: misc_feature
<223> OTHER INFORMATION: Nucleotides at positions 1, 2, 6-8, 13-15, 19
      and 20 are linked by phosphorothioate linkages
```

<400> SEQUENCE: 1594
ctctccactt ccacggcctg                                              20

<210> SEQ ID NO 1595
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 6-8 and 13-15 are
      2'-deoxy-2'-fluoro-arabinonucleotides
<220> FEATURE:
<221> NAME/KEY: misc_feature
<223> OTHER INFORMATION: Nucleotides at positions 1-3, 6, 8, 9-13, 15
      and 18-20 are linked by phosphorothioate linkages
<220> FEATURE:
<221> NAME/KEY: misc_feature
<223> OTHER INFORMATION: Nucleotides at positions 1-3, 6, 8-13, 15 and
      18-20 are linked by phosphorothioate linkages

<400> SEQUENCE: 1595
ctctccactt ccacggcctg                                              20

<210> SEQ ID NO 1596
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 8-13 are
      2'-deoxy-2'-fluoro-arabinonucleotides
<220> FEATURE:
<221> NAME/KEY: misc_feature
<223> OTHER INFORMATION: Nucleotides at positions 1-3, 8-14, 19 and 20
      are linnked by phosphorothioate linkages

<400> SEQUENCE: 1596
ctctccactt ccacggcctg                                              20

<210> SEQ ID NO 1597
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 8-13 are
      2'-deoxy-2'-fluoro-arabinonucleotides
<220> FEATURE:
<221> NAME/KEY: misc_feature
<223> OTHER INFORMATION: Nucleotides at positions 1-4, 8, 9, 12, 13 and
      17-20 are linked by phosphorothioate linkages

<400> SEQUENCE: 1597
ctctccactt ccacggcctg                                              20

<210> SEQ ID NO 1598
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides at positions 8-13 are
      2'-deoxy-2'-fluoro-arabinonucleotides
<220> FEATURE:
<221> NAME/KEY: misc_feature
<223> OTHER INFORMATION: Nucleotides at positions 1-4 and 17-20 are
      linked by phosphorothioate linkages

<400> SEQUENCE: 1598
ctctccactt ccacggcctg                                              20

```
<210> SEQ ID NO 1599
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-6 and 14-19 are
      2'-deoxy-2'-fluoro-arabinonucleotides
<220> FEATURE:
<221> NAME/KEY: misc_feature
<223> OTHER INFORMATION: All nucleotides are linked by phosphorothiate
      linkages

<400> SEQUENCE: 1599
cacctctgtc accagcatg                                                19

<210> SEQ ID NO 1600
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-8 and 16-19 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1600
cacctctgtc accagcatg                                                19

<210> SEQ ID NO 1601
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-5, 7-10, 18 and 19 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1601
cacctgtgtc accagcatg                                                19

<210> SEQ ID NO 1602
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 17-19 are 2'-deoxy-2'-fluoro-
      arabinonucleotides
<220> FEATURE:
<221> NAME/KEY: misc_feature
<223> OTHER INFORMATION: All nucleotides are linked by phosphorothioate
      linkages

<400> SEQUENCE: 1602
cacctctgtc accagcatg                                                19

<210> SEQ ID NO 1603
<211> LENGTH: 19
<212> TYPE: DNA
<213> ORGANISM: Homo sapiens
<220> FEATURE:
<221> NAME/KEY: misc_feature
```

```
<223> OTHER INFORMATION: Nucleotides 1, 2 and 17-19 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1603
cacctctgtc accagcatg                                                  19

<210> SEQ ID NO 1604
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-4 and 16-19 are
      2'-deoxy-2'-fluoro-arabinonucleotides
<220> FEATURE:
<221> NAME/KEY: misc_feature
<223> OTHER INFORMATION: All nucleotides are linked by phosphorothiate
      linkages

<400> SEQUENCE: 1604
cacctctgtc accagcatg                                                  19

<210> SEQ ID NO 1605
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-4, 8, 9, and 16-19 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1605
cacctctgtc accagcatg                                                  19

<210> SEQ ID NO 1606
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1, 3, 5, 7, 9, 1, 13, 15, 17 and
      19 are 2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1606
cacctctgtc accagcatg                                                  19

<210> SEQ ID NO 1607
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1, 2, 5, 6, 9, 10, 13, 14, and
      17-19 are 2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1607
```
cacctctgtc accagcatg                                                 19

<210> SEQ ID NO 1608
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-8 and 16-19 are
      2'-deoxy-2'-fluoro-arabinonucleotides
<220> FEATURE:
<221> NAME/KEY: misc_feature
<223> OTHER INFORMATION: Nucleotides 1-4 and 9-19 are linked by
      phosphorothioate linkages

<400> SEQUENCE: 1608
cacctctgtc accagcatg                                                 19

<210> SEQ ID NO 1609
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-8 and 16-19 are
      2'-deoxy-2'-fluoro-arabinonucleotides
<220> FEATURE:
<221> NAME/KEY: misc_feature
<223> OTHER INFORMATION: Nucleotides 1, 2, 9-15, 18 and 19 are linked by
      phosphorothioate linkages

<400> SEQUENCE: 1609
cacctctgtc accagcatg                                                 19

<210> SEQ ID NO 1610
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-8 and 16-19 are
      2'-deoxy-2'-fluoro-arabinonucleotides
<220> FEATURE:
<221> NAME/KEY: misc_feature
<223> OTHER INFORMATION: Nucleotides 1-8 and 13-19 are linked by
      phosphorothioate linkages

<400> SEQUENCE: 1610
cacctctgtc accagcatg                                                 19

<210> SEQ ID NO 1611
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-8 and 16-19 are
      2'-deoxy-2'-fluoro-arabinonucleotides
<220> FEATURE:
<221> NAME/KEY: misc_feature
<223> OTHER INFORMATION: Nucleotides 1-8 and 16-19 are linked by
      phosphorothiate linkages

<400> SEQUENCE: 1611
cacctctgtc accagcatg                                                 19

<210> SEQ ID NO 1612
<211> LENGTH: 19
<212> TYPE: DNA
<213> ORGANISM: Homo sapiens

```
<220> FEATURE:
<221> NAME/KEY: misc_feature
<223> OTHER INFORMATION: Nucleotides 1-6 and 16-19 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1612
cacctctgtc accagcatg                                              19

<210> SEQ ID NO 1613
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-8 and 16-19 are
      2'-deoxy-2'-fluoro-arabinonucleotides
<220> FEATURE:
<221> NAME/KEY: misc_feature
<223> OTHER INFORMATION: Nucleotides 1-4, 9-15, 18 and 19 are linked by
      phosphorothioate linkages

<400> SEQUENCE: 1613
cacctctgtc accagcatg                                              19

<210> SEQ ID NO 1614
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-8 and 16-19 are
      2'-deoxy-2'-fluoro-arabinonucleotides
<220> FEATURE:
<221> NAME/KEY: misc_feature
<223> OTHER INFORMATION: Nucleotides 1, 9-15, 18 and 19 are linked by
      phosphorothioate linkages

<400> SEQUENCE: 1614
cacctctgtc accagcatg                                              19

<210> SEQ ID NO 1615
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1-8 and 16-19 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (11)..(11)
<223> OTHER INFORMATION: n is 2-amino-2'-deoxyadenosine
<220> FEATURE:
<221> NAME/KEY: misc_feature
<222> LOCATION: (14)..(14)
<223> OTHER INFORMATION: n is 2-amino-2'-deoxyadenosine

<400> SEQUENCE: 1615
cacctctgtc nccngcatg                                              19

<210> SEQ ID NO 1616
<211> LENGTH: 19
<212> TYPE: DNA
<213> ORGANISM: Homo sapiens
```

```
<220> FEATURE:
<221> NAME/KEY: misc_feature
<223> OTHER INFORMATION: Nucleotides 1-6 and 16-19 are
      2'-deoxy-2'-fluoro-arabinonucleotides
<220> FEATURE:
<221> NAME/KEY: misc_feature
<223> OTHER INFORMATION: Nucleotides 1-8 and 13-19 are linked by
      phosphorothioate linkages

<400> SEQUENCE: 1616
cacctctgtc accagcatg                                              19

<210> SEQ ID NO 1617
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides 1, 2 and 16-20 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1617
gaatgggatg tatctgccca                                             20

<210> SEQ ID NO 1618
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides 1, 2, 11, 12, and 18-20 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1618
gaatgggatg tatctgccca                                             20

<210> SEQ ID NO 1619
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides 1, 2, and 16-20 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1619
accaggtcca gatgcttgct                                             20

<210> SEQ ID NO 1620
<211> LENGTH: 20
<212> TYPE: DNA
<213> ORGANISM: Homo sapiens
<220> FEATURE:
<221> NAME/KEY: misc_feature
<223> OTHER INFORMATION: Nucleotides 1, 2, 9, 10, and 18-20 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages
```

<400> SEQUENCE: 1620
accaggtcca gatgcttgct					20

<210> SEQ ID NO 1621
<211> LENGTH: 20
<212> TYPE: DNA
<213> ORGANISM: Homo sapiens
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (7)..(7)
<223> OTHER INFORMATION: n is 2-amino-2'-deoxyadenosine
<220> FEATURE:
<221> NAME/KEY: misc_feature
<222> LOCATION: (13)..(13)
<223> OTHER INFORMATION: n is 2-amino-2'-deoxyadenosine

<400> SEQUENCE: 1621
ctctccnctt ccncggcctg					20

<210> SEQ ID NO 1622
<211> LENGTH: 19
<212> TYPE: DNA
<213> ORGANISM: Homo sapiens
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (2)..(2)
<223> OTHER INFORMATION: n is 2-amino-2'-deoxyadenosine
<220> FEATURE:
<221> NAME/KEY: misc_feature
<222> LOCATION: (6)..(6)
<223> OTHER INFORMATION: n is 2-amino-2'-deoxyadenosine
<220> FEATURE:
<221> NAME/KEY: misc_feature
<222> LOCATION: (14)..(14)
<223> OTHER INFORMATION: n is 2-amino-2'-deoxyadenosine

<400> SEQUENCE: 1622
gnccgngctg gccncctcc					19

<210> SEQ ID NO 1623
<211> LENGTH: 20
<212> TYPE: DNA
<213> ORGANISM: Homo sapiens
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (4)..(4)
<223> OTHER INFORMATION: n is 2-amino-2'-deoxyadenosine
<220> FEATURE:
<221> NAME/KEY: misc_feature
<222> LOCATION: (11)..(11)
<223> OTHER INFORMATION: n is 2-amino-2'-deoxyadenosine
<220> FEATURE:
<221> NAME/KEY: misc_feature
<222> LOCATION: (16)..(16)
<223> OTHER INFORMATION: n is 2-amino-2'-deoxyadenosine
<220> FEATURE:
<221> NAME/KEY: misc_feature
<222> LOCATION: (19)..(19)
<223> OTHER INFORMATION: n is 2-amino-2'-deoxyadenosine

<400> SEQUENCE: 1623
tccnctggcc ngcccnggnc                                           20

<210> SEQ ID NO 1624
<211> LENGTH: 21
<212> TYPE: DNA
<213> ORGANISM: Homo sapiens
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (1)..(2)
<223> OTHER INFORMATION: n is 2-amino-2'-deoxyadenosine
<220> FEATURE:
<221> NAME/KEY: misc_feature
<222> LOCATION: (4)..(4)
<223> OTHER INFORMATION: n is 2-amino-2'-deoxyadenosine
<220> FEATURE:
<221> NAME/KEY: misc_feature
<222> LOCATION: (11)..(12)
<223> OTHER INFORMATION: n is 2-amino-2'-deoxyadenosine

<400> SEQUENCE: 1624
nngngtcctg nngccgcttg t                                         21

<210> SEQ ID NO 1625
<211> LENGTH: 20
<212> TYPE: DNA
<213> ORGANISM: Homo sapiens
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (1)..(1)
<223> OTHER INFORMATION: n is 2-amino-2'-deoxyadenosine
<220> FEATURE:
<221> NAME/KEY: misc_feature
<222> LOCATION: (3)..(3)
<223> OTHER INFORMATION: n is 2-amino-2'-deoxyadenosine
<220> FEATURE:
<221> NAME/KEY: misc_feature
<222> LOCATION: (7)..(7)
<223> OTHER INFORMATION: n is 2-amino-2'-deoxyadenosine
<220> FEATURE:
<221> NAME/KEY: misc_feature
<222> LOCATION: (9)..(9)
<223> OTHER INFORMATION: n is 2-amino-2'-deoxyadenosine

<400> SEQUENCE: 1625
ntngccncng ggctgtcctt                                           20

<210> SEQ ID NO 1626
<211> LENGTH: 18
<212> TYPE: DNA
<213> ORGANISM: Rattus norvegicus
<220> FEATURE:
<221> NAME/KEY: misc_feature
<223> OTHER INFORMATION: All nucleotides are linked by phosphorothioate
      linkages

<400> SEQUENCE: 1626
tggcacttta ggtggctg                                             18

<210> SEQ ID NO 1627
<211> LENGTH: 18
<212> TYPE: DNA
<213> ORGANISM: Rattus norvegicus
<220> FEATURE:
<221> NAME/KEY: misc_feature

```
<223> OTHER INFORMATION: Nucleotides 1, 2 and 14-18 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1627
tggcacttta ggtggctg                                                   18

<210> SEQ ID NO 1628
<211> LENGTH: 18
<212> TYPE: DNA
<213> ORGANISM: Rattus norvegicus
<220> FEATURE:
<221> NAME/KEY: misc_feature
<223> OTHER INFORMATION: All nucleotides are linked by phosphorothioate
      linkages

<400> SEQUENCE: 1628
actcatattc atagggtg                                                   18

<210> SEQ ID NO 1629
<211> LENGTH: 18
<212> TYPE: DNA
<213> ORGANISM: Rattus norvegicus
<220> FEATURE:
<221> NAME/KEY: misc_feature
<223> OTHER INFORMATION: Nucleotides 1, 2, and 15-18 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1629
actcatattc atagggtg                                                   18

<210> SEQ ID NO 1630
<211> LENGTH: 19
<212> TYPE: DNA
<213> ORGANISM: Homo sapiens
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (9)..(9)
<223> OTHER INFORMATION: n is 2-amino-2'-deoxyadenosine
<220> FEATURE:
<221> NAME/KEY: misc_feature
<222> LOCATION: (15)..(15)
<223> OTHER INFORMATION: n is 2-amino-2'-deoxyadenosine

<400> SEQUENCE: 1630
gggtctgcng cgggntggt                                                  19

<210> SEQ ID NO 1631
<211> LENGTH: 21
<212> TYPE: DNA
<213> ORGANISM: Homo sapiens
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (4)..(4)
<223> OTHER INFORMATION: n is 2-amino-2'-deoxyadenosine
<220> FEATURE:
<221> NAME/KEY: misc_feature
```

```
<222> LOCATION: (7)..(7)
<223> OTHER INFORMATION: n is 2-amino-2'-deoxyadenosine
<220> FEATURE:
<221> NAME/KEY: misc_feature
<222> LOCATION: (13)..(13)
<223> OTHER INFORMATION: n is 2-amino-2'-deoxyadenosine

<400> SEQUENCE: 1631
gttnctnctt ccncctgcct g                                              21

<210> SEQ ID NO 1632
<211> LENGTH: 19
<212> TYPE: DNA
<213> ORGANISM: Homo sapiens
<220> FEATURE:
<221> NAME/KEY: misc_feature
<223> OTHER INFORMATION: Nucleotides 1, 2 and 15-19 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages
<220> FEATURE:
<221> NAME/KEY: misc_feature
<222> LOCATION: (11)..(11)
<223> OTHER INFORMATION: n is inosine

<400> SEQUENCE: 1632
ggttgctcag ntctgcaca                                                 19

<210> SEQ ID NO 1633
<211> LENGTH: 21
<212> TYPE: DNA
<213> ORGANISM: Homo sapiens
<220> FEATURE:
<221> NAME/KEY: misc_feature
<223> OTHER INFORMATION: Nucleotides 1, 2 and 18-21 are
      2'-deoxy-2'-fluoro-arabinonucleotides
<220> FEATURE:
<221> NAME/KEY: misc_feature
<223> OTHER INFORMATION: All nucleotides are linked by phosphorothioate
      linkages

<400> SEQUENCE: 1633
tcatgagtgg cagctgcaat t                                              21

<210> SEQ ID NO 1634
<211> LENGTH: 22
<212> TYPE: RNA
<213> ORGANISM: Homo sapiens

<400> SEQUENCE: 1634
uuguacaugg uaggcuuuca uu                                             22

<210> SEQ ID NO 1635
<211> LENGTH: 22
<212> TYPE: RNA
<213> ORGANISM: Homo sapiens

<400> SEQUENCE: 1635
ugaaggucua cugugugcca gg                                             22

<210> SEQ ID NO 1636
<211> LENGTH: 21
<212> TYPE: RNA
<213> ORGANISM: Homo sapiens

<400> SEQUENCE: 1636
auccuugcua ucugggugcu a                                              21
```

<210> SEQ ID NO 1637
<211> LENGTH: 22
<212> TYPE: RNA
<213> ORGANISM: Homo sapiens

<400> SEQUENCE: 1637
aaugcaccug ggcaaggauu ca                                         22

<210> SEQ ID NO 1638
<211> LENGTH: 22
<212> TYPE: RNA
<213> ORGANISM: Homo sapiens

<400> SEQUENCE: 1638
auucuaauuu cuccacgucu uu                                         22

<210> SEQ ID NO 1639
<211> LENGTH: 22
<212> TYPE: RNA
<213> ORGANISM: Homo sapiens

<400> SEQUENCE: 1639
aagaugugga aaaauuggaa uc                                         22

<210> SEQ ID NO 1640
<211> LENGTH: 22
<212> TYPE: RNA
<213> ORGANISM: Homo sapiens

<400> SEQUENCE: 1640
aaaaguaauu gugguuuugg cc                                         22

<210> SEQ ID NO 1641
<211> LENGTH: 22
<212> TYPE: RNA
<213> ORGANISM: Homo sapiens

<400> SEQUENCE: 1641
caagaaccuc aguugcuuuu gu                                         22

<210> SEQ ID NO 1642
<211> LENGTH: 23
<212> TYPE: RNA
<213> ORGANISM: Homo sapiens

<400> SEQUENCE: 1642
acuccauuug uuuugaugau gga                                        23

<210> SEQ ID NO 1643
<211> LENGTH: 22
<212> TYPE: RNA
<213> ORGANISM: Homo sapiens

<400> SEQUENCE: 1643
caucaucguc ucaaugagu cu                                          22

<210> SEQ ID NO 1644
<211> LENGTH: 21
<212> TYPE: RNA
<213> ORGANISM: Homo sapiens

<400> SEQUENCE: 1644
cuuuuugcgg ucugggcuug c                                          21

-continued

<210> SEQ ID NO 1645
<211> LENGTH: 22
<212> TYPE: RNA
<213> ORGANISM: Homo sapiens

<400> SEQUENCE: 1645
aagcccuuac cccaaaaagc au                                              22

<210> SEQ ID NO 1646
<211> LENGTH: 22
<212> TYPE: RNA
<213> ORGANISM: Homo sapiens

<400> SEQUENCE: 1646
uggagagaaa ggcaguuccu ga                                              22

<210> SEQ ID NO 1647
<211> LENGTH: 22
<212> TYPE: RNA
<213> ORGANISM: Homo sapiens

<400> SEQUENCE: 1647
aggggcuggc uuccucugg uc                                               22

<210> SEQ ID NO 1648
<211> LENGTH: 24
<212> TYPE: RNA
<213> ORGANISM: Homo sapiens

<400> SEQUENCE: 1648
agcagaagca gggagguucu ccca                                            24

<210> SEQ ID NO 1649
<211> LENGTH: 23
<212> TYPE: RNA
<213> ORGANISM: Homo sapiens

<400> SEQUENCE: 1649
cgcauccccu agggcauugg ugu                                             23

<210> SEQ ID NO 1650
<211> LENGTH: 20
<212> TYPE: RNA
<213> ORGANISM: Homo sapiens

<400> SEQUENCE: 1650
acugccccag gugcugcugg                                                 20

<210> SEQ ID NO 1651
<211> LENGTH: 23
<212> TYPE: RNA
<213> ORGANISM: Homo sapiens

<400> SEQUENCE: 1651
ucccuguccu ccaggagcuc acg                                             23

<210> SEQ ID NO 1652
<211> LENGTH: 23
<212> TYPE: RNA
<213> ORGANISM: Homo sapiens

<400> SEQUENCE: 1652
ugagcgccuc gacgacagag ccg                                             23

```
<210> SEQ ID NO 1653
<211> LENGTH: 22
<212> TYPE: RNA
<213> ORGANISM: Homo sapiens

<400> SEQUENCE: 1653
agaggcuggc cgugaugaau uc                                              22

<210> SEQ ID NO 1654
<211> LENGTH: 22
<212> TYPE: RNA
<213> ORGANISM: Homo sapiens

<400> SEQUENCE: 1654
gucauacacg gcucuccucu cu                                              22

<210> SEQ ID NO 1655
<211> LENGTH: 20
<212> TYPE: RNA
<213> ORGANISM: Homo sapiens

<400> SEQUENCE: 1655
ccauggaucu ccaggugggu                                                 20

<210> SEQ ID NO 1656
<211> LENGTH: 22
<212> TYPE: RNA
<213> ORGANISM: Homo sapiens

<400> SEQUENCE: 1656
caaccuggag gacuccaugc ug                                              22

<210> SEQ ID NO 1657
<211> LENGTH: 22
<212> TYPE: RNA
<213> ORGANISM: Homo sapiens

<400> SEQUENCE: 1657
augcugacau auuuacuaga gg                                              22

<210> SEQ ID NO 1658
<211> LENGTH: 21
<212> TYPE: RNA
<213> ORGANISM: Homo sapiens

<400> SEQUENCE: 1658
ucuaguaaga guggcagucg a                                               21

<210> SEQ ID NO 1659
<211> LENGTH: 24
<212> TYPE: RNA
<213> ORGANISM: Homo sapiens

<400> SEQUENCE: 1659 acuggggcu uucgggcucu gcgu                                             24

<210> SEQ ID NO 1660
<211> LENGTH: 19
<212> TYPE: RNA
<213> ORGANISM: Homo sapiens

<400> SEQUENCE: 1660
ucuaggcugg uacugcuga                                                  19
```

<210> SEQ ID NO 1661
<211> LENGTH: 22
<212> TYPE: RNA
<213> ORGANISM: Homo sapiens

<400> SEQUENCE: 1661
aaaccugugu uguucaagag uc                                            22

<210> SEQ ID NO 1662
<211> LENGTH: 24
<212> TYPE: RNA
<213> ORGANISM: Homo sapiens

<400> SEQUENCE: 1662
ugccuggguc ucuggccugc gcgu                                          24

<210> SEQ ID NO 1663
<211> LENGTH: 21
<212> TYPE: RNA
<213> ORGANISM: Homo sapiens

<400> SEQUENCE: 1663
cccggagcca ggaugcagcu c                                             21

<210> SEQ ID NO 1664
<211> LENGTH: 21
<212> TYPE: RNA
<213> ORGANISM: Homo sapiens

<400> SEQUENCE: 1664
acucuagcug ccaaaggcgc u                                             21

<210> SEQ ID NO 1665
<211> LENGTH: 22
<212> TYPE: RNA
<213> ORGANISM: Homo sapiens

<400> SEQUENCE: 1665
ucuacaaagg aaagcgcuuu cu                                            22

<210> SEQ ID NO 1666
<211> LENGTH: 22
<212> TYPE: RNA
<213> ORGANISM: Homo sapiens

<400> SEQUENCE: 1666
aguuuugcau aguugcacua ca                                            22

<210> SEQ ID NO 1667
<211> LENGTH: 23
<212> TYPE: RNA
<213> ORGANISM: Homo sapiens

<400> SEQUENCE: 1667
ugugcaaauc uaugcaaaac uga                                           23

<210> SEQ ID NO 1668
<211> LENGTH: 23
<212> TYPE: RNA
<213> ORGANISM: Homo sapiens

<400> SEQUENCE: 1668 uaaagucuu auagugcagg uag                                            23

<210> SEQ ID NO 1669
<211> LENGTH: 22
<212> TYPE: RNA
<213> ORGANISM: Homo sapiens

<400> SEQUENCE: 1669
acugcauuau gagcacuuaa ag                                              22

<210> SEQ ID NO 1670
<211> LENGTH: 23
<212> TYPE: RNA
<213> ORGANISM: Homo sapiens

<400> SEQUENCE: 1670
caaagugcuc auagugcagg uag                                             23

<210> SEQ ID NO 1671
<211> LENGTH: 22
<212> TYPE: RNA
<213> ORGANISM: Homo sapiens

<400> SEQUENCE: 1671
acuguaguau gggcacuucc ag                                              22

<210> SEQ ID NO 1672
<211> LENGTH: 22
<212> TYPE: RNA
<213> ORGANISM: Homo sapiens

<400> SEQUENCE: 1672
agagcuuagc ugauugguga ac                                              22

<210> SEQ ID NO 1673
<211> LENGTH: 21
<212> TYPE: RNA
<213> ORGANISM: Homo sapiens

<400> SEQUENCE: 1673
uucacagugg cuaaguucug c                                               21

<210> SEQ ID NO 1674
<211> LENGTH: 21
<212> TYPE: RNA
<213> ORGANISM: Homo sapiens

<400> SEQUENCE: 1674
uaaagugcug acagugcaga u                                               21

<210> SEQ ID NO 1675
<211> LENGTH: 22
<212> TYPE: RNA
<213> ORGANISM: Homo sapiens

<400> SEQUENCE: 1675
ccgcacugug gguacuugcu gc                                              22

<210> SEQ ID NO 1676
<211> LENGTH: 22
<212> TYPE: RNA
<213> ORGANISM: Homo sapiens

<400> SEQUENCE: 1676
cugaagcuca gagggcucug au                                              22

-continued

<210> SEQ ID NO 1677
<211> LENGTH: 22
<212> TYPE: RNA
<213> ORGANISM: Homo sapiens

<400> SEQUENCE: 1677
ucggauccgu cugagcuugg cu                                          22

<210> SEQ ID NO 1678
<211> LENGTH: 22
<212> TYPE: RNA
<213> ORGANISM: Homo sapiens

<400> SEQUENCE: 1678
ugugacuggu ugaccagagg gg                                          22

<210> SEQ ID NO 1679
<211> LENGTH: 23
<212> TYPE: RNA
<213> ORGANISM: Homo sapiens

<400> SEQUENCE: 1679
agcugguguu gugaaucagg ccg                                         23

<210> SEQ ID NO 1680
<211> LENGTH: 22
<212> TYPE: RNA
<213> ORGANISM: Homo sapiens

<400> SEQUENCE: 1680
gcuauuucac gacaccaggg uu                                          22

<210> SEQ ID NO 1681
<211> LENGTH: 22
<212> TYPE: RNA
<213> ORGANISM: Homo sapiens

<400> SEQUENCE: 1681
aaaguucuga gacacuccga cu                                          22

<210> SEQ ID NO 1682
<211> LENGTH: 22
<212> TYPE: RNA
<213> ORGANISM: Homo sapiens

<400> SEQUENCE: 1682
ucagugcacu acagaacuuu gu                                          22

<210> SEQ ID NO 1683
<211> LENGTH: 23
<212> TYPE: RNA
<213> ORGANISM: Homo sapiens

<400> SEQUENCE: 1683
ucuggcuccg ugucuucacu ccc                                         23

<210> SEQ ID NO 1684
<211> LENGTH: 21
<212> TYPE: RNA
<213> ORGANISM: Homo sapiens

<400> SEQUENCE: 1684
agggagggac gggggcugug c                                           21

```
<210> SEQ ID NO 1685
<211> LENGTH: 22
<212> TYPE: RNA
<213> ORGANISM: Homo sapiens

<400> SEQUENCE: 1685
uagguuaucc guguugccuu cg                                              22

<210> SEQ ID NO 1686
<211> LENGTH: 22
<212> TYPE: RNA
<213> ORGANISM: Homo sapiens

<400> SEQUENCE: 1686
aaucauacac gguugaccua uu                                              22

<210> SEQ ID NO 1687
<211> LENGTH: 23
<212> TYPE: RNA
<213> ORGANISM: Homo sapiens

<400> SEQUENCE: 1687
uuaaugcuaa ucgugauagg ggu                                             23

<210> SEQ ID NO 1688
<211> LENGTH: 22
<212> TYPE: RNA
<213> ORGANISM: Homo sapiens

<400> SEQUENCE: 1688
cuccuacaua uuagcauuaa ca                                              22

<210> SEQ ID NO 1689
<211> LENGTH: 24
<212> TYPE: RNA
<213> ORGANISM: Homo sapiens

<400> SEQUENCE: 1689
uuuggcaaug guagaacuca cacu                                            24

<210> SEQ ID NO 1690
<211> LENGTH: 21
<212> TYPE: RNA
<213> ORGANISM: Homo sapiens

<400> SEQUENCE: 1690
ugguucuaga cuugccaacu a                                               21

<210> SEQ ID NO 1691
<211> LENGTH: 21
<212> TYPE: RNA
<213> ORGANISM: Homo sapiens

<400> SEQUENCE: 1691
caucccuugc augguggagg g                                               21

<210> SEQ ID NO 1692
<211> LENGTH: 21
<212> TYPE: RNA
<213> ORGANISM: Homo sapiens

<400> SEQUENCE: 1692
cucccacaug cagguuugc a                                                21
```

<210> SEQ ID NO 1693
<211> LENGTH: 22
<212> TYPE: RNA
<213> ORGANISM: Homo sapiens

<400> SEQUENCE: 1693
uucccuuugu cauccuaugc cu                                        22

<210> SEQ ID NO 1694
<211> LENGTH: 22
<212> TYPE: RNA
<213> ORGANISM: Homo sapiens

<400> SEQUENCE: 1694
uucccuuugu cauccuucgc cu                                        22

<210> SEQ ID NO 1695
<211> LENGTH: 22
<212> TYPE: RNA
<213> ORGANISM: Homo sapiens

<400> SEQUENCE: 1695
ugccugucua cacuugcugu gc                                        22

<210> SEQ ID NO 1696
<211> LENGTH: 22
<212> TYPE: RNA
<213> ORGANISM: Homo sapiens

<400> SEQUENCE: 1696
acagcaggca cagacaggca gu                                        22

<210> SEQ ID NO 1697
<211> LENGTH: 22
<212> TYPE: RNA
<213> ORGANISM: Homo sapiens

<400> SEQUENCE: 1697
cuggcccucu cugcccuucc gu                                        22

<210> SEQ ID NO 1698
<211> LENGTH: 22
<212> TYPE: RNA
<213> ORGANISM: Homo sapiens

<400> SEQUENCE: 1698
gcugacuccu aguccagggc uc                                        22

<210> SEQ ID NO 1699
<211> LENGTH: 22
<212> TYPE: RNA
<213> ORGANISM: Homo sapiens

<400> SEQUENCE: 1699
agagguugcc cuuggugaau uc                                        22

<210> SEQ ID NO 1700
<211> LENGTH: 22
<212> TYPE: RNA
<213> ORGANISM: Homo sapiens

<400> SEQUENCE: 1700
aucacacaaa ggcaacuuuu gu                                        22

-continued

```
<210> SEQ ID NO 1701
<211> LENGTH: 23
<212> TYPE: RNA
<213> ORGANISM: Homo sapiens

<400> SEQUENCE: 1701
agguuguccg uggugaguuc gca                                              23

<210> SEQ ID NO 1702
<211> LENGTH: 22
<212> TYPE: RNA
<213> ORGANISM: Homo sapiens

<400> SEQUENCE: 1702
aagacgggag gaaagaaggg ag                                               22

<210> SEQ ID NO 1703
<211> LENGTH: 21
<212> TYPE: RNA
<213> ORGANISM: Homo sapiens

<400> SEQUENCE: 1703
ucacuccucu ccucccgucu u                                                21

<210> SEQ ID NO 1704
<211> LENGTH: 24
<212> TYPE: RNA
<213> ORGANISM: Homo sapiens

<400> SEQUENCE: 1704
cugaagugau guguaacuga ucag                                             24

<210> SEQ ID NO 1705
<211> LENGTH: 23
<212> TYPE: RNA
<213> ORGANISM: Homo sapiens

<400> SEQUENCE: 1705
acuuacagac aagagccuug cuc                                              23

<210> SEQ ID NO 1706
<211> LENGTH: 22
<212> TYPE: RNA
<213> ORGANISM: Homo sapiens

<400> SEQUENCE: 1706
uggucuagga uuguuggagg ag                                               22

<210> SEQ ID NO 1707
<211> LENGTH: 23
<212> TYPE: RNA
<213> ORGANISM: Homo sapiens

<400> SEQUENCE: 1707
cuaauaguau cuaccacaau aaa                                              23

<210> SEQ ID NO 1708
<211> LENGTH: 21
<212> TYPE: RNA
<213> ORGANISM: Homo sapiens

<400> SEQUENCE: 1708
aggaggcagc gcucucagga c                                                21
```

<210> SEQ ID NO 1709
<211> LENGTH: 23
<212> TYPE: RNA
<213> ORGANISM: Homo sapiens

<400> SEQUENCE: 1709
ggcagguucu cacccucucu agg					23

<210> SEQ ID NO 1710
<211> LENGTH: 25
<212> TYPE: RNA
<213> ORGANISM: Homo sapiens

<400> SEQUENCE: 1710
ggcggaggga aguagguccg uuggu					25

<210> SEQ ID NO 1711
<211> LENGTH: 22
<212> TYPE: RNA
<213> ORGANISM: Homo sapiens

<400> SEQUENCE: 1711
aggcggggcg ccgcgggacc gc					22

<210> SEQ ID NO 1712
<211> LENGTH: 20
<212> TYPE: RNA
<213> ORGANISM: Homo sapiens

<400> SEQUENCE: 1712
guagaggaga uggcgcaggg					20

<210> SEQ ID NO 1713
<211> LENGTH: 21
<212> TYPE: RNA
<213> ORGANISM: Homo sapiens

<400> SEQUENCE: 1713
uccucuucuc ccuccuccca g					21

<210> SEQ ID NO 1714
<211> LENGTH: 23
<212> TYPE: RNA
<213> ORGANISM: Homo sapiens

<400> SEQUENCE: 1714
cgggucggag uuagcucaag cgg					23

<210> SEQ ID NO 1715
<211> LENGTH: 21
<212> TYPE: RNA
<213> ORGANISM: Homo sapiens

<400> SEQUENCE: 1715
cgcgggugcu uacugacccu u					21

<210> SEQ ID NO 1716
<211> LENGTH: 21
<212> TYPE: RNA
<213> ORGANISM: Homo sapiens

<400> SEQUENCE: 1716
aaggcagggc ccccgcuccc c					21

```
<210> SEQ ID NO 1717
<211> LENGTH: 22
<212> TYPE: RNA
<213> ORGANISM: Homo sapiens

<400> SEQUENCE: 1717
uauugcacau uacuaaguug ca                                              22

<210> SEQ ID NO 1718
<211> LENGTH: 22
<212> TYPE: RNA
<213> ORGANISM: Homo sapiens

<400> SEQUENCE: 1718
caauuuagug ugugugauau uu                                              22

<210> SEQ ID NO 1719
<211> LENGTH: 23
<212> TYPE: RNA
<213> ORGANISM: Homo sapiens

<400> SEQUENCE: 1719
uuauugcuua agaauacgcg uag                                             23

<210> SEQ ID NO 1720
<211> LENGTH: 21
<212> TYPE: RNA
<213> ORGANISM: Homo sapiens

<400> SEQUENCE: 1720
cauaaaguag aaagcacuac u                                               21

<210> SEQ ID NO 1721
<211> LENGTH: 23
<212> TYPE: RNA
<213> ORGANISM: Homo sapiens

<400> SEQUENCE: 1721
uguaguguuu ccuacuuuau gga                                             23

<210> SEQ ID NO 1722
<211> LENGTH: 23
<212> TYPE: RNA
<213> ORGANISM: Homo sapiens

<400> SEQUENCE: 1722
aacauucaac gcugucggug agu                                             23

<210> SEQ ID NO 1723
<211> LENGTH: 22
<212> TYPE: RNA
<213> ORGANISM: Homo sapiens

<400> SEQUENCE: 1723
accaucgacc guugauugua cc                                              22

<210> SEQ ID NO 1724
<211> LENGTH: 23
<212> TYPE: RNA
<213> ORGANISM: Homo sapiens

<400> SEQUENCE: 1724
aacauucauu gcugucggug ggu                                             23
```

```
<210> SEQ ID NO 1725
<211> LENGTH: 22
<212> TYPE: RNA
<213> ORGANISM: Homo sapiens

<400> SEQUENCE: 1725
aacauucaac cugucgguga gu                                              22

<210> SEQ ID NO 1726
<211> LENGTH: 22
<212> TYPE: RNA
<213> ORGANISM: Homo sapiens

<400> SEQUENCE: 1726
aaccaucgac cguugagugg ac                                              22

<210> SEQ ID NO 1727
<211> LENGTH: 23
<212> TYPE: RNA
<213> ORGANISM: Homo sapiens

<400> SEQUENCE: 1727
aacauucauu guugucggug ggu                                             23

<210> SEQ ID NO 1728
<211> LENGTH: 22
<212> TYPE: RNA
<213> ORGANISM: Homo sapiens

<400> SEQUENCE: 1728
uauacaaggg cagacucucu cu                                              22

<210> SEQ ID NO 1729
<211> LENGTH: 23
<212> TYPE: RNA
<213> ORGANISM: Homo sapiens

<400> SEQUENCE: 1729
ucaagagcaa uaacgaaaaa ugu                                             23

<210> SEQ ID NO 1730
<211> LENGTH: 22
<212> TYPE: RNA
<213> ORGANISM: Homo sapiens

<400> SEQUENCE: 1730
uuuuucauua uugcuccuga cc                                              22

<210> SEQ ID NO 1731
<211> LENGTH: 21
<212> TYPE: RNA
<213> ORGANISM: Homo sapiens

<400> SEQUENCE: 1731
gaacggcuuc auacaggagu u                                               21

<210> SEQ ID NO 1732
<211> LENGTH: 22
<212> TYPE: RNA
<213> ORGANISM: Homo sapiens

<400> SEQUENCE: 1732
cuccuauaug augccuuucu uc                                              22
```

```
<210> SEQ ID NO 1733
<211> LENGTH: 22
<212> TYPE: RNA
<213> ORGANISM: Homo sapiens

<400> SEQUENCE: 1733
guagauucuc cuucuaugag ua                                              22

<210> SEQ ID NO 1734
<211> LENGTH: 21
<212> TYPE: RNA
<213> ORGANISM: Homo sapiens

<400> SEQUENCE: 1734
aucauagagg aaaauccacg u                                               21

<210> SEQ ID NO 1735
<211> LENGTH: 22
<212> TYPE: RNA
<213> ORGANISM: Homo sapiens

<400> SEQUENCE: 1735
aucauagagg aaaauccaug uu                                              22

<210> SEQ ID NO 1736
<211> LENGTH: 22
<212> TYPE: RNA
<213> ORGANISM: Homo sapiens

<400> SEQUENCE: 1736
uauacaaggg caagcucucu gu                                              22

<210> SEQ ID NO 1737
<211> LENGTH: 22
<212> TYPE: RNA
<213> ORGANISM: Homo sapiens

<400> SEQUENCE: 1737
gaaguuguuc gugguggauu cg                                              22

<210> SEQ ID NO 1738
<211> LENGTH: 23
<212> TYPE: RNA
<213> ORGANISM: Homo sapiens

<400> SEQUENCE: 1738
agguuacccg agcaacuuug cau                                             23

<210> SEQ ID NO 1739
<211> LENGTH: 22
<212> TYPE: RNA
<213> ORGANISM: Homo sapiens

<400> SEQUENCE: 1739
gaauguugcu cggugaaccc cu                                              22

<210> SEQ ID NO 1740
<211> LENGTH: 22
<212> TYPE: RNA
<213> ORGANISM: Homo sapiens

<400> SEQUENCE: 1740
uuuugcaaua uguuccugaa ua                                              22
```

-continued

<210> SEQ ID NO 1741
<211> LENGTH: 22
<212> TYPE: RNA
<213> ORGANISM: Homo sapiens

<400> SEQUENCE: 1741
uugggaucau uuugcaucca ua                                              22

<210> SEQ ID NO 1742
<211> LENGTH: 22
<212> TYPE: RNA
<213> ORGANISM: Homo sapiens

<400> SEQUENCE: 1742
uucacaagga ggugucauuu au                                              22

<210> SEQ ID NO 1743
<211> LENGTH: 22
<212> TYPE: RNA
<213> ORGANISM: Homo sapiens

<400> SEQUENCE: 1743
cucuagaggg aagcgcuuuc ug                                              22

<210> SEQ ID NO 1744
<211> LENGTH: 22
<212> TYPE: RNA
<213> ORGANISM: Homo sapiens

<400> SEQUENCE: 1744
aaaaugguuc ccuuuagagu gu                                              22

<210> SEQ ID NO 1745
<211> LENGTH: 22
<212> TYPE: RNA
<213> ORGANISM: Homo sapiens

<400> SEQUENCE: 1745
aaacauucgc ggugcacuuc uu                                              22

<210> SEQ ID NO 1746
<211> LENGTH: 22
<212> TYPE: RNA
<213> ORGANISM: Homo sapiens

<400> SEQUENCE: 1746
aaaaguaauu gcgaguuuua cc                                              22

<210> SEQ ID NO 1747
<211> LENGTH: 22
<212> TYPE: RNA
<213> ORGANISM: Homo sapiens

<400> SEQUENCE: 1747
caaaacuggc aauuacuuuu gc                                              22

<210> SEQ ID NO 1748
<211> LENGTH: 22
<212> TYPE: RNA
<213> ORGANISM: Homo sapiens

<400> SEQUENCE: 1748
aaaaguaauu gcgguuuuug cc                                              22

```
<210> SEQ ID NO 1749
<211> LENGTH: 22
<212> TYPE: RNA
<213> ORGANISM: Homo sapiens

<400> SEQUENCE: 1749
caaaaaucuc aauuacuuuu gc                                              22

<210> SEQ ID NO 1750
<211> LENGTH: 22
<212> TYPE: RNA
<213> ORGANISM: Homo sapiens

<400> SEQUENCE: 1750
aaaaguaauu gugguuuuug cc                                              22

<210> SEQ ID NO 1751
<211> LENGTH: 22
<212> TYPE: RNA
<213> ORGANISM: Homo sapiens

<400> SEQUENCE: 1751
caaaaaccac aguucuuuu gc                                               22

<210> SEQ ID NO 1752
<211> LENGTH: 22
<212> TYPE: RNA
<213> ORGANISM: Homo sapiens

<400> SEQUENCE: 1752
aaaaguaauc gcgguuuuug uc                                              22

<210> SEQ ID NO 1753
<211> LENGTH: 22
<212> TYPE: RNA
<213> ORGANISM: Homo sapiens

<400> SEQUENCE: 1753
aaaaguaauu gcggauuuug cc                                              22

<210> SEQ ID NO 1754
<211> LENGTH: 22
<212> TYPE: RNA
<213> ORGANISM: Homo sapiens

<400> SEQUENCE: 1754
aaaaguaauu gcggucuuug gu                                              22

<210> SEQ ID NO 1755
<211> LENGTH: 22
<212> TYPE: RNA
<213> ORGANISM: Homo sapiens

<400> SEQUENCE: 1755
aaaaguauuu gcggguuuug uc                                              22

<210> SEQ ID NO 1756
<211> LENGTH: 22
<212> TYPE: RNA
<213> ORGANISM: Homo sapiens

<400> SEQUENCE: 1756
caaaaguaau uguggauuuu gu                                              22
```

<210> SEQ ID NO 1757
<211> LENGTH: 22
<212> TYPE: RNA
<213> ORGANISM: Homo sapiens

<400> SEQUENCE: 1757
uagcaaaaac ugcaguuacu uu                                              22

<210> SEQ ID NO 1758
<211> LENGTH: 22
<212> TYPE: RNA
<213> ORGANISM: Homo sapiens

<400> SEQUENCE: 1758
cgaaaacagc aauuaccuuu gc                                              22

<210> SEQ ID NO 1759
<211> LENGTH: 21
<212> TYPE: RNA
<213> ORGANISM: Homo sapiens

<400> SEQUENCE: 1759
uaaaguaaau augcaccaaa a                                               21

<210> SEQ ID NO 1760
<211> LENGTH: 24
<212> TYPE: RNA
<213> ORGANISM: Homo sapiens

<400> SEQUENCE: 1760
aaagacauag gauagaguca ccuc                                            24

<210> SEQ ID NO 1761
<211> LENGTH: 22
<212> TYPE: RNA
<213> ORGANISM: Homo sapiens

<400> SEQUENCE: 1761 ugguggggccg cagaacaugu gc                                             22

<210> SEQ ID NO 1762
<211> LENGTH: 22
<212> TYPE: RNA
<213> ORGANISM: Homo sapiens

<400> SEQUENCE: 1762
uaugucugcu gaccaucacc uu                                              22

<210> SEQ ID NO 1763
<211> LENGTH: 22
<212> TYPE: RNA
<213> ORGANISM: Homo sapiens

<400> SEQUENCE: 1763
cuugguucag ggagggucccc ca                                             22

<210> SEQ ID NO 1764
<211> LENGTH: 23
<212> TYPE: RNA
<213> ORGANISM: Homo sapiens

<400> SEQUENCE: 1764
aggaagcccu ggagggggcug gag                                            23

```
<210> SEQ ID NO 1765
<211> LENGTH: 21
<212> TYPE: RNA
<213> ORGANISM: Homo sapiens

<400> SEQUENCE: 1765
uccgguucuc agggcuccac c                                            21

<210> SEQ ID NO 1766
<211> LENGTH: 23
<212> TYPE: RNA
<213> ORGANISM: Homo sapiens

<400> SEQUENCE: 1766
caguaacaaa gauucauccu ugu                                          23

<210> SEQ ID NO 1767
<211> LENGTH: 22
<212> TYPE: RNA
<213> ORGANISM: Homo sapiens

<400> SEQUENCE: 1767
uggauuucuu ugugaaucac ca                                           22

<210> SEQ ID NO 1768
<211> LENGTH: 22
<212> TYPE: RNA
<213> ORGANISM: Homo sapiens

<400> SEQUENCE: 1768
uggugguuua caaaguaauu ca                                           22

<210> SEQ ID NO 1769
<211> LENGTH: 21
<212> TYPE: RNA
<213> ORGANISM: Homo sapiens

<400> SEQUENCE: 1769
uuaauaucgg acaaccauug u                                            21

<210> SEQ ID NO 1770
<211> LENGTH: 20
<212> TYPE: RNA
<213> ORGANISM: Homo sapiens

<400> SEQUENCE: 1770
gugucugggc ggacagcugc                                              20

<210> SEQ ID NO 1771
<211> LENGTH: 20
<212> TYPE: RNA
<213> ORGANISM: Homo sapiens

<400> SEQUENCE: 1771
ugagcccugu ccucccgcag                                              20

<210> SEQ ID NO 1772
<211> LENGTH: 27
<212> TYPE: RNA
<213> ORGANISM: Homo sapiens

<400> SEQUENCE: 1772
auugaucauc gacacuucga acgcaau                                      27
```

<210> SEQ ID NO 1773
<211> LENGTH: 22
<212> TYPE: RNA
<213> ORGANISM: Homo sapiens

<400> SEQUENCE: 1773
agaucagaag gugauugugg cu                                        22

<210> SEQ ID NO 1774
<211> LENGTH: 23
<212> TYPE: RNA
<213> ORGANISM: Homo sapiens

<400> SEQUENCE: 1774
uaauccuugc uaccugggug aga                                       23

<210> SEQ ID NO 1775
<211> LENGTH: 22
<212> TYPE: RNA
<213> ORGANISM: Homo sapiens

<400> SEQUENCE: 1775
augcaccugg gcaaggauuc ug                                        22

<210> SEQ ID NO 1776
<211> LENGTH: 21
<212> TYPE: RNA
<213> ORGANISM: Homo sapiens

<400> SEQUENCE: 1776
aagccugccc ggcuccucgg g                                         21

<210> SEQ ID NO 1777
<211> LENGTH: 21
<212> TYPE: RNA
<213> ORGANISM: Homo sapiens

<400> SEQUENCE: 1777
acagucugcu gagguuggag c                                         21

<210> SEQ ID NO 1778
<211> LENGTH: 20
<212> TYPE: RNA
<213> ORGANISM: Homo sapiens

<400> SEQUENCE: 1778
guguguggaa augcuucugc                                           20

<210> SEQ ID NO 1779
<211> LENGTH: 19
<212> TYPE: DNA
<213> ORGANISM: Homo sapiens

<400> SEQUENCE: 1779
ctggctcgac cggtggagg                                            19

<210> SEQ ID NO 1780
<211> LENGTH: 20
<212> TYPE: DNA
<213> ORGANISM: Homo sapiens

<400> SEQUENCE: 1780
gagaggtgaa ggtgccggac                                           20

```
<210> SEQ ID NO 1781
<211> LENGTH: 22
<212> TYPE: DNA
<213> ORGANISM: Homo sapiens

<400> SEQUENCE: 1781
gtctccggtg aggtcccagg ag                                            22

<210> SEQ ID NO 1782
<211> LENGTH: 19
<212> TYPE: DNA
<213> ORGANISM: Homo sapiens

<400> SEQUENCE: 1782
gtggagacag tggtcgtac                                                19

<210> SEQ ID NO 1783
<211> LENGTH: 19
<212> TYPE: DNA
<213> ORGANISM: Homo sapiens

<400> SEQUENCE: 1783
gtggagacag tggtcgtac                                                19

<210> SEQ ID NO 1784
<211> LENGTH: 21
<212> TYPE: DNA
<213> ORGANISM: Homo sapiens

<400> SEQUENCE: 1784
catgaaggcc ttggagagag g                                             21

<210> SEQ ID NO 1785
<211> LENGTH: 18
<212> TYPE: DNA
<213> ORGANISM: Homo sapiens

<400> SEQUENCE: 1785
atatccttgt cgtatccc                                                 18
```